United States Patent
Vanhollebeke

(10) Patent No.: US 11,840,557 B2
(45) Date of Patent: Dec. 12, 2023

(54) WNT7 VARIANTS CAPABLE OF ACTIVATING G-PROTEIN COUPLED RECEPTOR (GPR)124/RECK/FRIZZLED/LIPOPROTEIN RECEPTOR-RELATED PROTEIN (LRP)-MEDIATED WNT SIGNALING

(71) Applicant: UNIVERSITÉ LIBRE DE BRUXELLES, Brussels (BE)

(72) Inventor: Benoit Vanhollebeke, Auderghem (BE)

(73) Assignee: UNIVERSITÉ LIBRE DE BRUXELLES, Brussels (BE)

( * ) Notice: Subject to any disclaimer, the term of this patent is extended or adjusted under 35 U.S.C. 154(b) by 32 days.

(21) Appl. No.: 17/040,418

(22) PCT Filed: Mar. 22, 2019

(86) PCT No.: PCT/EP2019/057243
§ 371 (c)(1),
(2) Date: Sep. 22, 2020

(87) PCT Pub. No.: WO2019/180204
PCT Pub. Date: Sep. 26, 2019

(65) Prior Publication Data
US 2021/0309704 A1    Oct. 7, 2021

(30) Foreign Application Priority Data
Mar. 23, 2018 (EP) ..................... 18163777

(51) Int. Cl.
| C12P 21/00 | (2006.01) |
| C12P 21/02 | (2006.01) |
| C12N 15/00 | (2006.01) |
| C07K 14/00 | (2006.01) |
| A61K 38/00 | (2006.01) |
| C07K 14/47 | (2006.01) |
| A61P 25/00 | (2006.01) |
| G01N 33/50 | (2006.01) |

(52) U.S. Cl.
CPC .......... *C07K 14/4705* (2013.01); *A61P 25/00* (2018.01); *G01N 33/5041* (2013.01); *A61K 38/00* (2013.01); *G01N 2333/726* (2013.01)

(58) Field of Classification Search
CPC ............... A61K 38/00; C07K 14/4702; C07K 14/4705; C07K 14/00; A61P 25/00; A61P 9/00; A61P 9/10; C12N 15/11; C12N 2501/415
See application file for complete search history.

(56) References Cited

U.S. PATENT DOCUMENTS

2014/0044713 A1*  2/2014  De Lau .................. A61K 45/06
                                                      424/134.1

FOREIGN PATENT DOCUMENTS

| WO | WO2012/140274   | * 10/2012 |
| WO | WO 2012/140274 A2 | 10/2012 |

OTHER PUBLICATIONS

Cho et al.,Neuron, 2017; 95:1056-1073.dx.doi.org/10.1016/j.neuron.2017.07.031.*
Vanhollebeke et al. (eLife, 2005; 4:406489. DOI:107554/eLife.06489.*
Foulquier et al., Pharmacol. Rev. 2018. 70:68-141. doi.org/10.1124/pr.117.013896.*
Burgess et al. J of Cell Bio. 1990, 111:2129-2138.*
Bowie et al. Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
The Wnt7A-V5 plasmid catalog # 43816 retrieved from the Addgene website www.addgene.org/43816/ on Dec. 1, 2021.*
The Wnt7B-V5 plasmid catalog #43817 retrieved from the Addgene website www.addgene.org/43817/ on Dec. 1, 2021.*
Vallon et al. Cell Rep. 2018; 25:339-349. e9.doi:10.1016/j.celrep.2018.09.045.*
Chow et al., Trends in Neurosc. 2015; 38:598-608. dx.doi.org/10.1016/j.tins.2015.08.003.*
Alok et al. J. Cell Sci. 2017; 130:1532-1544. doi:10.1242/jcs.198093.*
Bostaille et al. Biology Open, 2016; 5:1874-1881. doi:10.1242/bio.021287.*
Posokhova et al. Cell Rep. 2015; 10:123-130.*
Kuo et al. PNAS, 2001; 98:4605-4610.*
Maltzahn et al. Nat. Comm. 2013; 4:2869. DOI:10.1038/ncomms3869.*
PAd/CMV/V-vector user guide retrieved from the Invitrogen published Jan. 4, 2012.*
MacDonald et al.,J. Biol. Chem. 2014; 289:18122-18136.*
Chang et al., Nat. Med. 2017; 23:450-, published Online Mar. 13, 2017. doi:10.1038/nm.4309.*
Vanhollebeke et al. "Tip cell-specific requirement for an atypical Gpr124- and Reck-dependent Wnt/ß-catenin pathway during brain angiogenesis ". eLife, Jan. 1, 2015, pp. 1-25.
Cho et al. "Reck and Gpr124 Are Essential Receptor Cofactors for Wnt7a/Wnt7b-Specific Signaling in Mammalian CNS Angiogenesis and Blood-Brain Barrier Regulation". Neuron, Aug. 30, 2017, pp. 1056-1073.

(Continued)

*Primary Examiner* — Chang-Yu Wang
(74) *Attorney, Agent, or Firm* — Knobbe Martens Olson & Bear, LLP

(57) ABSTRACT

Novel therapeutic agents, particularly those capable of activating (GPR)124/RECK/Frizzled/lipoprotein receptor-related protein (LRP)-mediated Wnt signaling, while not activating Frizzled/LRP-mediated Wnt signaling in the absence of RECK and/or GPR124. The agents are particularly useful for the prevention or treatment of neurovascular disorders or central nervous system (CNS) disorders including neurovascular dysfunction.

4 Claims, 36 Drawing Sheets
Specification includes a Sequence Listing.

(56) References Cited

OTHER PUBLICATIONS

Martin, Maud, et al., "Engineered Wnt ligands enable blood-brain barrier repair in neurological disorders." Science, 375 (6582), eabm4459. · DOI: 10.1126/science.abm4459; Downloaded from https://www.science.org at Universite Libre de Bruxelles on Feb. 18, 2022.
Office Action in Chinese Application No. 201980021129 dated Nov. 4, 2022.
First Search Report in Chinese Application No. 201980021129 dated Oct. 31, 2022.
Accession No. NP_004616.2, Genbank, Mar. 13, 2018.
Accession No. NP_478679.1, Genbank, Feb. 19, 2018.

* cited by examiner

FIG. 1
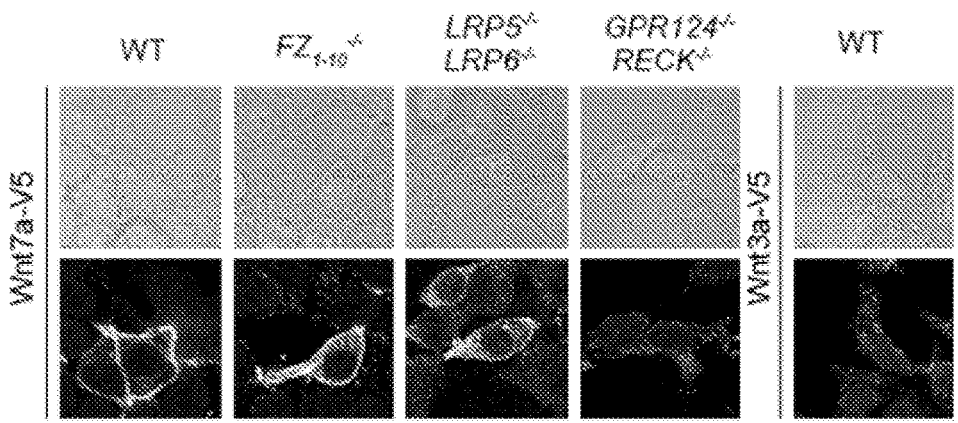
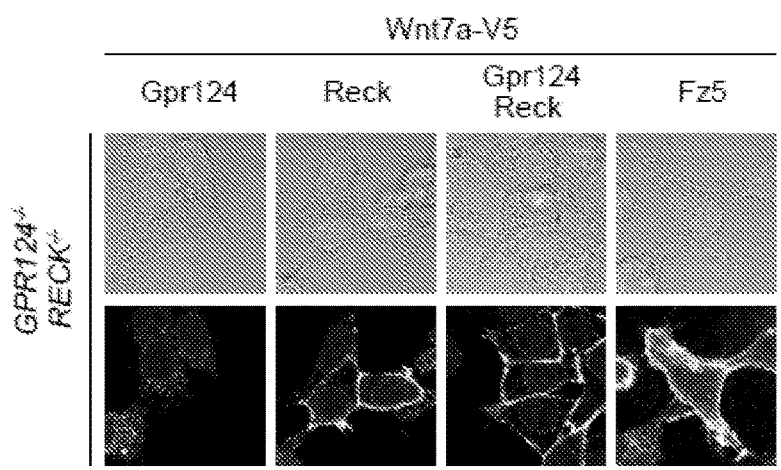
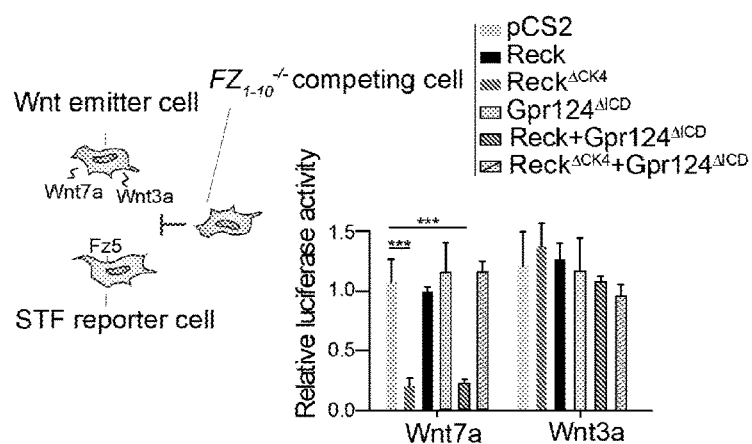

FIG. 1 (continued)
F
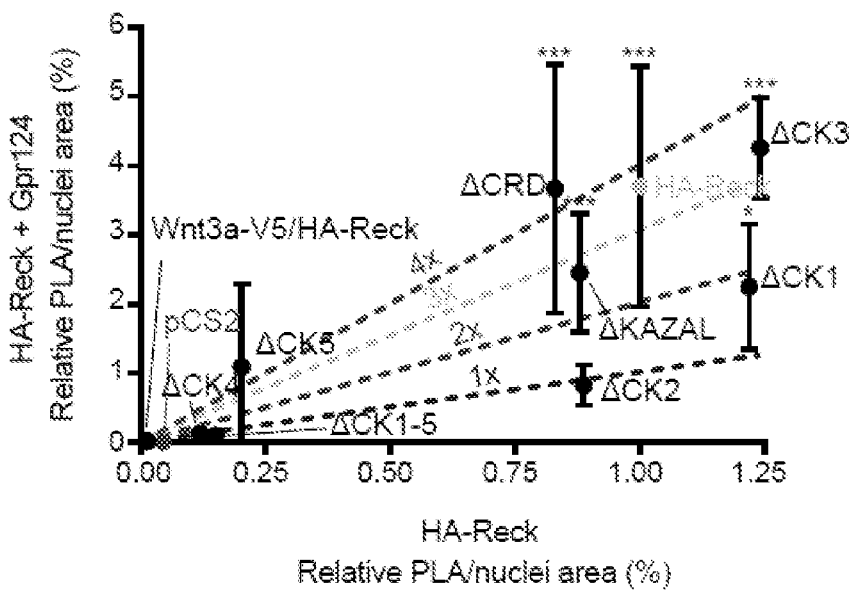
G
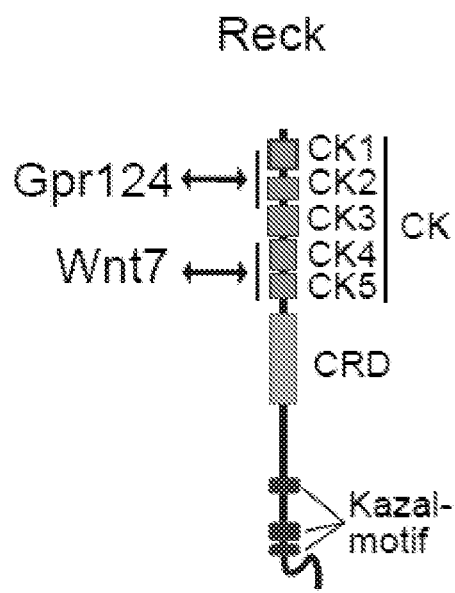

FIG. 2
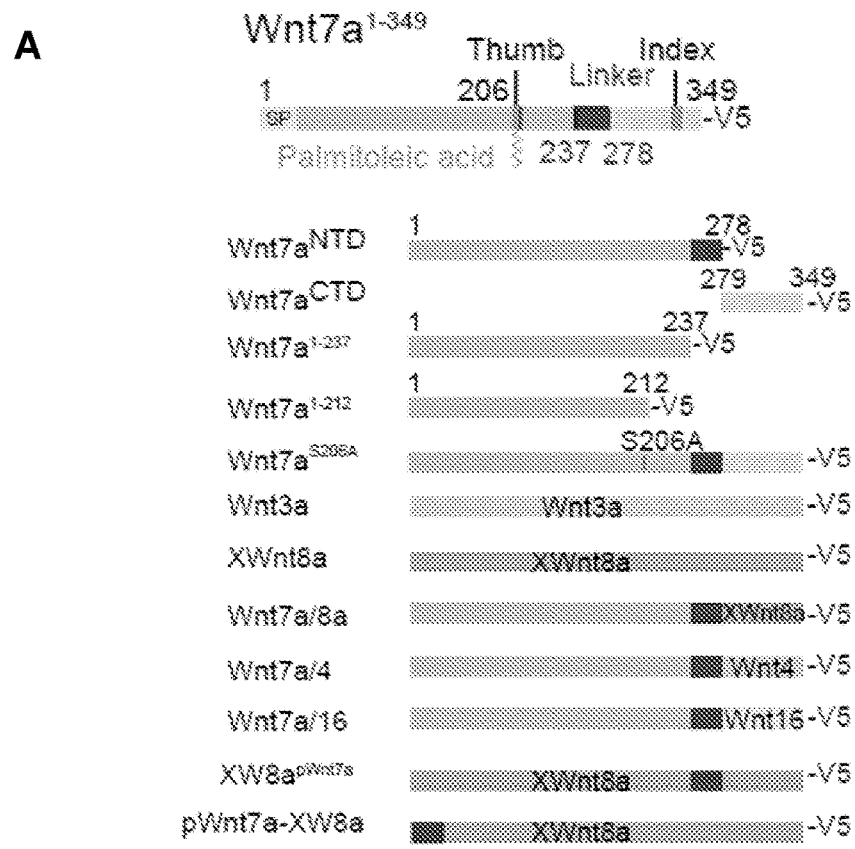
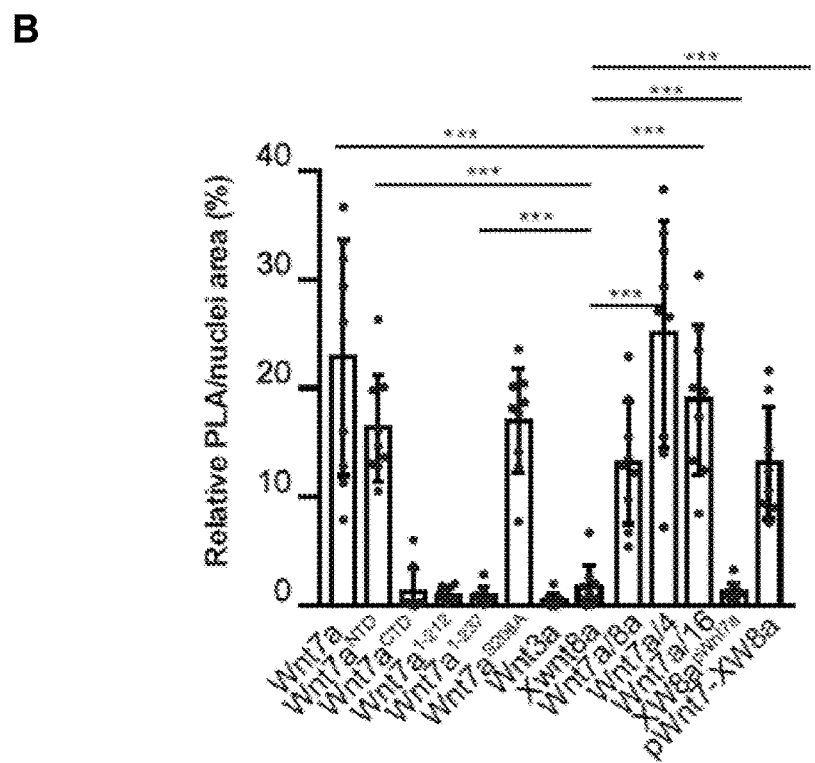

FIG. 2 (continued)
C
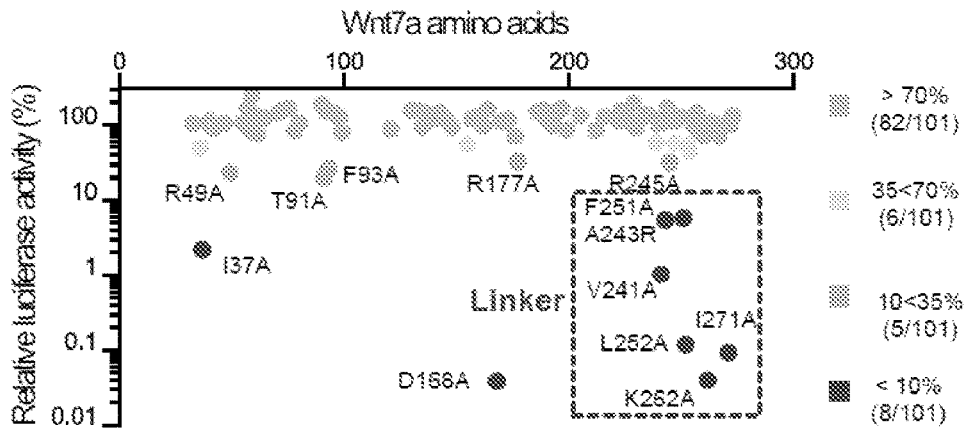
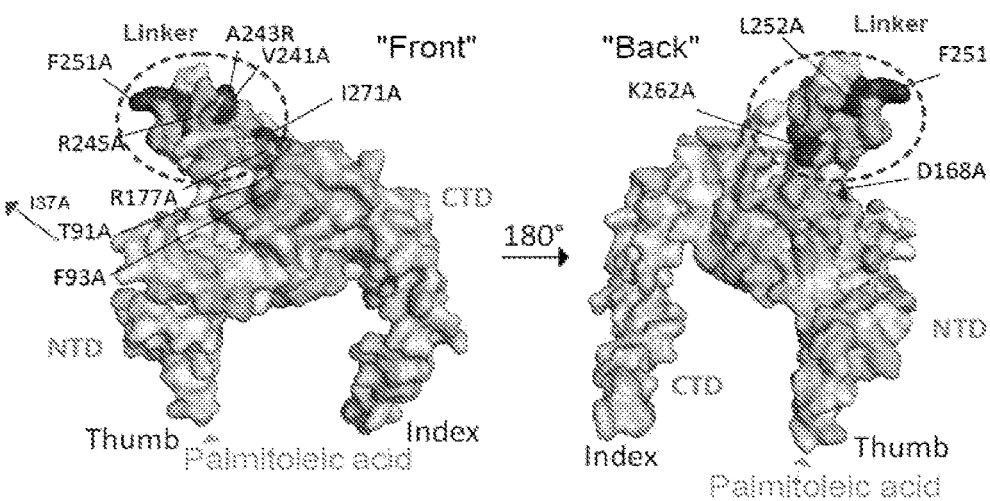
D
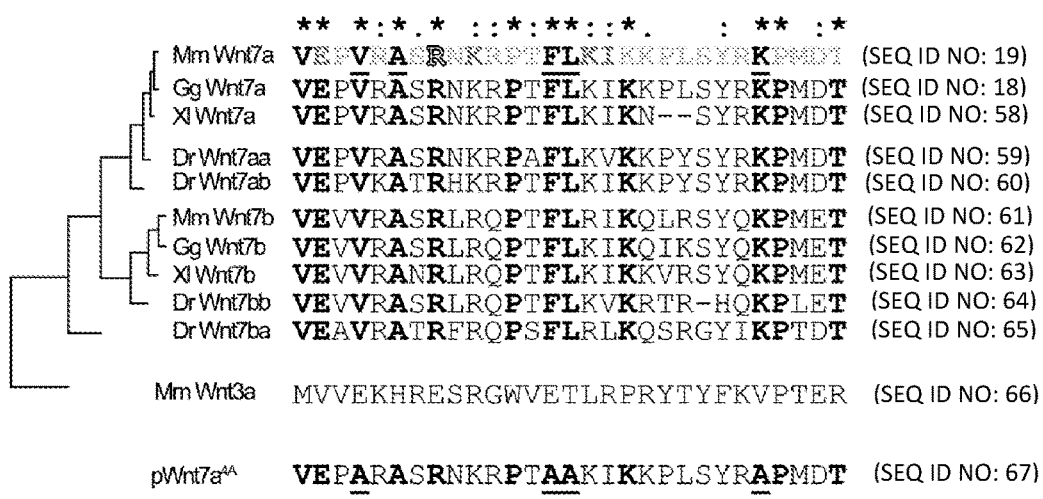

FIG. 2 (continued)
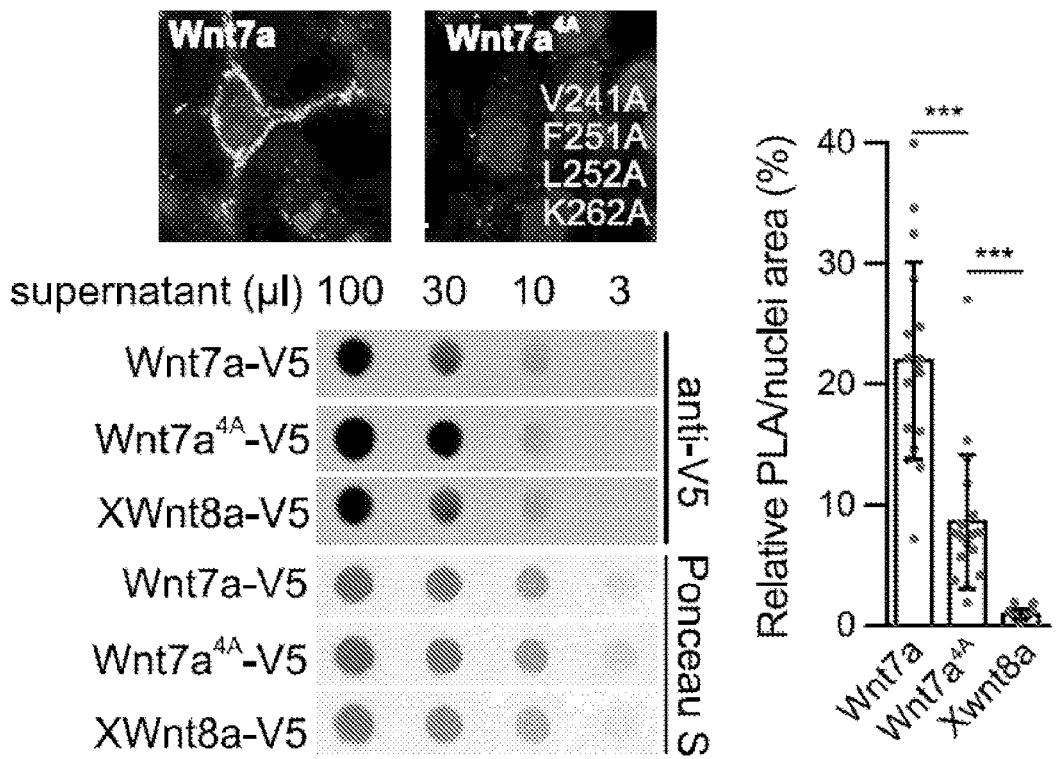
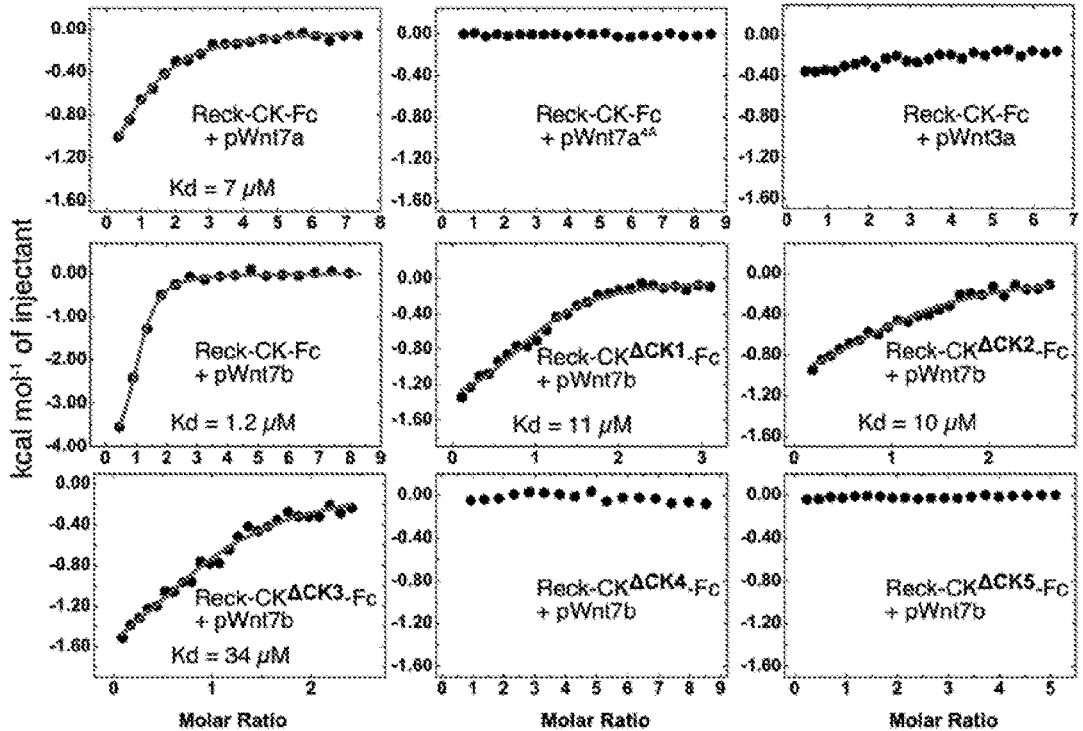

G

FIG. 3
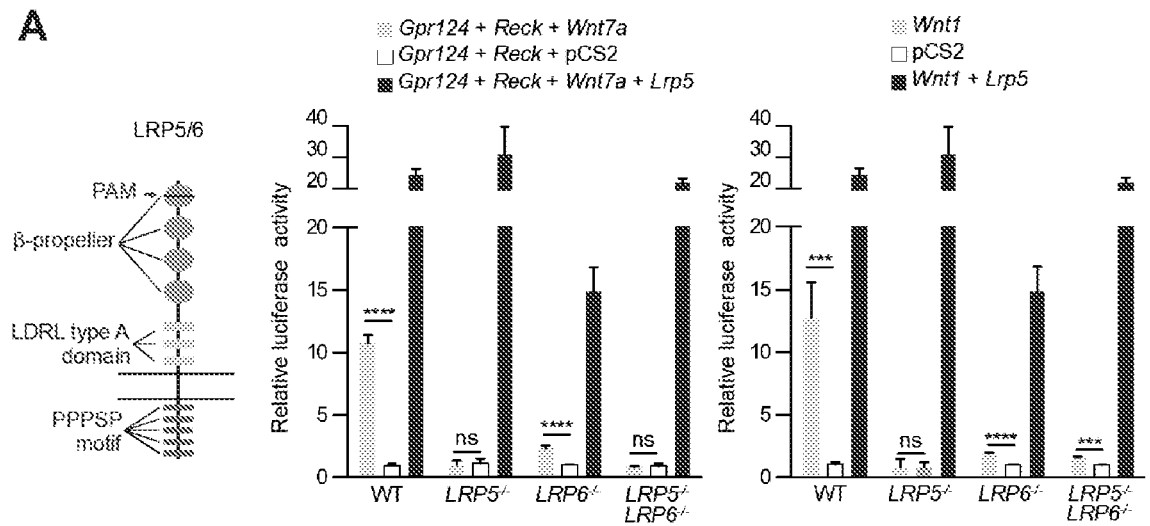
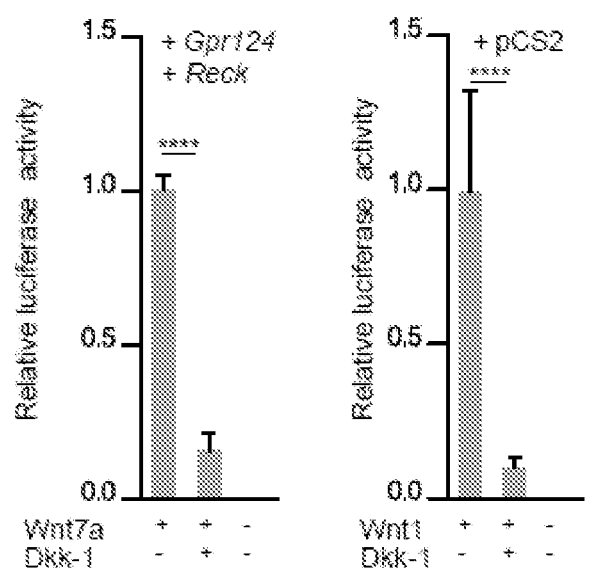

FIG. 3 (continued)
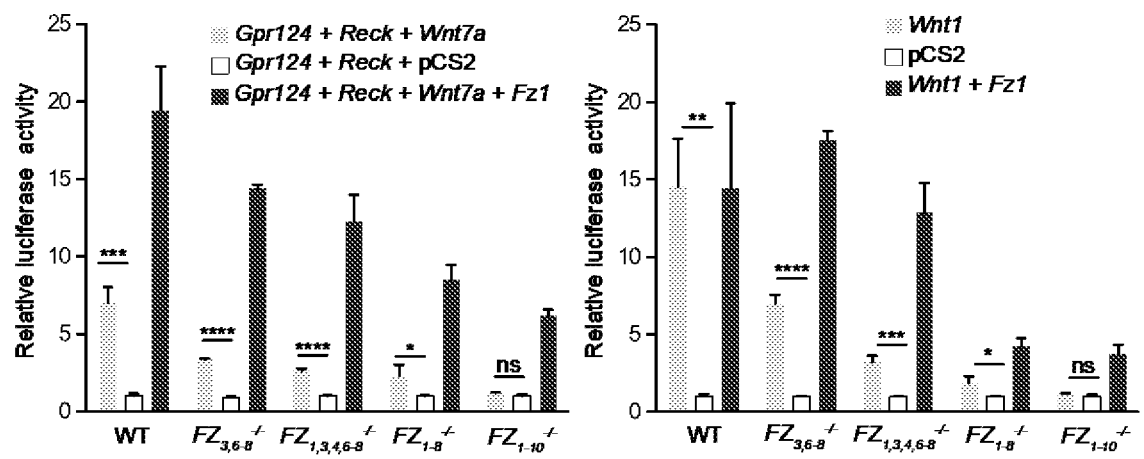
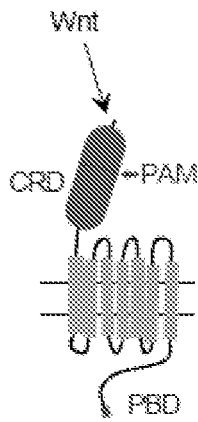
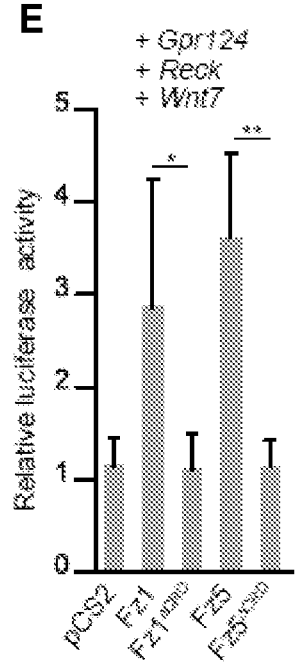

FIG. 4
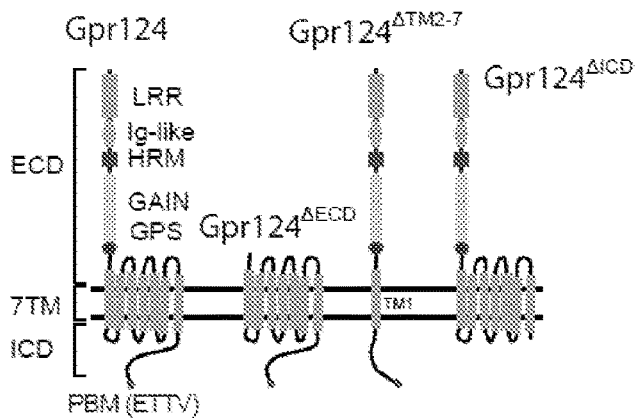
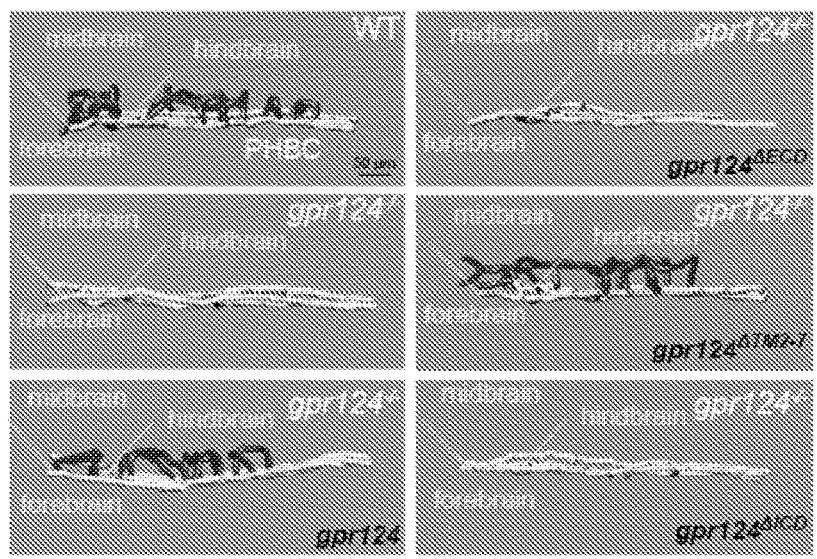
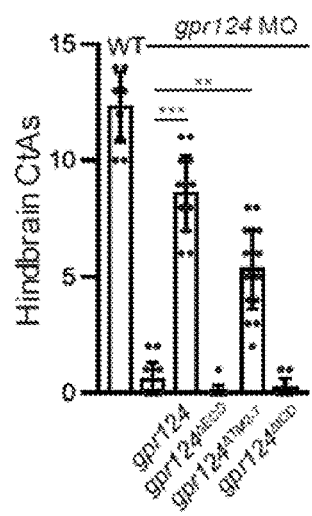

FIG. 4 (continued)
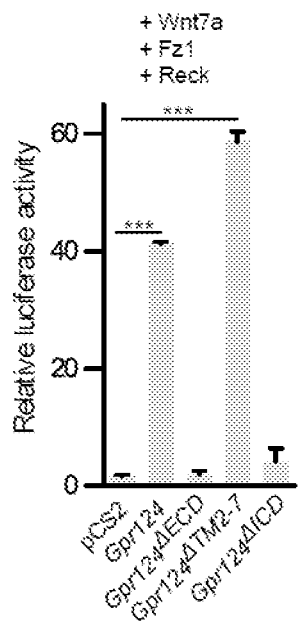
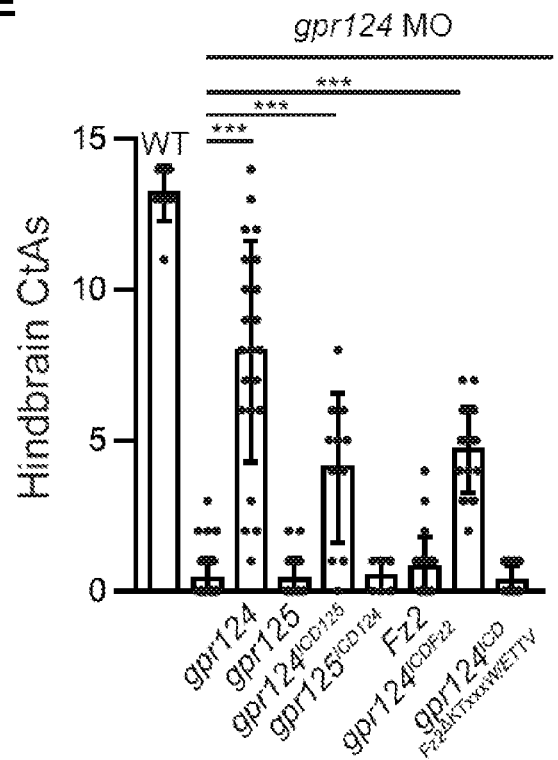

FIG. 5
A
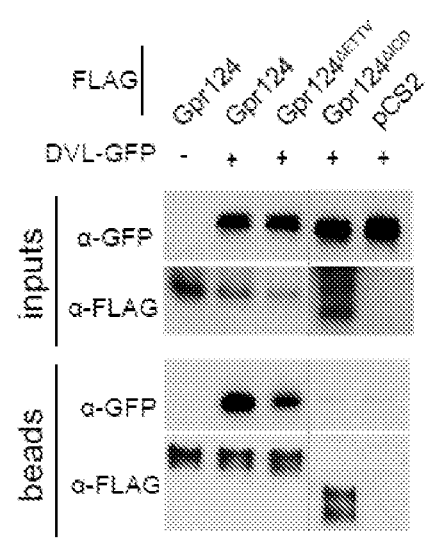
B
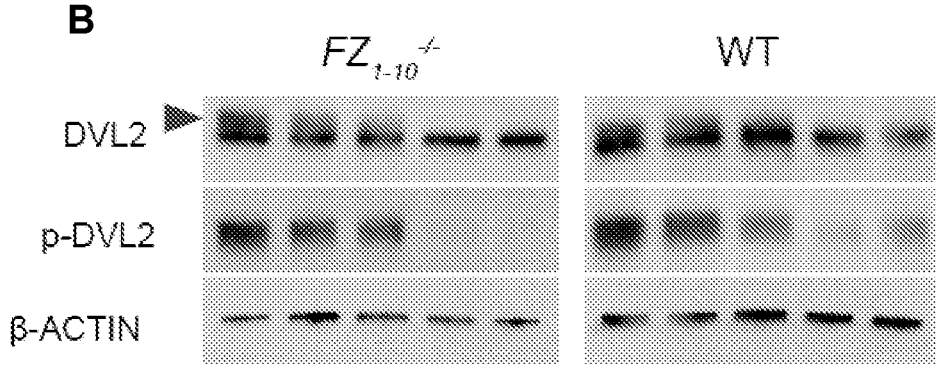

FIG. 5 (continued)
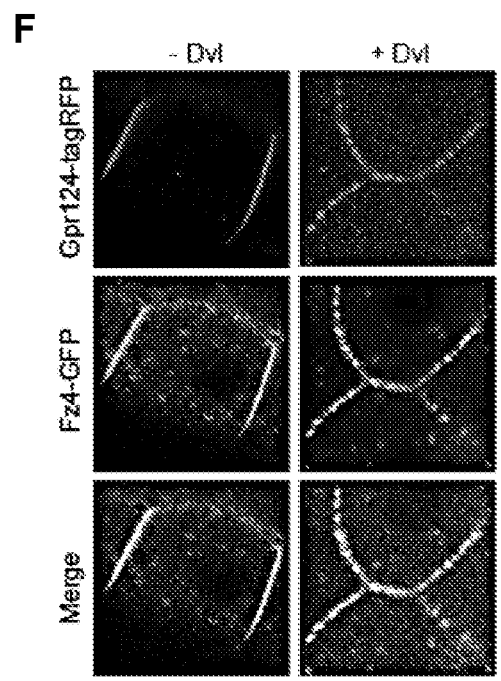
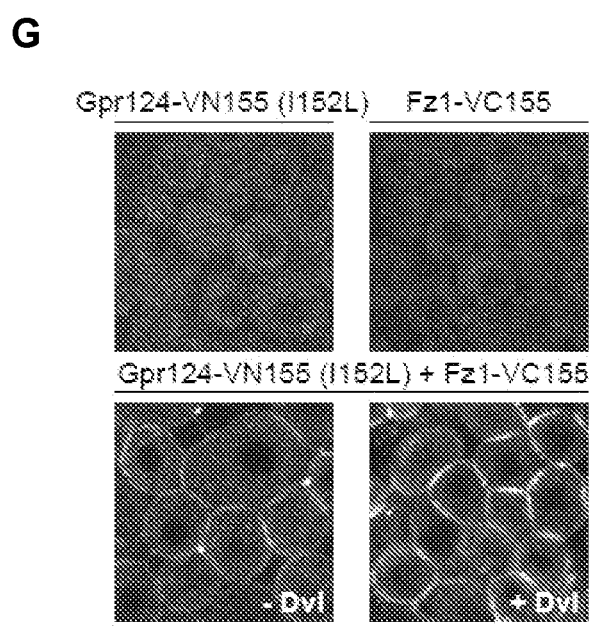

FIG. 7
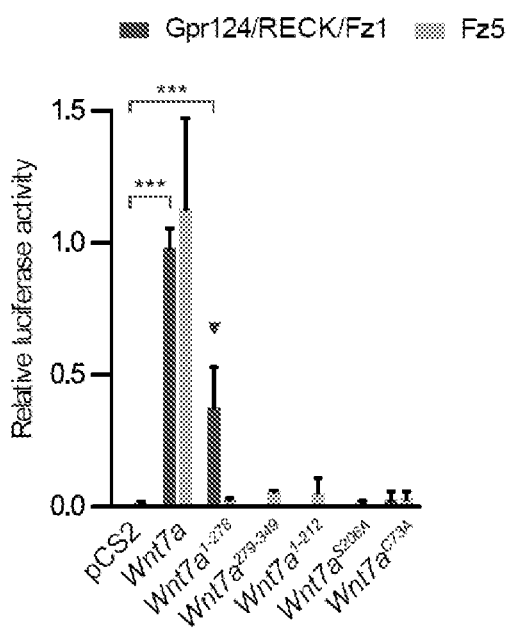
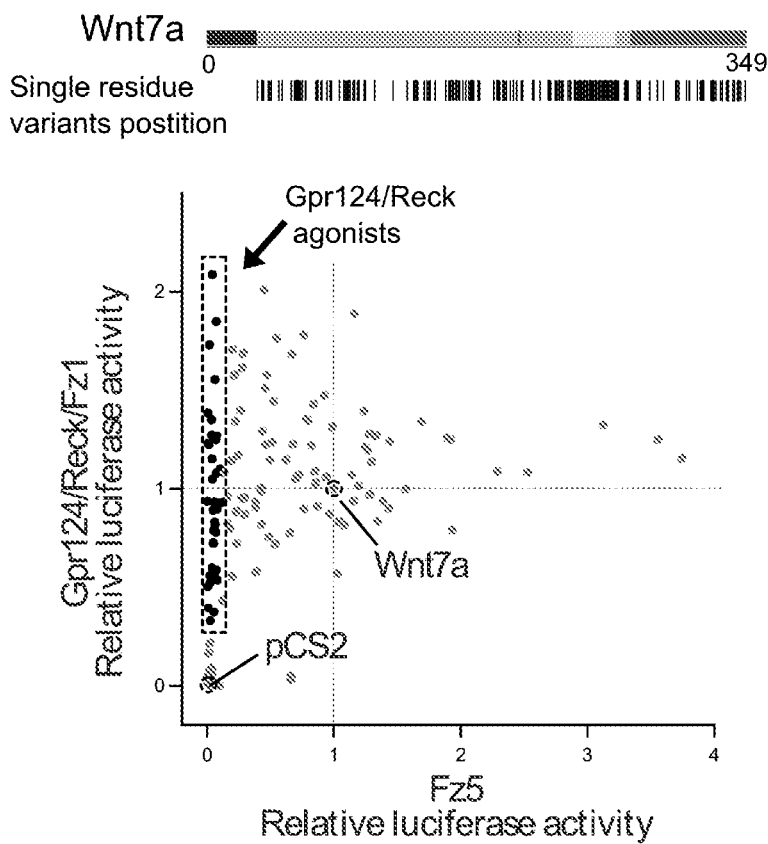

FIG. 7 (continued)
D
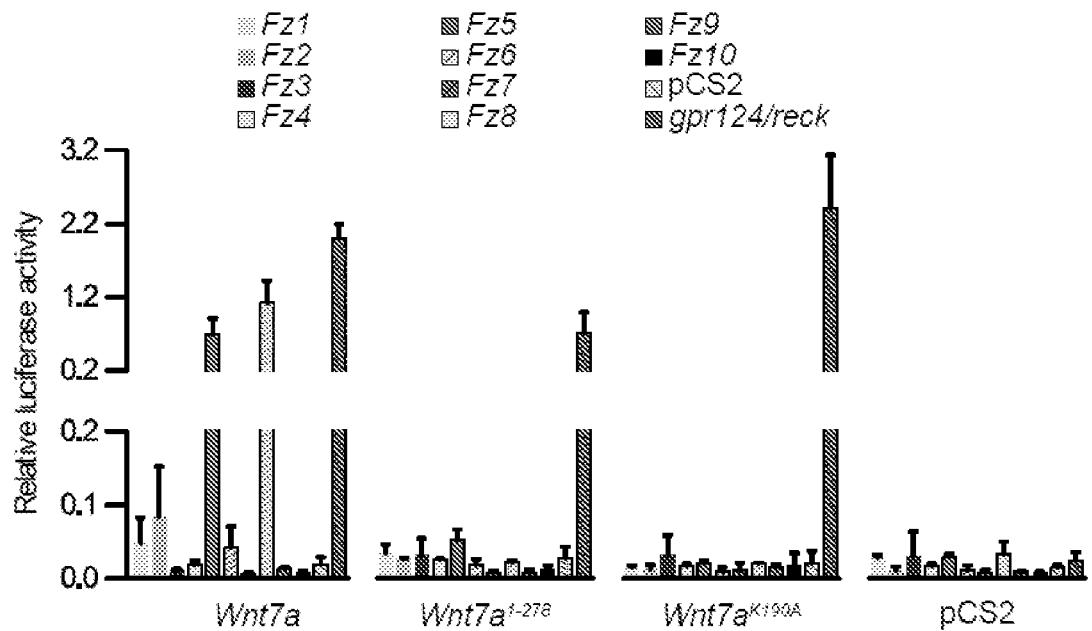
E
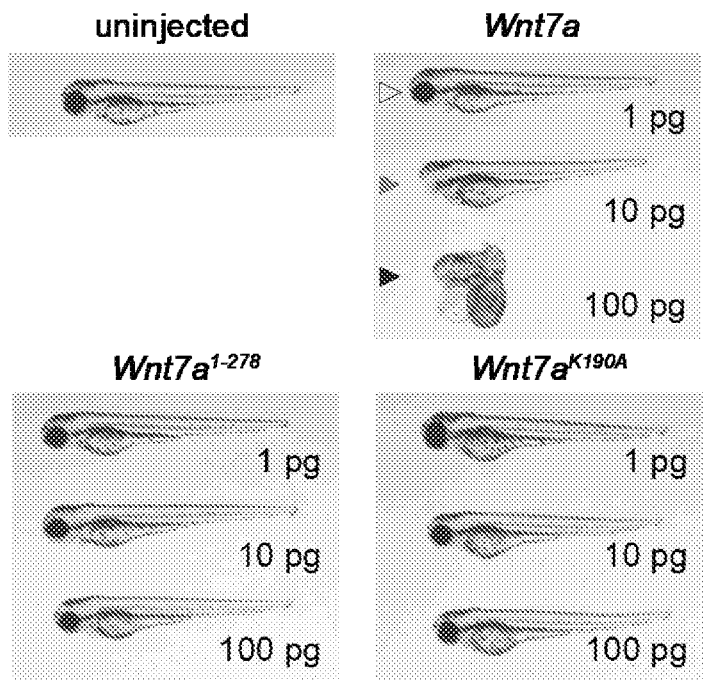

FIG. 7 (continued)
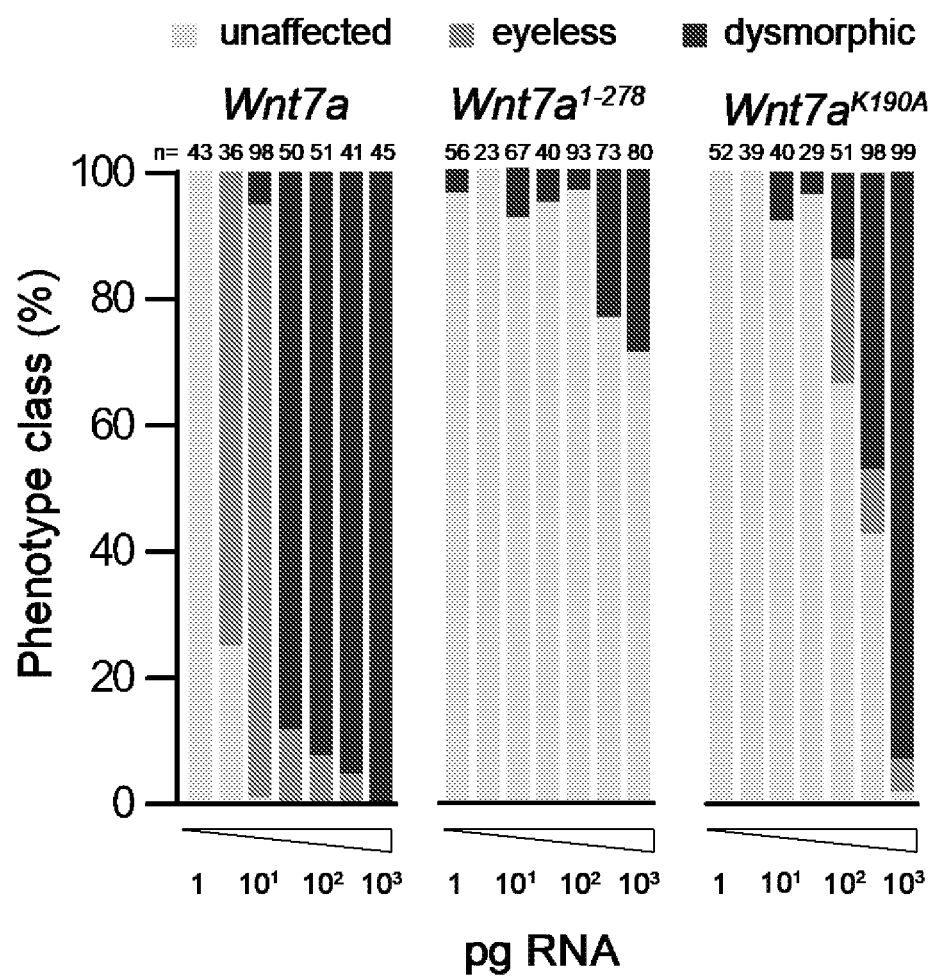
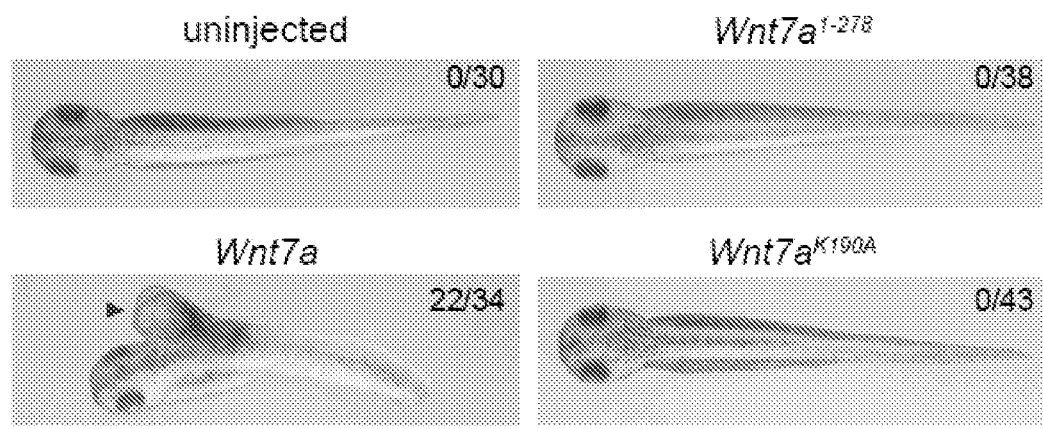

FIG. 7 (continued)

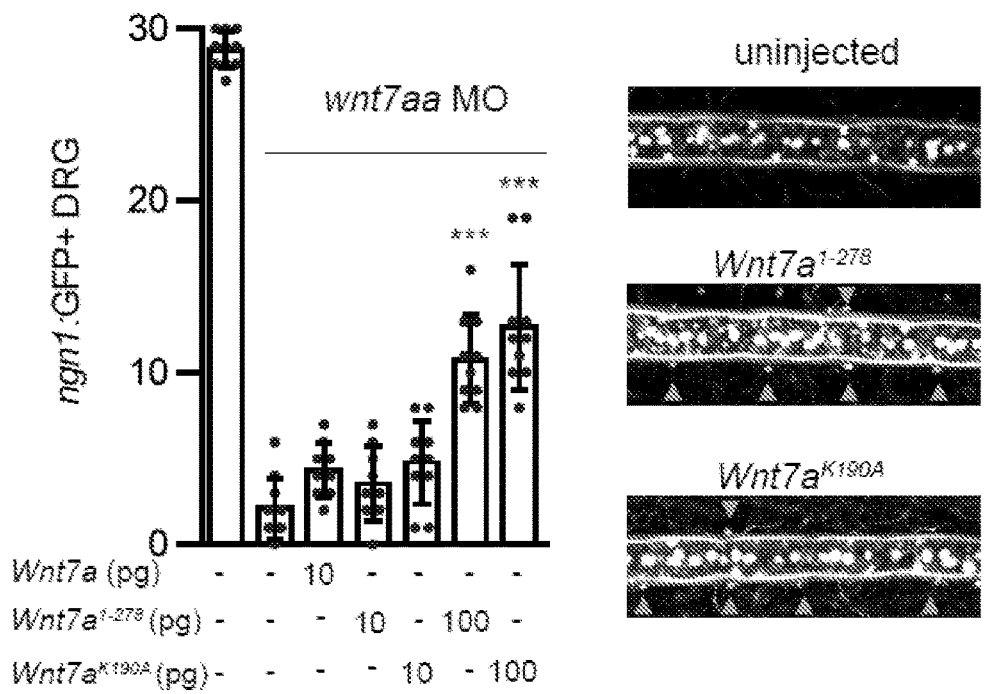

FIG. 8 hWnt7a[NTD-K159A]:
    LGASIICNKIPGLAPRQRAICQSRPDAIIVIGEGSQMGLDECQFQFRNGRWNCSALGERTVFGKE
    LKVGSREAAFTYAIIAAGVAHAITAACTQGNLSDCGCDKEKQGQYHRDEGWKWGGCSADIRY
    GIGFAKVFVDAREIKQNARTLMNLHNNEAGR<u>A</u>ILEENMKLECKCHGVSGSCTTKTCWTTLPQF
    RELGYVLKDKYNEAVHVEPVRASRNKRPTFLKIKKPLSYRKPMDTDLVYIEKSPNYC (SEQ ID
    NO: 28)

hWnt7a[K159A]:
    LGASIICNKIPGLAPRQRAICQSRPDAIIVIGEGSQMGLDECQFQFRNGRWNCSALGERTVFGKE
    LKVGSREAAFTYAIIAAGVAHAITAACTQGNLSDCGCDKEKQGQYHRDEGWKWGGCSADIRY
    GIGFAKVFVDAREIKQNARTLMNLHNNEAGR<u>A</u>ILEENMKLECKCHGVSGSCTTKTCWTTLPQF
    RELGYVLKDKYNEAVHVEPVRASRNKRPTFLKIKKPLSYRKPMDTDLVYIEKSPNYCEEDPVT
    GSVGTQGRACNKTAPQASGCDLMCCGRGYNTHQYARVWQCNCKFHWCCYVKCNTCSERTE
    MYTCK (SEQ ID NO: 85)

FIG. 8 (continued)

hWnt7a$^{NTD-A27R}$:

LGASIICNKIPGLAPRQRAICQSRPDRIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYC (SEQ ID NO: 29)

hWnt7a$^{A27R}$:

LGASIICNKIPGLAPRQRAICQSRPDRIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 86)

hWnt7a$^{NTD-E33A}$:

LGASIICNKIPGLAPRQRAICQSRPDAIIVIGAGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYC (SEQ ID NO: 30)

hWnt7a$^{E33A}$:

LGASIICNKIPGLAPRQRAICQSRPDAIIVIGAGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 87)

hWnt7a$^{NTD-E41A}$:

LGASIICNKIPGLAPRQRAICQSRPDAIIVIGEGSQMGLDACQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYC (SEQ ID NO: 31)

hWnt7a$^{E41A}$:

LGASIICNKIPGLAPRQRAICQSRPDAIIVIGEGSQMGLDACQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 88)

FIG. 8 (continued)

hWnt7a<sup>NTD-F44A</sup>:
> LGASIICNKIPGLAPRQRAICQSRPDAIIVIGEGSQMGLDECQ<u>A</u>QFRNGRWNCSALGERTVFGKE
> LKVGSREAAFTYAIIAAGVAHAITAACTQGNLSDCGCDKEKQGQYHRDEGWKWGGCSADIRY
> GIGFAKVFVDAREIKQNARTLMNLHNNEAGRKILEENMKLECKCHGVSGSCTTKTCWTTLPQF
> RELGYVLKDKYNEAVHVEPVRASRNKRPTFLKIKKPLSYRKPMDTDLVYIEKSPNYC (SEQ ID
> NO: 32)

hWnt7a<sup>F44A</sup>:
> LGASIICNKIPGLAPRQRAICQSRPDAIIVIGEGSQMGLDECQ<u>A</u>QFRNGRWNCSALGERTVFGKE
> LKVGSREAAFTYAIIAAGVAHAITAACTQGNLSDCGCDKEKQGQYHRDEGWKWGGCSADIRY
> GIGFAKVFVDAREIKQNARTLMNLHNNEAGRKILEENMKLECKCHGVSGSCTTKTCWTTLPQF
> RELGYVLKDKYNEAVHVEPVRASRNKRPTFLKIKKPLSYRKPMDTDLVYIEKSPNYCEEDPVT
> GSVGTQGRACNKTAPQASGCDLMCCGRGYNTHQYARVWQCNCKFHWCCYVKCNTCSERTE
> MYTCK (SEQ ID NO: 89)

hWnt7a<sup>NTD-N52Q</sup>:
> LGASIICNKIPGLAPRQRAICQSRPDAIIVIGEGSQMGLDECQFQFRNGRW<u>Q</u>CSALGERTVFGKE
> LKVGSREAAFTYAIIAAGVAHAITAACTQGNLSDCGCDKEKQGQYHRDEGWKWGGCSADIRY
> GIGFAKVFVDAREIKQNARTLMNLHNNEAGRKILEENMKLECKCHGVSGSCTTKTCWTTLPQF
> RELGYVLKDKYNEAVHVEPVRASRNKRPTFLKIKKPLSYRKPMDTDLVYIEKSPNYC (SEQ ID
> NO: 33)

hWnt7a<sup>N52Q</sup>:
> LGASIICNKIPGLAPRQRAICQSRPDAIIVIGEGSQMGLDECQFQFRNGRW<u>Q</u>CSALGERTVFGKE
> LKVGSREAAFTYAIIAAGVAHAITAACTQGNLSDCGCDKEKQGQYHRDEGWKWGGCSADIRY
> GIGFAKVFVDAREIKQNARTLMNLHNNEAGRKILEENMKLECKCHGVSGSCTTKTCWTTLPQF
> RELGYVLKDKYNEAVHVEPVRASRNKRPTFLKIKKPLSYRKPMDTDLVYIEKSPNYCEEDPVT
> GSVGTQGRACNKTAPQASGCDLMCCGRGYNTHQYARVWQCNCKFHWCCYVKCNTCSERTE
> MYTCK (SEQ ID NO: 90)

hWnt7a<sup>NTD-I129A</sup>:
> LGASIICNKIPGLAPRQRAICQSRPDAIIVIGEGSQMGLDECQFQFRNGRWNCSALGERTVFGKE
> LKVGSREAAFTYAIIAAGVAHAITAACTQGNLSDCGCDKEKQGQYHRDEGWKWGGCSADIRY
> G<u>A</u>GFAKVFVDAREIKQNARTLMNLHNNEAGRKILEENMKLECKCHGVSGSCTTKTCWTTLPQ
> FRELGYVLKDKYNEAVHVEPVRASRNKRPTFLKIKKPLSYRKPMDTDLVYIEKSPNYC (SEQ
> ID NO: 34)

hWnt7a<sup>I129A</sup>:
> LGASIICNKIPGLAPRQRAICQSRPDAIIVIGEGSQMGLDECQFQFRNGRWNCSALGERTVFGKE
> LKVGSREAAFTYAIIAAGVAHAITAACTQGNLSDCGCDKEKQGQYHRDEGWKWGGCSADIRY
> G<u>A</u>GFAKVFVDAREIKQNARTLMNLHNNEAGRKILEENMKLECKCHGVSGSCTTKTCWTTLPQ
> FRELGYVLKDKYNEAVHVEPVRASRNKRPTFLKIKKPLSYRKPMDTDLVYIEKSPNYCEEDPV
> TGSVGTQGRACNKTAPQASGCDLMCCGRGYNTHQYARVWQCNCKFHWCCYVKCNTCSERT
> EMYTCK (SEQ ID NO: 91)

FIG. 8 (continued)

hWnt7a<sup>NTD-F131A</sup>:
LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIG<u>A</u>AKVFVDAREIKQNARTLMNLHNNEAGRKILEENMKLECKCHGVSGSCTTKTCWTTLPQ
FRELGYVLKDKYNEAVHVEPVRASRNKRPTFLKIKKPLSYRKPMDTDLVYIEKSPNYC (SEQ
ID NO: 35)

hWnt7a<sup>F131A</sup>:
LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIG<u>A</u>AKVFVDAREIKQNARTLMNLHNNEAGRKILEENMKLECKCHGVSGSCTTKTCWTTLPQ
FRELGYVLKDKYNEAVHVEPVRASRNKRPTFLKIKKPLSYRKPMDTDLVYIEKSPNYCEEDPV
TGSVGTQGRACNKTAPQASGCDLMCCGRGYNTHQYARVWQCNCKFHWCCYVKCNTCSERT
EMYTCK (SEQ ID NO: 92)

hWnt7a<sup>NTD-K133A</sup>:
LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFA<u>A</u>VFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYC (SEQ ID
NO: 36)

hWnt7a<sup>K133A</sup>:
LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFA<u>A</u>VFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 93)

hWnt7a<sup>NTD-I141A</sup>:
LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDARE<u>A</u>KQNARTLMNLHNNEAGRKILEENMKLECKCHGVSGSCTTKTCWTTLPQ
FRELGYVLKDKYNEAVHVEPVRASRNKRPTFLKIKKPLSYRKPMDTDLVYIEKSPNYC (SEQ
ID NO: 37)

hWnt7a<sup>I141A</sup>:
LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDARE<u>A</u>KQNARTLMNLHNNEAGRKILEENMKLECKCHGVSGSCTTKTCWTTLPQ
FRELGYVLKDKYNEAVHVEPVRASRNKRPTFLKIKKPLSYRKPMDTDLVYIEKSPNYCEEDPV
TGSVGTQGRACNKTAPQASGCDLMCCGRGYNTHQYARVWQCNCKFHWCCYVKCNTCSERT
EMYTCK (SEQ ID NO: 94)

FIG. 8 (continued)

hWnt7a$^{NTD-R158A}$:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAG<u>A</u>KILEENMKLECKCHGVSGSCTTKTCWTTLPQF
RELGYVLKDKYNEAVHVEPVRASRNKRPTFLKIKKPLSYRKPMDTDLVYIEKSPNYC (SEQ ID
NO: 38)

hWnt7a$^{R158A}$:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAG<u>A</u>KILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 95)

hWnt7a$^{NTD-K181A}$:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTT<u>A</u>TCWTTLPQF
RELGYVLKDKYNEAVHVEPVRASRNKRPTFLKIKKPLSYRKPMDTDLVYIEKSPNYC (SEQ ID
NO: 39)

hWnt7a$^{K181A}$:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTT<u>A</u>TCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 96)

hWnt7a$^{NTD-R191A}$:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
<u>A</u>ELGYVLKDKYNEAVHVEPVRASRNKRPTFLKIKKPLSYRKPMDTDLVYIEKSPNYC (SEQ ID
NO: 40)

hWnt7a$^{R191A}$:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
<u>A</u>ELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 97)

FIG. 8 (continued)

hWnt7a<sup>NTD-K198A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLADKYNEAVHVEPVRASRNKRPTFLKIKKPLSYRKPMDTDLVYIEKSPNYC (SEQ ID NO: 41)

hWnt7a<sup>K198A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLADKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 98)

hWnt7a<sup>NTD-V205A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAAHVEPVRASRNKRPTFLKIKKPLSYRKPMDTDLVYIEKSPNYC (SEQ ID NO: 42)

hWnt7a<sup>V205A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAAHVEPVRASRNKRPTFLKIKKPLSYRKPMDTDLVYIEKSPNYEEDPVTG
SVGTQGRACNKTAPQASGCDLMCCGRGYNTHQYARVWQCNCKFHWCCYVKCNTCSERTEM
YTCK (SEQ ID NO: 99)

hWnt7a<sup>NTD-E208A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVAPVRASRNKRPTFLKIKKPLSYRKPMDTDLVYIEKSPNYC (SEQ ID NO: 43)

hWnt7a<sup>E208A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVAPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 100)

FIG. 8 (continued)

hWnt7a<sup>NTD-K216A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNARPTFLKIKKPLSYRKPMDTDLVYIEKSPNYC (SEQ ID
NO: 44)

hWnt7a<sup>K216A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNARPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 101)

hWnt7a<sup>NTD-K222A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLAIKKPLSYRKPMDTDLVYIEKSPNYC (SEQ ID
NO: 45)

hWnt7a<sup>K222A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLAIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 102)

hWnt7a<sup>NTD-I223A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKAKKPLSYRKPMDTDLVYIEKSPNYC (SEQ ID
NO: 46)

hWnt7a<sup>I223A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKAKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 103)

FIG. 8 (continued)

hWnt7a<sup>NTD-Y229A</sup>:
   LGASIICNKIPGLAPRQRAICQSRPDAIIVIGEGSQMGLDECQFQFRNGRWNCSALGERTVFGKE
   LKVGSREAAFTYAIIAAGVAHAITAACTQGNLSDCGCDKEKQGQYHRDEGWKWGGCSADIRY
   GIGFAKVFVDAREIKQNARTLMNLHNNEAGRKILEENMKLECKCHGVSGSCTTKTCWTTLPQF
   RELGYVLKDKYNEAVHVEPVRASRNKRPTFLKIKKPLSARKPMDTDLVYIEKSPNYC (SEQ ID
   NO: 47)

hWnt7a<sup>Y229A</sup>:
   LGASIICNKIPGLAPRQRAICQSRPDAIIVIGEGSQMGLDECQFQFRNGRWNCSALGERTVFGKE
   LKVGSREAAFTYAIIAAGVAHAITAACTQGNLSDCGCDKEKQGQYHRDEGWKWGGCSADIRY
   GIGFAKVFVDAREIKQNARTLMNLHNNEAGRKILEENMKLECKCHGVSGSCTTKTCWTTLPQF
   RELGYVLKDKYNEAVHVEPVRASRNKRPTFLKIKKPLSARKPMDTDLVYIEKSPNYCEEDPVT
   GSVGTQGRACNKTAPQASGCDLMCCGRGYNTHQYARVWQCNCKFHWCCYVKCNTCSERTE
   MYTCK (SEQ ID NO: 104)

hWnt7a<sup>NTD-P232A</sup>:
   LGASIICNKIPGLAPRQRAICQSRPDAIIVIGEGSQMGLDECQFQFRNGRWNCSALGERTVFGKE
   LKVGSREAAFTYAIIAAGVAHAITAACTQGNLSDCGCDKEKQGQYHRDEGWKWGGCSADIRY
   GIGFAKVFVDAREIKQNARTLMNLHNNEAGRKILEENMKLECKCHGVSGSCTTKTCWTTLPQF
   RELGYVLKDKYNEAVHVEPVRASRNKRPTFLKIKKPLSYRKAMDTDLVYIEKSPNYC (SEQ ID
   NO: 48)

hWnt7a<sup>P232A</sup>:
   LGASIICNKIPGLAPRQRAICQSRPDAIIVIGEGSQMGLDECQFQFRNGRWNCSALGERTVFGKE
   LKVGSREAAFTYAIIAAGVAHAITAACTQGNLSDCGCDKEKQGQYHRDEGWKWGGCSADIRY
   GIGFAKVFVDAREIKQNARTLMNLHNNEAGRKILEENMKLECKCHGVSGSCTTKTCWTTLPQF
   RELGYVLKDKYNEAVHVEPVRASRNKRPTFLKIKKPLSYRKAMDTDLVYIEKSPNYCEEDPVT
   GSVGTQGRACNKTAPQASGCDLMCCGRGYNTHQYARVWQCNCKFHWCCYVKCNTCSERTE
   MYTCK (SEQ ID NO: 105)

hWnt7a<sup>NTD-T235A</sup>:
   LGASIICNKIPGLAPRQRAICQSRPDAIIVIGEGSQMGLDECQFQFRNGRWNCSALGERTVFGKE
   LKVGSREAAFTYAIIAAGVAHAITAACTQGNLSDCGCDKEKQGQYHRDEGWKWGGCSADIRY
   GIGFAKVFVDAREIKQNARTLMNLHNNEAGRKILEENMKLECKCHGVSGSCTTKTCWTTLPQF
   RELGYVLKDKYNEAVHVEPVRASRNKRPTFLKIKKPLSYRKPMDADLVYIEKSPNYC (SEQ ID
   NO: 49)

hWnt7a<sup>T235A</sup>:
   LGASIICNKIPGLAPRQRAICQSRPDAIIVIGEGSQMGLDECQFQFRNGRWNCSALGERTVFGKE
   LKVGSREAAFTYAIIAAGVAHAITAACTQGNLSDCGCDKEKQGQYHRDEGWKWGGCSADIRY
   GIGFAKVFVDAREIKQNARTLMNLHNNEAGRKILEENMKLECKCHGVSGSCTTKTCWTTLPQF
   RELGYVLKDKYNEAVHVEPVRASRNKRPTFLKIKKPLSYRKPMDADLVYIEKSPNYCEEDPVT
   GSVGTQGRACNKTAPQASGCDLMCCGRGYNTHQYARVWQCNCKFHWCCYVKCNTCSERTE
   MYTCK (SEQ ID NO: 106)

FIG. 8 (continued)

hWnt7a$^{E248A}$:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYCAEDPVT
GSVGTQGRACNKTAPQASGCDLMCCGRGYNTHQYARVWQCNCKFHWCCYVKCNTCSERTE
MYTCK (SEQ ID NO: 50)

hWnt7a$^{R289A}$:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYAAVWQCNCKFHWCCYVKCNTCSERTE
MYTCK (SEQ ID NO: 52)

hWnt7a$^{W291A}$:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVAQCNCKFHWCCYVKCNTCSERTE
MYTCK (SEQ ID NO: 53)

hWnt7a$^{T307A}$:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNACSERTE
MYTCK (SEQ ID NO: 54)

hWnt7a$^{NTD-Q17A}$:

LGASIICNKIPGLAPRARAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYC (SEQ ID
NO: 68)

hWnt7a$^{Q17A}$:

LGASIICNKIPGLAPRARAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 107)

FIG. 8 (continued)

hWnt7a$^{NTD-I20A}$:

LGASIICNKIPGLAPRQRAACQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYC (SEQ ID
NO: 69)

hWnt7a$^{I20A}$:

LGASIICNKIPGLAPRQRAACQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 108)

hWnt7a$^{NTD-P25A}$:

LGASIICNKIPGLAPRQRAICQSRADAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYC (SEQ ID
NO: 70)

hWnt7a$^{P25A}$:

LGASIICNKIPGLAPRQRAICQSRADAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 109)

hWnt7a$^{NTD-M37A}$:

LGASIICNKIPGLAPRQRAICQSRPDAIIVIGEGSQAGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYC (SEQ ID
NO: 71)

hWnt7a$^{M37A}$:

LGASIICNKIPGLAPRQRAICQSRPDAIIVIGEGSQAGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 110)

FIG. 8 (continued)

hWnt7a<sup>NTD-L39A</sup>:
LGASIICNKIPGLAPRQRAICQSRPDAIIVIGEGSQMGADECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYC (SEQ ID
NO: 72)

hWnt7a<sup>L39A</sup>:
LGASIICNKIPGLAPRQRAICQSRPDAIIVIGEGSQMGADECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 111)

hWnt7a<sup>NTD-I28A</sup>:
LGASIICNKIPGLAPRQRAICQSRPDAAIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYC (SEQ ID
NO: 74)

hWnt7a<sup>I28A</sup>:
LGASIICNKIPGLAPRQRAICQSRPDAAIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 112)

hWnt7a<sup>NTD-R50A</sup>:
LGASIICNKIPGLAPRQRAICQSRPDAIIVIGEGSQMGLDECQFQFRNGAWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYC (SEQ ID
NO: 75)

hWnt7a<sup>R50A</sup>:
LGASIICNKIPGLAPRQRAICQSRPDAIIVIGEGSQMGLDECQFQFRNGAWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 113)

FIG. 8 (continued)

hWnt7a<sup>NTD-V68A</sup>:

LGASIICNKIPGLAPRQRAICQSRPDAIIVIGEGSQMGLDECQFQFRNGRWNCSALGERTVFGKE
LKAGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYC (SEQ ID
NO: 76)

hWnt7a<sup>V68A</sup>:

LGASIICNKIPGLAPRQRAICQSRPDAIIVIGEGSQMGLDECQFQFRNGRWNCSALGERTVFGKE
LKAGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 114)

hWnt7a<sup>NTD-F135A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVAVDAREIKQNARTLMNLHNNEAGRKILEENMKLECKCHGVSGSCTTKTCWTTLPQ
FRELGYVLKDKYNEAVHVEPVRASRNKRPTFLKIKKPLSYRKPMDTDLVYIEKSPNYC (SEQ
ID NO: 77)

hWnt7a<sup>F135A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVAVDAREIKQNARTLMNLHNNEAGRKILEENMKLECKCHGVSGSCTTKTCWTTLPQ
FRELGYVLKDKYNEAVHVEPVRASRNKRPTFLKIKKPLSYRKPMDTDLVYIEKSPNYCEEDPV
TGSVGTQGRACNKTAPQASGCDLMCCGRGYNTHQYARVWQCNCKFHWCCYVKCNTCSERT
EMYTCK (SEQ ID NO: 115)

hWnt7a<sup>NTD-R146A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNAATLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYC (SEQ ID
NO: 78)

hWnt7a<sup>R146A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNAATLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 116)

FIG. 8 (continued)

hWnt7a$^{NTD\text{-}K159S}$:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRSILEENMKLECKCHGVSGSCTTKTCWTTLPQF
RELGYVLKDKYNEAVHVEPVRASRNKRPTFLKIKKPLSYRKPMDTDLVYIEKSPNYC (SEQ ID
NO: 79)

hWnt7a$^{K159S}$:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRSILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 117)

hWnt7a$^{NTD\text{-}K159L}$:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRLILEENMKLECKCHGVSGSCTTKTCWTTLPQF
RELGYVLKDKYNEAVHVEPVRASRNKRPTFLKIKKPLSYRKPMDTDLVYIEKSPNYC (SEQ ID
NO: 80)

hWnt7a$^{K159L}$:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRLILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 118)

hWnt7a$^{NTD\text{-}K200A}$:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDAYNEAVHVEPVRASRNKRPTFLKIKKPLSYRKPMDTDLVYIEKSPNYC (SEQ ID
NO: 81)

hWnt7a$^{K200A}$:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDAYNEAVHVEPVRASRNKRPTFLKIKKPLSYRKPMDTDLVYIEKSPNYC
EEDPVTGSVGTQGRACNKTAPQASGCDLMCCGRGYNTHQYARVWQCNCKFHWCCYVKCNT
CSERTEMYTCK (SEQ ID NO: 119)

FIG. 8 (continued)

hWnt7a<sup>NTD-R214A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASANKRPTFLKIKKPLSYRKPMDTDLVYIEKSPNYC (SEQ ID
NO: 82)

hWnt7a<sup>R214A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASANKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 120)

hWnt7a<sup>NTD-P218A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYC (SEQ ID
NO: 83)

hWnt7a<sup>P218A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCK (SEQ ID NO: 121)

hWnt7a<sup>K318A</sup>:

LGASIICNKIPGLAPRQRAICQSRPDAIIVIGEGSQMGLDECQFQFRNGRWNCSALGERTVFGKE
LKVGSREAAFTYAIIAAGVAHAITAACTQGNLSDCGCDKEKQGQYHRDEGWKWGGCSADIRY
GIGFAKVFVDAREIKQNARTLMNLHNNEAGRKILEENMKLECKCHGVSGSCTTKTCWTTLPQF
RELGYVLKDKYNEAVHVEPVRASRNKRPTFLKIKKPLSYRKPMDTDLVYIEKSPNYCEEDPVT
GSVGTQGRACNKTAPQASGCDLMCCGRGYNTHQYARVWQCNCKFHWCCYVKCNTCSERTE
MYTCA (SEQ ID NO: 84)

Fig. 9
A
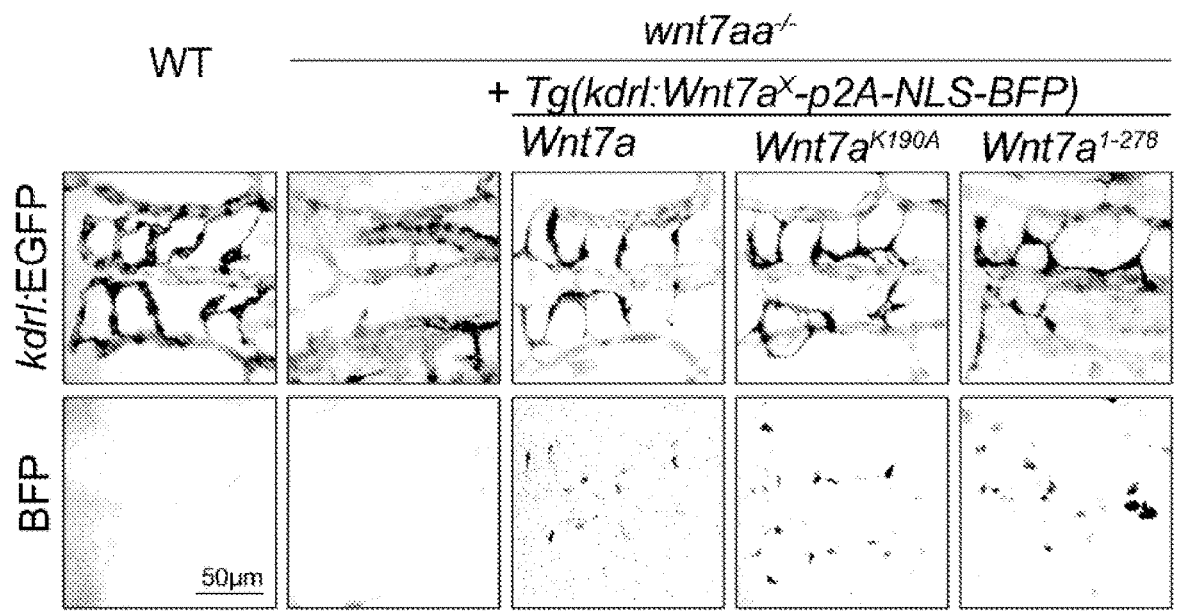
B
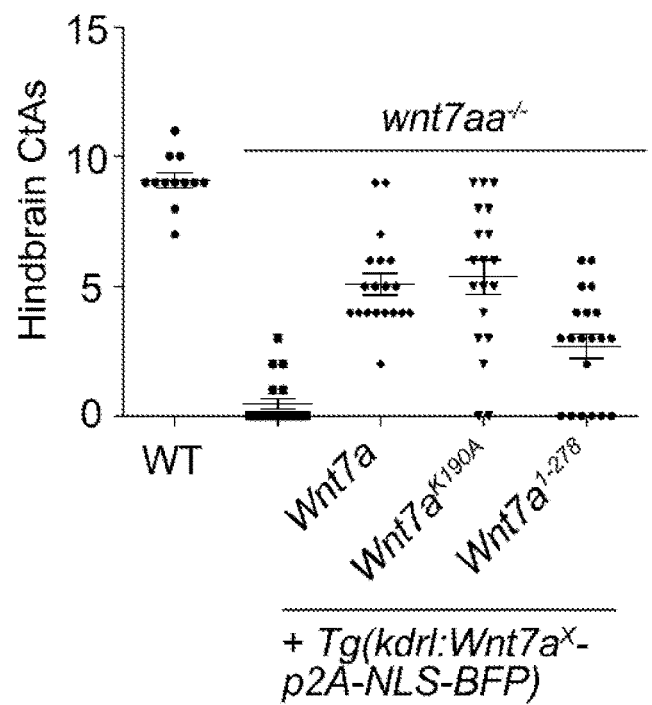

Fig. 10
A
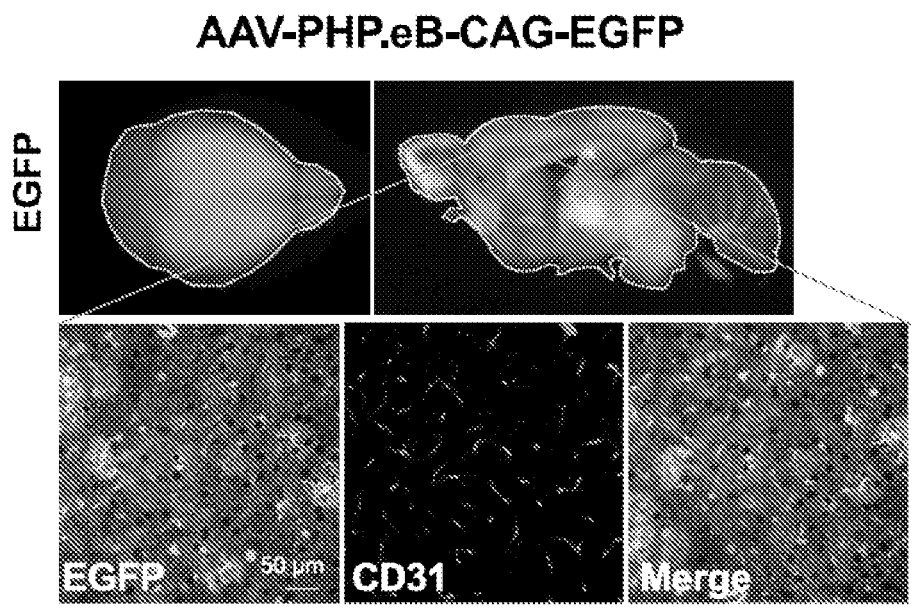
B
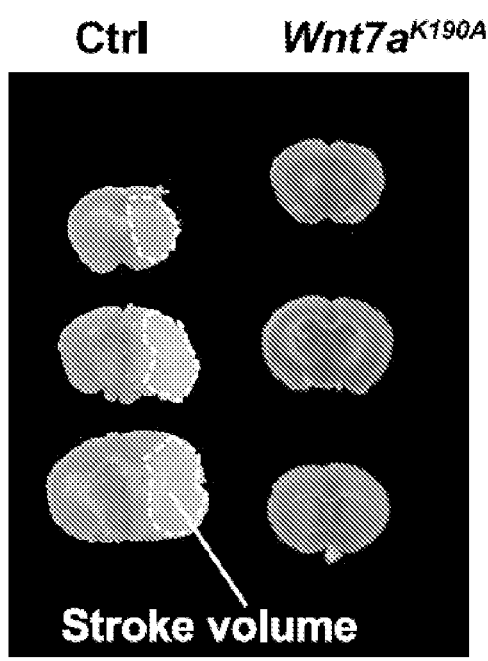
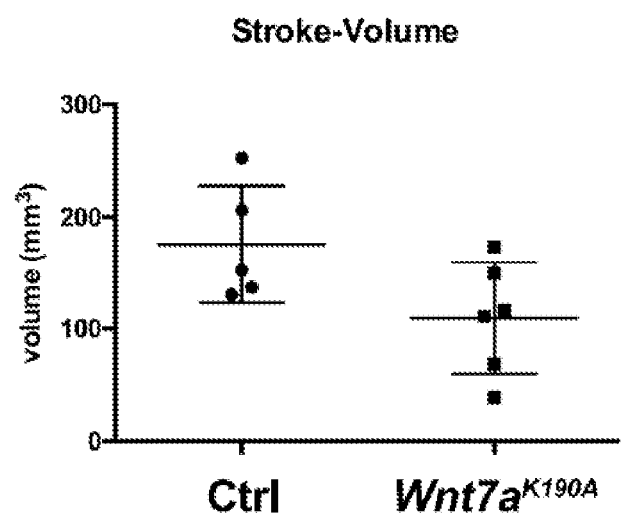

SEQUENCE LISTING

```
<160> NUMBER OF SEQ ID NOS: 123

<210> SEQ ID NO 1
<211> LENGTH: 1338
<212> TYPE: PRT
<213> ORGANISM: homo sapiens

<400> SEQUENCE: 1

Met Gly Ala Gly Gly Arg Arg Met Arg Gly Ala Pro Ala Arg Leu Leu
1               5                   10                  15

Leu Pro Leu Leu Pro Trp Leu Leu Leu Leu Ala Pro Glu Ala Arg
                20                  25                  30

Gly Ala Pro Gly Cys Pro Leu Ser Ile Arg Ser Cys Lys Cys Ser Gly
            35                  40                  45

Glu Arg Pro Lys Gly Leu Ser Gly Val Pro Gly Pro Ala Arg Arg
        50                  55                  60

Arg Val Val Cys Ser Gly Gly Asp Leu Pro Glu Pro Pro Glu Pro Gly
65                  70                  75                  80

Leu Leu Pro Asn Gly Thr Val Thr Leu Leu Leu Ser Asn Asn Lys Ile
                85                  90                  95

Thr Gly Leu Arg Asn Gly Ser Phe Leu Gly Leu Ser Leu Leu Glu Lys
            100                 105                 110

Leu Asp Leu Arg Asn Asn Ile Ile Ser Thr Val Gln Pro Gly Ala Phe
        115                 120                 125

Leu Gly Leu Gly Glu Leu Lys Arg Leu Asp Leu Ser Asn Asn Arg Ile
    130                 135                 140

Gly Cys Leu Thr Ser Glu Thr Phe Gln Gly Leu Pro Arg Leu Leu Arg
145                 150                 155                 160

Leu Asn Ile Ser Gly Asn Ile Phe Ser Ser Leu Gln Pro Gly Val Phe
```

```
                165                 170                 175
Asp Glu Leu Pro Ala Leu Lys Val Val Asp Leu Gly Thr Glu Phe Leu
                    180                 185                 190

Thr Cys Asp Cys His Leu Arg Trp Leu Leu Pro Trp Ala Gln Asn Arg
                195                 200                 205

Ser Leu Gln Leu Ser Glu His Thr Leu Cys Ala Tyr Pro Ser Ala Leu
            210                 215                 220

His Ala Gln Ala Leu Gly Ser Leu Gln Glu Ala Gln Leu Cys Cys Glu
225                 230                 235                 240

Gly Ala Leu Glu Leu His Thr His Leu Ile Pro Ser Leu Arg Gln
                    245                 250                 255

Val Val Phe Gln Gly Asp Arg Leu Pro Phe Gln Cys Ser Ala Ser Tyr
                260                 265                 270

Leu Gly Asn Asp Thr Arg Ile Arg Trp Tyr His Asn Arg Ala Pro Val
            275                 280                 285

Glu Gly Asp Glu Gln Ala Gly Ile Leu Leu Ala Glu Ser Leu Ile His
290                 295                 300

Asp Cys Thr Phe Ile Thr Ser Glu Leu Thr Leu Ser His Ile Gly Val
305                 310                 315                 320

Trp Ala Ser Gly Glu Trp Glu Cys Thr Val Ser Met Ala Gln Gly Asn
                    325                 330                 335

Ala Ser Lys Lys Val Glu Ile Val Val Leu Glu Thr Ser Ala Ser Tyr
                340                 345                 350

Cys Pro Ala Glu Arg Val Ala Asn Asn Arg Gly Asp Phe Arg Trp Pro
            355                 360                 365

Arg Thr Leu Ala Gly Ile Thr Ala Tyr Gln Ser Cys Leu Gln Tyr Pro
        370                 375                 380

Phe Thr Ser Val Pro Leu Gly Gly Ala Pro Gly Thr Arg Ala Ser
385                 390                 395                 400

Arg Arg Cys Asp Arg Ala Gly Arg Trp Glu Pro Gly Asp Tyr Ser His
                    405                 410                 415

Cys Leu Tyr Thr Asn Asp Ile Thr Arg Val Leu Tyr Thr Phe Val Leu
                420                 425                 430

Met Pro Ile Asn Ala Ser Asn Ala Leu Thr Leu Ala His Gln Leu Arg
            435                 440                 445

Val Tyr Thr Ala Glu Ala Ser Phe Ser Asp Met Met Asp Val Val
        450                 455                 460

Tyr Val Ala Gln Met Ile Gln Lys Phe Leu Gly Tyr Val Asp Gln Ile
465                 470                 475                 480

Lys Glu Leu Val Glu Val Met Val Asp Met Ala Ser Asn Leu Met Leu
                    485                 490                 495

Val Asp Glu His Leu Leu Trp Leu Ala Gln Arg Glu Asp Lys Ala Cys
                500                 505                 510

Ser Arg Ile Val Gly Ala Leu Glu Arg Ile Gly Gly Ala Ala Leu Ser
            515                 520                 525

Pro His Ala Gln His Ile Ser Val Asn Ala Arg Asn Val Ala Leu Glu
        530                 535                 540

Ala Tyr Leu Ile Lys Pro His Ser Tyr Val Gly Leu Thr Cys Thr Ala
545                 550                 555                 560

Phe Gln Arg Arg Glu Gly Val Pro Gly Thr Arg Pro Gly Ser Pro
                    565                 570                 575

Gly Gln Asn Pro Pro Glu Pro Glu Pro Ala Asp Gln Gln Leu
                580                 585                 590
```

```
Arg Phe Arg Cys Thr Thr Gly Arg Pro Asn Val Ser Leu Ser Ser Phe
        595                 600                 605

His Ile Lys Asn Ser Val Ala Leu Ala Ser Ile Gln Leu Pro Pro Ser
        610                 615                 620

Leu Phe Ser Ser Leu Pro Ala Ala Leu Ala Pro Pro Val Pro Pro Asp
625                 630                 635                 640

Cys Thr Leu Gln Leu Leu Val Phe Arg Asn Gly Arg Leu Phe His Ser
                645                 650                 655

His Ser Asn Thr Ser Arg Pro Gly Ala Ala Gly Pro Gly Lys Arg Arg
            660                 665                 670

Gly Val Ala Thr Pro Val Ile Phe Ala Gly Thr Ser Gly Cys Gly Val
        675                 680                 685

Gly Asn Leu Thr Glu Pro Val Ala Val Ser Leu Arg His Trp Ala Glu
    690                 695                 700

Gly Ala Glu Pro Val Ala Ala Trp Trp Ser Gln Gly Pro Gly Gly Glu
705                 710                 715                 720

Ala Gly Gly Trp Thr Ser Glu Gly Cys Gln Leu Arg Ser Ser Gln Pro
                725                 730                 735

Asn Val Ser Ala Leu His Cys Gln His Leu Gly Asn Val Ala Val Leu
            740                 745                 750

Met Glu Leu Ser Ala Phe Pro Arg Glu Val Gly Gly Ala Gly Ala Gly
        755                 760                 765

Leu His Pro Val Val Tyr Pro Cys Thr Ala Leu Leu Leu Cys Leu
    770                 775                 780

Phe Ala Thr Ile Ile Thr Tyr Ile Leu Asn His Ser Ser Ile Arg Val
785                 790                 795                 800

Ser Arg Lys Gly Trp His Met Leu Leu Asn Leu Cys Phe His Ile Ala
                805                 810                 815

Met Thr Ser Ala Val Phe Ala Gly Gly Ile Thr Leu Thr Asn Tyr Gln
            820                 825                 830

Met Val Cys Gln Ala Val Gly Ile Thr Leu His Tyr Ser Ser Leu Ser
        835                 840                 845

Thr Leu Leu Trp Met Gly Val Lys Ala Arg Val Leu His Lys Glu Leu
    850                 855                 860

Thr Trp Arg Ala Pro Pro Gln Glu Gly Asp Pro Ala Leu Pro Thr
865                 870                 875                 880

Pro Ser Pro Met Leu Arg Phe Tyr Leu Ile Ala Gly Ile Pro Leu
                885                 890                 895

Ile Ile Cys Gly Ile Thr Ala Ala Val Asn Ile His Asn Tyr Arg Asp
            900                 905                 910

His Ser Pro Tyr Cys Trp Leu Val Trp Arg Pro Ser Leu Gly Ala Phe
        915                 920                 925

Tyr Ile Pro Val Ala Leu Ile Leu Leu Ile Thr Trp Ile Tyr Phe Leu
    930                 935                 940

Cys Ala Gly Leu Arg Leu Arg Gly Pro Leu Ala Gln Asn Pro Lys Ala
945                 950                 955                 960

Gly Asn Ser Arg Ala Ser Leu Glu Ala Gly Glu Glu Leu Arg Gly Ser
                965                 970                 975

Thr Arg Leu Arg Gly Ser Gly Pro Leu Leu Ser Asp Ser Gly Ser Leu
            980                 985                 990

Leu Ala Thr Gly Ser Ala Arg Val  Gly Thr Pro Gly Pro  Pro Glu Asp
        995                 1000                 1005
```

-continued

Gly Asp Ser Leu Tyr Ser Pro Gly Val Gln Leu Gly Ala Leu Val
1010                1015                1020

Thr Thr His Phe Leu Tyr Leu Ala Met Trp Ala Cys Gly Ala Leu
    1025                1030                1035

Ala Val Ser Gln Arg Trp Leu Pro Arg Val Val Cys Ser Cys Leu
    1040                1045                1050

Tyr Gly Val Ala Ala Ser Ala Leu Gly Leu Phe Val Phe Thr His
    1055                1060                1065

His Cys Ala Arg Arg Arg Asp Val Arg Ala Ser Trp Arg Ala Cys
    1070                1075                1080

Cys Pro Pro Ala Ser Pro Ala Ala Pro His Ala Pro Pro Arg Ala
    1085                1090                1095

Leu Pro Ala Ala Ala Glu Asp Gly Ser Pro Val Phe Gly Glu Gly
    1100                1105                1110

Pro Pro Ser Leu Lys Ser Ser Pro Ser Gly Ser Ser Gly His Pro
    1115                1120                1125

Leu Ala Leu Gly Pro Cys Lys Leu Thr Asn Leu Gln Leu Ala Gln
    1130                1135                1140

Ser Gln Val Cys Glu Ala Gly Ala Ala Ala Gly Gly Glu Gly Glu
    1145                1150                1155

Pro Glu Pro Ala Gly Thr Arg Gly Asn Leu Ala His Arg His Pro
    1160                1165                1170

Asn Asn Val His His Gly Arg Arg Ala His Lys Ser Arg Ala Lys
    1175                1180                1185

Gly His Arg Ala Gly Glu Ala Cys Gly Lys Asn Arg Leu Lys Ala
    1190                1195                1200

Leu Arg Gly Gly Ala Ala Gly Ala Leu Glu Leu Ser Ser Glu
    1205                1210                1215

Ser Gly Ser Leu His Asn Ser Pro Thr Asp Ser Tyr Leu Gly Ser
    1220                1225                1230

Ser Arg Asn Ser Pro Gly Ala Gly Leu Gln Leu Glu Gly Glu Pro
    1235                1240                1245

Met Leu Thr Pro Ser Glu Gly Ser Asp Thr Ser Ala Ala Pro Leu
    1250                1255                1260

Ser Glu Ala Gly Arg Ala Gly Gln Arg Arg Ser Ala Ser Arg Asp
    1265                1270                1275

Ser Leu Lys Gly Gly Gly Ala Leu Glu Lys Glu Ser His Arg Arg
    1280                1285                1290

Ser Tyr Pro Leu Asn Ala Ala Ser Leu Asn Gly Ala Pro Lys Gly
    1295                1300                1305

Gly Lys Tyr Asp Asp Val Thr Leu Met Gly Ala Glu Val Ala Ser
    1310                1315                1320

Gly Gly Cys Met Lys Thr Gly Leu Trp Lys Ser Glu Thr Thr Val
    1325                1330                1335

<210> SEQ ID NO 2
<211> LENGTH: 971
<212> TYPE: PRT
<213> ORGANISM: homo sapiens

<400> SEQUENCE: 2

Met Ala Thr Val Arg Ala Ser Leu Arg Gly Ala Leu Leu Leu Leu
1               5                   10                  15

Ala Val Ala Gly Val Ala Glu Val Ala Gly Gly Leu Ala Pro Gly Ser
            20                  25                  30

-continued

```
Ala Gly Ala Leu Cys Cys Asn His Ser Lys Asp Asn Gln Met Cys Arg
        35                  40                  45

Asp Val Cys Glu Gln Ile Phe Ser Ser Lys Ser Glu Ser Arg Leu Lys
 50                  55                  60

His Leu Leu Gln Arg Ala Pro Asp Tyr Cys Pro Glu Thr Met Val Glu
 65                  70                  75                  80

Ile Trp Asn Cys Met Asn Ser Ser Leu Pro Gly Val Phe Lys Lys Ser
                 85                  90                  95

Asp Gly Trp Val Gly Leu Gly Cys Cys Glu Leu Ala Ile Ala Leu Glu
                100                 105                 110

Cys Arg Gln Ala Cys Lys Gln Ala Ser Ser Lys Asn Asp Ile Ser Lys
            115                 120                 125

Val Cys Arg Lys Glu Tyr Glu Asn Ala Leu Phe Ser Cys Ile Ser Arg
        130                 135                 140

Asn Glu Met Gly Ser Val Cys Cys Ser Tyr Ala Gly His His Thr Asn
145                 150                 155                 160

Cys Arg Glu Tyr Cys Gln Ala Ile Phe Arg Thr Asp Ser Ser Pro Gly
                165                 170                 175

Pro Ser Gln Ile Lys Ala Val Glu Asn Tyr Cys Ala Ser Ile Ser Pro
                180                 185                 190

Gln Leu Ile His Cys Val Asn Asn Tyr Thr Gln Ser Tyr Pro Met Arg
            195                 200                 205

Asn Pro Thr Asp Ser Leu Tyr Cys Cys Asp Arg Ala Glu Asp His Ala
        210                 215                 220

Cys Gln Asn Ala Cys Lys Arg Ile Leu Met Ser Lys Lys Thr Glu Met
225                 230                 235                 240

Glu Ile Val Asp Gly Leu Ile Glu Gly Cys Lys Thr Gln Pro Leu Pro
                245                 250                 255

Gln Asp Pro Leu Trp Gln Cys Phe Leu Glu Ser Ser Gln Ser Val His
                260                 265                 270

Pro Gly Val Thr Val His Pro Pro Ser Thr Gly Leu Asp Gly Ala
            275                 280                 285

Lys Leu His Cys Cys Ser Lys Ala Asn Thr Ser Thr Cys Arg Glu Leu
        290                 295                 300

Cys Thr Lys Leu Tyr Ser Met Ser Trp Gly Asn Thr Gln Ser Trp Gln
305                 310                 315                 320

Glu Phe Asp Arg Phe Cys Glu Tyr Asn Pro Val Glu Val Ser Met Leu
                325                 330                 335

Thr Cys Leu Ala Asp Val Arg Glu Pro Cys Gln Leu Gly Cys Arg Asn
            340                 345                 350

Leu Thr Tyr Cys Thr Asn Phe Asn Asn Arg Pro Thr Glu Leu Phe Arg
        355                 360                 365

Ser Cys Asn Ala Gln Ser Asp Gln Gly Ala Met Asn Asp Met Lys Leu
    370                 375                 380

Trp Glu Lys Gly Ser Ile Lys Met Pro Phe Ile Asn Ile Pro Val Leu
385                 390                 395                 400

Asp Ile Lys Lys Cys Gln Pro Glu Met Trp Lys Ala Ile Ala Cys Ser
                405                 410                 415

Leu Gln Ile Lys Pro Cys His Ser Lys Ser Arg Gly Ser Ile Ile Cys
            420                 425                 430

Lys Ser Asp Cys Val Glu Ile Leu Lys Lys Cys Gly Asp Gln Asn Lys
        435                 440                 445
```

```
Phe Pro Glu Asp His Thr Ala Glu Ser Ile Cys Glu Leu Leu Ser Pro
    450                 455                 460

Thr Asp Asp Leu Lys Asn Cys Ile Pro Leu Asp Thr Tyr Leu Arg Pro
465                 470                 475                 480

Ser Thr Leu Gly Asn Ile Val Glu Val Thr His Pro Cys Asn Pro
                485                 490                 495

Asn Pro Cys Pro Ala Asn Glu Leu Cys Glu Val Asn Arg Lys Gly Cys
        500                 505                 510

Pro Ser Gly Asp Pro Cys Leu Pro Tyr Phe Cys Val Gln Gly Cys Lys
        515                 520                 525

Leu Gly Glu Ala Ser Asp Phe Ile Val Arg Gln Gly Thr Leu Ile Gln
530                 535                 540

Val Pro Ser Ser Ala Gly Glu Val Gly Cys Tyr Lys Ile Cys Ser Cys
545                 550                 555                 560

Gly Gln Ser Gly Leu Leu Glu Asn Cys Met Glu Met His Cys Ile Asp
                565                 570                 575

Leu Gln Lys Ser Cys Ile Val Gly Gly Lys Arg Lys Ser His Gly Thr
        580                 585                 590

Ser Phe Ser Ile Asp Cys Asn Val Cys Ser Cys Phe Ala Gly Asn Leu
        595                 600                 605

Val Cys Ser Thr Arg Leu Cys Leu Ser Glu His Ser Ser Glu Asp Asp
        610                 615                 620

Arg Arg Thr Phe Thr Gly Leu Pro Cys Asn Cys Ala Asp Gln Phe Val
625                 630                 635                 640

Pro Val Cys Gly Gln Asn Gly Arg Thr Tyr Pro Ser Ala Cys Ile Ala
                645                 650                 655

Arg Cys Val Gly Leu Gln Asp His Gln Phe Glu Phe Gly Ser Cys Met
            660                 665                 670

Ser Lys Asp Pro Cys Asn Pro Asn Pro Cys Gln Lys Asn Gln Arg Cys
        675                 680                 685

Ile Pro Lys Pro Gln Val Cys Leu Thr Thr Phe Asp Lys Phe Gly Cys
        690                 695                 700

Ser Gln Tyr Glu Cys Val Pro Arg Gln Leu Ala Cys Asp Gln Val Gln
705                 710                 715                 720

Asp Pro Val Cys Asp Thr Asp His Met Glu His Asn Asn Leu Cys Thr
                725                 730                 735

Leu Tyr Gln Arg Gly Lys Ser Leu Ser Tyr Lys Gly Pro Cys Gln Pro
            740                 745                 750

Phe Cys Arg Ala Thr Glu Pro Val Cys Gly His Asn Gly Glu Thr Tyr
        755                 760                 765

Ser Ser Val Cys Ala Ala Tyr Ser Asp Arg Val Ala Val Asp Tyr Tyr
770                 775                 780

Gly Asp Cys Gln Ala Val Gly Val Leu Ser Glu His Ser Ser Val Ala
785                 790                 795                 800

Glu Cys Ala Ser Val Lys Cys Pro Ser Leu Leu Ala Ala Gly Cys Lys
                805                 810                 815

Pro Ile Ile Pro Pro Gly Ala Cys Cys Pro Leu Cys Ala Gly Met Leu
            820                 825                 830

Arg Val Leu Phe Asp Lys Glu Lys Leu Asp Thr Ile Ala Lys Val Thr
        835                 840                 845

Asn Lys Lys Pro Ile Thr Val Leu Glu Ile Leu Gln Lys Ile Arg Met
850                 855                 860

His Val Ser Val Pro Gln Cys Asp Val Phe Gly Tyr Phe Ser Ile Glu
```

```
            865                 870                 875                 880
Ser Glu Ile Val Ile Leu Ile Ile Pro Val Asp His Tyr Pro Lys Ala
                    885                 890                 895

Leu Gln Ile Glu Ala Cys Asn Lys Glu Ala Lys Ile Glu Ser Leu
                900                 905                 910

Ile Asn Ser Asp Ser Pro Thr Leu Ala Ser His Val Pro Leu Ser Ala
                915                 920                 925

Leu Ile Ile Ser Gln Val Gln Val Ser Ser Val Pro Ser Ala Gly
                930                 935                 940

Val Arg Ala Arg Pro Ser Cys His Ser Leu Leu Pro Leu Ser Leu
945                 950                 955                 960

Gly Leu Ala Leu His Leu Leu Trp Thr Tyr Asn
                965                 970

<210> SEQ ID NO 3
<211> LENGTH: 1615
<212> TYPE: PRT
<213> ORGANISM: homo sapiens

<400> SEQUENCE: 3

Met Glu Ala Ala Pro Pro Gly Pro Pro Trp Pro Leu Leu Leu Leu
1                   5                   10                  15

Leu Leu Leu Ala Leu Cys Gly Cys Pro Ala Pro Ala Ala Ala Ser
                20                  25                  30

Pro Leu Leu Leu Phe Ala Asn Arg Arg Asp Val Arg Leu Val Asp Ala
                35                  40                  45

Gly Gly Val Lys Leu Glu Ser Thr Ile Val Val Ser Gly Leu Glu Asp
50                  55                  60

Ala Ala Ala Val Asp Phe Gln Phe Ser Lys Gly Ala Val Tyr Trp Thr
65                  70                  75                  80

Asp Val Ser Glu Glu Ala Ile Lys Gln Thr Tyr Leu Asn Gln Thr Gly
                85                  90                  95

Ala Ala Val Gln Asn Val Val Ile Ser Gly Leu Val Ser Pro Asp Gly
                100                 105                 110

Leu Ala Cys Asp Trp Val Gly Lys Lys Leu Tyr Trp Thr Asp Ser Glu
                115                 120                 125

Thr Asn Arg Ile Glu Val Ala Asn Leu Asn Gly Thr Ser Arg Lys Val
                130                 135                 140

Leu Phe Trp Gln Asp Leu Asp Gln Pro Arg Ala Ile Ala Leu Asp Pro
145                 150                 155                 160

Ala His Gly Tyr Met Tyr Trp Thr Asp Trp Gly Glu Thr Pro Arg Ile
                165                 170                 175

Glu Arg Ala Gly Met Asp Gly Ser Thr Arg Lys Ile Ile Val Asp Ser
                180                 185                 190

Asp Ile Tyr Trp Pro Asn Gly Leu Thr Ile Asp Leu Glu Glu Gln Lys
                195                 200                 205

Leu Tyr Trp Ala Asp Ala Lys Leu Ser Phe Ile His Arg Ala Asn Leu
                210                 215                 220

Asp Gly Ser Phe Arg Gln Lys Val Val Glu Gly Ser Leu Thr His Pro
225                 230                 235                 240

Phe Ala Leu Thr Leu Ser Gly Asp Thr Leu Tyr Trp Thr Asp Trp Gln
                245                 250                 255

Thr Arg Ser Ile His Ala Cys Asn Lys Arg Thr Gly Gly Lys Arg Lys
                260                 265                 270
```

-continued

```
Glu Ile Leu Ser Ala Leu Tyr Ser Pro Met Asp Ile Gln Val Leu Ser
            275                 280                 285

Gln Glu Arg Gln Pro Phe Phe His Thr Arg Cys Glu Glu Asp Asn Gly
    290                 295                 300

Gly Cys Ser His Leu Cys Leu Leu Ser Pro Ser Glu Pro Phe Tyr Thr
305                 310                 315                 320

Cys Ala Cys Pro Thr Gly Val Gln Leu Gln Asp Asn Gly Arg Thr Cys
                325                 330                 335

Lys Ala Gly Ala Glu Glu Val Leu Leu Leu Ala Arg Arg Thr Asp Leu
            340                 345                 350

Arg Arg Ile Ser Leu Asp Thr Pro Asp Phe Thr Asp Ile Val Leu Gln
    355                 360                 365

Val Asp Asp Ile Arg His Ala Ile Ala Ile Asp Tyr Asp Pro Leu Glu
370                 375                 380

Gly Tyr Val Tyr Trp Thr Asp Asp Glu Val Arg Ala Ile Arg Arg Ala
385                 390                 395                 400

Tyr Leu Asp Gly Ser Gly Ala Gln Thr Leu Val Asn Thr Glu Ile Asn
                405                 410                 415

Asp Pro Asp Gly Ile Ala Val Asp Trp Val Ala Arg Asn Leu Tyr Trp
            420                 425                 430

Thr Asp Thr Gly Thr Asp Arg Ile Glu Val Thr Arg Leu Asn Gly Thr
    435                 440                 445

Ser Arg Lys Ile Leu Val Ser Glu Asp Leu Asp Glu Pro Arg Ala Ile
450                 455                 460

Ala Leu His Pro Val Met Gly Leu Met Tyr Trp Thr Asp Trp Gly Glu
465                 470                 475                 480

Asn Pro Lys Ile Glu Cys Ala Asn Leu Asp Gly Gln Glu Arg Arg Val
                485                 490                 495

Leu Val Asn Ala Ser Leu Gly Trp Pro Asn Gly Leu Ala Leu Asp Leu
            500                 505                 510

Gln Glu Gly Lys Leu Tyr Trp Gly Asp Ala Lys Thr Asp Lys Ile Glu
    515                 520                 525

Val Ile Asn Val Asp Gly Thr Lys Arg Arg Thr Leu Leu Glu Asp Lys
530                 535                 540

Leu Pro His Ile Phe Gly Phe Thr Leu Leu Gly Asp Phe Ile Tyr Trp
545                 550                 555                 560

Thr Asp Trp Gln Arg Arg Ser Ile Glu Arg Val His Lys Val Lys Ala
                565                 570                 575

Ser Arg Asp Val Ile Ile Asp Gln Leu Pro Asp Leu Met Gly Leu Lys
            580                 585                 590

Ala Val Asn Val Ala Lys Val Val Gly Thr Asn Pro Cys Ala Asp Arg
    595                 600                 605

Asn Gly Gly Cys Ser His Leu Cys Phe Phe Thr Pro His Ala Thr Arg
610                 615                 620

Cys Gly Cys Pro Ile Gly Leu Glu Leu Leu Ser Asp Met Lys Thr Cys
625                 630                 635                 640

Ile Val Pro Glu Ala Phe Leu Val Phe Thr Ser Arg Ala Ala Ile His
                645                 650                 655

Arg Ile Ser Leu Glu Thr Asn Asn Asn Asp Val Ala Ile Pro Leu Thr
            660                 665                 670

Gly Val Lys Glu Ala Ser Ala Leu Asp Phe Asp Val Ser Asn Asn His
    675                 680                 685

Ile Tyr Trp Thr Asp Val Ser Leu Lys Thr Ile Ser Arg Ala Phe Met
```

-continued

```
            690                 695                 700
Asn Gly Ser Ser Val Glu His Val Val Glu Phe Gly Leu Asp Tyr Pro
705                 710                 715                 720

Glu Gly Met Ala Val Asp Trp Met Gly Lys Asn Leu Tyr Trp Ala Asp
                725                 730                 735

Thr Gly Thr Asn Arg Ile Glu Val Ala Arg Leu Asp Gly Gln Phe Arg
                740                 745                 750

Gln Val Leu Val Trp Arg Asp Leu Asp Asn Pro Arg Ser Leu Ala Leu
                755                 760                 765

Asp Pro Thr Lys Gly Tyr Ile Tyr Trp Thr Glu Trp Gly Gly Lys Pro
770                 775                 780

Arg Ile Val Arg Ala Phe Met Asp Gly Thr Asn Cys Met Thr Leu Val
785                 790                 795                 800

Asp Lys Val Gly Arg Ala Asn Asp Leu Thr Ile Asp Tyr Ala Asp Gln
                805                 810                 815

Arg Leu Tyr Trp Thr Asp Leu Asp Thr Asn Met Ile Glu Ser Ser Asn
                820                 825                 830

Met Leu Gly Gln Glu Arg Val Val Ile Ala Asp Asp Leu Pro His Pro
                835                 840                 845

Phe Gly Leu Thr Gln Tyr Ser Asp Tyr Ile Tyr Trp Thr Asp Trp Asn
850                 855                 860

Leu His Ser Ile Glu Arg Ala Asp Lys Thr Ser Gly Arg Asn Arg Thr
865                 870                 875                 880

Leu Ile Gln Gly His Leu Asp Phe Val Met Asp Ile Leu Val Phe His
                885                 890                 895

Ser Ser Arg Gln Asp Gly Leu Asn Asp Cys Met His Asn Asn Gly Gln
                900                 905                 910

Cys Gly Gln Leu Cys Leu Ala Ile Pro Gly Gly His Arg Cys Gly Cys
                915                 920                 925

Ala Ser His Tyr Thr Leu Asp Pro Ser Ser Arg Asn Cys Ser Pro Pro
                930                 935                 940

Thr Thr Phe Leu Leu Phe Ser Gln Lys Ser Ala Ile Ser Arg Met Ile
945                 950                 955                 960

Pro Asp Asp Gln His Ser Pro Asp Leu Ile Leu Pro Leu His Gly Leu
                965                 970                 975

Arg Asn Val Lys Ala Ile Asp Tyr Asp Pro Leu Asp Lys Phe Ile Tyr
                980                 985                 990

Trp Val Asp Gly Arg Gln Asn Ile Lys Arg Ala Lys Asp Asp Gly Thr
                995                 1000                1005

Gln Pro Phe Val Leu Thr Ser Leu Ser Gln Gly Gln Asn Pro Asp
        1010                1015                1020

Arg Gln Pro His Asp Leu Ser Ile Asp Ile Tyr Ser Arg Thr Leu
        1025                1030                1035

Phe Trp Thr Cys Glu Ala Thr Asn Thr Ile Asn Val His Arg Leu
        1040                1045                1050

Ser Gly Glu Ala Met Gly Val Val Leu Arg Gly Asp Arg Asp Lys
        1055                1060                1065

Pro Arg Ala Ile Val Val Asn Ala Glu Arg Gly Tyr Leu Tyr Phe
        1070                1075                1080

Thr Asn Met Gln Asp Arg Ala Ala Lys Ile Glu Arg Ala Ala Leu
        1085                1090                1095

Asp Gly Thr Glu Arg Glu Val Leu Phe Thr Thr Gly Leu Ile Arg
        1100                1105                1110
```

```
Pro Val Ala Leu Val Val Asp Asn Thr Leu Gly Lys Leu Phe Trp
1115                1120                1125

Val Asp Ala Asp Leu Lys Arg Ile Glu Ser Cys Asp Leu Ser Gly
1130                1135                1140

Ala Asn Arg Leu Thr Leu Glu Asp Ala Asn Ile Val Gln Pro Leu
1145                1150                1155

Gly Leu Thr Ile Leu Gly Lys His Leu Tyr Trp Ile Asp Arg Gln
1160                1165                1170

Gln Gln Met Ile Glu Arg Val Glu Lys Thr Thr Gly Asp Lys Arg
1175                1180                1185

Thr Arg Ile Gln Gly Arg Val Ala His Leu Thr Gly Ile His Ala
1190                1195                1200

Val Glu Glu Val Ser Leu Glu Glu Phe Ser Ala His Pro Cys Ala
1205                1210                1215

Arg Asp Asn Gly Gly Cys Ser His Ile Cys Ile Ala Lys Gly Asp
1220                1225                1230

Gly Thr Pro Arg Cys Ser Cys Pro Val His Leu Val Leu Leu Gln
1235                1240                1245

Asn Leu Leu Thr Cys Gly Glu Pro Pro Thr Cys Ser Pro Asp Gln
1250                1255                1260

Phe Ala Cys Ala Thr Gly Glu Ile Asp Cys Ile Pro Gly Ala Trp
1265                1270                1275

Arg Cys Asp Gly Phe Pro Glu Cys Asp Asp Gln Ser Asp Glu Glu
1280                1285                1290

Gly Cys Pro Val Cys Ser Ala Ala Gln Phe Pro Cys Ala Arg Gly
1295                1300                1305

Gln Cys Val Asp Leu Arg Leu Arg Cys Asp Gly Glu Ala Asp Cys
1310                1315                1320

Gln Asp Arg Ser Asp Glu Ala Asp Cys Asp Ala Ile Cys Leu Pro
1325                1330                1335

Asn Gln Phe Arg Cys Ala Ser Gly Gln Cys Val Leu Ile Lys Gln
1340                1345                1350

Gln Cys Asp Ser Phe Pro Asp Cys Ile Asp Gly Ser Asp Glu Leu
1355                1360                1365

Met Cys Glu Ile Thr Lys Pro Pro Ser Asp Asp Ser Pro Ala His
1370                1375                1380

Ser Ser Ala Ile Gly Pro Val Ile Gly Ile Ile Leu Ser Leu Phe
1385                1390                1395

Val Met Gly Gly Val Tyr Phe Val Cys Gln Arg Val Val Cys Gln
1400                1405                1410

Arg Tyr Ala Gly Ala Asn Gly Pro Phe Pro His Glu Tyr Val Ser
1415                1420                1425

Gly Thr Pro His Val Pro Leu Asn Phe Ile Ala Pro Gly Gly Ser
1430                1435                1440

Gln His Gly Pro Phe Thr Gly Ile Ala Cys Gly Lys Ser Met Met
1445                1450                1455

Ser Ser Val Ser Leu Met Gly Gly Arg Gly Gly Val Pro Leu Tyr
1460                1465                1470

Asp Arg Asn His Val Thr Gly Ala Ser Ser Ser Ser Ser Ser Ser
1475                1480                1485

Thr Lys Ala Thr Leu Tyr Pro Pro Ile Leu Asn Pro Pro Pro Ser
1490                1495                1500
```

```
Pro Ala Thr Asp Pro Ser Leu Tyr Asn Met Asp Met Phe Tyr Ser
    1505                1510                1515

Ser Asn Ile Pro Ala Thr Ala Arg Pro Tyr Arg Pro Tyr Ile Ile
1520                1525                1530

Arg Gly Met Ala Pro Pro Thr Thr Pro Cys Ser Thr Asp Val Cys
    1535                1540                1545

Asp Ser Asp Tyr Ser Ala Ser Arg Trp Lys Ala Ser Lys Tyr Tyr
    1550                1555                1560

Leu Asp Leu Asn Ser Asp Ser Asp Pro Tyr Pro Pro Pro Pro Thr
1565                1570                1575

Pro His Ser Gln Tyr Leu Ser Ala Glu Asp Ser Cys Pro Pro Ser
    1580                1585                1590

Pro Ala Thr Glu Arg Ser Tyr Phe His Leu Phe Pro Pro Pro Pro
1595                1600                1605

Ser Pro Cys Thr Asp Ser Ser
    1610                1615

<210> SEQ ID NO 4
<211> LENGTH: 1613
<212> TYPE: PRT
<213> ORGANISM: homo sapiens

<400> SEQUENCE: 4

Met Gly Ala Val Leu Arg Ser Leu Leu Ala Cys Ser Phe Cys Val Leu
1               5                   10                  15

Leu Arg Ala Ala Pro Leu Leu Leu Tyr Ala Asn Arg Arg Asp Leu Arg
            20                  25                  30

Leu Val Asp Ala Thr Asn Gly Lys Glu Asn Ala Thr Ile Val Val Gly
        35                  40                  45

Gly Leu Glu Asp Ala Ala Ala Val Asp Phe Val Phe Ser His Gly Leu
    50                  55                  60

Ile Tyr Trp Ser Asp Val Ser Glu Glu Ala Ile Lys Arg Thr Glu Phe
65                  70                  75                  80

Asn Lys Thr Glu Ser Val Gln Asn Val Val Val Ser Gly Leu Leu Ser
                85                  90                  95

Pro Asp Gly Leu Ala Cys Asp Trp Leu Gly Glu Lys Leu Tyr Trp Thr
            100                 105                 110

Asp Ser Glu Thr Asn Arg Ile Glu Val Ser Asn Leu Asp Gly Ser Leu
        115                 120                 125

Arg Lys Val Leu Phe Trp Gln Glu Leu Asp Gln Pro Arg Ala Ile Ala
    130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Ile Ile
                165                 170                 175

Ile Asn Ser Glu Ile Tyr Trp Pro Asn Gly Leu Thr Leu Asp Tyr Glu
            180                 185                 190

Glu Gln Lys Leu Tyr Trp Ala Asp Ala Lys Leu Asn Phe Ile His Lys
        195                 200                 205

Ser Asn Leu Asp Gly Thr Asn Arg Gln Ala Val Val Lys Gly Ser Leu
    210                 215                 220

Pro His Pro Phe Ala Leu Thr Leu Phe Glu Asp Ile Leu Tyr Trp Thr
225                 230                 235                 240

Asp Trp Ser Thr His Ser Ile Leu Ala Cys Asn Lys Tyr Thr Gly Glu
                245                 250                 255
```

-continued

Gly Leu Arg Glu Ile His Ser Asp Ile Phe Ser Pro Met Asp Ile His
            260                 265                 270

Ala Phe Ser Gln Gln Arg Gln Pro Asn Ala Thr Asn Pro Cys Gly Ile
            275                 280                 285

Asp Asn Gly Gly Cys Ser His Leu Cys Leu Met Ser Pro Val Lys Pro
290                 295                 300

Phe Tyr Gln Cys Ala Cys Pro Thr Gly Val Lys Leu Leu Glu Asn Gly
305                 310                 315                 320

Lys Thr Cys Lys Asp Gly Ala Thr Glu Leu Leu Leu Ala Arg Arg
            325                 330                 335

Thr Asp Leu Arg Arg Ile Ser Leu Asp Thr Pro Asp Phe Thr Asp Ile
            340                 345                 350

Val Leu Gln Leu Glu Asp Ile Arg His Ala Ile Ala Ile Asp Tyr Asp
            355                 360                 365

Pro Val Glu Gly Tyr Ile Tyr Trp Thr Asp Asp Glu Val Arg Ala Ile
            370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
            405                 410                 415

Leu Tyr Trp Thr Asp Thr Gly Thr Asp Arg Ile Glu Val Thr Arg Leu
            420                 425                 430

Asn Gly Thr Met Arg Lys Ile Leu Ile Ser Glu Asp Leu Glu Glu Pro
            435                 440                 445

Arg Ala Ile Val Leu Asp Pro Met Val Gly Tyr Met Tyr Trp Thr Asp
450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
            485                 490                 495

Leu Asp Tyr Asp Glu Gly Lys Ile Tyr Trp Gly Asp Ala Lys Thr Asp
            500                 505                 510

Lys Ile Glu Val Met Asn Thr Asp Gly Thr Gly Arg Arg Val Leu Val
            515                 520                 525

Glu Asp Lys Ile Pro His Ile Phe Gly Phe Thr Leu Leu Gly Asp Tyr
            530                 535                 540

Val Tyr Trp Thr Asp Trp Gln Arg Arg Ser Ile Glu Arg Val His Lys
545                 550                 555                 560

Arg Ser Ala Glu Arg Glu Val Ile Ile Asp Gln Leu Pro Asp Leu Met
            565                 570                 575

Gly Leu Lys Ala Thr Asn Val His Arg Val Ile Gly Ser Asn Pro Cys
            580                 585                 590

Ala Glu Glu Asn Gly Gly Cys Ser His Leu Cys Leu Tyr Arg Pro Gln
            595                 600                 605

Gly Leu Arg Cys Ala Cys Pro Ile Gly Phe Glu Leu Ile Ser Asp Met
            610                 615                 620

Lys Thr Cys Ile Val Pro Glu Ala Phe Leu Leu Phe Ser Arg Arg Ala
625                 630                 635                 640

Asp Ile Arg Arg Ile Ser Leu Glu Thr Asn Asn Asn Val Ala Ile
            645                 650                 655

Pro Leu Thr Gly Val Lys Glu Ala Ser Ala Leu Asp Phe Asp Val Thr
            660                 665                 670

```
Asp Asn Arg Ile Tyr Trp Thr Asp Ile Ser Leu Lys Thr Ile Ser Arg
            675                 680                 685

Ala Phe Met Asn Gly Ser Ala Leu Glu His Val Val Glu Phe Gly Leu
    690                 695                 700

Asp Tyr Pro Glu Gly Met Ala Val Asp Trp Leu Gly Lys Asn Leu Tyr
705                 710                 715                 720

Trp Ala Asp Thr Gly Thr Asn Arg Ile Glu Val Ser Lys Leu Asp Gly
                725                 730                 735

Gln His Arg Gln Val Leu Val Trp Lys Asp Leu Asp Ser Pro Arg Ala
            740                 745                 750

Leu Ala Leu Asp Pro Ala Glu Gly Phe Met Tyr Trp Thr Glu Trp Gly
            755                 760                 765

Gly Lys Pro Lys Ile Asp Arg Ala Ala Met Asp Gly Ser Glu Arg Thr
    770                 775                 780

Thr Leu Val Pro Asn Val Gly Arg Ala Asn Gly Leu Thr Ile Asp Tyr
785                 790                 795                 800

Ala Lys Arg Arg Leu Tyr Trp Thr Asp Leu Asp Thr Asn Leu Ile Glu
                805                 810                 815

Ser Ser Asn Met Leu Gly Leu Asn Arg Glu Val Ile Ala Asp Asp Leu
            820                 825                 830

Pro His Pro Phe Gly Leu Thr Gln Tyr Gln Asp Tyr Ile Tyr Trp Thr
            835                 840                 845

Asp Trp Ser Arg Arg Ser Ile Glu Arg Ala Asn Lys Thr Ser Gly Gln
            850                 855                 860

Asn Arg Thr Ile Ile Gln Gly His Leu Asp Tyr Val Met Asp Ile Leu
865                 870                 875                 880

Val Phe His Ser Ser Arg Gln Ser Gly Trp Asn Glu Cys Ala Ser Ser
                885                 890                 895

Asn Gly His Cys Ser His Leu Cys Leu Ala Val Pro Val Gly Gly Phe
            900                 905                 910

Val Cys Gly Cys Pro Ala His Tyr Ser Leu Asn Ala Asp Asn Arg Thr
            915                 920                 925

Cys Ser Ala Pro Thr Thr Phe Leu Leu Phe Ser Gln Lys Ser Ala Ile
930                 935                 940

Asn Arg Met Val Ile Asp Glu Gln Gln Ser Pro Asp Ile Ile Leu Pro
945                 950                 955                 960

Ile His Ser Leu Arg Asn Val Arg Ala Ile Asp Tyr Asp Pro Leu Asp
                965                 970                 975

Lys Gln Leu Tyr Trp Ile Asp Ser Arg Gln Asn Met Ile Arg Lys Ala
            980                 985                 990

Gln Glu Asp Gly Ser Gln Gly Phe Thr Val Val Val Ser Ser Val Pro
            995                 1000                1005

Ser Gln Asn Leu Glu Ile Gln Pro Tyr Asp Leu Ser Ile Asp Ile
    1010                1015                1020

Tyr Ser Arg Tyr Ile Tyr Trp Thr Cys Glu Ala Thr Asn Val Ile
    1025                1030                1035

Asn Val Thr Arg Leu Asp Gly Arg Ser Val Gly Val Val Leu Lys
    1040                1045                1050

Gly Glu Gln Asp Arg Pro Arg Ala Val Val Val Asn Pro Glu Lys
    1055                1060                1065

Gly Tyr Met Tyr Phe Thr Asn Leu Gln Glu Arg Ser Pro Lys Ile
    1070                1075                1080

Glu Arg Ala Ala Leu Asp Gly Thr Glu Arg Glu Val Leu Phe Phe
```

-continued

```
            1085                1090                1095
Ser Gly Leu Ser Lys Pro Ile Ala Leu Ala Leu Asp Ser Arg Leu
            1100                1105                1110
Gly Lys Leu Phe Trp Ala Asp Ser Asp Leu Arg Arg Ile Glu Ser
            1115                1120                1125
Ser Asp Leu Ser Gly Ala Asn Arg Ile Val Leu Glu Asp Ser Asn
            1130                1135                1140
Ile Leu Gln Pro Val Gly Leu Thr Val Phe Glu Asn Trp Leu Tyr
            1145                1150                1155
Trp Ile Asp Lys Gln Gln Gln Met Ile Glu Lys Ile Asp Met Thr
            1160                1165                1170
Gly Arg Glu Gly Arg Thr Lys Val Gln Ala Arg Ile Ala Gln Leu
            1175                1180                1185
Ser Asp Ile His Ala Val Lys Glu Leu Asn Leu Gln Glu Tyr Arg
            1190                1195                1200
Gln His Pro Cys Ala Gln Asp Asn Gly Gly Cys Ser His Ile Cys
            1205                1210                1215
Leu Val Lys Gly Asp Gly Thr Thr Arg Cys Ser Cys Pro Met His
            1220                1225                1230
Leu Val Leu Leu Gln Asp Glu Leu Ser Cys Gly Glu Pro Pro Thr
            1235                1240                1245
Cys Ser Pro Gln Gln Phe Thr Cys Phe Thr Gly Glu Ile Asp Cys
            1250                1255                1260
Ile Pro Val Ala Trp Arg Cys Asp Gly Phe Thr Glu Cys Glu Asp
            1265                1270                1275
His Ser Asp Glu Leu Asn Cys Pro Val Cys Ser Glu Ser Gln Phe
            1280                1285                1290
Gln Cys Ala Ser Gly Gln Cys Ile Asp Gly Ala Leu Arg Cys Asn
            1295                1300                1305
Gly Asp Ala Asn Cys Gln Asp Lys Ser Asp Glu Lys Asn Cys Glu
            1310                1315                1320
Val Leu Cys Leu Ile Asp Gln Phe Arg Cys Ala Asn Gly Gln Cys
            1325                1330                1335
Ile Gly Lys His Lys Lys Cys Asp His Asn Val Asp Cys Ser Asp
            1340                1345                1350
Lys Ser Asp Glu Leu Asp Cys Tyr Pro Thr Glu Glu Pro Ala Pro
            1355                1360                1365
Gln Ala Thr Asn Thr Val Gly Ser Val Ile Gly Val Ile Val Thr
            1370                1375                1380
Ile Phe Val Ser Gly Thr Val Tyr Phe Ile Cys Gln Arg Met Leu
            1385                1390                1395
Cys Pro Arg Met Lys Gly Asp Gly Glu Thr Met Thr Asn Asp Tyr
            1400                1405                1410
Val Val His Gly Pro Ala Ser Val Pro Leu Gly Tyr Val Pro His
            1415                1420                1425
Pro Ser Ser Leu Ser Gly Ser Leu Pro Gly Met Ser Arg Gly Lys
            1430                1435                1440
Ser Met Ile Ser Ser Leu Ser Ile Met Gly Gly Ser Ser Gly Pro
            1445                1450                1455
Pro Tyr Asp Arg Ala His Val Thr Gly Ala Ser Ser Ser Ser Ser
            1460                1465                1470
Ser Ser Thr Lys Gly Thr Tyr Phe Pro Ala Ile Leu Asn Pro Pro
            1475                1480                1485
```

```
Pro Ser  Pro Ala Thr Glu Arg  Ser His Tyr Thr Met  Glu Phe Gly
    1490             1495              1500

Tyr Ser  Ser Asn Ser Pro Ser  Thr His Arg Ser Tyr  Ser Tyr Arg
    1505             1510              1515

Pro Tyr  Ser Tyr Arg His Phe  Ala Pro Pro Thr Thr  Pro Cys Ser
    1520             1525              1530

Thr Asp  Val Cys Asp Ser Asp  Tyr Ala Pro Ser Arg  Arg Met Thr
    1535             1540              1545

Ser Val  Ala Thr Ala Lys Gly  Tyr Thr Ser Asp Leu  Asn Tyr Asp
    1550             1555              1560

Ser Glu  Pro Val Pro Pro Pro  Pro Thr Pro Arg Ser  Gln Tyr Leu
    1565             1570              1575

Ser Ala  Glu Glu Asn Tyr Glu  Ser Cys Pro Pro Ser  Pro Tyr Thr
    1580             1585              1590

Glu Arg  Ser Tyr Ser His His  Leu Tyr Pro Pro Pro  Pro Ser Pro
    1595             1600              1605

Cys Thr  Asp Ser Ser
    1610
```

```
<210> SEQ ID NO 5
<211> LENGTH: 48
<212> TYPE: PRT
<213> ORGANISM: homo sapiens

<400> SEQUENCE: 5

Cys Cys Asp Arg Ala Glu Asp His Ala Cys Gln Asn Ala Cys Lys Arg
1               5                   10                  15

Ile Leu Met Ser Lys Lys Thr Glu Met Glu Ile Val Asp Gly Leu Ile
            20                  25                  30

Glu Gly Cys Lys Thr Gln Pro Leu Pro Gln Asp Pro Leu Trp Gln Cys
        35                  40                  45

<210> SEQ ID NO 6
<211> LENGTH: 47
<212> TYPE: PRT
<213> ORGANISM: homo sapiens

<400> SEQUENCE: 6

Cys Cys Ser Lys Ala Asn Thr Ser Thr Cys Arg Glu Leu Cys Thr Lys
1               5                   10                  15

Leu Tyr Ser Met Ser Trp Gly Asn Thr Gln Ser Trp Gln Phe Asp
            20                  25                  30

Arg Phe Cys Glu Tyr Asn Pro Val Glu Val Ser Met Leu Thr Cys
        35                  40                  45

<210> SEQ ID NO 7
<211> LENGTH: 6
<212> TYPE: PRT
<213> ORGANISM: artificial sequence
<220> FEATURE:
<223> OTHER INFORMATION: fragment of Frizzled receptor
<220> FEATURE:
<221> NAME/KEY: SITE
<222> LOCATION: (3)..(5)
<223> OTHER INFORMATION: any amino acid

<400> SEQUENCE: 7

Lys Thr Xaa Xaa Xaa Trp
1               5
```

```
<210> SEQ ID NO 8
<211> LENGTH: 4
<212> TYPE: PRT
<213> ORGANISM: artificial sequence
<220> FEATURE:
<223> OTHER INFORMATION: LRP repeat domain

<400> SEQUENCE: 8

Tyr Trp Thr Asp
1

<210> SEQ ID NO 9
<211> LENGTH: 4
<212> TYPE: PRT
<213> ORGANISM: artificial sequence
<220> FEATURE:
<223> OTHER INFORMATION: LRP motif
<220> FEATURE:
<221> NAME/KEY: SITE
<222> LOCATION: (3)..(3)
<223> OTHER INFORMATION: any amino acid

<400> SEQUENCE: 9

Asn Pro Xaa Tyr
1

<210> SEQ ID NO 10
<211> LENGTH: 5
<212> TYPE: PRT
<213> ORGANISM: artificial sequence
<220> FEATURE:
<223> OTHER INFORMATION: LRP motif

<400> SEQUENCE: 10

Pro Pro Pro Ser Pro
1               5

<210> SEQ ID NO 11
<211> LENGTH: 16
<212> TYPE: PRT
<213> ORGANISM: artificial sequence
<220> FEATURE:
<223> OTHER INFORMATION: Frizzled-binding domain
<220> FEATURE:
<221> NAME/KEY: SITE
<222> LOCATION: (1)..(1)
<223> OTHER INFORMATION: any amino acid
<220> FEATURE:
<221> NAME/KEY: SITE
<222> LOCATION: (3)..(6)
<223> OTHER INFORMATION: any amino acid
<220> FEATURE:
<221> NAME/KEY: SITE
<222> LOCATION: (9)..(15)
<223> OTHER INFORMATION: any amino acid

<400> SEQUENCE: 11

Xaa Lys Xaa Xaa Xaa Xaa Ser Gly Xaa Xaa Xaa Xaa Xaa Xaa Xaa Trp
1               5                   10                  15

<210> SEQ ID NO 12
<211> LENGTH: 16
<212> TYPE: PRT
<213> ORGANISM: homo sapiens

<400> SEQUENCE: 12

Cys Lys Cys His Gly Val Ser Gly Ser Cys Thr Thr Lys Thr Cys Trp
1               5                   10                  15
```

```
<210> SEQ ID NO 13
<211> LENGTH: 5
<212> TYPE: PRT
<213> ORGANISM: artificial sequence
<220> FEATURE:
<223> OTHER INFORMATION: Frizzled-binding domain
<220> FEATURE:
<221> NAME/KEY: SITE
<222> LOCATION: (2)..(2)
<223> OTHER INFORMATION: any amino acid
<220> FEATURE:
<221> NAME/KEY: SITE
<222> LOCATION: (4)..(4)
<223> OTHER INFORMATION: any amino acid

<400> SEQUENCE: 13

Trp Xaa Cys Xaa Val
1               5

<210> SEQ ID NO 14
<211> LENGTH: 89
<212> TYPE: PRT
<213> ORGANISM: homo sapiens

<400> SEQUENCE: 14

Met Tyr His Thr Lys Gly Gln Glu Gly Ser Val Cys Leu Arg Ser Ser
1               5                   10                  15

Asp Cys Ala Ser Gly Leu Cys Cys Ala Arg His Phe Trp Ser Lys Ile
            20                  25                  30

Cys Lys Pro Val Leu Lys Glu Gly Gln Val Cys Thr Lys His Arg Arg
        35                  40                  45

Lys Gly Ser His Gly Leu Glu Ile Phe Gln Arg Cys Tyr Cys Gly Glu
    50                  55                  60

Gly Leu Ser Cys Arg Ile Gln Lys Asp His His Gln Ala Ser Asn Ser
65                  70                  75                  80

Ser Arg Leu His Thr Cys Gln Arg His
                85

<210> SEQ ID NO 15
<211> LENGTH: 349
<212> TYPE: PRT
<213> ORGANISM: homo sapiens

<400> SEQUENCE: 15

Met Asn Arg Lys Ala Arg Arg Cys Leu Gly His Leu Phe Leu Ser Leu
1               5                   10                  15

Gly Met Val Tyr Leu Arg Ile Gly Gly Phe Ser Ser Val Val Ala Leu
            20                  25                  30

Gly Ala Ser Ile Ile Cys Asn Lys Ile Pro Gly Leu Ala Pro Arg Gln
        35                  40                  45

Arg Ala Ile Cys Gln Ser Arg Pro Asp Ala Ile Ile Val Ile Gly Glu
    50                  55                  60

Gly Ser Gln Met Gly Leu Asp Glu Cys Gln Phe Gln Phe Arg Asn Gly
65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
            100                 105                 110

Ala Gly Val Ala His Ala Ile Thr Ala Ala Cys Thr Gln Gly Asn Leu
        115                 120                 125
```

```
Ser Asp Cys Gly Cys Asp Lys Glu Lys Gln Gly Gln Tyr His Arg Asp
    130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ser Gly Ser
            195                 200                 205

Cys Thr Thr Lys Thr Cys Trp Thr Thr Leu Pro Gln Phe Arg Glu Leu
    210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
            260                 265                 270

Lys Ser Pro Asn Tyr Cys Glu Glu Asp Pro Val Thr Gly Ser Val Gly
            275                 280                 285

Thr Gln Gly Arg Ala Cys Asn Lys Thr Ala Pro Gln Ala Ser Gly Cys
    290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Met Tyr Thr Cys Lys
            340                 345

<210> SEQ ID NO 16
<211> LENGTH: 349
<212> TYPE: PRT
<213> ORGANISM: homo sapiens

<400> SEQUENCE: 16

Met His Arg Asn Phe Arg Lys Trp Ile Phe Tyr Val Phe Leu Cys Phe
1               5                   10                  15

Gly Val Leu Tyr Val Lys Leu Gly Ala Leu Ser Ser Val Val Ala Leu
            20                  25                  30

Gly Ala Asn Ile Ile Cys Asn Lys Ile Pro Gly Leu Ala Pro Arg Gln
            35                  40                  45

Arg Ala Ile Cys Gln Ser Arg Pro Asp Ala Ile Ile Val Ile Gly Glu
    50                  55                  60

Gly Ala Gln Met Gly Ile Asn Glu Cys Gln Tyr Gln Phe Arg Phe Gly
65                  70                  75                  80

Arg Trp Asn Cys Ser Ala Leu Gly Glu Lys Thr Val Phe Gly Gln Glu
                85                  90                  95

Leu Arg Val Gly Ser Arg Glu Ala Ala Phe Thr Tyr Ala Ile Thr Ala
            100                 105                 110

Ala Gly Val Ala His Ala Val Thr Ala Ala Cys Ser Gln Gly Asn Leu
            115                 120                 125

Ser Asn Cys Gly Cys Asp Arg Glu Lys Gln Gly Tyr Tyr Asn Gln Ala
    130                 135                 140

Glu Gly Trp Lys Trp Gly Gly Cys Ser Ala Asp Val Arg Tyr Gly Ile
145                 150                 155                 160
```

-continued

```
Asp Phe Ser Arg Arg Phe Val Asp Ala Arg Glu Ile Lys Lys Asn Ala
            165                 170                 175

Arg Arg Leu Met Asn Leu His Asn Asn Glu Ala Gly Arg Lys Val Leu
        180                 185                 190

Glu Asp Arg Met Gln Leu Glu Cys Lys Cys His Gly Val Ser Gly Ser
            195                 200                 205

Cys Thr Thr Lys Thr Cys Trp Thr Thr Leu Pro Lys Phe Arg Glu Val
        210                 215                 220

Gly His Leu Leu Lys Glu Lys Tyr Asn Ala Ala Val Gln Val Glu Val
225                 230                 235                 240

Val Arg Ala Ser Arg Leu Arg Gln Pro Thr Phe Leu Arg Ile Lys Gln
            245                 250                 255

Leu Arg Ser Tyr Gln Lys Pro Met Glu Thr Asp Leu Val Tyr Ile Glu
        260                 265                 270

Lys Ser Pro Asn Tyr Cys Glu Glu Asp Ala Ala Thr Gly Ser Val Gly
        275                 280                 285

Thr Gln Gly Arg Leu Cys Asn Arg Thr Ser Pro Gly Ala Asp Gly Cys
    290                 295                 300

Asp Thr Met Cys Cys Gly Arg Gly Tyr Asn Thr His Gln Tyr Thr Lys
305                 310                 315                 320

Val Trp Gln Cys Asn Cys Lys Phe His Trp Cys Cys Phe Val Lys Cys
            325                 330                 335

Asn Thr Cys Ser Glu Arg Thr Glu Val Phe Thr Cys Lys
            340                 345

<210> SEQ ID NO 17
<211> LENGTH: 42
<212> TYPE: PRT
<213> ORGANISM: homo sapiens

<400> SEQUENCE: 17

His Val Glu Pro Val Arg Ala Ser Arg Asn Lys Arg Pro Thr Phe Leu
1               5                   10                  15

Lys Ile Lys Lys Pro Leu Ser Tyr Arg Lys Pro Met Asp Thr Asp Leu
            20                  25                  30

Val Tyr Ile Glu Lys Ser Pro Asn Tyr Cys
        35                  40

<210> SEQ ID NO 18
<211> LENGTH: 29
<212> TYPE: PRT
<213> ORGANISM: homo sapiens

<400> SEQUENCE: 18

Val Glu Pro Val Arg Ala Ser Arg Asn Lys Arg Pro Thr Phe Leu Lys
1               5                   10                  15

Ile Lys Lys Pro Leu Ser Tyr Arg Lys Pro Met Asp Thr
            20                  25

<210> SEQ ID NO 19
<211> LENGTH: 29
<212> TYPE: PRT
<213> ORGANISM: homo sapiens

<400> SEQUENCE: 19

Val Glu Val Val Arg Ala Ser Arg Leu Arg Gln Pro Thr Phe Leu Arg
1               5                   10                  15
```

Ile Lys Gln Leu Arg Ser Tyr Gln Lys Pro Met Glu Thr
            20                  25

<210> SEQ ID NO 20
<211> LENGTH: 29
<212> TYPE: PRT
<213> ORGANISM: artificial sequence
<220> FEATURE:
<223> OTHER INFORMATION: RECK-binding domain
<220> FEATURE:
<221> NAME/KEY: SITE
<222> LOCATION: (1)..(3)
<223> OTHER INFORMATION: any amino acid
<220> FEATURE:
<221> NAME/KEY: SITE
<222> LOCATION: (5)..(5)
<223> OTHER INFORMATION: any amino acid
<220> FEATURE:
<221> NAME/KEY: SITE
<222> LOCATION: (7)..(7)
<223> OTHER INFORMATION: any amino acid
<220> FEATURE:
<221> NAME/KEY: SITE
<222> LOCATION: (9)..(13)
<223> OTHER INFORMATION: any amino acid
<220> FEATURE:
<221> NAME/KEY: SITE
<222> LOCATION: (16)..(16)
<223> OTHER INFORMATION: any amino acid
<220> FEATURE:
<221> NAME/KEY: SITE
<222> LOCATION: (18)..(22)
<223> OTHER INFORMATION: any amino acid
<220> FEATURE:
<221> NAME/KEY: SITE
<222> LOCATION: (24)..(24)
<223> OTHER INFORMATION: any amino acid
<220> FEATURE:
<221> NAME/KEY: SITE
<222> LOCATION: (26)..(29)
<223> OTHER INFORMATION: any amino acid

<400> SEQUENCE: 20

Xaa Xaa Xaa Val Xaa Ala Xaa Arg Xaa Xaa Xaa Xaa Xaa Phe Leu Xaa
1               5                   10                  15

Ile Xaa Xaa Xaa Xaa Xaa Tyr Xaa Lys Xaa Xaa Xaa Xaa
            20                  25

<210> SEQ ID NO 21
<211> LENGTH: 22
<212> TYPE: PRT
<213> ORGANISM: artificial sequence
<220> FEATURE:
<223> OTHER INFORMATION: RECK-binding domain
<220> FEATURE:
<221> NAME/KEY: SITE
<222> LOCATION: (2)..(2)
<223> OTHER INFORMATION: any amino acid
<220> FEATURE:
<221> NAME/KEY: SITE
<222> LOCATION: (4)..(4)
<223> OTHER INFORMATION: any amino acid
<220> FEATURE:
<221> NAME/KEY: SITE
<222> LOCATION: (6)..(10)
<223> OTHER INFORMATION: any amino acid
<220> FEATURE:
<221> NAME/KEY: SITE
<222> LOCATION: (13)..(13)
<223> OTHER INFORMATION: any amino acid
<220> FEATURE:
<221> NAME/KEY: SITE
<222> LOCATION: (15)..(19)
<223> OTHER INFORMATION: any amino acid
<220> FEATURE:

```
<221> NAME/KEY: SITE
<222> LOCATION: (21)..(21)
<223> OTHER INFORMATION: any amino acid

<400> SEQUENCE: 21

Val Xaa Ala Xaa Arg Xaa Xaa Xaa Xaa Phe Leu Xaa Ile Xaa Xaa
1               5                   10                  15

Xaa Xaa Xaa Tyr Xaa Lys
            20

<210> SEQ ID NO 22
<211> LENGTH: 29
<212> TYPE: PRT
<213> ORGANISM: artificial sequence
<220> FEATURE:
<223> OTHER INFORMATION: RECK-binding domain
<220> FEATURE:
<221> NAME/KEY: SITE
<222> LOCATION: (1)..(3)
<223> OTHER INFORMATION: any amino acid
<220> FEATURE:
<221> NAME/KEY: SITE
<222> LOCATION: (5)..(5)
<223> OTHER INFORMATION: any amino acid
<220> FEATURE:
<221> NAME/KEY: SITE
<222> LOCATION: (7)..(7)
<223> OTHER INFORMATION: any amino acid
<220> FEATURE:
<221> NAME/KEY: SITE
<222> LOCATION: (9)..(13)
<223> OTHER INFORMATION: any amino acid
<220> FEATURE:
<221> NAME/KEY: SITE
<222> LOCATION: (16)..(24)
<223> OTHER INFORMATION: any amino acid
<220> FEATURE:
<221> NAME/KEY: SITE
<222> LOCATION: (26)..(29)
<223> OTHER INFORMATION: any amino acid

<400> SEQUENCE: 22

Xaa Xaa Xaa Val Xaa Ala Xaa Arg Xaa Xaa Xaa Xaa Phe Leu Xaa
1               5                   10                  15

Xaa Xaa Xaa Xaa Xaa Xaa Xaa Xaa Lys Xaa Xaa Xaa Xaa
            20                  25

<210> SEQ ID NO 23
<211> LENGTH: 22
<212> TYPE: PRT
<213> ORGANISM: artificial sequence
<220> FEATURE:
<223> OTHER INFORMATION: RECK-binding domain
<220> FEATURE:
<221> NAME/KEY: SITE
<222> LOCATION: (2)..(2)
<223> OTHER INFORMATION: any amino acid
<220> FEATURE:
<221> NAME/KEY: SITE
<222> LOCATION: (4)..(4)
<223> OTHER INFORMATION: any amino acid
<220> FEATURE:
<221> NAME/KEY: SITE
<222> LOCATION: (6)..(10)
<223> OTHER INFORMATION: any amino acid
<220> FEATURE:
<221> NAME/KEY: SITE
<222> LOCATION: (13)..(21)
<223> OTHER INFORMATION: any amino acid

<400> SEQUENCE: 23

Val Xaa Ala Xaa Arg Xaa Xaa Xaa Xaa Xaa Phe Leu Xaa Xaa Xaa Xaa
```

```
1               5                   10                  15

Xaa Xaa Xaa Xaa Xaa Lys
                    20
```

<210> SEQ ID NO 24
<211> LENGTH: 247
<212> TYPE: PRT
<213> ORGANISM: artificial sequence
<220> FEATURE:
<223> OTHER INFORMATION: N-terminal domain (NTD) of human Wnt7a
      polypeptide

<400> SEQUENCE: 24

```
Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245
```

<210> SEQ ID NO 25
<211> LENGTH: 247
<212> TYPE: PRT
<213> ORGANISM: artificial sequence
<220> FEATURE:
<223> OTHER INFORMATION: N-terminal domain (NTD) of human Wnt7b
      polypeptide

<400> SEQUENCE: 25

```
Leu Gly Ala Asn Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
```

```
                20                  25                  30
Glu Gly Ala Gln Met Gly Ile Asn Glu Cys Gln Tyr Gln Phe Arg Phe
            35                  40                  45
Gly Arg Trp Asn Cys Ser Ala Leu Gly Glu Lys Thr Val Phe Gly Gln
        50                  55                  60
Glu Leu Arg Val Gly Ser Arg Glu Ala Ala Phe Thr Tyr Ala Ile Thr
65                  70                  75                  80
Ala Ala Gly Val Ala His Ala Val Thr Ala Ala Cys Ser Gln Gly Asn
                85                  90                  95
Leu Ser Asn Cys Gly Cys Asp Arg Glu Lys Gln Gly Tyr Tyr Asn Gln
            100                 105                 110
Ala Glu Gly Trp Lys Trp Gly Gly Cys Ser Ala Asp Val Arg Tyr Gly
        115                 120                 125
Ile Asp Phe Ser Arg Arg Phe Val Asp Ala Arg Glu Ile Lys Lys Asn
        130                 135                 140
Ala Arg Arg Leu Met Asn Leu His Asn Asn Glu Ala Gly Arg Lys Val
145                 150                 155                 160
Leu Glu Asp Arg Met Gln Leu Glu Cys Lys Cys His Gly Val Ser Gly
                165                 170                 175
Ser Cys Thr Thr Lys Thr Cys Trp Thr Thr Leu Pro Lys Phe Arg Glu
            180                 185                 190
Val Gly His Leu Leu Lys Glu Lys Tyr Asn Ala Ala Val Gln Val Glu
        195                 200                 205
Val Val Arg Ala Ser Arg Leu Arg Gln Pro Thr Phe Leu Arg Ile Lys
210                 215                 220
Gln Leu Arg Ser Tyr Gln Lys Pro Met Glu Thr Asp Leu Val Tyr Ile
225                 230                 235                 240
Glu Lys Ser Pro Asn Tyr Cys
            245
```

<210> SEQ ID NO 26
<211> LENGTH: 31
<212> TYPE: PRT
<213> ORGANISM: artificial sequence
<220> FEATURE:
<223> OTHER INFORMATION: signal peptide human Wnt7a polypeptide

<400> SEQUENCE: 26

```
Met Asn Arg Lys Ala Arg Arg Cys Leu Gly His Leu Phe Leu Ser Leu
1               5                   10                  15
Gly Met Val Tyr Leu Arg Ile Gly Gly Phe Ser Ser Val Val Ala
            20                  25                  30
```

<210> SEQ ID NO 27
<211> LENGTH: 31
<212> TYPE: PRT
<213> ORGANISM: artificial sequence
<220> FEATURE:
<223> OTHER INFORMATION: signal peptide human Wnt7b polypeptide

<400> SEQUENCE: 27

```
Met His Arg Asn Phe Arg Lys Trp Ile Phe Tyr Val Phe Leu Cys Phe
1               5                   10                  15
Gly Val Leu Tyr Val Lys Leu Gly Ala Leu Ser Ser Val Val Ala
            20                  25                  30
```

<210> SEQ ID NO 28
<211> LENGTH: 247

```
<212> TYPE: PRT
<213> ORGANISM: artificial sequence
<220> FEATURE:
<223> OTHER INFORMATION: human N-terminal domain (NTD) Wnt7a variant
      K159A

<400> SEQUENCE: 28

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Ala Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 29
<211> LENGTH: 247
<212> TYPE: PRT
<213> ORGANISM: artificial sequence
<220> FEATURE:
<223> OTHER INFORMATION: human N-terminal domain (NTD) Wnt7a variant
      A27R

<400> SEQUENCE: 29

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Arg Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60
```

```
Glu Leu Lys Val Gly Ser Arg Glu Ala Ala Phe Thr Tyr Ala Ile Ile
 65                  70                  75                  80

Ala Ala Gly Val Ala His Ala Ile Thr Ala Ala Cys Thr Gln Gly Asn
                 85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 30
<211> LENGTH: 247
<212> TYPE: PRT
<213> ORGANISM: artificial sequence
<220> FEATURE:
<223> OTHER INFORMATION: human N-terminal domain (NTD) Wnt7a variant
      E33A

<400> SEQUENCE: 30

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Ala Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
 65                  70                  75                  80

Ala Ala Gly Val Ala His Ala Ile Thr Ala Ala Cys Thr Gln Gly Asn
                 85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175
```

```
Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 31
<211> LENGTH: 247
<212> TYPE: PRT
<213> ORGANISM: artificial sequence
<220> FEATURE:
<223> OTHER INFORMATION: human N-terminal domain (NTD) Wnt7a variant
      E41A

<400> SEQUENCE: 31

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Val Ile Gly
            20                  25                  30

Glu Gly Ser Gln Met Gly Leu Asp Ala Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 32
<211> LENGTH: 247
<212> TYPE: PRT
```

<213> ORGANISM: artificial sequence
<220> FEATURE:
<223> OTHER INFORMATION: human N-terminal domain (NTD) Wn

```
                65                  70                  75                  80
Ala Ala Gly Val Ala His Ala Ile Thr Ala Ala Cys Thr Gln Gly Asn
                    85                  90                  95

Leu Ser Asp Cys Gly Cys Asp Lys Glu Lys Gln Gly Gln Tyr His Arg
                    100                 105                 110

Asp Glu Gly Trp Lys Trp Gly Gly Cys Ser Ala Asp Ile Arg Tyr Gly
                    115                 120                 125

Ile Gly Phe Ala Lys Val Phe Val Asp Ala Arg Glu Ile Lys Gln Asn
                    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                    165                 170                 175

Ser Cys Thr Thr Lys Thr Cys Trp Thr Thr Leu Pro Gln Phe Arg Glu
                    180                 185                 190

Leu Gly Tyr Val Leu Lys Asp Lys Tyr Asn Glu Ala Val His Val Glu
                    195                 200                 205

Pro Val Arg Ala Ser Arg Asn Lys Arg Pro Thr Phe Leu Lys Ile Lys
                    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                    245

<210> SEQ ID NO 34
<211> LENGTH: 247
<212> TYPE: PRT
<213> ORGANISM: artificial sequence
<220> FEATURE:
<223> OTHER INFORMATION: human N-terminal domain (NTD) Wnt7a variant
      I129A

<400> SEQUENCE: 34

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
                    20                  25                  30

Glu Gly Ser Gln Met Gly Leu Asp Glu Cys Gln Phe Gln Phe Arg Asn
                    35                  40                  45

Gly Arg Trp Asn Cys Ser Ala Leu Gly Glu Arg Thr Val Phe Gly Lys
                    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                    85                  90                  95

Leu Ser Asp Cys Gly Cys Asp Lys Glu Lys Gln Gly Gln Tyr His Arg
                    100                 105                 110

Asp Glu Gly Trp Lys Trp Gly Gly Cys Ser Ala Asp Ile Arg Tyr Gly
                    115                 120                 125

Ala Gly Phe Ala Lys Val Phe Val Asp Ala Arg Glu Ile Lys Gln Asn
                    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                    165                 170                 175
```

```
Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
        210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 35
<211> LENGTH: 247
<212> TYPE: PRT
<213> ORGANISM: artificial sequence
<220> FEATURE:
<223> OTHER INFORMATION: human N-terminal domain (NTD) Wnt7a variant
      F131A

<400> SEQUENCE: 35

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Ala Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
        210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 36
<211> LENGTH: 247
<212> TYPE: PRT
<213> ORGANISM: artificial sequence
```

<220> FEATURE:
<223> OTHER INFORMATION: human N-terminal domain (NTD) Wnt7a variant
      K133A

<400> SEQUENCE: 36

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Ala Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 37
<211> LENGTH: 247
<212> TYPE: PRT
<213> ORGANISM: artificial sequence
<220> FEATURE:
<223> OTHER INFORMATION: human N-terminal domain (NTD) Wnt7a variant
      I141A

<400> SEQUENCE: 37

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

```
Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ala Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 38
<211> LENGTH: 247
<212> TYPE: PRT
<213> ORGANISM: artificial sequence
<220> FEATURE:
<223> OTHER INFORMATION: human N-terminal domain (NTD) Wnt7a variant
      R158A

<400> SEQUENCE: 38

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Ala Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
```

```
                180                 185                 190
Leu Gly Tyr Val Leu Lys Asp Lys Tyr Asn Glu Ala Val His Val Glu
                195                 200                 205

Pro Val Arg Ala Ser Arg Asn Lys Arg Pro Thr Phe Leu Lys Ile Lys
            210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 39
<211> LENGTH: 247
<212> TYPE: PRT
<213> ORGANISM: artificial sequence
<220> FEATURE:
<223> OTHER INFORMATION: human N-terminal domain (NTD) Wnt7a variant
      K181A

<400> SEQUENCE: 39

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Ala Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 40
<211> LENGTH: 247
<212> TYPE: PRT
<213> ORGANISM: artificial sequence
<220> FEATURE:
```

<223> OTHER INFORMATION: human N-terminal domain (NTD) Wnt7a variant R191A

<400> SEQUENCE: 40

```
Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Ala Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245
```

<210> SEQ ID NO 41
<211> LENGTH: 247
<212> TYPE: PRT
<213> ORGANISM: artificial sequence
<220> FEATURE:
<223> OTHER INFORMATION: human N-terminal domain (NTD) Wnt7a variant K198A

<400> SEQUENCE: 41

```
Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80
```

```
Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
            115                 120                 125

Ile Gly Phe Ala Lys Val Phe Val Asp Ala Arg Glu Ile Lys Gln Asn
130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Ala Asp Lys Tyr Asn Glu Ala Val His Val Glu
        195                 200                 205

Pro Val Arg Ala Ser Arg Asn Leu Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 42
<211> LENGTH: 247
<212> TYPE: PRT
<213> ORGANISM: artificial sequence
<220> FEATURE:
<223> OTHER INFORMATION: human N-terminal domain (NTD) Wnt7a variant
      V205A

<400> SEQUENCE: 42

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
            115                 120                 125

Ile Gly Phe Ala Lys Val Phe Val Asp Ala Arg Glu Ile Lys Gln Asn
130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190
```

-continued

Leu Gly Tyr Val Leu Lys Asp Lys Tyr Asn Glu Ala Ala His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
            245

<210> SEQ ID NO 43
<211> LENGTH: 247
<212> TYPE: PRT
<213> ORGANISM: artificial sequence
<220> FEATURE:
<223> OTHER INFORMATION: human N-terminal domain (NTD) Wnt7a variant
      E208A

<400> SEQUENCE: 43

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Ala
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
            245

<210> SEQ ID NO 44
<211> LENGTH: 247
<212> TYPE: PRT
<213> ORGANISM: artificial sequence
<220> FEATURE:
<223> OTHER INFORMATION: human N-terminal domain (NTD) Wnt7a variant

K216A

<400> SEQUENCE: 44

| | | | | | | | | | | | | | | |
|---|---|---|---|---|---|---|---|---|---|---|---|---|---|---|
Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Ala Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 45
<211> LENGTH: 247
<212> TYPE: PRT
<213> ORGANISM: artificial sequence
<220> FEATURE:
<223> OTHER INFORMATION: human N-terminal domain (NTD) Wnt7a variant
      K222A

<400> SEQUENCE: 45

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn

```
            85                  90                  95
Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
            115                 120                 125

Ile Gly Phe Ala Lys Val Phe Val Asp Ala Arg Glu Ile Lys Gln Asn
        130                 135                 140

Ala Arg Thr Leu Met Asn Leu His Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
            195                 200                 205

Pro Val Arg Ala Ser Arg Asn Lys Arg Pro Thr Phe Leu Ala Ile Lys
        210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 46
<211> LENGTH: 247
<212> TYPE: PRT
<213> ORGANISM: artificial sequence
<220> FEATURE:
<223> OTHER INFORMATION: human N-terminal domain (NTD) Wnt7a variant
      I223A

<400> SEQUENCE: 46

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
            115                 120                 125

Ile Gly Phe Ala Lys Val Phe Val Asp Ala Arg Glu Ile Lys Gln Asn
        130                 135                 140

Ala Arg Thr Leu Met Asn Leu His Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190
```

```
Leu Gly Tyr Val Leu Lys Asp Lys Tyr Asn Glu Ala Val His Val Glu
            195                 200                 205

Pro Val Arg Ala Ser Arg Asn Lys Arg Pro Thr Phe Leu Lys Ala Lys
        210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245
```

<210> SEQ ID NO 47
<211> LENGTH: 247
<212> TYPE: PRT
<213> ORGANISM: artificial sequence
<220> FEATURE:
<223> OTHER INFORMATION: human N-terminal domain (NTD) Wnt7a variant
      Y229A

<400> SEQUENCE: 47

```
Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Ala Arg Lys Pro Met Asp Thr Asp Leu Val Tyr Ile
225                 230                 235                 240

Glu Lys Ser Pro Asn Tyr Cys
                245
```

<210> SEQ ID NO 48
<211> LENGTH: 247
<212> TYPE: PRT
<213> ORGANISM: artificial sequence
<220> FEATURE:
<223> OTHER INFORMATION: human N-terminal domain (NTD) Wnt7a variant
      P232A

<400> SEQUENCE: 48

```
Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Ala Met Asp Thr Asp Leu Val Tyr Ile
225                 230                 235                 240

Glu Lys Ser Pro Asn Tyr Cys
                245
```

<210> SEQ ID NO 49
<211> LENGTH: 247
<212> TYPE: PRT
<213> ORGANISM: artificial sequence
<220> FEATURE:
<223> OTHER INFORMATION: human N-terminal domain (NTD) Wnt7a variant T235A

<400> SEQUENCE: 49

```
Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95
```

Leu Ser Asp Cys Gly Cys Asp Lys Glu Lys Gln Gly Gln Tyr His Arg
            100                 105                 110

Asp Glu Gly Tr

```
Pro Val Arg Ala Ser Arg Asn Lys Arg Pro Thr Phe Leu Lys Ile Lys
    210                 215                 220
Lys Pro Leu Ser Tyr Arg Lys Pro Met Asp Thr Asp Leu Val Tyr Ile
225                 230                 235                 240
Glu Lys Ser Pro Asn Tyr Cys Ala Glu Asp Pro Val Thr Gly Ser Val
                245                 250                 255
Gly Thr Gln Gly Arg Ala Cys Asn Lys Thr Ala Pro Gln Ala Ser Gly
            260                 265                 270
Cys Asp Leu Met Cys Cys Gly Arg Gly Tyr Asn Thr His Gln Tyr Ala
        275                 280                 285
Arg Val Trp Gln Cys Asn Cys Lys Phe His Trp Cys Cys Tyr Val Lys
    290                 295                 300
Cys Asn Thr Cys Ser Glu Arg Thr Glu Met Tyr Thr Cys Lys
305                 310                 315
```

<210> SEQ ID NO 51
<211> LENGTH: 318
<212> TYPE: PRT
<213> ORGANISM: homo sapiens

<400> SEQUENCE: 51

```
Leu Gly Ala Ser Ile Ile Cys Asn Lys Ile Pro Gly Leu Ala Pro Arg
1               5                   10                  15
Gln Arg Ala Ile Cys Gln Ser Arg Pro Asp Ala Ile Ile Val Ile Gly
            20                  25                  30
Glu Gly Ser Gln Met Gly Leu Asp Glu Cys Gln Phe Gln Phe Arg Asn
        35                  40                  45
Gly Arg Trp Asn Cys Ser Ala Leu Gly Glu Arg Thr Val Phe Gly Lys
    50                  55                  60
Glu Leu Lys Val Gly Ser Arg Glu Ala Ala Phe Thr Tyr Ala Ile Ile
65                  70                  75                  80
Ala Ala Gly Val Ala His Ala Ile Thr Ala Ala Cys Thr Gln Gly Asn
                85                  90                  95
Leu Ser Asp Cys Gly Cys Asp Lys Glu Lys Gln Gly Gln Tyr His Arg
            100                 105                 110
Asp Glu Gly Trp Lys Trp Gly Gly Cys Ser Ala Asp Ile Arg Tyr Gly
        115                 120                 125
Ile Gly Phe Ala Lys Val Phe Val Asp Ala Arg Glu Ile Lys Gln Asn
    130                 135                 140
Ala Arg Thr Leu Met Asn Leu His Asn Asn Glu Ala Gly Arg Lys Ile
145                 150                 155                 160
Leu Glu Glu Asn Met Lys Leu Glu Cys Lys Cys His Gly Val Ser Gly
                165                 170                 175
Ser Cys Thr Thr Lys Thr Cys Trp Thr Thr Leu Pro Gln Phe Arg Glu
            180                 185                 190
Leu Gly Tyr Val Leu Lys Asp Lys Tyr Asn Glu Ala Val His Val Glu
        195                 200                 205
Pro Val Arg Ala Ser Arg Asn Lys Arg Pro Thr Phe Leu Lys Ile Lys
    210                 215                 220
Lys Pro Leu Ser Tyr Arg Lys Pro Met Asp Thr Asp Leu Val Tyr Ile
225                 230                 235                 240
Glu Lys Ser Pro Asn Tyr Cys Glu Glu Asp Pro Val Thr Gly Ser Val
                245                 250                 255
Gly Thr Gln Gly Arg Ala Cys Asn Lys Thr Ala Pro Gln Ala Ser Gly
```

```
                260                 265                 270
Cys Asp Leu Met Cys Cys Gly Arg Gly Tyr Asn Thr His Gln Tyr Ala
            275                 280                 285

Arg Val Trp Gln Cys Asn Cys Lys Phe His Trp Cys Cys Tyr Val Lys
        290                 295                 300

Cys Asn Thr Cys Ser Glu Arg Thr Glu Met Tyr Thr Cys Lys
305                 310                 315

<210> SEQ ID NO 52
<211> LENGTH: 318
<212> TYPE: PRT
<213> ORGANISM: artificial sequence
<220> FEATURE:
<223> OTHER INFORMATION: human full Wnt7a variant R289A

<400> SEQUENCE: 52

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Ala Val Trp Gln Cys Asn Cys Lys Phe His Trp Cys Cys Tyr Val Lys
    290                 295                 300

Cys Asn Thr Cys Ser Glu Arg Thr Glu Met Tyr Thr Cys Lys
```

<210> SEQ ID NO 53
<211> LENGTH: 318
<212> TYPE: PRT
<213> ORGANISM: artificial sequence
<220> FEATURE:
<223> OTHER INFORMATION: human full Wnt7a variant W291A

<400> SEQUENCE: 53

```
Leu Gly Ala Ser Ile Ile Cys Asn Lys Ile Pro Gly Leu Ala Pro Arg
1               5                   10                  15
Gln Arg Ala Ile Cys Gln Ser Arg Pro Asp Ala Ile Ile Val Ile Gly
            20                  25                  30
Glu Gly Ser Gln Met Gly Leu Asp Glu Cys Gln Phe Gln Phe Arg Asn
        35                  40                  45
Gly Arg Trp Asn Cys Ser Ala Leu Gly Glu Arg Thr Val Phe Gly Lys
    50                  55                  60
Glu Leu Lys Val Gly Ser Arg Glu Ala Ala Phe Thr Tyr Ala Ile Ile
65                  70                  75                  80
Ala Ala Gly Val Ala His Ala Ile Thr Ala Ala Cys Thr Gln Gly Asn
                85                  90                  95
Leu Ser Asp Cys Gly Cys Asp Lys Glu Lys Gln Gly Gln Tyr His Arg
            100                 105                 110
Asp Glu Gly Trp Lys Trp Gly Gly Cys Ser Ala Asp Ile Arg Tyr Gly
        115                 120                 125
Ile Gly Phe Ala Lys Val Phe Val Asp Ala Arg Glu Ile Lys Gln Asn
    130                 135                 140
Ala Arg Thr Leu Met Asn Leu His Asn Asn Glu Ala Gly Arg Lys Ile
145                 150                 155                 160
Leu Glu Glu Asn Met Lys Leu Glu Cys Lys Cys His Gly Val Ser Gly
                165                 170                 175
Ser Cys Thr Thr Lys Thr Cys Trp Thr Thr Leu Pro Gln Phe Arg Glu
            180                 185                 190
Leu Gly Tyr Val Leu Lys Asp Lys Tyr Asn Glu Ala Val His Val Glu
        195                 200                 205
Pro Val Arg Ala Ser Arg Asn Lys Arg Pro Thr Phe Leu Lys Ile Lys
    210                 215                 220
Lys Pro Leu Ser Tyr Arg Lys Pro Met Asp Thr Asp Leu Val Tyr Ile
225                 230                 235                 240
Glu Lys Ser Pro Asn Tyr Cys Glu Glu Asp Pro Val Thr Gly Ser Val
                245                 250                 255
Gly Thr Gln Gly Arg Ala Cys Asn Lys Thr Ala Pro Gln Ala Ser Gly
            260                 265                 270
Cys Asp Leu Met Cys Cys Gly Arg Gly Tyr Asn Thr His Gln Tyr Ala
        275                 280                 285
Arg Val Ala Gln Cys Asn Cys Lys Phe His Trp Cys Cys Tyr Val Lys
    290                 295                 300
Cys Asn Thr Cys Ser Glu Arg Thr Glu Met Tyr Thr Cys Lys
305                 310                 315
```

<210> SEQ ID NO 54
<211> LENGTH: 318
<212> TYPE: PRT
<213> ORGANISM: artificial sequence
<220> FEATURE:
<223> OTHER INFORMATION: human full Wnt7a variant T307A

<400> SEQUENCE: 54

```
Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
    290                 295                 300

Cys Asn Ala Cys Ser Glu Arg Thr Glu Met Tyr Thr Cys Lys
305                 310                 315
```

<210> SEQ ID NO 55
<211> LENGTH: 11
<212> TYPE: PRT
<213> ORGANISM: artificial sequence
<220> FEATURE:
<223> OTHER INFORMATION: peptide displayed on AAV-PHP.B

<400> SEQUENCE: 55

```
Ser Ala Gln Thr Leu Ala Val Pro Phe Lys Ala
1               5                   10
```

<210> SEQ ID NO 56
<211> LENGTH: 11

```
<212> TYPE: PRT
<213> ORGANISM: artificial sequence
<220> FEATURE:
<223> OTHER INFORMATION: peptide displayed on AAV-PHP.eB

<400> SEQUENCE: 56

Ser Asp Gly Thr Leu Ala Val Pro Phe Lys Ala
1               5                   10

<210> SEQ ID NO 57
<211> LENGTH: 7
<212> TYPE: PRT
<213> ORGANISM: artificial sequence
<220> FEATURE:
<223> OTHER INFORMATION: peptide displayed on AAV-BR1

<400> SEQUENCE: 57

Asn Arg Gly Thr Glu Trp Asp
1               5

<210> SEQ ID NO 58
<211> LENGTH: 27
<212> TYPE: PRT
<213> ORGANISM: artificial sequence
<220> FEATURE:
<223> OTHER INFORMATION: xenopus Levis

<400> SEQUENCE: 58

Val Glu Pro Val Arg Ala Ser Arg Asn Lys Arg Pro Thr Phe Leu Lys
1               5                   10                  15

Ile Lys Asn Ser Tyr Arg Lys Pro Met Asp Thr
            20                  25

<210> SEQ ID NO 59
<211> LENGTH: 29
<212> TYPE: PRT
<213> ORGANISM: artificial sequence
<220> FEATURE:
<223> OTHER INFORMATION: danio rerio

<400> SEQUENCE: 59

Val Glu Pro Val Arg Ala Ser Arg Asn Lys Arg Pro Ala Phe Leu Lys
1               5                   10                  15

Val Lys Lys Pro Tyr Ser Tyr Arg Lys Pro Met Asp Thr
            20                  25

<210> SEQ ID NO 60
<211> LENGTH: 29
<212> TYPE: PRT
<213> ORGANISM: artificial sequence
<220> FEATURE:
<223> OTHER INFORMATION: danio rerio

<400> SEQUENCE: 60

Val Glu Pro Val Lys Ala Thr Arg His Lys Arg Pro Thr Phe Leu Lys
1               5                   10                  15

Ile Lys Lys Pro Tyr Ser Tyr Arg Lys Pro Met Asp Thr
            20                  25

<210> SEQ ID NO 61
<211> LENGTH: 29
<212> TYPE: PRT
<213> ORGANISM: artificial sequence
<220> FEATURE:
<223> OTHER INFORMATION: mus musculus
```

```
<400> SEQUENCE: 61

Val Glu Val Val Arg Ala Ser Arg Leu Arg Gln Pro Thr Phe Leu Arg
1               5                   10                  15

Ile Lys Gln Leu Arg Ser Tyr Gln Lys Pro Met Glu Thr
            20                  25

<210> SEQ ID NO 62
<211> LENGTH: 29
<212> TYPE: PRT
<213> ORGANISM: artificial sequence
<220> FEATURE:
<223> OTHER INFORMATION: gallus gallus

<400> SEQUENCE: 62

Val Glu Val Val Arg Ala Ser Arg Leu Arg Gln Pro Thr Phe Leu Lys
1               5                   10                  15

Ile Lys Gln Ile Lys Ser Tyr Gln Lys Pro Met Glu Thr
            20                  25

<210> SEQ ID NO 63
<211> LENGTH: 29
<212> TYPE: PRT
<213> ORGANISM: artificial sequence
<220> FEATURE:
<223> OTHER INFORMATION: xenopus Levis

<400> SEQUENCE: 63

Val Glu Val Val Arg Ala Asn Arg Leu Arg Gln Pro Thr Phe Leu Lys
1               5                   10                  15

Ile Lys Lys Val Arg Ser Tyr Gln Lys Pro Met Glu Thr
            20                  25

<210> SEQ ID NO 64
<211> LENGTH: 28
<212> TYPE: PRT
<213> ORGANISM: artificial sequence
<220> FEATURE:
<223> OTHER INFORMATION: Danio rerio

<400> SEQUENCE: 64

Val Glu Val Val Arg Ala Ser Arg Leu Arg Gln Pro Thr Phe Leu Lys
1               5                   10                  15

Val Lys Arg Thr Arg His Gln Lys Pro Leu Glu Thr
            20                  25

<210> SEQ ID NO 65
<211> LENGTH: 29
<212> TYPE: PRT
<213> ORGANISM: artificial sequence
<220> FEATURE:
<223> OTHER INFORMATION: Danio rerio

<400> SEQUENCE: 65

Val Glu Ala Val Arg Ala Thr Arg Phe Arg Gln Pro Ser Phe Leu Arg
1               5                   10                  15

Leu Lys Gln Ser Arg Gly Tyr Ile Lys Pro Thr Asp Thr
            20                  25

<210> SEQ ID NO 66
<211> LENGTH: 29
<212> TYPE: PRT
<213> ORGANISM: artificial sequence
<220> FEATURE:
<223> OTHER INFORMATION: mus musculus
```

-continued

<400> SEQUENCE: 66

Met Val Val Glu Lys His Arg Glu Ser Arg Gly Trp Val Glu Thr Leu
1               5                   10                  15

Arg Pro Arg Tyr Thr Tyr Phe Lys Val Pro Thr Glu Arg
            20                  25

<210> SEQ ID NO 67
<211> LENGTH: 29
<212> TYPE: PRT
<213> ORGANISM: artificial sequence
<220> FEATURE:
<223> OTHER INFORMATION: quadruple pWnt7a4A variant

<400> SEQUENCE: 67

Val Glu Pro Ala Arg Ala Ser Arg Asn Lys Arg Pro Thr Ala Ala Lys
1               5                   10                  15

Ile Lys Lys Pro Leu Ser Tyr Arg Ala Pro Met Asp Thr
            20                  25

<210> SEQ ID NO 68
<211> LENGTH: 247
<212> TYPE: PRT
<213> ORGANISM: artificial sequence
<220> FEATURE:
<223> OTHER INFORMATION: human N-terminal domain (NTD) Wnt7a variant
      Q17A

<400> SEQUENCE: 68

Leu Gly Ala Ser Ile Ile Cys Asn Lys Ile Pro Gly Leu Ala Pro Arg
1               5                   10                  15

Ala Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile

Glu Lys Ser Pro Asn Tyr Cys
225                 245

<210> SEQ ID NO 69
<211> LENGTH: 247
<212> TYPE: PRT
<213> ORGANISM: artificial sequence
<220> FEATURE:
<223> OTHER INFORMATION: human N-terminal domain (NTD) Wnt7a variant
      I20A

<400> SEQUENCE: 69

Leu Gly Ala Ser Ile Ile Cys Asn Lys Ile Pro Gly Leu Ala Pro Arg
1               5                   10                  15

Gln Arg Ala Ala Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 70
<211> LENGTH: 247
<212> TYPE: PRT
<213> ORGANISM: artificial sequence
<220> FEATURE:
<223> OTHER INFORMATION: human N-terminal domain (NTD) Wnt7a variant
      P25A

<400> SEQUENCE: 70

Leu Gly Ala Ser Ile Ile Cys Asn Lys Ile Pro Gly Leu Ala Pro Arg
1               5                   10                  15

Gln Arg Ala Ile Cys Gln Ser Arg Ala Asp Ala Ile Ile Val Ile Gly

```
                20                  25                  30
Glu Gly Ser Gln Met Gly Leu Asp Glu Cys Gln Phe Gln Phe Arg Asn
            35                  40                  45
Gly Arg Trp Asn Cys Ser Ala Leu Gly Glu Arg Thr Val Phe Gly Lys
        50                  55                  60
Glu Leu Lys Val Gly Ser Arg Glu Ala Ala Phe Thr Tyr Ala Ile Ile
65                  70                  75                  80
Ala Ala Gly Val Ala His Ala Ile Thr Ala Ala Cys Thr Gln Gly Asn
                85                  90                  95
Leu Ser Asp Cys Gly Cys Asp Lys Glu Lys Gln Gly Gln Tyr His Arg
            100                 105                 110
Asp Glu Gly Trp Lys Trp Gly Gly Cys Ser Ala Asp Ile Arg Tyr Gly
        115                 120                 125
Ile Gly Phe Ala Lys Val Phe Val Asp Ala Arg Glu Ile Lys Gln Asn
            130                 135                 140
Ala Arg Thr Leu Met Asn Leu His Asn Asn Glu Ala Gly Arg Lys Ile
145                 150                 155                 160
Leu Glu Glu Asn Met Lys Leu Glu Cys Lys Cys His Gly Val Ser Gly
                165                 170                 175
Ser Cys Thr Thr Lys Thr Cys Trp Thr Thr Leu Pro Gln Phe Arg Glu
            180                 185                 190
Leu Gly Tyr Val Leu Lys Asp Lys Tyr Asn Glu Ala Val His Val Glu
        195                 200                 205
Pro Val Arg Ala Ser Arg Asn Lys Arg Pro Thr Phe Leu Lys Ile Lys
210                 215                 220
Lys Pro Leu Ser Tyr Arg Lys Pro Met Asp Thr Asp Leu Val Tyr Ile
225                 230                 235                 240
Glu Lys Ser Pro Asn Tyr Cys
                245

<210> SEQ ID NO 71
<211> LENGTH: 247
<212> TYPE: PRT
<213> ORGANISM: artificial sequence
<220> FEATURE:
<223> OTHER INFORMATION: human N-terminal domain (NTD) Wnt7a variant
      M37A

<400> SEQUENCE: 71

Leu Gly Ala Ser Ile Ile Cys Asn Lys Ile Pro Gly Leu Ala Pro Arg
1               5                   10                  15
Gln Arg Ala Ile Cys Gln Ser Arg Pro Asp Ala Ile Ile Val Ile Gly
            20                  25                  30
Glu Gly Ser Gln Ala Gly Leu Asp Glu Cys Gln Phe Gln Phe Arg Asn
        35                  40                  45
Gly Arg Trp Asn Cys Ser Ala Leu Gly Glu Arg Thr Val Phe Gly Lys
    50                  55                  60
Glu Leu Lys Val Gly Ser Arg Glu Ala Ala Phe Thr Tyr Ala Ile Ile
65                  70                  75                  80
Ala Ala Gly Val Ala His Ala Ile Thr Ala Ala Cys Thr Gln Gly Asn
                85                  90                  95
Leu Ser Asp Cys Gly Cys Asp Lys Glu Lys Gln Gly Gln Tyr His Arg
            100                 105                 110
Asp Glu Gly Trp Lys Trp Gly Gly Cys Ser Ala Asp Ile Arg Tyr Gly
        115                 120                 125
```

```
Ile Gly Phe Ala Lys Val Phe Val Asp Ala Arg Glu Ile Lys Gln Asn
            130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                    165                 170                 175

Ser Cys Thr Thr Lys Thr Cys Trp Thr Thr Leu Pro Gln Phe Arg Glu
                180                 185                 190

Leu Gly Tyr Val Leu Lys Asp Lys Tyr Asn Glu Ala Val His Val Glu
            195                 200                 205

Pro Val Arg Ala Ser Arg Asn Lys Arg Pro Thr Phe Leu Lys Ile Lys
            210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 72
<211> LENGTH: 247
<212> TYPE: PRT
<213> ORGANISM: artificial sequence
<220> FEATURE:
<223> OTHER INFORMATION: human N-terminal domain (NTD) Wnt7a variant
      L39A

<400> SEQUENCE: 72

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Ala Asp Glu Cys Gln Phe Gln Phe Arg Asn
            35                  40                  45

Gly Arg Trp Asn Cys Ser Ala Leu Gly Glu Arg Thr Val Phe Gly Lys
50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
                100                 105                 110

Asp Glu Gly Trp Lys Trp Gly Gly Cys Ser Ala Asp Ile Arg Tyr Gly
            115                 120                 125

Ile Gly Phe Ala Lys Val Phe Val Asp Ala Arg Glu Ile Lys Gln Asn
            130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                    165                 170                 175

Ser Cys Thr Thr Lys Thr Cys Trp Thr Thr Leu Pro Gln Phe Arg Glu
                180                 185                 190

Leu Gly Tyr Val Leu Lys Asp Lys Tyr Asn Glu Ala Val His Val Glu
            195                 200                 205

Pro Val Arg Ala Ser Arg Asn Lys Arg Pro Thr Phe Leu Lys Ile Lys
            210                 215                 220

Lys Pro Leu Ser Tyr Arg Lys Pro Met Asp Thr Asp Leu Val Tyr Ile
225                 230                 235                 240
```

Glu Lys Ser Pro Asn Tyr Cys
            245

<210> SEQ ID NO 73
<211> LENGTH: 25
<212> TYPE: DNA
<213> ORGANISM: artificial sequence
<220> FEATURE:
<223> OTHER INFORMATION: wnt7aa Morpholino

<400> SEQUENCE: 73
ttccatttga ccctacttac ccaat                                               25

<210> SEQ ID NO 74
<211> LENGTH: 247
<212> TYPE: PRT
<213> ORGANISM: artificial sequence
<220> FEATURE:
<223> OTHER INFORMATION: human N-terminal domain (NTD) Wnt7a variant
      I28A

<400> SEQUENCE: 74

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ala Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
            245

<210> SEQ ID NO 75
<211> LENGTH: 247
<212> TYPE: PRT

<213> ORGANISM: artificial sequence
<220> FEATURE:
<223> OTHER INFORMATION: human N-terminal domain (NTD) Wnt7a variant R50A

<400> SEQUENCE: 75

```
Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Ala Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245
```

<210> SEQ ID NO 76
<211> LENGTH: 247
<212> TYPE: PRT
<213> ORGANISM: artificial sequence
<220> FEATURE:
<223> OTHER INFORMATION: human N-terminal domain (NTD) Wnt7a variant V68A

<400> SEQUENCE: 76

```
Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Ala Gly Ser Arg Glu Ala Ala Phe Thr Tyr Ala Ile Ile
```

```
                65                  70                  75                  80
Ala Ala Gly Val Ala His Ala Ile Thr Ala Ala Cys Thr Gln Gly Asn
                    85                  90                  95

Leu Ser Asp Cys Gly Cys Asp Lys Glu Lys Gln Gly Gln Tyr His Arg
                100                 105                 110

Asp Glu Gly Trp Lys Trp Gly Gly Cys Ser Ala Asp Ile Arg Tyr Gly
                115                 120                 125

Ile Gly Phe Ala Lys Val Phe Val Asp Ala Arg Glu Ile Lys Gln Asn
            130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
                180                 185                 190

Leu Gly Tyr Val Leu Lys Asp Lys Tyr Asn Glu Ala Val His Val Glu
            195                 200                 205

Pro Val Arg Ala Ser Arg Asn Lys Arg Pro Thr Phe Leu Lys Ile Lys
            210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 77
<211> LENGTH: 247
<212> TYPE: PRT
<213> ORGANISM: artificial sequence
<220> FEATURE:
<223> OTHER INFORMATION: human N-terminal domain (NTD) Wnt7a variant
      F135A

<400> SEQUENCE: 77

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                    85                  90                  95

Leu Ser Asp Cys Gly Cys Asp Lys Glu Lys Gln Gly Gln Tyr His Arg
                100                 105                 110

Asp Glu Gly Trp Lys Trp Gly Gly Cys Ser Ala Asp Ile Arg Tyr Gly
                115                 120                 125

Ile Gly Phe Ala Lys Val Ala Val Asp Ala Arg Glu Ile Lys Gln Asn
            130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175
```

```
Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
        210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 78
<211> LENGTH: 247
<212> TYPE: PRT
<213> ORGANISM: artificial sequence
<220> FEATURE:
<223> OTHER INFORMATION: human N-terminal domain (NTD) Wnt7a variant
      R146A

<400> SEQUENCE: 78

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Ala Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
        210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 79
<211> LENGTH: 247
<212> TYPE: PRT
<213> ORGANISM: artificial sequence
```

<220> FEATURE:
<223> OTHER INFORMATION: human N-terminal domain (NTD) Wnt7a variant
      K159S

<400> SEQUENCE: 79

```
Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Ser Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245
```

<210> SEQ ID NO 80
<211> LENGTH: 247
<212> TYPE: PRT
<213> ORGANISM: artificial sequence
<220> FEATURE:
<223> OTHER INFORMATION: human N-terminal domain (NTD) Wnt7a variant
      K159L

<400> SEQUENCE: 80

```
Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80
```

```
Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Leu Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 81
<211> LENGTH: 247
<212> TYPE: PRT
<213> ORGANISM: artificial sequence
<220> FEATURE:
<223> OTHER INFORMATION: human N-terminal domain (NTD) Wnt7a variant
      K200A

<400> SEQUENCE: 81

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
```

180                 185                 190

Leu Gly Tyr Val Leu Lys Asp Ala Tyr Asn Glu Ala Val His Val Glu
                195                 200                 205

Pro Val Arg Ala Ser Arg Asn Lys Arg Pro Thr Phe Leu Lys Ile Lys
            210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 82
<211> LENGTH: 247
<212> TYPE: PRT
<213> ORGANISM: artificial sequence
<220> FEATURE:
<223> OTHER INFORMATION: human N-terminal domain (NTD) Wnt7a variant
      R214A

<400> SEQUENCE: 82

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Leu Tyr Asn Glu Ala Val His Val Glu
        195                 200                 205

Pro Val Arg Ala Ser Ala Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys
                245

<210> SEQ ID NO 83
<211> LENGTH: 247
<212> TYPE: PRT
<213> ORGANISM: artificial sequence
<220> FEATURE:

<223> OTHER INFORMATION: human N-terminal domain (NTD) Wnt7a variant P218A

<400> SEQUENCE: 83

| | | | | | | | | | | | | | | | |
|---|---|---|---|---|---|---|---|---|---|---|---|---|---|---|---|
| Leu | Gly | Ala | Ser | Ile | Ile | Cys | Asn | Lys | Ile | Pro | Gly | Leu | Ala | Pro | Arg |
| 1 | | | | 5 | | | | | 10 | | | | | 15 | |
| Gln | Arg | Ala | Ile | Cys | Gln | Ser | Arg | Pro | Asp | Ala | Ile | Ile | Val | Ile | Gly |
| | | | 20 | | | | | 25 | | | | | 30 | | |
| Glu | Gly | Ser | Gln | Met | Gly | Leu | Asp | Glu | Cys | Gln | Phe | Gln | Phe | Arg | Asn |
| | | | 35 | | | | 40 | | | | | 45 | | | |
| Gly | Arg | Trp | Asn | Cys | Ser | Ala | Leu | Gly | Glu | Arg | Thr | Val | Phe | Gly | Lys |
| | 50 | | | | | 55 | | | | | 60 | | | | |
| Glu | Leu | Lys | Val | Gly | Ser | Arg | Glu | Ala | Ala | Phe | Thr | Tyr | Ala | Ile | Ile |
| 65 | | | | | 70 | | | | | 75 | | | | | 80 |
| Ala | Ala | Gly | Val | Ala | His | Ala | Ile | Thr | Ala | Ala | Cys | Thr | Gln | Gly | Asn |
| | | | | 85 | | | | | 90 | | | | | 95 | |
| Leu | Ser | Asp | Cys | Gly | Cys | Asp | Lys | Glu | Lys | Gln | Gly | Gln | Tyr | His | Arg |
| | | | 100 | | | | | 105 | | | | | 110 | | |
| Asp | Glu | Gly | Trp | Lys | Trp | Gly | Gly | Cys | Ser | Ala | Asp | Ile | Arg | Tyr | Gly |
| | | 115 | | | | | 120 | | | | | 125 | | | |
| Ile | Gly | Phe | Ala | Lys | Val | Phe | Val | Asp | Ala | Arg | Glu | Ile | Lys | Gln | Asn |
| 130 | | | | | 135 | | | | | 140 | | | | | |
| Ala | Arg | Thr | Leu | Met | Asn | Leu | His | Asn | Asn | Glu | Ala | Gly | Arg | Lys | Ile |
| 145 | | | | | 150 | | | | | 155 | | | | | 160 |
| Leu | Glu | Glu | Asn | Met | Lys | Leu | Glu | Cys | Lys | Cys | His | Gly | Val | Ser | Gly |
| | | | | 165 | | | | | 170 | | | | | 175 | |
| Ser | Cys | Thr | Thr | Lys | Thr | Cys | Trp | Thr | Thr | Leu | Pro | Gln | Phe | Arg | Glu |
| | | | 180 | | | | | 185 | | | | | 190 | | |
| Leu | Gly | Tyr | Val | Leu | Lys | Asp | Lys | Tyr | Asn | Glu | Ala | Val | His | Val | Glu |
| | | | 195 | | | | | 200 | | | | | 205 | | |
| Pro | Val | Arg | Ala | Ser | Arg | Asn | Lys | Arg | Pro | Thr | Phe | Leu | Lys | Ile | Lys |
| | | 210 | | | | | 215 | | | | | 220 | | | |
| Lys | Pro | Leu | Ser | Tyr | Arg | Lys | Pro | Met | Asp | Thr | Asp | Leu | Val | Tyr | Ile |
| 225 | | | | | 230 | | | | | 235 | | | | | 240 |
| Glu | Lys | Ser | Pro | Asn | Tyr | Cys | | | | | | | | | |
| | | | | 245 | | | | | | | | | | | |

<210> SEQ ID NO 84
<211> LENGTH: 318
<212> TYPE: PRT
<213> ORGANISM: artificial sequence
<220> FEATURE:
<223> OTHER INFORMATION: human Wnt7a variant K318A

<400> SEQUENCE: 84

| | | | | | | | | | | | | | | | |
|---|---|---|---|---|---|---|---|---|---|---|---|---|---|---|---|
| Leu | Gly | Ala | Ser | Ile | Ile | Cys | Asn | Lys | Ile | Pro | Gly | Leu | Ala | Pro | Arg |
| 1 | | | | 5 | | | | | 10 | | | | | 15 | |
| Gln | Arg | Ala | Ile | Cys | Gln | Ser | Arg | Pro | Asp | Ala | Ile | Ile | Val | Ile | Gly |
| | | | 20 | | | | | 25 | | | | | 30 | | |
| Glu | Gly | Ser | Gln | Met | Gly | Leu | Asp | Glu | Cys | Gln | Phe | Gln | Phe | Arg | Asn |
| | | | 35 | | | | 40 | | | | | 45 | | | |
| Gly | Arg | Trp | Asn | Cys | Ser | Ala | Leu | Gly | Glu | Arg | Thr | Val | Phe | Gly | Lys |
| | 50 | | | | | 55 | | | | | 60 | | | | |
| Glu | Leu | Lys | Val | Gly | Ser | Arg | Glu | Ala | Ala | Phe | Thr | Tyr | Ala | Ile | Ile |
| 65 | | | | | 70 | | | | | 75 | | | | | 80 |
| Ala | Ala | Gly | Val | Ala | His | Ala | Ile | Thr | Ala | Ala | Cys | Thr | Gln | Gly | Asn |

85                  90                  95
Leu Ser Asp Cys Gly Cys Asp Lys Glu Lys Gln Gly Gln Tyr His Arg
                100                 105                 110
Asp Glu Gly Trp Lys Trp Gly Gly Cys Ser Ala Asp Ile Arg Tyr Gly
                115                 120                 125
Ile Gly Phe Ala Lys Val Phe Val Asp Ala Arg Glu Ile Lys Gln Asn
            130                 135                 140
Ala Arg Thr Leu Met Asn Leu His Asn Glu Ala Gly Arg Lys Ile
145                 150                 155                 160
Leu Glu Glu Asn Met Lys Leu Glu Cys Lys Cys His Gly Val Ser Gly
                165                 170                 175
Ser Cys Thr Thr Lys Thr Cys Trp Thr Thr Leu Pro Gln Phe Arg Glu
                180                 185                 190
Leu Gly Tyr Val Leu Lys Asp Lys Tyr Asn Glu Ala Val His Val Glu
                195                 200                 205
Pro Val Arg Ala Ser Arg Asn Lys Arg Pro Thr Phe Leu Lys Ile Lys
            210                 215                 220
Lys Pro Leu Ser Tyr Arg Lys Pro Met Asp Thr Asp Leu Val Tyr Ile
225                 230                 235                 240
Glu Lys Ser Pro Asn Tyr Cys Glu Glu Asp Pro Val Thr Gly Ser Val
                245                 250                 255
Gly Thr Gln Gly Arg Ala Cys Asn Lys Thr Ala Pro Gln Ala Ser Gly
            260                 265                 270
Cys Asp Leu Met Cys Cys Gly Arg Gly Tyr Asn Thr His Gln Tyr Ala
                275                 280                 285
Arg Val Trp Gln Cys Asn Cys Lys Phe His Trp Cys Cys Tyr Val Lys
            290                 295                 300
Cys Asn Thr Cys Ser Glu Arg Thr Glu Met Tyr Thr Cys Ala
305                 310                 315

<210> SEQ ID NO 85
<211> LENGTH: 318
<212> TYPE: PRT
<213> ORGANISM: artificial sequence
<220> FEATURE:
<223> OTHER INFORMATION: human Wnt7a variant K159A

<400> SEQUENCE: 85

Leu Gly Ala Ser Ile Ile Cys Asn Lys Ile Pro Gly Leu Ala Pro Arg
1               5                   10                  15
Gln Arg Ala Ile Cys Gln Ser Arg Pro Asp Ala Ile Ile Val Ile Gly
            20                  25                  30
Glu Gly Ser Gln Met Gly Leu Asp Glu Cys Gln Phe Gln Phe Arg Asn
        35                  40                  45
Gly Arg Trp Asn Cys Ser Ala Leu Gly Glu Arg Thr Val Phe Gly Lys
    50                  55                  60
Glu Leu Lys Val Gly Ser Arg Glu Ala Ala Phe Thr Tyr Ala Ile Ile
65                  70                  75                  80
Ala Ala Gly Val Ala His Ala Ile Thr Ala Ala Cys Thr Gln Gly Asn
                85                  90                  95
Leu Ser Asp Cys Gly Cys Asp Lys Glu Lys Gln Gly Gln Tyr His Arg
                100                 105                 110
Asp Glu Gly Trp Lys Trp Gly Gly Cys Ser Ala Asp Ile Arg Tyr Gly
                115                 120                 125
Ile Gly Phe Ala Lys Val Phe Val Asp Ala Arg Glu Ile Lys Gln Asn

```
            130                 135                 140
Ala Arg Thr Leu Met Asn Leu His Asn Asn Glu Ala Gly Arg Ala Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
                195                 200                 205

Pro Val Arg Ala Ser Arg Asn Lys Arg Pro Thr Phe Leu Lys Ile Lys
210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
                260                 265                 270

Cys Asp Leu Met Cys Cys Gly Arg Gly Tyr Asn Thr His Gln Tyr Ala
                275                 280                 285

Arg Val Trp Gln Cys Asn Cys Lys Phe His Trp Cys Cys Tyr Val Lys
            290                 295                 300

Cys Asn Thr Cys Ser Glu Arg Thr Glu Met Tyr Thr Cys Lys
305                 310                 315

<210> SEQ ID NO 86
<211> LENGTH: 318
<212> TYPE: PRT
<213> ORGANISM: artificial sequence
<220> FEATURE:
<223> OTHER INFORMATION: human Wnt7a variant A27R

<400> SEQUENCE: 86

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Arg Ile Ile Val Ile Gly
                20                  25                  30

Glu Gly Ser Gln Met Gly Leu Asp Glu Cys Gln Phe Gln Phe Arg Asn
            35                  40                  45

Gly Arg Trp Asn Cys Ser Ala Leu Gly Glu Arg Thr Val Phe Gly Lys
        50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
```

```
                180                 185                 190
Leu Gly Tyr Val Leu Lys Asp Lys Tyr Asn Glu Ala Val His Val Glu
                    195                 200                 205

Pro Val Arg Ala Ser Arg Asn Lys Arg Pro Thr Phe Leu Lys Ile Lys
        210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
    290                 295                 300

Cys Asn Thr Cys Ser Glu Arg Thr Glu Met Tyr Thr Cys Lys
305                 310                 315
```

<210> SEQ ID NO 87
<211> LENGTH: 318
<212> TYPE: PRT
<213> ORGANISM: artificial sequence
<220> FEATURE:
<223> OTHER INFORMATION: human Wnt7a variant E33A

<400> SEQUENCE: 87

```
Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Ala Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
```

```
                225                 230                 235                 240
Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
            275                 280                 285

Arg Val Trp Gln Cys Asn Cys Lys Phe His Trp Cys Cys Tyr Val Lys
            290                 295                 300

Cys Asn Thr Cys Ser Glu Arg Thr Glu Met Tyr Thr Cys Lys
305                 310                 315

<210> SEQ ID NO 88
<211> LENGTH: 318
<212> TYPE: PRT
<213> ORGANISM: artificial sequence
<220> FEATURE:
<223> OTHER INFORMATION: human Wnt7a variant E41A

<400> SEQUENCE: 88

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Ala Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
```

```
                275                 280                 285
Arg Val Trp Gln Cys Asn Cys Lys Phe His Trp Cys Cys Tyr Val Lys
    290                 295                 300

Cys Asn Thr Cys Ser Glu Arg Thr Glu Met Tyr Thr Cys Lys
305                 310                 315

<210> SEQ ID NO 89
<211> LENGTH: 318
<212> TYPE: PRT
<213> ORGANISM: artificial sequence
<220> FEATURE:
<223> OTHER INFORMATION: human Wnt7a variant F44A

<400> SEQUENCE: 89

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Ala Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
    290                 295                 300

Cys Asn Thr Cys Ser Glu Arg Thr Glu Met Tyr Thr Cys Lys
305                 310                 315
```

-continued

```
<210> SEQ ID NO 90
<211> LENGTH: 318
<212> TYPE: PRT
<213> ORGANISM: artificial sequence
<220> FEATURE:
<223> OTHER INFORMATION: human Wnt7a variant N52Q

<400> SEQUENCE: 90

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Gln Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
    290                 295                 300

Cys Asn Thr Cys Ser Glu Arg Thr Glu Met Tyr Thr Cys Lys
305                 310                 315

<210> SEQ ID NO 91
<211> LENGTH: 318
<212> TYPE: PRT
<213> ORGANISM: artificial sequence
<220> FEATURE:
<223> OTHER INFORMATION: human Wnt7a variant I129A

<400> SEQUENCE: 91
```

-continued

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
            115                 120                 125

Ala Gly Phe Ala Lys Val Phe Val Asp Ala Arg Glu Ile Lys Gln Asn
        130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
    290                 295                 300

Cys Asn Thr Cys Ser Glu Arg Thr Glu Met Tyr Thr Cys Lys
305                 310                 315

<210> SEQ ID NO 92
<211> LENGTH: 318
<212> TYPE: PRT
<213> ORGANISM: artificial sequence
<220> FEATURE:
<223> OTHER INFORMATION: human Wnt7a variant F131A

<400> SEQUENCE: 92

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Ala Ala Lys Val Phe Val Asp Ala Arg Glu Ile Lys Gln Asn
130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
290                 295                 300

Cys Asn Thr Cys Ser Glu Arg Thr Glu Met Tyr Thr Cys Lys
305                 310                 315

<210> SEQ ID NO 93
<211> LENGTH: 318
<212> TYPE: PRT
<213> ORGANISM: artificial sequence
<220> FEATURE:
<223> OTHER INFORMATION: human Wnt7a variant K133A

<400> SEQUENCE: 93

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
                100                 105                 110

Asp Glu Gly Trp Lys Trp Gly Gly Cys Ser Ala Asp Ile Arg Tyr Gly
            115                 120                 125

Ile Gly Phe Ala Ala Val Phe Val Asp Ala Arg Glu Ile Lys Gln Asn
        130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
    290                 295                 300

Cys Asn Thr Cys Ser Glu Arg Thr Glu Met Tyr Thr Cys Lys
305                 310                 315

<210> SEQ ID NO 94
<211> LENGTH: 318
<212> TYPE: PRT
<213> ORGANISM: artificial sequence
<220> FEATURE:
<223> OTHER INFORMATION: human Wnt7a variant I141A

<400> SEQUENCE: 94

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
                100                 105                 110

Asp Glu Gly Trp Lys Trp Gly Gly Cys Ser Ala Asp Ile Arg Tyr Gly
            115                 120                 125

Ile Gly Phe Ala Lys Val Phe Val Asp Ala Arg Glu Ala Lys Gln Asn
        130                 135                 140

```
Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
    290                 295                 300

Cys Asn Thr Cys Ser Glu Arg Thr Glu Met Tyr Thr Cys Lys
305                 310                 315

<210> SEQ ID NO 95
<211> LENGTH: 318
<212> TYPE: PRT
<213> ORGANISM: artificial sequence
<220> FEATURE:
<223> OTHER INFORMATION: human Wnt7a variant R158A

<400> SEQUENCE: 95

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Ala Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190
```

```
Leu Gly Tyr Val Leu Lys Asp Lys Tyr Asn Glu Ala Val His Val Glu
            195                 200                 205

Pro Val Arg Ala Ser Arg Asn Lys Arg Pro Thr Phe Leu Lys Ile Lys
        210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
        290                 295                 300

Cys Asn Thr Cys Ser Glu Arg Thr Glu Met Tyr Thr Cys Lys
305                 310                 315
```

<210> SEQ ID NO 96
<211> LENGTH: 318
<212> TYPE: PRT
<213> ORGANISM: artificial sequence
<220> FEATURE:
<223> OTHER INFORMATION: human Wnt7a variant K181A

<400> SEQUENCE: 96

```
Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Ala Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240
```

```
Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
            275                 280                 285

Arg Val Trp Gln Cys Asn Cys Lys Phe His Trp Cys Cys Tyr Val Lys
            290                 295                 300

Cys Asn Thr Cys Ser Glu Arg Thr Glu Met Tyr Thr Cys Lys
305                 310                 315

<210> SEQ ID NO 97
<211> LENGTH: 318
<212> TYPE: PRT
<213> ORGANISM: artificial sequence
<220> FEATURE:
<223> OTHER INFORMATION: human Wnt7a variant R191A

<400> SEQUENCE: 97

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Ala Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
            275                 280                 285
```

```
Arg Val Trp Gln Cys Asn Cys Lys Phe His Trp Cys Cys Tyr Val Lys
            290                 295                 300
Cys Asn Thr Cys Ser Glu Arg Thr Glu Met Tyr Thr Cys Lys
305                 310                 315

<210> SEQ ID NO 98
<211> LENGTH: 318
<212> TYPE: PRT
<213> ORGANISM: artificial sequence
<220> FEATURE:
<223> OTHER INFORMATION: human Wnt7a variant K198A

<400> SEQUENCE: 98

Leu Gly Ala Ser Ile Ile Cys Asn Lys Ile Pro Gly Leu Ala Pro Arg
1               5                   10                  15
Gln Arg Ala Ile Cys Gln Ser Arg Pro Asp Ala Ile Ile Val Ile Gly
            20                  25                  30
Glu Gly Ser Gln Met Gly Leu Asp Glu Cys Gln Phe Gln Phe Arg Asn
        35                  40                  45
Gly Arg Trp Asn Cys Ser Ala Leu Gly Glu Arg Thr Val Phe Gly Lys
    50                  55                  60
Glu Leu Lys Val Gly Ser Arg Glu Ala Ala Phe Thr Tyr Ala Ile Ile
65                  70                  75                  80
Ala Ala Gly Val Ala His Ala Ile Thr Ala Ala Cys Thr Gln Gly Asn
                85                  90                  95
Leu Ser Asp Cys Gly Cys Asp Lys Glu Lys Gln Gly Gln Tyr His Arg
            100                 105                 110
Asp Glu Gly Trp Lys Trp Gly Gly Cys Ser Ala Asp Ile Arg Tyr Gly
        115                 120                 125
Ile Gly Phe Ala Lys Val Phe Val Asp Ala Arg Glu Ile Lys Gln Asn
    130                 135                 140
Ala Arg Thr Leu Met Asn Leu His Asn Asn Glu Ala Gly Arg Lys Ile
145                 150                 155                 160
Leu Glu Glu Asn Met Lys Leu Glu Cys Lys Cys His Gly Val Ser Gly
                165                 170                 175
Ser Cys Thr Thr Lys Thr Cys Trp Thr Thr Leu Pro Gln Phe Arg Glu
            180                 185                 190
Leu Gly Tyr Val Leu Ala Asp Lys Tyr Asn Glu Ala Val His Val Glu
        195                 200                 205
Pro Val Arg Ala Ser Arg Asn Lys Arg Pro Thr Phe Leu Lys Ile Lys
    210                 215                 220
Lys Pro Leu Ser Tyr Arg Lys Pro Met Asp Thr Asp Leu Val Tyr Ile
225                 230                 235                 240
Glu Lys Ser Pro Asn Tyr Cys Glu Glu Asp Pro Val Thr Gly Ser Val
                245                 250                 255
Gly Thr Gln Gly Arg Ala Cys Asn Lys Thr Ala Pro Gln Ala Ser Gly
            260                 265                 270
Cys Asp Leu Met Cys Cys Gly Arg Gly Tyr Asn Thr His Gln Tyr Ala
        275                 280                 285
Arg Val Trp Gln Cys Asn Cys Lys Phe His Trp Cys Cys Tyr Val Lys
    290                 295                 300
Cys Asn Thr Cys Ser Glu Arg Thr Glu Met Tyr Thr Cys Lys
305                 310                 315

<210> SEQ ID NO 99
<211> LENGTH: 317
```

```
<212> TYPE: PRT
<213> ORGANISM: artificial sequence
<220> FEATURE:
<223> OTHER INFORMATION: human Wnt7a variant V205A

<400> SEQUENCE: 99
```

| | | | | | | | | | | | | | | | |
|---|---|---|---|---|---|---|---|---|---|---|---|---|---|---|---|
| Leu | Gly | Ala | Ser | Ile | Ile | Cys | Asn | Lys | Ile | Pro | Gly | Leu | Ala | Pro | Arg |
| 1 | | | | 5 | | | | | 10 | | | | | 15 | |
| Gln | Arg | Ala | Ile | Cys | Gln | Ser | Arg | Pro | Asp | Ala | Ile | Ile | Val | Ile | Gly |
| | | | 20 | | | | | 25 | | | | | 30 | | |
| Glu | Gly | Ser | Gln | Met | Gly | Leu | Asp | Glu | Cys | Gln | Phe | Gln | Phe | Arg | Asn |
| | | | 35 | | | | | 40 | | | | | 45 | | |
| Gly | Arg | Trp | Asn | Cys | Ser | Ala | Leu | Gly | Glu | Arg | Thr | Val | Phe | Gly | Lys |
| | 50 | | | | | 55 | | | | | 60 | | | | |
| Glu | Leu | Lys | Val | Gly | Ser | Arg | Glu | Ala | Ala | Phe | Thr | Tyr | Ala | Ile | Ile |
| 65 | | | | | 70 | | | | | 75 | | | | | 80 |
| Ala | Ala | Gly | Val | Ala | His | Ala | Ile | Thr | Ala | Ala | Cys | Thr | Gln | Gly | Asn |
| | | | | 85 | | | | | 90 | | | | | 95 | |
| Leu | Ser | Asp | Cys | Gly | Cys | Asp | Lys | Glu | Lys | Gln | Gly | Gln | Tyr | His | Arg |
| | | | 100 | | | | | 105 | | | | | 110 | | |
| Asp | Glu | Gly | Trp | Lys | Trp | Gly | Gly | Cys | Ser | Ala | Asp | Ile | Arg | Tyr | Gly |
| | | | 115 | | | | | 120 | | | | | 125 | | |
| Ile | Gly | Phe | Ala | Lys | Val | Phe | Val | Asp | Ala | Arg | Glu | Ile | Lys | Gln | Asn |
| | 130 | | | | | 135 | | | | | 140 | | | | |
| Ala | Arg | Thr | Leu | Met | Asn | Leu | His | Asn | Asn | Glu | Ala | Gly | Arg | Lys | Ile |
| 145 | | | | | 150 | | | | | 155 | | | | | 160 |
| Leu | Glu | Glu | Asn | Met | Lys | Leu | Glu | Cys | Lys | Cys | His | Gly | Val | Ser | Gly |
| | | | | 165 | | | | | 170 | | | | | 175 | |
| Ser | Cys | Thr | Thr | Lys | Thr | Cys | Trp | Thr | Thr | Leu | Pro | Gln | Phe | Arg | Glu |
| | | | 180 | | | | | 185 | | | | | 190 | | |
| Leu | Gly | Tyr | Val | Leu | Lys | Asp | Lys | Tyr | Asn | Glu | Ala | Ala | His | Val | Glu |
| | | | 195 | | | | | 200 | | | | | 205 | | |
| Pro | Val | Arg | Ala | Ser | Arg | Asn | Lys | Arg | Pro | Thr | Phe | Leu | Lys | Ile | Lys |
| | 210 | | | | | 215 | | | | | 220 | | | | |
| Lys | Pro | Leu | Ser | Tyr | Arg | Lys | Pro | Met | Asp | Thr | Asp | Leu | Val | Tyr | Ile |
| 225 | | | | | 230 | | | | | 235 | | | | | 240 |
| Glu | Lys | Ser | Pro | Asn | Tyr | Glu | Glu | Asp | Pro | Val | Thr | Gly | Ser | Val | Gly |
| | | | | 245 | | | | | 250 | | | | | 255 | |
| Thr | Gln | Gly | Arg | Ala | Cys | Asn | Lys | Thr | Ala | Pro | Gln | Ala | Ser | Gly | Cys |
| | | | 260 | | | | | 265 | | | | | 270 | | |
| Asp | Leu | Met | Cys | Cys | Gly | Arg | Gly | Tyr | Asn | Thr | His | Gln | Tyr | Ala | Arg |
| | | | 275 | | | | | 280 | | | | | 285 | | |
| Val | Trp | Gln | Cys | Asn | Cys | Lys | Phe | His | Trp | Cys | Cys | Tyr | Val | Lys | Cys |
| | 290 | | | | | 295 | | | | | 300 | | | | |
| Asn | Thr | Cys | Ser | Glu | Arg | Thr | Glu | Met | Tyr | Thr | Cys | Lys | | | |
| 305 | | | | | 310 | | | | | 315 | | | | | |

```
<210> SEQ ID NO 100
<211> LENGTH: 318
<212> TYPE: PRT
<213> ORGANISM: artificial sequence
<220> FEATURE:
<223> OTHER INFORMATION: human Wnt7a variant E208A

<400> SEQUENCE: 100
```

| | | | | | | | | | | | | | | | |
|---|---|---|---|---|---|---|---|---|---|---|---|---|---|---|---|
| Leu | Gly | Ala | Ser | Ile | Ile | Cys | Asn | Lys | Ile | Pro | Gly | Leu | Ala | Pro | Arg |
| 1 | | | | 5 | | | | | 10 | | | | | 15 | |

-continued

```
Gln Arg Ala Ile Cys Gln Ser Arg Pro Asp Ala Ile Ile Val Ile Gly
             20                  25                  30

Glu Gly Ser Gln Met Gly Leu Asp Glu Cys Gln Phe Gln Phe Arg Asn
         35                  40                  45

Gly Arg Trp Asn Cys Ser Ala Leu Gly Glu Arg Thr Val Phe Gly Lys
 50                  55                  60

Glu Leu Lys Val Gly Ser Arg Glu Ala Ala Phe Thr Tyr Ala Ile Ile
 65                  70                  75                  80

Ala Ala Gly Val Ala His Ala Ile Thr Ala Ala Cys Thr Gln Gly Asn
                 85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Ala
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
    290                 295                 300

Cys Asn Thr Cys Ser Glu Arg Thr Glu Met Tyr Thr Cys Lys
305                 310                 315

<210> SEQ ID NO 101
<211> LENGTH: 318
<212> TYPE: PRT
<213> ORGANISM: artificial sequence
<220> FEATURE:
<223> OTHER INFORMATION: human Wnt7a variant K216A

<400> SEQUENCE: 101

Leu Gly Ala Ser Ile Ile Cys Asn Lys Ile Pro Gly Leu Ala Pro Arg
1                5                  10                  15

Gln Arg Ala Ile Cys Gln Ser Arg Pro Asp Ala Ile Ile Val Ile Gly
             20                  25                  30

Glu Gly Ser Gln Met Gly Leu Asp Glu Cys Gln Phe Gln Phe Arg Asn
         35                  40                  45

Gly Arg Trp Asn Cys Ser Ala Leu Gly Glu Arg Thr Val Phe Gly Lys
 50                  55                  60
```

```
Glu Leu Lys Val Gly Ser Arg Glu Ala Ala Phe Thr Tyr Ala Ile Ile
 65                  70                  75                  80

Ala Ala Gly Val Ala His Ala Ile Thr Ala Ala Cys Thr Gln Gly Asn
                 85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Ala Arg Pro Thr Phe Leu Lys Ile Lys
210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
290                 295                 300

Cys Asn Thr Cys Ser Glu Arg Thr Glu Met Tyr Thr Cys Lys
305                 310                 315

<210> SEQ ID NO 102
<211> LENGTH: 318
<212> TYPE: PRT
<213> ORGANISM: artificial sequence
<220> FEATURE:
<223> OTHER INFORMATION: human Wnt7a variant K222A

<400> SEQUENCE: 102

Leu Gly Ala Ser Ile Ile Cys Asn Lys Ile Pro Gly Leu Ala Pro Arg
 1               5                  10                  15

Gln Arg Ala Ile Cys Gln Ser Arg Pro Asp Ala Ile Ile Val Ile Gly
             20                  25                  30

Glu Gly Ser Gln Met Gly Leu Asp Glu Cys Gln Phe Gln Phe Arg Asn
         35                  40                  45

Gly Arg Trp Asn Cys Ser Ala Leu Gly Glu Arg Thr Val Phe Gly Lys
     50                  55                  60

Glu Leu Lys Val Gly Ser Arg Glu Ala Ala Phe Thr Tyr Ala Ile Ile
 65                  70                  75                  80

Ala Ala Gly Val Ala His Ala Ile Thr Ala Ala Cys Thr Gln Gly Asn
                 85                  90                  95

Leu Ser Asp Cys Gly Cys Asp Lys Glu Lys Gln Gly Gln Tyr His Arg
            100                 105                 110
```

```
Asp Glu Gly Trp Lys Trp Gly Gly Cys Ser Ala Asp Ile Arg Tyr Gly
            115                 120                 125

Ile Gly Phe Ala Lys Val Phe Val Asp Ala Arg Glu Ile Lys Gln Asn
            130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
                180                 185                 190

Leu Gly Tyr Val Leu Lys Asp Lys Tyr Asn Glu Ala Val His Val Glu
            195                 200                 205

Pro Val Arg Ala Ser Arg Asn Lys Arg Pro Thr Phe Leu Ala Ile Lys
            210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
                260                 265                 270

Cys Asp Leu Met Cys Cys Gly Arg Gly Tyr Asn Thr His Gln Tyr Ala
                275                 280                 285

Arg Val Trp Gln Cys Asn Cys Lys Phe His Trp Cys Cys Tyr Val Lys
            290                 295                 300

Cys Asn Thr Cys Ser Glu Arg Thr Glu Met Tyr Thr Cys Lys
305                 310                 315

<210> SEQ ID NO 103
<211> LENGTH: 318
<212> TYPE: PRT
<213> ORGANISM: artificial sequence
<220> FEATURE:
<223> OTHER INFORMATION: human Wnt7a variant I223A

<400> SEQUENCE: 103

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
            115                 120                 125

Ile Gly Phe Ala Lys Val Phe Val Asp Ala Arg Glu Ile Lys Gln Asn
            130                 135                 140

Ala Arg Thr Leu Met Asn Leu His Asn Asn Glu Ala Gly Arg Lys Ile
145                 150                 155                 160
```

Leu Glu Glu Asn Met Lys Leu Glu Cys Lys Cys His Gly Val Ser Gly
            165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
            195                 200                 205

Pro Val Arg Ala Ser Arg Asn Lys Arg Pro Thr Phe Leu Lys Ala Lys
210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
            245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
            275                 280                 285

Arg Val Trp Gln Cys Asn Cys Lys Phe His Trp Cys Cys Tyr Val Lys
            290                 295                 300

Cys Asn Thr Cys Ser Glu Arg Thr Glu Met Tyr Thr Cys Lys
305                 310                 315

<210> SEQ ID NO 104
<211> LENGTH: 318
<212> TYPE: PRT
<213> ORGANISM: artificial sequence
<220> FEATURE:
<223> OTHER INFORMATION: human Wnt7a variant Y229A

<400> SEQUENCE: 104

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
            35                  40                  45

Gly Arg Trp Asn Cys Ser Ala Leu Gly Glu Arg Thr Val Phe Gly Lys
        50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
            85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
            115                 120                 125

Ile Gly Phe Ala Lys Val Phe Val Asp Ala Arg Glu Ile Lys Gln Asn
            130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
            165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
            195                 200                 205

```
Pro Val Arg Ala Ser Arg Asn Lys Arg Pro Thr Phe Leu Lys Ile Lys
    210                 215                 220

Lys Pro Leu Ser Ala Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
    290                 295                 300

Cys Asn Thr Cys Ser Glu Arg Thr Glu Met Tyr Thr Cys Lys
305                 310                 315

<210> SEQ ID NO 105
<211> LENGTH: 318
<212> TYPE: PRT
<213> ORGANISM: artificial sequence
<220> FEATURE:
<223> OTHER INFORMATION: human Wnt7a variant P232A

<400> SEQUENCE: 105

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Ala Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255
```

```
Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
            275                 280                 285

Arg Val Trp Gln Cys Asn Cys Lys Phe His Trp Cys Cys Tyr Val Lys
290                 295                 300

Cys Asn Thr Cys Ser Glu Arg Thr Glu Met Tyr Thr Cys Lys
305                 310                 315

<210> SEQ ID NO 106
<211> LENGTH: 318
<212> TYPE: PRT
<213> ORGANISM: artificial sequence
<220> FEATURE:
<223> OTHER INFORMATION: human Wnt7a variant T235A

<400> SEQUENCE: 106

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
                20                  25                  30

Glu Gly Ser Gln Met Gly Leu Asp Glu Cys Gln Phe Gln Phe Arg Asn
            35                  40                  45

Gly Arg Trp Asn Cys Ser Ala Leu Gly Glu Arg Thr Val Phe Gly Lys
        50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
210                 215                 220

Lys Pro Leu Ser Tyr Arg Lys Pro Met Asp Ala Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
290                 295                 300
```

```
Cys Asn Thr Cys Ser Glu Arg Thr Glu Met Tyr Thr Cys Lys
305                 310                 315

<210> SEQ ID NO 107
<211> LENGTH: 318
<212> TYPE: PRT
<213> ORGANISM: artificial sequence
<220> FEATURE:
<223> OTHER INFORMATION: human Wnt7a variant Q17A

<400> SEQUENCE: 107

Leu Gly Ala Ser Ile Ile Cys Asn Lys Ile Pro Gly Leu Ala Pro Arg
1               5                   10                  15

Ala Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65              70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
    290                 295                 300

Cys Asn Thr Cys Ser Glu Arg Thr Glu Met Tyr Thr Cys Lys
305                 310                 315

<210> SEQ ID NO 108
<211> LENGTH: 318
<212> TYPE: PRT
<213> ORGANISM: artificial sequence
```

<220> FEATURE:
<223> OTHER INFORMATION: human Wnt7a variant I20A

<400> SEQUENCE: 108

Leu Gly Ala Ser Ile Ile Cys Asn Lys Ile Pro Gly Leu Ala Pro Arg
1               5                   10                  15

Gln Arg Ala Ala Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
    290                 295                 300

Cys Asn Thr Cys Ser Glu Arg Thr Glu Met Tyr Thr Cys Lys
305                 310                 315

<210> SEQ ID NO 109
<211> LENGTH: 318
<212> TYPE: PRT
<213> ORGANISM: artificial sequence
<220> FEATURE:
<223> OTHER INFORMATION: human Wnt7a variant P25A

<400> SEQUENCE: 109

Leu Gly Ala Ser Ile Ile Cys Asn Lys Ile Pro Gly Leu Ala Pro Arg
1               5                   10                  15

Gln Arg Ala Ile Cys Gln Ser Arg Ala Asp Ala Ile Ile Val Ile Gly

```
            20                  25                  30
Glu Gly Ser Gln Met Gly Leu Asp Glu Cys Gln Phe Gln Phe Arg Asn
            35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
            115                 120                 125

Ile Gly Phe Ala Lys Val Phe Val Asp Ala Arg Glu Ile Lys Gln Asn
        130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
    290                 295                 300

Cys Asn Thr Cys Ser Glu Arg Thr Glu Met Tyr Thr Cys Lys
305                 310                 315

<210> SEQ ID NO 110
<211> LENGTH: 318
<212> TYPE: PRT
<213> ORGANISM: artificial sequence
<220> FEATURE:
<223> OTHER INFORMATION: human Wnt7a variant M37A

<400> SEQUENCE: 110

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Ala Gly Leu Asp Glu Cys Gln Phe Gln Phe Arg Asn
            35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
```

```
                65                  70                  75                  80
Ala Ala Gly Val Ala His Ala Ile Thr Ala Ala Cys Thr Gln Gly Asn
                    85                  90                  95

Leu Ser Asp Cys Gly Cys Asp Lys Glu Lys Gln Gly Gln Tyr His Arg
                    100                 105                 110

Asp Glu Gly Trp Lys Trp Gly Gly Cys Ser Ala Asp Ile Arg Tyr Gly
                    115                 120                 125

Ile Gly Phe Ala Lys Val Phe Val Asp Ala Arg Glu Ile Lys Gln Asn
                    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                    165                 170                 175

Ser Cys Thr Thr Lys Thr Cys Trp Thr Thr Leu Pro Gln Phe Arg Glu
                    180                 185                 190

Leu Gly Tyr Val Leu Lys Asp Lys Tyr Asn Glu Ala Val His Val Glu
                    195                 200                 205

Pro Val Arg Ala Ser Arg Asn Lys Arg Pro Thr Phe Leu Lys Ile Lys
                    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                    245                 250                 255

Gly Thr Gln Gly Arg Ala Cys Asn Lys Thr Ala Pro Gln Ala Ser Gly
                    260                 265                 270

Cys Asp Leu Met Cys Cys Gly Arg Gly Tyr Asn Thr His Gln Tyr Ala
                    275                 280                 285

Arg Val Trp Gln Cys Asn Cys Lys Phe His Trp Cys Cys Tyr Val Lys
                    290                 295                 300

Cys Asn Thr Cys Ser Glu Arg Thr Glu Met Tyr Thr Cys Lys
305                 310                 315

<210> SEQ ID NO 111
<211> LENGTH: 318
<212> TYPE: PRT
<213> ORGANISM: artificial sequence
<220> FEATURE:
<223> OTHER INFORMATION: human Wnt7a variant L39A

<400> SEQUENCE: 111

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
                    20                  25                  30

Glu Gly Ser Gln Met Gly Ala Asp Glu Cys Gln Phe Gln Phe Arg Asn
                35                  40                  45

Gly Arg Trp Asn Cys Ser Ala Leu Gly Glu Arg Thr Val Phe Gly Lys
            50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                    85                  90                  95

Leu Ser Asp Cys Gly Cys Asp Lys Glu Lys Gln Gly Gln Tyr His Arg
                    100                 105                 110

Asp Glu Gly Trp Lys Trp Gly Gly Cys Ser Ala Asp Ile Arg Tyr Gly
```

```
            115                 120                 125
Ile Gly Phe Ala Lys Val Phe Val Asp Ala Arg Glu Ile Lys Gln Asn
        130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
    290                 295                 300

Cys Asn Thr Cys Ser Glu Arg Thr Glu Met Tyr Thr Cys Lys
305                 310                 315

<210> SEQ ID NO 112
<211> LENGTH: 318
<212> TYPE: PRT
<213> ORGANISM: artificial sequence
<220> FEATURE:
<223> OTHER INFORMATION: human Wnt7a variant I28A

<400> SEQUENCE: 112

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ala Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
```

```
                 165                 170                 175
Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
    290                 295                 300

Cys Asn Thr Cys Ser Glu Arg Thr Glu Met Tyr Thr Cys Lys
305                 310                 315

<210> SEQ ID NO 113
<211> LENGTH: 318
<212> TYPE: PRT
<213> ORGANISM: artificial sequence
<220> FEATURE:
<223> OTHER INFORMATION: human Wnt7a variant R50A

<400> SEQUENCE: 113

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Ala Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
```

```
                210                 215                 220
Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
            275                 280                 285

Arg Val Trp Gln Cys Asn Cys Lys Phe His Trp Cys Cys Tyr Val Lys
            290                 295                 300

Cys Asn Thr Cys Ser Glu Arg Thr Glu Met Tyr Thr Cys Lys
305                 310                 315

<210> SEQ ID NO 114
<211> LENGTH: 318
<212> TYPE: PRT
<213> ORGANISM: artificial sequence
<220> FEATURE:
<223> OTHER INFORMATION: human Wnt7a variant V68A

<400> SEQUENCE: 114

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Ala Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
```

```
              260                 265                 270
Cys Asp Leu Met Cys Cys Gly Arg Gly Tyr Asn Thr His Gln Tyr Ala
            275                 280                 285

Arg Val Trp Gln Cys Asn Cys Lys Phe His Trp Cys Cys Tyr Val Lys
            290                 295                 300

Cys Asn Thr Cys Ser Glu Arg Thr Glu Met Tyr Thr Cys Lys
305                 310                 315

<210> SEQ ID NO 115
<211> LENGTH: 318
<212> TYPE: PRT
<213> ORGANISM: artificial sequence
<220> FEATURE:
<223> OTHER INFORMATION: human Wnt7a variant F135A

<400> SEQUENCE: 115

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Ala Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
    290                 295                 300

Cys Asn Thr Cys Ser Glu Arg Thr Glu Met Tyr Thr Cys Lys
```

<210> SEQ ID NO 116
<211> LENGTH: 318
<212> TYPE: PRT
<213> ORGANISM: artificial sequence
<220> FEATURE:
<223> OTHER INFORMATION: human Wnt7a variant R146A

<400> SEQUENCE: 116

```
Leu Gly Ala Ser Ile Ile Cys Asn Lys Ile Pro Gly Leu Ala Pro Arg
1               5                   10                  15
Gln Arg Ala Ile Cys Gln Ser Arg Pro Asp Ala Ile Ile Val Ile Gly
            20                  25                  30
Glu Gly Ser Gln Met Gly Leu Asp Glu Cys Gln Phe Gln Phe Arg Asn
        35                  40                  45
Gly Arg Trp Asn Cys Ser Ala Leu Gly Glu Arg Thr Val Phe Gly Lys
    50                  55                  60
Glu Leu Lys Val Gly Ser Arg Glu Ala Ala Phe Thr Tyr Ala Ile Ile
65                  70                  75                  80
Ala Ala Gly Val Ala His Ala Ile Thr Ala Ala Cys Thr Gln Gly Asn
                85                  90                  95
Leu Ser Asp Cys Gly Cys Asp Lys Glu Lys Gln Gly Gln Tyr His Arg
            100                 105                 110
Asp Glu Gly Trp Lys Trp Gly Gly Cys Ser Ala Asp Ile Arg Tyr Gly
        115                 120                 125
Ile Gly Phe Ala Lys Val Phe Val Asp Ala Arg Glu Ile Lys Gln Asn
    130                 135                 140
Ala Ala Thr Leu Met Asn Leu His Asn Asn Glu Ala Gly Arg Lys Ile
145                 150                 155                 160
Leu Glu Glu Asn Met Lys Leu Glu Cys Lys Cys His Gly Val Ser Gly
                165                 170                 175
Ser Cys Thr Thr Lys Thr Cys Trp Thr Thr Leu Pro Gln Phe Arg Glu
            180                 185                 190
Leu Gly Tyr Val Leu Lys Asp Lys Tyr Asn Glu Ala Val His Val Glu
        195                 200                 205
Pro Val Arg Ala Ser Arg Asn Lys Arg Pro Thr Phe Leu Lys Ile Lys
    210                 215                 220
Lys Pro Leu Ser Tyr Arg Lys Pro Met Asp Thr Asp Leu Val Tyr Ile
225                 230                 235                 240
Glu Lys Ser Pro Asn Tyr Cys Glu Glu Asp Pro Val Thr Gly Ser Val
                245                 250                 255
Gly Thr Gln Gly Arg Ala Cys Asn Lys Thr Ala Pro Gln Ala Ser Gly
            260                 265                 270
Cys Asp Leu Met Cys Cys Gly Arg Gly Tyr Asn Thr His Gln Tyr Ala
        275                 280                 285
Arg Val Trp Gln Cys Asn Cys Lys Phe His Trp Cys Cys Tyr Val Lys
    290                 295                 300
Cys Asn Thr Cys Ser Glu Arg Thr Glu Met Tyr Thr Cys Lys
305                 310                 315
```

<210> SEQ ID NO 117
<211> LENGTH: 318
<212> TYPE: PRT
<213> ORGANISM: artificial sequence
<220> FEATURE:
<223> OTHER INFORMATION: human Wnt7a variant K159S

<400> SEQUENCE: 117

| Leu | Gly | Ala | Ser | Ile | Ile | Cys | Asn | Lys | Ile | Pro | Gly | Leu | Ala | Pro | Arg |
| 1 | | | | 5 | | | | | 10 | | | | | 15 | |

| Gln | Arg | Ala | Ile | Cys | Gln | Ser | Arg | Pro | Asp | Ala | Ile | Ile | Val | Ile | Gly |
| | | | 20 | | | | | 25 | | | | | 30 | | |

| Glu | Gly | Ser | Gln | Met | Gly | Leu | Asp | Glu | Cys | Gln | Phe | Gln | Phe | Arg | Asn |
| | | 35 | | | | | 40 | | | | | 45 | | | |

| Gly | Arg | Trp | Asn | Cys | Ser | Ala | Leu | Gly | Glu | Arg | Thr | Val | Phe | Gly | Lys |
| | 50 | | | | | 55 | | | | | 60 | | | | |

| Glu | Leu | Lys | Val | Gly | Ser | Arg | Glu | Ala | Ala | Phe | Thr | Tyr | Ala | Ile | Ile |
| 65 | | | | | 70 | | | | | 75 | | | | | 80 |

| Ala | Ala | Gly | Val | Ala | His | Ala | Ile | Thr | Ala | Ala | Cys | Thr | Gln | Gly | Asn |
| | | | | 85 | | | | | 90 | | | | | 95 | |

| Leu | Ser | Asp | Cys | Gly | Cys | Asp | Lys | Glu | Lys | Gln | Gly | Gln | Tyr | His | Arg |
| | | | 100 | | | | | 105 | | | | | 110 | | |

| Asp | Glu | Gly | Trp | Lys | Trp | Gly | Gly | Cys | Ser | Ala | Asp | Ile | Arg | Tyr | Gly |
| | | 115 | | | | | 120 | | | | | 125 | | | |

| Ile | Gly | Phe | Ala | Lys | Val | Phe | Val | Asp | Ala | Arg | Glu | Ile | Lys | Gln | Asn |
| | 130 | | | | | 135 | | | | | 140 | | | | |

| Ala | Arg | Thr | Leu | Met | Asn | Leu | His | Asn | Asn | Glu | Ala | Gly | Arg | Ser | Ile |
| 145 | | | | | 150 | | | | | 155 | | | | | 160 |

| Leu | Glu | Glu | Asn | Met | Lys | Leu | Glu | Cys | Lys | Cys | His | Gly | Val | Ser | Gly |
| | | | | 165 | | | | | 170 | | | | | 175 | |

| Ser | Cys | Thr | Thr | Lys | Thr | Cys | Trp | Thr | Thr | Leu | Pro | Gln | Phe | Arg | Glu |
| | | | 180 | | | | | 185 | | | | | 190 | | |

| Leu | Gly | Tyr | Val | Leu | Lys | Asp | Lys | Tyr | Asn | Glu | Ala | Val | His | Val | Glu |
| | | 195 | | | | | 200 | | | | | 205 | | | |

| Pro | Val | Arg | Ala | Ser | Arg | Asn | Lys | Arg | Pro | Thr | Phe | Leu | Lys | Ile | Lys |
| | 210 | | | | | 215 | | | | | 220 | | | | |

| Lys | Pro | Leu | Ser | Tyr | Arg | Lys | Pro | Met | Asp | Thr | Asp | Leu | Val | Tyr | Ile |
| 225 | | | | | 230 | | | | | 235 | | | | | 240 |

| Glu | Lys | Ser | Pro | Asn | Tyr | Cys | Glu | Glu | Asp | Pro | Val | Thr | Gly | Ser | Val |
| | | | | 245 | | | | | 250 | | | | | 255 | |

| Gly | Thr | Gln | Gly | Arg | Ala | Cys | Asn | Lys | Thr | Ala | Pro | Gln | Ala | Ser | Gly |
| | | | 260 | | | | | 265 | | | | | 270 | | |

| Cys | Asp | Leu | Met | Cys | Cys | Gly | Arg | Gly | Tyr | Asn | Thr | His | Gln | Tyr | Ala |
| | | 275 | | | | | 280 | | | | | 285 | | | |

| Arg | Val | Trp | Gln | Cys | Asn | Cys | Lys | Phe | His | Trp | Cys | Cys | Tyr | Val | Lys |
| | 290 | | | | | 295 | | | | | 300 | | | | |

| Cys | Asn | Thr | Cys | Ser | Glu | Arg | Thr | Glu | Met | Tyr | Thr | Cys | Lys | | |
| 305 | | | | | 310 | | | | | 315 | | | | | |

<210> SEQ ID NO 118
<211> LENGTH: 318
<212> TYPE: PRT
<213> ORGANISM: artificial sequence
<220> FEATURE:
<223> OTHER INFORMATION: human Wnt7a variant K159L

<400> SEQUENCE: 118

| Leu | Gly | Ala | Ser | Ile | Ile | Cys | Asn | Lys | Ile | Pro | Gly | Leu | Ala | Pro | Arg |
| 1 | | | | 5 | | | | | 10 | | | | | 15 | |

| Gln | Arg | Ala | Ile | Cys | Gln | Ser | Arg | Pro | Asp | Ala | Ile | Ile | Val | Ile | Gly |
| | | | 20 | | | | | 25 | | | | | 30 | | |

```
Glu Gly Ser Gln Met Gly Leu Asp Glu Cys Gln Phe Gln Phe Arg Asn
             35                  40                  45

Gly Arg Trp Asn Cys Ser Ala Leu Gly Glu Arg Thr Val Phe Gly Lys
 50                  55                  60

Glu Leu Lys Val Gly Ser Arg Glu Ala Ala Phe Thr Tyr Ala Ile Ile
 65                  70                  75                  80

Ala Ala Gly Val Ala His Ala Ile Thr Ala Ala Cys Thr Gln Gly Asn
                 85                  90                  95

Leu Ser Asp Cys Gly Cys Asp Lys Glu Lys Gln Gly Gln Tyr His Arg
                100                 105                 110

Asp Glu Gly Trp Lys Trp Gly Gly Cys Ser Ala Asp Ile Arg Tyr Gly
            115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Leu Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
    195                 200                 205

Pro Val Arg Ala Ser Arg Asn Lys Arg Pro Thr Phe Leu Lys Ile Lys
        210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
    275                 280                 285

Arg Val Trp Gln Cys Asn Cys Lys Phe His Trp Cys Cys Tyr Val Lys
        290                 295                 300

Cys Asn Thr Cys Ser Glu Arg Thr Glu Met Tyr Thr Cys Lys
305                 310                 315
```

<210> SEQ ID NO 119
<211> LENGTH: 318
<212> TYPE: PRT
<213> ORGANISM: artificial sequence
<220> FEATURE:
<223> OTHER INFORMATION: human Wnt7a variant K200A

<400> SEQUENCE: 119

```
Leu Gly Ala Ser Ile Ile Cys Asn Lys Ile Pro Gly Leu Ala Pro Arg
 1               5                  10                  15

Gln Arg Ala Ile Cys Gln Ser Arg Pro Asp Ala Ile Ile Val Ile Gly
                 20                  25                  30

Glu Gly Ser Gln Met Gly Leu Asp Glu Cys Gln Phe Gln Phe Arg Asn
             35                  40                  45

Gly Arg Trp Asn Cys Ser Ala Leu Gly Glu Arg Thr Val Phe Gly Lys
 50                  55                  60

Glu Leu Lys Val Gly Ser Arg Glu Ala Ala Phe Thr Tyr Ala Ile Ile
 65                  70                  75                  80
```

```
Ala Ala Gly Val Ala His Ala Ile Thr Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
            115                 120                 125

Ile Gly Phe Ala Lys Val Phe Val Asp Ala Arg Glu Ile Lys Gln Asn
130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Ala Tyr Asn Glu Ala Val His Val Glu
            195                 200                 205

Pro Val Arg Ala Ser Arg Asn Lys Arg Pro Thr Phe Leu Lys Ile Lys
            210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
            275                 280                 285

Arg Val Trp Gln Cys Asn Cys Lys Phe His Trp Cys Cys Tyr Val Lys
            290                 295                 300

Cys Asn Thr Cys Ser Glu Arg Thr Glu Met Tyr Thr Cys Lys
305                 310                 315

<210> SEQ ID NO 120
<211> LENGTH: 318
<212> TYPE: PRT
<213> ORGANISM: artificial sequence
<220> FEATURE:
<223> OTHER INFORMATION: human Wnt7a variant R214A

<400> SEQUENCE: 120

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
            35                  40                  45

Gly Arg Trp Asn Cys Ser Ala Leu Gly Glu Arg Thr Val Phe Gly Lys
50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
            115                 120                 125
```

```
Ile Gly Phe Ala Lys Val Phe Val Asp Ala Arg Glu Ile Lys Gln Asn
            130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                    165                 170                 175

Ser Cys Thr Thr Lys Thr Cys Trp Thr Thr Leu Pro Gln Phe Arg Glu
                180                 185                 190

Leu Gly Tyr Val Leu Lys Asp Lys Tyr Asn Glu Ala Val His Val Glu
                195                 200                 205

Pro Val Arg Ala Ser Ala Asn Lys Arg Pro Thr Phe Leu Lys Ile Lys
        210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                    245                 250                 255

Gly Thr Gln Gly Arg Ala Cys Asn Lys Thr Ala Pro Gln Ala Ser Gly
                260                 265                 270

Cys Asp Leu Met Cys Cys Gly Arg Gly Tyr Asn Thr His Gln Tyr Ala
                275                 280                 285

Arg Val Trp Gln Cys Asn Cys Lys Phe His Trp Cys Cys Tyr Val Lys
        290                 295                 300

Cys Asn Thr Cys Ser Glu Arg Thr Glu Met Tyr Thr Cys Lys
305                 310                 315

<210> SEQ ID NO 121
<211> LENGTH: 318
<212> TYPE: PRT
<213> ORGANISM: artificial sequence
<220> FEATURE:
<223> OTHER INFORMATION: human Wnt7a variant P218A

<400> SEQUENCE: 121

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
            20                  25                  30

Glu Gly Ser Gln Met Gly Leu Asp Glu Cys Gln Phe Gln Phe Arg Asn
        35                  40                  45

Gly Arg Trp Asn Cys Ser Ala Leu Gly Glu Arg Thr Val Phe Gly Lys
    50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
                100                 105                 110

Asp Glu Gly Trp Lys Trp Gly Gly Cys Ser Ala Asp Ile Arg Tyr Gly
            115                 120                 125

Ile Gly Phe Ala Lys Val Phe Val Asp Ala Arg Glu Ile Lys Gln Asn
            130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                    165                 170                 175
```

```
Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
        210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
            275                 280                 285

Arg Val Trp Gln Cys Asn Cys Lys Phe His Trp Cys Cys Tyr Val Lys
            290                 295                 300

Cys Asn Thr Cys Ser Glu Arg Thr Glu Met Tyr Thr Cys Lys
305                 310                 315

<210> SEQ ID NO 122
<211> LENGTH: 25
<212> TYPE: DNA
<213> ORGANISM: artificial sequence
<220> FEATURE:
<223> OTHER INFORMATION: Splice-blocking morpholino against gpr124

<400> SEQUENCE: 122
actgatattg atttaactca ccaca                                    25

<210> SEQ ID NO 123
<211> LENGTH: 25
<212> TYPE: DNA
<213> ORGANISM: artificial sequence
<220> FEATURE:
<223> OTHER INFORMATION: Splice-blocking morpholino

<400> SEQUENCE: 123
ttccatttga ccctacttac ccaat                                    25
```

WNT7 VARIANTS CAPABLE OF ACTIVATING G-PROTEIN COUPLED RECEPTOR (GPR)124/RECK/FRIZZLED/LIPOPROTEIN RECEPTOR-RELATED PROTEIN (LRP)-MEDIATED WNT SIGNALING

CROSS-REFERENCE TO RELATED APPLICATIONS

This application is the U.S. National Phase under 35 U.S.C. § 371 of International Application PCT/EP2019/057243, filed Mar. 22, 2019, designating the U.S., and published in English as WO 2019/180204 on Sep. 26, 2019 which claims priority to European Patent Application No. 18163777.8, filed Mar. 23, 2018, the entire content of which is incorporated herein by reference.

A Sequence Listing submitted as an ASCII text file via EFS-Web is hereby incorporated by reference in accordance with 35 U.S.C. § 1.52(e). The name of the ASCII text file for the Sequence Listing is 56562516.txt, the date of creation of the ASCII text file is Nov. 30, 2022, and the size of the ASCII text file is 270 KB.

FIELD

The invention is broadly in the medical field, and more precisely relates to treatments of neurovascular disorders or central nervous system (CNS) disorders comprising neurovascular dysfunction. The invention provides novel Wnt signaling agonist molecules useful in therapy, and particularly useful in the treatment of neurovascular disorders or CNS disorders comprising neurovascular dysfunction, and related products, methods and uses.

BACKGROUND

Wnt proteins constitute a large family of highly conserved, secreted, lipid-modified proteins that mediate intercellular communications during animal development and adult tissue homeostasis. They exert pleiotropic functions by regulating cell proliferation, differentiation, migration, apoptosis, polarity and genetic stability. Dysregulated Wnt signaling levels are associated with a large spectrum of human pathologies, including cancer and CNS disorders such as neurodegeneration.

The ten members of the Frizzled (Fz) family are seven-pass transmembrane proteins that serve as receptors for Wnt proteins. Greatly contributing to the complexity of Wnt signaling, the Wnt/Fz binding relationships are promiscuous, with multiple Wnts competing for binding to individual Fzs and several Fzs capable of responding to a given Wnt. Recent crystallographic studies confirmed that the Wnt/Fz interaction chemistry is incompatible with unambiguous Wnt and Fz pairing, with both contact sites between Wnt and Fz being dominated by strictly or chemically-conserved residues (Janda et al. Science 2012, vol. 337, 59-64). These observations raise the question of how cells interpret the intermingled expression patterns of simultaneous and sometimes conflicting signaling inputs from multiple Wnt ligands. In some biological settings, cells may integrate all signal inputs non-discriminately and trigger appropriate responses by considering their total net balance as well as their coordinated interpretation by functionally intertwined intracellular signaling cascades. However, other biological processes exhibit surprisingly strict Wnt ligand selectivity, despite complex Wnt/Fz expression landscapes.

Cerebrovascular development of the mammalian forebrain and ventral spinal cord operates under the exclusive control of Wnt7a and Wnt7b and hence serves as a paradigm for highly selective Wnt responsive processes. In order to respond to neural progenitor-derived Wnt7 and activate Wnt/β-catenin signaling, cerebral endothelial cells must express Gpr124, an orphan member of the adhesion class of G protein-coupled receptors as well as the GPI-anchored glycoprotein Reck (Vanhollebeke et al. Elife 2015, vol. 4, 1-25). Furthermore, when expressed in cultured cells, Gpr124 and Reck physically interact and synergistically stimulate Wnt7-specific responses (ibid.).

Importantly, endothelial Wnt/β-catenin signaling is an important regulator of blood-brain barrier (BBB) physiology, controlling the expansion and maturation of the CNS vascular network during embryogenesis and contributing to BBB maintenance in adults. While BBB dysfunction has long been implicated in multiple neurological disorders, recent evidence suggests that the sheer stimulation of Wnt/β-catenin signaling at the dysfunctional BBB is sufficient to significantly ameliorate ischemic stroke and brain cancer in mouse. Accordingly, therapies capable of stimulating Wnt/β-catenin signaling in cerebral endothelial cells substantially without cross-reactivity with other Frizzled pathways, would be highly advantageous for the treatment of various neurological disorders.

SUMMARY

The present invention is at least in part based on the discovery and characterisation of the first ever "Wnt decoding module" used by cells to selectively respond to Wnt7 ligands. In particular, in the herein characterised Wnt decoding module, selectivity is conferred by RECK, which mediates Wnt7-specific binding in a Frizzled-independent manner. Wnt7 availability for Frizzled signaling relies on GPR124, a RECK binding partner that acts as a signaling-deficient trans-membrane tether between RECK-bound Wnt7 and intracellular Dishevelled (Dvl) scaffolds. By bridging Frizzled and GPR124, Dvl polymers assemble ligand-specific RECK/Gpr124/Frizzled/LRP signalosomes. The present inventors thus propose a model in which higher-order RECK/GPR124/Frizzled/LRP receptor complexes form within ligand-specific Wnt signalosomes through the simultaneous binding of Frizzled and GPR124 by Dvl polymers and the specific binding of Wnt7 to RECK.

Having uncovered this novel mechanism, further investigations unexpectedly revealed that novel agonists could be designed capable of activating Wnt signaling selectively in cells expressing RECK and GPR124, such agonists being useful as therapeutics, such as particularly for the treatment of CNS disorders with neurovascular implications, including inter alia stroke, multiple sclerosis, brain cancer, epilepsy and neurodegenerative disorders Accordingly, an aspect provides an agent capable of activating GPR124/RECK/Frizzled/LRP-mediated Wnt signaling, wherein said agent does not activate Frizzled/LRP-mediated Wnt signaling in the absence of RECK and/or GPR124.

In certain embodiments, said agent may be a protein, polypeptide or a peptide. Accordingly, another aspect provides a nucleic acid encoding said agent, wherein said agent is a protein, polypeptide or a peptide.

A further aspect provides a nucleic acid expression cassette comprising said nucleic acid operably linked to a promoter and/or transcriptional and translational regulatory signals. Also provided is a vector comprising said nucleic acid or nucleic acid expression cassette.

Another aspect provides a pharmaceutical composition comprising said agent, said nucleic acid or nucleic acid expression cassette or said vector, and a pharmaceutically acceptable carrier.

A further aspect provides said agent, said nucleic acid or nucleic acid expression cassette, said vector or said pharmaceutical composition, for use as a medicament.

Also provided is said agent, said nucleic acid or nucleic acid expression cassette, said vector or said pharmaceutical composition, for use in the prevention or treatment of a neurovascular disorder or a central nervous system (CNS) disorder comprising neurovascular dysfunction.

Another aspect provides an in vitro method for identifying an agent useful as a therapeutic, such as in particular useful for the prevention or treatment of a neurovascular disorder or a CNS disorder comprising neurovascular dysfunction, said method comprising determining whether a test agent activates GPR124/RECK/Frizzled/LRP-mediated Wnt signaling but not Frizzled/LRP-mediated Wnt signaling in the absence of RECK and/or GPR124.

These and further aspects and preferred embodiments of the invention are described in the following sections and in the appended claims. The subject-matter of the appended claims is hereby specifically incorporated in this specification.

BRIEF DESCRIPTION OF DRAWINGS

FIG. 3 shows (A) the schematic illustration of the CRISPR/Cas9 protospacer adjacent motif (PAM) site in Lrp5/6 (left panel) and luciferase activities in WT HEK293T cells or LRP5−/−, LRP6−/− or double mutant LRP5−/−; LRP6−/− HEK293T cell clones 48 h after transfection with STF reporter plasmids and the indicated combinations of plasmids stimulating either Reck/Gpr124-dependent Wnt7a signaling or Gpr124/Reck independent Wnt1 signaling. (B) STF activity of Gpr124/Reck-dependent and -independent signaling in WT HEK293T cells in the presence or absence of co-expressed Dkk-1. (C) Luciferase activities in WT HEK293T cells or FZ mutant HEK293T cell clones 48 h after transfection with STF reporter plasmids and the indicated combinations of expression plasmids, stimulating Reck/Gpr124-dependent Wnt7a signaling or Gpr124/Reck-independent Wnt1 signaling. (D) Schematic representation of the CRISPR/Cas9 PAM site within Fz CRD. (E) STF activity of Gpr124/Reck-dependent signaling in $FZ1-10^{-/-}$ HEK293T after co-transfection with the indicated Fz or Fz CRD variant. *p<0.05, p<0.01, *p<0.001; data represent mean±SD.

FIG. 4 shows (A) a schematic representation of Gpr124 and its domain variants. (B) Representative 3D wire diagrams of the 60 hpf cerebrovasculatures of WT and gpr124 mutant embryos injected with 100 pg of the indicated RNA. Black vessels represent the Gpr124/Reck-dependent intracerebral CtAs that sprout from the grey perineural primordial hindbrain channels (PHBC) (C) Hindbrain central arteries (CtAs) of 60 hpf gpr124 morphant embryos injected at the one-cell stage with 100 pg of the indicated mRNA. (D) Relative luciferase activity of HEK293-STF cells co-transfected with Reck, Fz1, Wnt7a and the indicated Gpr124 variants. *p<0.001; data represent mean±SD. (E) Hindbrain CtAs of 60 hpf gpr124 morphant embryos injected at the one-cell stage with 100 pg of the indicated mRNAs. *P<0.001; data represent mean±SD.

Phosphorylated DVL2 (T224) could be detected as a slowly migrating band with anti-DVL2 antibodies (arrowhead) or by a phosphospecific antibody recognizing phosphothreonine 224 (p-DVL2) in whole cell extracts obtained after 48 h post-transfection with the different combinations of constructs as indicated. (C) Intracellular distribution of Fz4-GFP and Gpr124-tagRFP expressed individually or in the presence of Dvl in zebrafish blastula deep layer (DEL) cells (D) Intracellular distribution of Dvl-GFP co-expressed with Fz4 or Gpr124 in zebrafish blastula DEL cells. (E) Intracellular distribution of co-expressed Fz4-GFP and Gpr124-tagRFP in the absence or presence of Dvl in zebrafish blastula DEL cells. The cells annotated with an asterisk is magnified in the right panels and the pixel intensity of the green and red channels along a virtual clockwise path following the cell cortex from a to b is plotted below. (F) same as (E) in EVL cells. (G) BiFC signals in zebrafish DEL cells expressing Gpr124-VN155 (I152L) and Fz1-VC155 in the presence or absence of Dvl overexpression. ***P<0.001; data represent mean±SD.

Figure 6:
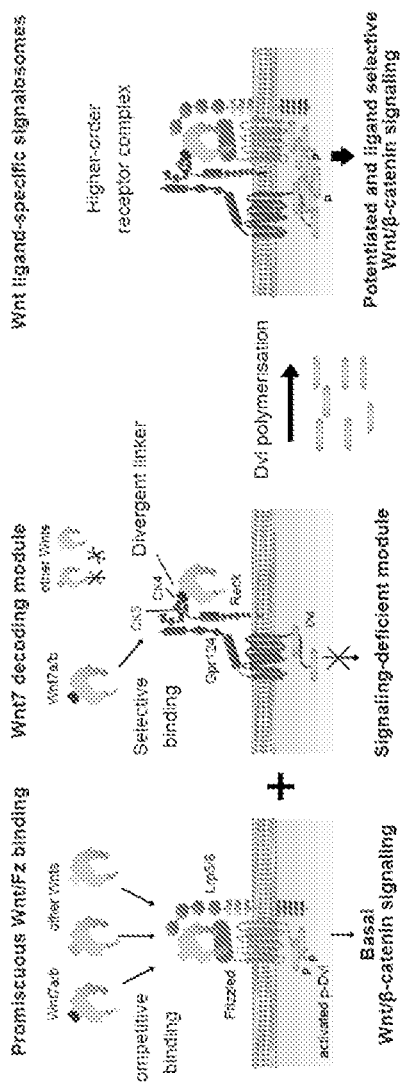

FIG. 6 represents an exemplary integrated model for Gpr124/Reck-dependent, Wnt7-specific Fz signaling.

Figure 7:
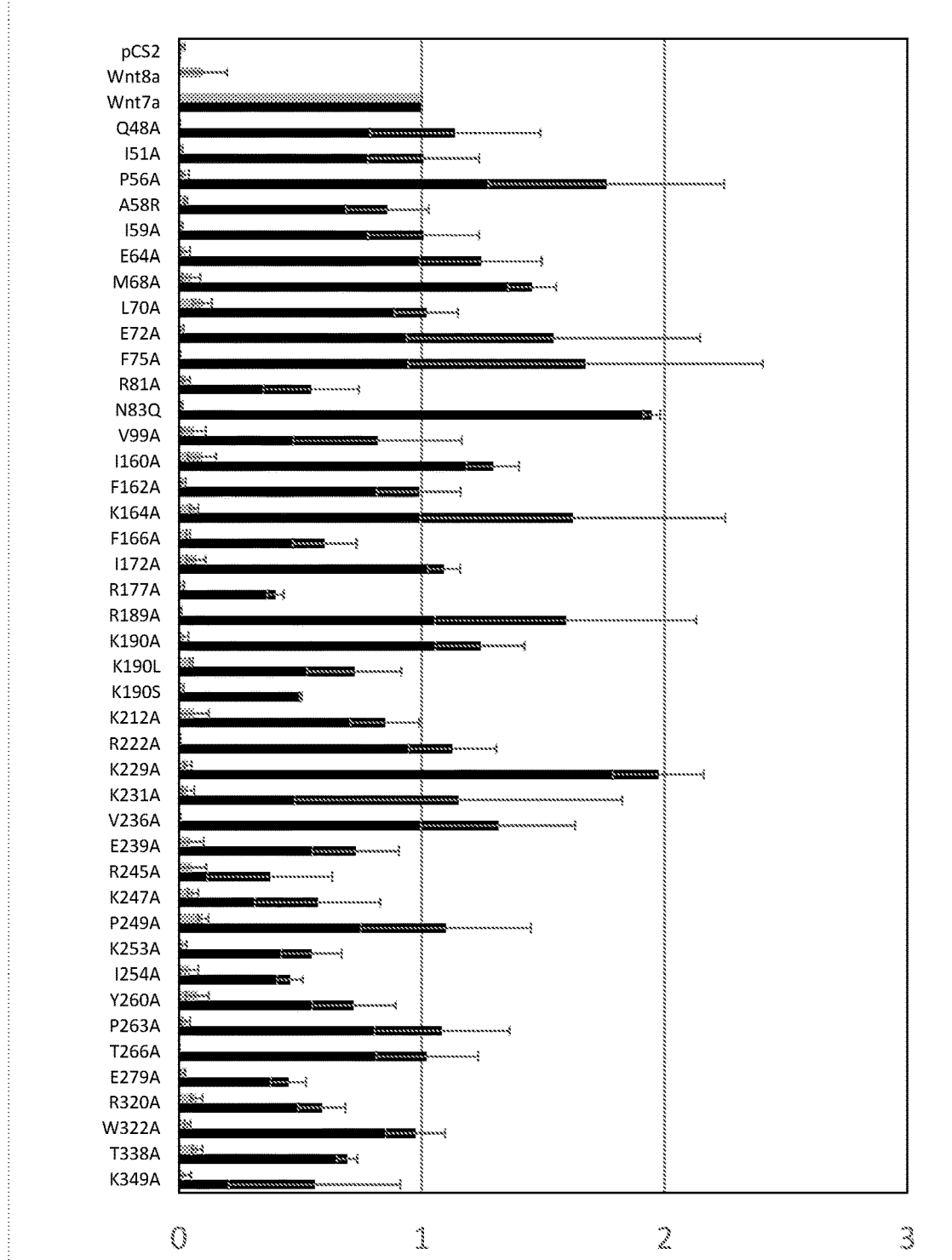

FIG. 7 shows (A) Relative luciferase activity in HEK293-STF cells of Fz5-dependent pathways (light gray, Fz5 transfection) or Gpr124/Reck-dependent pathways (black, Gpr124, RECK and Fz1 transfection) stimulated with different Wnt7 variants. (B) Gpr124/Reck-dependent and Fzd5 relative STF luciferase activities in HEK293-STF cells of signaling of 101 different single-residue variants of Wnt7a and their position on the Wnt7a structure. The relative luciferase activities are normalized to the WT Wnt7a values. 42 different single-residue variants of Wnt7a activate Gpr124/Reck/Fz/LRP-mediated Wnt signaling by at least 35% of the Gpr124/Reck/Fz/LRP-mediated Wnt signaling activity of the wild-type Wnt7a (rectangular box). (C) Gpr124/Reck-dependent and Fzd5 relative STF luciferase activities in HEK293-STF cells of signaling of 42 different single-residue variants of Wnt7a showing selective activation of the Gpr124/Reck pathway (D) Relative luciferase activity in HEK-STF after co-transfection of Wnt7a or Wnt7a$^{1-278}$ or Wnt7a$^{K190A}$ with all 10 Fz genes. (E) Lateral views of 3 dpf larvae injected at the one-cell stage with wnt7a or wnt7a$^{1-278}$ or wnt7a$^{K190A}$ mRNA at the indicated doses. (F) Phenotypic scoring of the 3 dpf larvae of (D). (G) Dorsal views of stage 36 *Xenopus laevis* embryos injected in one ventral blastomere of the 4-cell embryo with 15 pg of the indicated mRNA. The fraction of secondary axis formation (arrowhead) is indicated for each condition. (H) Trunk DRG of 72 hpf wnt7aa morphant larvae injected at the one-cell stage with the indicated mRNA. Representative images of Tg(neurog1:GFP) DRG are shown on the right. ***P<0.001; data represent mean±SD.

FIG. 8 shows the amino acid sequences of the human Wnt7a variants as taught herein. The amino acid substitutions versus the wild-type Wnt7a NTD domain or full length Wnt7a are in bold and underlined font.

Figure 9:
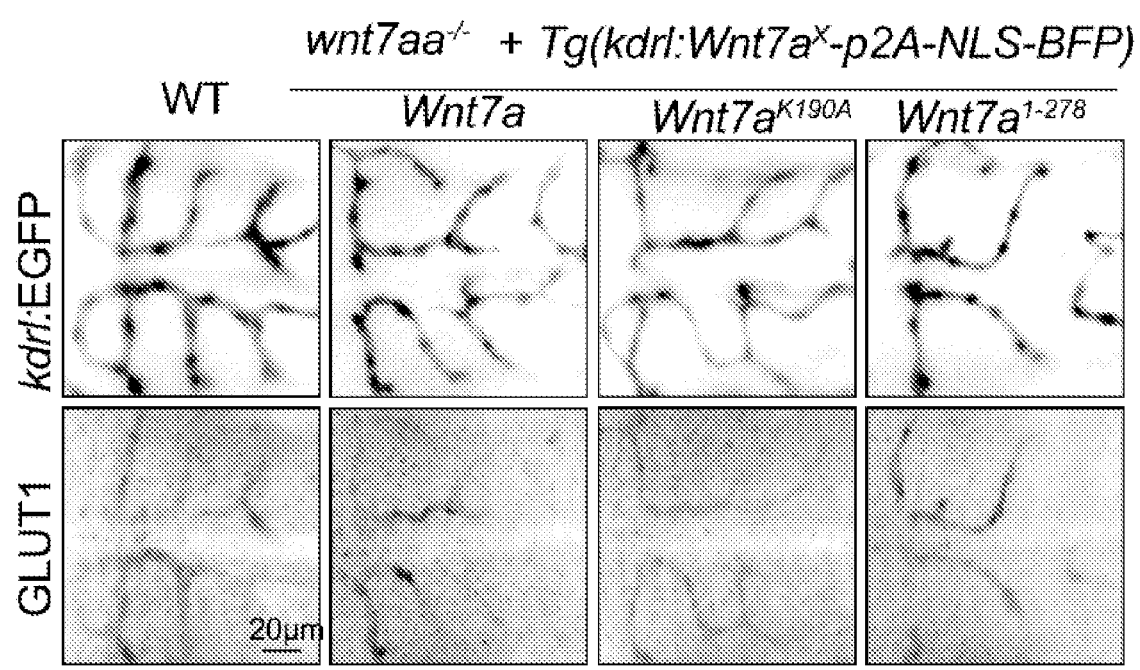

FIG. 9 shows that transgenic endothelial expression of Wnt7a$^{K190A}$ and Wnt7a$^{1-278}$ trigger GPR124/RECK-dependent brain angiogenesis and restores blood-brain barrier in Wnt7aa$^{-/-}$ zebrafish. (A) Dorsal views of the cerebral vasculatures of 60 hpf WT or Wnt7aa$^{-/-}$ Tg(kdrl:EGFP) embryos. In Wnt7a$^{-/-}$ mutants, the intracerebral CtAs are lacking. Wnt7, Wnt7a$^{K190A}$ or Wnt7a$^{1-278}$ were transiently expressed in the endothelium of Wnt7aa$^{-/-}$ embryos under the control of an endothelial-specific kdrl (Vascular endothelial growth factor receptor kdr-like) promoter. The Wnt7 ligands were expressed as a biscistronic construct with BFP (Blue Fluorescent Protein) used as transgenesis marker. In contrast to uninjected embryos, Wnt7, Wnt7a$^{K190A}$ or Wnt7a$^{1-278}$ restore hindbrain CtAs formation in Wnt7aa$^{-/-}$ mutants as quantified in (B). (C) Anti-GLUT1 staining of the CtAs after transgenic expression of Wnt7, Wnt7a$^{K190A}$ and Wnt7a$^{1-278}$ in 60 hpf Wnt7aa$^{-/-}$ embryos. Transgenic expression was achieved as in (A). Together this data demonstrates that the uncovered Wnt7a$^{K190A}$ or Wnt7a$^{1-278}$ agonists are active in vivo in Gpr124/Reck-dependent processes.

FIG. 10 represents GPR124/RECK-based gene therapy in a mouse model of stroke. AVV-PHP.eB viruses were used to deliver Wnt7a$^{K190A}$ or a corresponding empty AAV control (Ctrl) to the brains of 8 weeks-old mice. (A) a GFP encoding AAV-PHP.eB (AAV-PHP.eB-CAG-EGFP) was used to demonstrate widespread transgenic expression in the mouse brains (8-week old mice, 2 weeks post injection). The CAG promoter is a strong synthetic promoter used in mammalian expression vectors. Left panel, dorsal view on an intact isolated brain, right panel sagittal section. The section was stained with anti-CD31 to label the vasculature. (B) Intravenous injection of a $1 \cdot 10^{11}$ AAV-PHP.eB-CAG-Wnt7a$^{K190A}$-p2A-EGFP viral particles two weeks prior to tMCAO (transient middle cerebral artery occlusion, stroke model) reduced the stroke volume (mm$^3$), demonstrating that the uncovered agonists ameliorated stroke in pre-clinical models. The AAV-PHP.eB-CAG-EGFP viruses were used as control.

DESCRIPTION OF EMBODIMENTS

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members. In another example, "one or more" or "at least one" may refer to 1, 2, 3, 4, 5, 6, 7 or more.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

The present inventors have characterised the first ever "Wnt decoding module" capable of discriminating Wnt ligands that are otherwise largely synonymous in their capacity to bind Frizzled, thereby helping cells interpret the complexity of Wnt signaling inputs in order to orchestrate tissue development and homeostasis. In the herein characterised Wnt decoding module, selectivity is conferred by RECK, which mediates Wnt7-specific binding in a Frizzled-independent manner. G-protein coupled receptor GPR124, a RECK binding partner, acts as a signaling-deficient transmembrane protein which is able to recruit intracellular Dishevelled (Dvl). Dvl scaffolds bridge GPR124 and Frizzled, thereby assembling Wnt7 ligand-specific RECK/GPR124/Frizzled/lipoprotein receptor-related protein (LRP) signalosomes.

The inventors further unexpectedly demonstrated the design of novel agonists capable of activating Wnt signaling selectively in cells expressing RECK and GPR124, such agonists being useful as therapeutics, such as particularly for the treatment of neurovascular disorders or central nervous system (CNS) disorders comprising neurovascular dysfunction, including inter alia stroke, multiple sclerosis and brain cancer. Hence, the invention allows to provide inter alia novel agonists capable of stimulating Wnt/β-catenin signaling in cerebral endothelial cells substantially without cross-reactivity with other Frizzled pathways, and useful as therapeutics, particularly for neurovascular disorders or central nervous system (CNS) disorders comprising neurovascular dysfunction.

Accordingly, an aspect provides an agent capable of activating Wnt signaling mediated by the GPR124/RECK/Frizzled/LRP receptor complex, wherein said agent does not activate Wnt signaling mediated by the Frizzled/LRP receptor complex in the absence of RECK and/or GPR124.

References to any peptides, polypeptides, proteins or nucleic acids denote the respective peptides, polypeptides, proteins or nucleic acids as commonly known under the respective designations in the art. More particularly, the references to "G-protein coupled receptor 124" (GPR124), "Reversion-inducing cysteine-rich protein with Kazal motifs" (RECK), "Frizzled" (FZD), or "lipoprotein receptor-related protein" (LRP) denote the respective peptides, polypeptides, proteins or nucleic acids, as apparent from the context, as commonly known under said designations in the art.

The terms encompass the peptides, polypeptides, proteins or nucleic acids when forming a part of a living organism, organ, tissue or cell, when forming a part of a biological sample, as well as when at least partly isolated from such sources. The terms also encompass the peptides, polypeptides, proteins or nucleic acids when produced by recombinant or synthetic means.

Unless otherwise apparent from the context, reference herein to any peptide, polypeptide, protein or nucleic acid also encompasses modified forms of said peptide, polypeptide, protein or nucleic acid, such as forms bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

By means of additional guidance, G protein-coupled receptor 124 is also known in the art as Adhesion G protein-coupled receptor A2 (ADGRA2) or Tumor endothelial marker 5 (TEM5). By means of an example, human GPR124 gene is annotated under NCBI Genbank (http://www.ncbi.nlm.nih.gov/) Gene ID 25960. Human GPR124 mRNA is annotated under NCBI Genbank accession number NM_032777.9. Nucleotides 387 (start codon) to 4403 (stop codon) of NM_032777.9 constitute the GPR124 coding sequence. Human GPR124 protein sequence is annotated under NCBI Genbank accession number NP_116166.9, and Uniprot (www.uniprot.org) accession number Q96PE1-1, and is further reproduced below (SEQ ID NO: 1):

NP_116166.9 Adhesion G Protein-Coupled Receptor A2 Precursor [*Homo sapiens*]

```
MGAGGRRMRGAPARLLLPLLPWLLLLLAPEARGAPGCPLSIRSCKCSGER

PKGLSGGVPGPARRRVVCSGGDLPEPPEPGLLPNGTVTLLLSNNKITGLR

NGSFLGLSLLEKLDLRNNIISTVQPGAFLGLGELKRLDLSNNRIGCLTSE

TFQGLPRLLRLNISGNIFSSLQPGVFDELPALKVVDLGTEFLTCDCHLRW
```

-continued

LLPWAQNRSLQLSEHTLCAYPSALHAQALGSLQEAQLCCEGALELHTHHL

IPSLRQVVFQGDRLPFQCSASYLGNDTRIRWYHNRAPVEGDEQAGILLAE

SLIHDCTFITSELTLSHIGVWASGEWECTVSMAQGNASKKVEIVVLETSA

SYCPAERVANNRGDFRWPRTLAGITAYQSCLQYPFTSVPLGGGAPGTRAS

RRCDRAGRWEPGDYSHCLYTNDITRVLYTFVLMPINASNALTLAHQLRVY

TAEAASFSDMMDVVYVAQMIQKFLGYVDQIKELVEVMVDMASNLMLVDEH

LLWLAQREDKACSRIVGALERIGGAALSPHAQHISVNARNVALEAYLIKP

HSYVGLTCTAFQRREGGVPGTRPGSPGQNPPPEPEPPADQQLRFRCTTGR

PNVSLSSFHIKNSVALASIQLPPSLFSSLPAALAPPVPPDCTLQLLVFRN

GRLFHSHSNTSRPGAAGPGKRRGVATPVIFAGTSGCGVGNLTEPVAVSLR

HWAEGAEPVAAWWSQEGPGEAGGWTSEGCQLRSSQPNVSALHCQHLGNVA

VLMELSAFPREVGGAGAGLHPVVYPCTALLLLCLFATIITYILNHSSIRV

SRKGWHMLLNLCFHIAMTSAVFAGGITLTNYQMVCQAVGITLHYSSLSTL

LWMGVKARVLHKELTWRAPPPQEGDPALPTPSPMLRFYLIAGGIPLIICG

ITAAVNIHNYRDHSPYCWLVWRPSLGAFYIPVALILLITWIYFLCAGLRL

RGPLAQNPKAGNSRASLEAGEELRGSTRLRGSGPLLSDSGSLLATGSARV

GTPGPPEDGDSLYSPGVQLGALVTTHFLYLAMWACGALAVSQRWLPRVVC

SCLYGVAASALGLFVFTHHCARRRDVRASWRACCPPASPAAPHAPPRALP

AAAEDGSPVFGEGPPSLKSSPSGSSGHPLALGPCKLTNLQLAQSQVCEAG

AAAGGEGEPEPAGTRGNLAHRHPNNVHHGRRAHKSRAKGHRAGEACGKNR

LKALRGGAAGALELLSSESGSLHNSPTDSYLGSSRNSPGAGLQLEGEPML

TPSEGSDTSAAPLSEAGRAGQRRSASRDSLKGGGALEKESHRRSYPLNAA

SLNGAPKGGKYDDVTLMGAEVASGGCMKTGLWKSETTV

By means of additional guidance, RECK (Reversion-Inducing Cysteine-Rich Protein With Kazal Motifs) is also known in the art as Suppressor of tumorigenicity 15 protein (ST15). By means of an example, human RECK gene is annotated under NCBI Genbank (http://www.ncbi.nlm.nih.gov/) Gene ID 8434. Human RECK mRNA (transcript variant 1) is annotated under NCBI Genbank accession number NM_021111.2. Nucleotides 87 (start codon) to 3002 (stop codon) of NM_021111.2 constitute the RECK coding sequence. Human RECK protein sequence is annotated under NCBI Genbank accession number NP_066934.1, and Uniprot accession number O95980-1, and is further reproduced below (SEQ ID NO: 2):

NP_066934.1 Reversion-Inducing Cysteine-Rich Protein with Kazal Motifs Isoform 1 Precursor [*Homo sapiens*]

MATVRASLRGALLLLLAVAGVAEVAGGLAPGSAGALCCNHSKDNQMCRDV

CEQIFSSKSESRLKHLLQRAPDYCPETMVEIWNCMNSSLPGVFKKSDGWV

GLGCCELAIALECRQACKQASSKNDISKVCRKEYENALFSCISRNEMGSV

CCSYAGHHTNCREYCQAIFRTDSSPGPSQIKAVENYCASISPQLIHCVNN

YTQSYPMRNPTDSLYCCDRAEDHACQNACKRILMSKKTEMEIVDGLIEGC

KTQPLPQDPLWQCFLESSQSVHPGVTVHPPPSTGLDGAKLHCCSKANTST

CRELCTKLYSMSWGNTQSWQEFDRFCEYNPVEVSMLTCLADVREPCQLGC

RNLTYCTNFNNRPTELFRSCNAQSDQGAMNDMKLWEKGSIKMPFINIPVL

DIKKCQPEMWKAIACSLQIKPCHSKSRGSIICKSDCVEILKKCGDQNKFP

EDHTAESICELLSPTDDLKNCIPLDTYLRPSTLGNIVEEVTHPCNPNPCP

ANELCEVNRKGCPSGDPCLPYFCVQGCKLGEASDFIVRQGTLIQVPSSAG

EVGCYKICSCGQSGLLENCMEMHCIDLQKSCIVGGKRKSHGTSFSIDCNV

CSCFAGNLVCSTRLCLSEHSSEDDRRTFTGLPCNCADQFVPVCGQNGRTY

PSACIARCVGLQDHQFEFGSCMSKDPCNPNPCQKNQRCIPKPQVCLTTFD

KFGCSQYECVPRQLACDQVQDPVCDTDHMEHNNLCTLYQRGKSLSYKGPC

QPFCRATEPVCGHNGETYSSVCAAYSDRVAVDYYGDCQAVGVLSEHSSVA

ECASVKCPSLLAAGCKPIIPPGACCPLCAGMLRVLFDKEKLDTIAKVTNK

KPITVLEILQKIRMHVSVPQCDVFGYFSIESEIVILIIPVDHYPKALQIE

ACNKEAEKIESLINSDSPTLASHVPLSALIISQVQVSSSVPSAGVRARPS

CHSLLLPLSLGLALHLLWTYN

The term "Frizzled" or "FZD" or "FZ" encompasses any and all members of the Frizzled family. By means of additional guidance, Table 1 presents 10 known human Frizzled family members, as annotated in NCBI Genbank and Uniprot.

TABLE 1

| | NCBI Genbank | | | |
|---|---|---|---|---|
| | GeneID | mRNA | Start-Stop codon | Protein | Uniprot Protein |
| FZD1 | 8321 | NM_003505.1 | 414-2357 | NP_003496.1 | Q9UP38-1 |
| FZD2 | 2535 | NM_001466.3 | 246-1943 | NP_001457.1 | Q14332-1 |
| FZD3 | 7976 | NM_017412.3 | 530-2530 | NP_059108.1 | Q9NPG1-1 |
| | | NM_145866.1 | 484-2484 | NP_665873.1 | |
| FZD4 | 8322 | NM_012193.3 | 314-1927 | NP_036325.2 | Q9ULV1-1 |
| FZD5 | 7855 | NM_003468.3 | 411-2168 | NP_003459.2 | Q13467-1 |
| FZD6 | 8323 | NM_001164615.1 | 291-2411 | NP_001158087.1 | O60353-1 |
| | | NM_001164616.1 | 299-2323 | NP_001158088.1 | O60353-2 |
| | | NM_001317796.1 | 463-1668 | NP_001304725.1 | |
| | | NM_003506.3 | 318-2438 | NP_003497.2 | |
| FZD7 | 8324 | NM_003507.1 | 62-1786 | NP_003498.1 | O75084-1 |
| FZD8 | 8325 | NM_031866.2 | 6-2090 | NP_114072.1 | Q9H461-1 |
| FZD9 | 8326 | NM_003508.2 | 230-2005 | NP_003499.1 | O00144-1 |
| FZD10 | 11211 | NM_007197.3 | 485-2230 | NP_009128.1 | Q9ULW2-1 |

The term "lipoprotein receptor-related protein" or "LRP" encompasses any and all lipoprotein receptor-related proteins, also known in the art as low density lipoprotein receptor-related proteins or prolow-density lipoprotein receptor-related proteins, and particularly denote LPR proteins involved in Wnt signaling. In certain particularly preferred embodiments, the terms denote LRP5 (GeneID: 4041), LRP6 (GeneID: 4040), or LRP5 and LRP6 (LRP5/6).

Hence, also disclosed is an agent capable of activating GPR124/RECK/Frizzled/LRP5/6-mediated Wnt signaling, wherein said agent does not activate Frizzled/LRP5/6-mediated Wnt signaling in the absence of RECK and/or GPR124.

Further disclosed is an in vitro method for identifying an agent useful as a therapeutic, such as in particular useful for the prevention or treatment of a neurovascular disorder or a CNS disorder comprising neurovascular dysfunction, said method comprising determining whether a test agent activates GPR124/RECK/Frizzled/LRP5/6-mediated Wnt signaling but not Frizzled/LRP5/6-mediated Wnt signaling in the absence of RECK and/or GPR124.

By means of additional guidance, human LRP5 mRNA is annotated under NCBI Genbank accession numbers NM_002335.3 (transcript variant 1; nucleotides 107 (start codon) to 4954 (stop codon) of NM_002335.3 constitute the LRP5 coding sequence) or NM_001291902.1 (transcript variant 2; nucleotides 1872 (start codon) to 4976 (stop codon) of NM_001291902.1 constitute the LRP5 coding sequence). Human LRP5 protein sequence is annotated under NCBI Genbank accession numbers NP_002326.2 (isoform 1 precursor) or NP_001278831.1 (isoform 2), and Uniprot accession number O75197-1, the LRP5 protein sequence annotated as NP_002326.2 being reproduced below (SEQ ID NO: 3):

NP_002326.2 Low-Density Lipoprotein Receptor-Related Protein 5 Isoform 1 Precursor [*Homo sapiens*]

```
MEAAPPGPPWPLLLLLLLLLALCGCPAPAAASPLLLFANRRDVRLVDAGG
VKLESTIVVSGLEDAAAVDFQFSKGAVYWTDVSEEAIKQTYLNQTGAAVQ
NVVISGLVSPDGLACDWVGKKLYWTDSETNRIEVANLNGTSRKVLFWQDL
DQPRAIALDPAHGYMYWTDWGETPRIERAGMDGSTRKIIVDSDIYWPNGL
TIDLEEQKLYWADAKLSFIHRANLDGSFRQKVVEGSLTHPFALTLSGDTL
YWTDWQTRSIHACNKRTGGKRKEILSALYSPMDIQVLSQERQPFFHTRCE
EDNGGCSHLCLLSPSEPFYTCACPTGVQLQDNGRTCKAGAEEVLLLARRT
DLRRISLDTPDFTDIVLQVDDIRHAIAIDYDPLEGYVYWTDDEVRAIRRA
YLDGSGAQTLVNTEINDPDGIAVDWVARNLYWTDTGTDRIEVTRLNGTSR
KILVSEDLDEPRAIALHPVMGLMYWTDWGENPKIECANLDGQERRVLVNA
SLGWPNGLALDLQEGKLYWGDAKTDKIEVINVDGTKRRTLLEDKLPHIFG
FTLLGDFIYWTDWQRRSIERVHKVKASRDVIIDQLPDLMGLKAVNVAKVV
GTNPCADRNGGCSHLCFFTPHATRCGCPIGLELLSDMKTCIVPEAFLVFT
SRAAIHRISLETNNNDVAIPLTGVKEASALDFDVSNNHIYWTDVSLKTIS
RAFMNGSSVEHVVEFGLDYPEGMAVDWMGKNLYWADTGTNRIEVARLDGQ
FRQVLVWRDLDNPRSLALDPTKGYIYWTEWGGKPRIVRAFMDGTNCMTLV
DKVGRANDLTIDYADQRLYWTDLDTNMIESSNMLGQERVVIADDLPHPFG
LTQYSDYIYWTDWNLHSIERADKTSGRNRTLIQGHLDFVMDILVFHSSRQ
DGLNDCMHNNGQCGQLCLAIPGGHRCGCASHYTLDPSSRNCSPPTTFLLF
SQKSAISRMIPDDQHSPDLILPLHGLRNVKAIDYDPLDKFIYWVDGRQNI
KRAKDDGTQPFVLTSLSQGQNPDRQPHDLSIDIYSRTLFWTCEATNTINV
HRLSGEAMGVVLRGDRDKPRAIVVNAERGYLYFTNMQDRAAKIERAALDG
TEREVLFTTGLIRPVALVVDNTLGKLFWVDADLKRIESCDLSGANRLTLE
DANIVQPLGLTILGKHLYWIDRQQQMIERVEKTTGDKRTRIQGRVAHLTG
IHAVEEVSLEEFSAHPCARDNGGCSHICIAKGDGTPRCSCPVHLVLLQNL
LTCGEPPTCSPDQFACATGEIDCIPGAWRCDGFPECDDQSDEEGCPVCSA
AQFPCARGQCVDLRLRCDGEADCQDRSDEADCDAICLPNQFRCASGQCVL
IKQQCDSFPDCIDGSDELMCEITKPPSDDSPAHSSAIGPVIGIILSLFVM
GGVYFVCQRVVCQRYAGANGPFPHEYVSGTPHVPLNFIAPGGSQHGPFTG
IACGKSMMSSVSLMGGRGGVPLYDRNHVTGASSSSSSSTKATLYPPILNP
PPSPATDPSLYNMDMFYSSNIPATARPYRPYIIRGMAPPTTPCSTDVCDS
DYSASRWKASKYYLDLNSDSDPYPPPPTPHSQYLSAEDSCPPSPATERSY
FHLFPPPPSPCTDSS
```

By means of additional guidance, human LRP6 mRNA is annotated under NCBI Genbank accession number NM_002336.2. Nucleotides 143 (start codon) to 4984 (stop codon) of NM_002336.2 constitute the LRP6 coding sequence. Human LRP6 protein sequence is annotated under NCBI Genbank accession number NP_002327.2 and Uniprot accession number O75581-1, and is further reproduced below (SEQ ID NO: 4):

NP_002327.2 Low-Density Lipoprotein Receptor-Related Protein 6 Precursor [*Homo sapiens*]

```
MGAVLRSLLACSFCVLLRAAPLLLYANRRDLRLVDATNGKENATIVVGGL
EDAAAVDFVFSHGLIYWSDVSEEAIKRTEFNKTESVQNVVVSGLLSPDGL
ACDWLGEKLYWTDSETNRIEVSNLDGSLRKVLFWQELDQPRAIALDPSSG
FMYWTDWGEVPKIERAGMDGSSRFIIINSEIYWPNGLTLDYEEQKLYWAD
AKLNFIHKSNLDGTNRQAVVKGSLPHPFALTLFEDILYWTDWSTHSILAC
NKYTGEGLREIHSDIFSPMDIHAFSQQRQPNATNPCGIDNGGCSHLCLMS
PVKPFYQCACPTGVKLLENGKTCKDGATELLLLARRTDLRRISLDTPDFT
DIVLQLEDIRHAIAIDYDPVEGYIYWTDDEVRAIRRSFIDGSGSQFVVTA
QIAHPDGIAVDWVARNLYWTDTGTDRIEVTRLNGTMRKILISEDLEEPRA
IVLDPMVGYMYWTDWGEIPKIERAALDGSDRVVLVNTSLGWPNGLALDYD
EGKIYWGDAKTDKIEVMNTDGTGRRVLVEDKIPHIFGFTLLGDYVYWTDW
QRRSIERVHKRSAEREVIIDQLPDLMGLKATNVHRVIGSNPCAEENGGCS
HLCLYRPQGLRCACPIGFELISDMKTCIVPEAFLLFSRRADIRRISLETN
NNNVAIPLTGVKEASALDFDVTDNRIYWTDISLKTISRAFMNGSALEHVV
EFGLDYPEGMAVDWLGKNLYWADTGTNRIEVSKLDGQHRQVLVWKDLDSP
RALALDPAEGFMYWTEWGGKPKIDRAAMDGSERTTLVPNVGRANGLTIDY
AKRRLYWTDLDTNLIESSNMLGLNREVIADDLPHPFGLTQYQDYIYWTDW
SRRSIERANKTSGQNRTIIQGHLDYVMDILVFHSSRQSGWNECASSNGHC
```

-continued

```
SHLCLAVPVGGFVCGCPAHYSLNADNRTCSAPTTFLLFSQKSAINRMVID

EQQSPDIILPIHSLRNVRAIDYDPLDKQLYWIDSRQNMIRKAQEDGSQGF

TVVVSSVPSQNLEIQPYDLSIDIYSRYIYWTCEATNVINVTRLDGRSVGV

VLKGEQDRPRAVVVNPEKGYMYFTNLQERSPKIERAALDGTEREVLFFSG

LSKPIALALDSRLGKLFWADSDLRRIESSDLSGANRIVLEDSNILQPVGL

TVFENWLYWIDKQQQMIEKIDMTGREGRTKVQARIAQLSDIHAVKELNLQ

EYRQHPCAQDNGGCSHICLVKGDGTTRCSCPMHLVLLQDELSCGEPPTCS

PQQFTCFTGEIDCIPVAWRCDGFTECEDHSDELNCPVCSESQFQCASGQC

IDGALRCNGDANCQDKSDEKNCEVLCLIDQFRCANGQCIGKHKKCDHNVD

CSDKSDELDCYPTEEPAPQATNTVGSVIGVIVTIFVSGTVYFICQRMLCP

RMKGDGETMTNDYVVHGPASVPLGYVPHPSSLSGSLPGMSRGKSMISSLS

IMGGSSGPPYDRAHVTGASSSSSSSTKGTYFPAILNPPPSPATERSHYTM

EFGYSSNSPSTHRSYSYRPYSYRHFAPPTTPCSTDVCDSDYAPSRRMTSV

ATAKGYTSDLNYDSEPVPPPPTPRSQYLSAEENYESCPPSPYTERSYSHH

LYPPPPSPCTDSS
```

A skilled person can appreciate that any sequences represented in sequence databases or in the present specification may be of precursors of the respective peptides, polypeptides, proteins or nucleic acids and may include parts which are processed away from mature molecules.

The term "protein" as used throughout this specification generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes protein variants or mutants which carry amino acid sequence variations vis-à-vis a corresponding native proteins, such as, e.g., amino acid deletions, additions and/or substitutions. The term contemplates both full-length proteins and protein parts or fragments, e.g., naturally-occurring protein parts that ensue from processing of such full-length proteins.

The term "polypeptide" as used throughout this specification generally encompasses polymeric chains of amino acid residues linked by peptide bonds. Hence, especially when a protein is only composed of a single polypeptide chain, the terms "protein" and "polypeptide" may be used interchangeably herein to denote such a protein. The term is not limited to any minimum length of the polypeptide chain. The term may encompass naturally, recombinantly, semi-synthetically or synthetically produced polypeptides. The term also encompasses polypeptides that carry one or more co- or post-expression-type modifications of the polypeptide chain, such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes polypeptide variants or mutants which carry amino acid sequence variations vis-à-vis a corresponding native polypeptide, such as, e.g., amino acid deletions, additions and/or substitutions. The term contemplates both full-length polypeptides and polypeptide parts or fragments, e.g., naturally-occurring polypeptide parts that ensue from processing of such full-length polypeptides.

The term "peptide" as used throughout this specification preferably refers to a polypeptide as used herein consisting essentially of 50 amino acids or less, e.g., 45 amino acids or less, preferably 40 amino acids or less, e.g., 35 amino acids or less, more preferably 30 amino acids or less, e.g., 25 or less, 20 or less, 15 or less, 10 or less or 5 or less amino acids.

A peptide, polypeptide or protein can be naturally occurring, e.g., present in or isolated from nature, e.g., produced or expressed natively or endogenously by a cell or tissue and optionally isolated therefrom. A peptide, polypeptide or protein can be recombinant, i.e., produced by recombinant DNA technology, and/or can be, partly or entirely, chemically or biochemically synthesised. Without limitation, a peptide, polypeptide or protein can be produced recombinantly by a suitable host or host cell expression system and optionally isolated therefrom (e.g., a suitable bacterial, yeast, fungal, plant or animal host or host cell expression system), or produced recombinantly by cell-free translation or cell-free transcription and translation, or non-biological peptide, polypeptide or protein synthesis.

The term "nucleic acid" as used throughout this specification typically refers to a polymer (preferably a linear polymer) of any length composed essentially of nucleoside units. A nucleoside unit commonly includes a heterocyclic base and a sugar group. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Exemplary modified nucleobases include without limitation 5-substituted pyrimidines, 6-azapyrimidines and N-2, N-6 and 0-6 substituted purines, including 2-aminopropyladenine, 5-propynyluracil and 5-propynylcytosine. In particular, 5-methylcytosine substitutions have been shown to increase nucleic acid duplex stability and may be preferred base substitutions in for example antisense agents, even more particularly when combined with 2'-O-methoxyethyl sugar modifications. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups (such as without limitation 2'-O-alkylated, e.g., 2'-O-methylated or 2'-O-ethylated sugars such as ribose; 2'-O-alkyloxyalkylated, e.g., 2'-O-methoxyethylated sugars such as ribose; or 2'-0,4'-C-alkylene-linked, e.g., 2'-0,4'-C-methylene-linked or 2'-0,4'-C-ethylene-linked sugars such as ribose; 2'-fluoroarabinose, etc.). Nucleic acid molecules comprising at least one ribonucleoside unit may be typically referred to as ribonucleic acids or RNA. Such ribonucleoside unit(s) comprise a 2'-OH moiety, wherein —H may be substituted as known in the art for ribonucleosides (e.g., by a methyl, ethyl, alkyl, or alkyloxyalkyl). Preferably, ribonucleic acids or RNA may be composed primarily of ribonucleoside units, for example, ≥80%, ≥85%, ≥90%, ≥95%, ≥96%, ≥97%, ≥98%, ≥99% or even 100% (by number) of nucleoside units constituting the nucleic acid molecule may be ribonucleoside units. Nucleic acid molecules comprising at least one deoxyribonucleoside unit may be typically referred to as deoxyribonucleic acids or DNA. Such deoxyribonucleoside unit(s) comprise 2'-H. Preferably, deoxyribonucleic acids or DNA may be composed primarily of deoxyribonucleoside units, for example, ≥80%, ≥85%, ≥90%, ≥95%, ≥96%, ≥97%, ≥98%, ≥99% or even 100% (by number) of nucleoside units constituting the nucleic acid molecule may be deoxyribonucleoside units. Nucleoside units may be linked to one another by any one of numerous known internucleoside linkages, including inter alia phosphodiester linkages common in naturally-occurring nucleic acids, and further modified phosphate- or phosphonate-based linkages such as phosphorothioate, alkyl phosphorothioate such as methyl phosphorothioate, phosphorodithioate, alkylphosphonate such as methylphosphonate, alkylphosphonothioate, phosphotriester such as alkylphosphotriester, phosphoramidate, phosphoropiperazidate, phosphoromorpholidate, bridged phosphoramidate, bridged methylene phosphonate, bridged phosphorothioate; and further siloxane, carbonate, sulfamate, carboalkoxy, acetamidate, carbamate such as 3'-N-carbamate, morpholino, borano, thioether, 3'-thioacetal, and sulfone internucleoside linkages. Preferably, internucleoside linkages may be phosphate-based linkages including modified phosphate-based linkages, such as more preferably phosphodiester, phosphorothioate or phosphorodithioate linkages or combinations thereof. The term "nucleic acid" also encompasses any other nucleobase containing polymers such as nucleic acid mimetics, including, without limitation, peptide nucleic acids (PNA), peptide nucleic acids with phosphate groups (PHONA), locked nucleic acids (LNA), morpholino phosphorodiamidate-backbone nucleic acids (PMO), cyclohexene nucleic acids (CeNA), tricyclo-DNA (tcDNA), and nucleic acids having backbone sections with alkyl linkers or amino linkers (see, e.g., Kurreck 2003 (Eur J Biochem 270: 1628-1644)). "Alkyl" as used herein particularly encompasses lower hydrocarbon moieties, e.g., C1-C4 linear or branched, saturated or unsaturated hydrocarbon, such as methyl, ethyl, ethenyl, propyl, 1-propenyl, 2-propenyl, and isopropyl. Nucleic acids as intended herein may include naturally occurring nucleosides, modified nucleosides or mixtures thereof. A modified nucleoside may include a modified heterocyclic base, a modified sugar moiety, a modified inter-nucleoside linkage or a combination thereof.

The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g., chemically synthesised) DNA, RNA or DNA/RNA hybrids. RNA is inclusive of RNAi (inhibitory RNA), dsRNA (double stranded RNA), siRNA (small interfering RNA), mRNA (messenger RNA), miRNA (micro-RNA), tRNA (transfer RNA, whether charged or discharged with a corresponding acylated amino acid), and cRNA (complementary RNA). A nucleic acid can be naturally occurring, e.g., present in or isolated from nature, e.g., produced natively or endogenously by a cell or a tissue and optionally isolated therefrom. A nucleic acid can be recombinant, i.e., produced by recombinant DNA technology, and/or can be, partly or entirely, chemically or biochemically synthesised. Without limitation, a nucleic acid can be produced recombinantly by a suitable host or host cell expression system and optionally isolated therefrom (e.g., a suitable bacterial, yeast, fungal, plant or animal host or host cell expression system), or produced recombinantly by cell-free transcription, or non-biological nucleic acid synthesis. A nucleic acid can be double-stranded, partly double stranded, or single-stranded. Where single-stranded, the nucleic acid can be the sense strand or the antisense strand. In addition, nucleic acid can be circular or linear.

The reference to any peptides, polypeptides, proteins or nucleic acids encompass such peptides, polypeptides, proteins or nucleic acids of any organism where found, and particularly of animals, preferably warm-blooded animals, more preferably vertebrates, yet more preferably mammals, including humans and non-human mammals, still more preferably of humans.

Hence, in certain embodiments, one or more and preferably all of GPR124, RECK, FZD and LRP as employed herein is or are of animal origin, preferably warm-blooded animal origin, more preferably vertebrate origin, yet more preferably mammalian origin, including human origin and non-human mammalian origin, still more preferably human origin.

The reference to any peptides, polypeptides, proteins or nucleic acids may particularly encompass such peptides, polypeptides, proteins or nucleic acids with a native sequence, i.e., ones of which the primary sequence is the same as that of the peptides, polypeptides, proteins or nucleic acids found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to somatic mutations, or post-transcriptional or post-translational modifications. Any such variants or isoforms of peptides, polypeptides, proteins or nucleic acids are intended herein. Accordingly, all sequences of peptides, polypeptides, proteins or nucleic acids found in or derived from nature are considered "native".

In certain embodiments, the peptides, polypeptides, proteins or nucleic acids may be human, i.e., their primary sequence may be the same as a corresponding primary sequence of or present in naturally occurring human peptides, polypeptides, proteins or nucleic acids. In certain embodiments the qualifier "human" relates to the primary sequence of the respective peptides, polypeptides, proteins or nucleic acids, rather than to their origin or source. For example, such peptides, polypeptides, proteins or nucleic acids may be present in or isolated from samples of human subjects or may be obtained by other means (e.g., by recombinant expression, cell-free transcription or translation, or non-biological nucleic acid or peptide synthesis).

In certain embodiments, the peptides, polypeptides, proteins or nucleic acids may be wild-type. While most native peptides, polypeptides, proteins or nucleic acids may be considered wild-type, those carrying naturally-occurring mutations leading to partial or complete loss of function, which may contribute to or be causative of a disease phenotype, are generally excluded from the scope of the term "wild-type".

The reference to any peptides, polypeptides, proteins or nucleic acids may also encompass variants or fragments of such peptides, polypeptides, proteins or nucleic acids, particularly of naturally-occurring, native or wild-type forms thereof.

The term "fragment" as used throughout this specification with reference to a peptide, polypeptide, or protein generally denotes a portion of the peptide, polypeptide, or protein, such as typically an N- and/or C-terminally truncated form of the peptide, polypeptide, or protein. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of said peptide, polypeptide, or protein. For example, insofar not exceeding the length of the full-length peptide, polypeptide, or protein, a fragment may include a sequence of ≥5 consecutive amino acids, or ≥10 consecutive amino acids, or ≥20 consecutive amino acids, or ≥30 consecutive amino acids, e.g., ≥40 consecutive amino acids, such as for example ≥50 consecutive amino acids, e.g., ≥60, ≥70, ≥80, ≥90, ≥100, ≥200, ≥300, ≥400, ≥500, ≥600, ≥700, ≥800, ≥900 or ≥1000 consecutive amino acids of the corresponding full-length peptide, polypeptide, or protein.

The term "fragment" with reference to a nucleic acid (polynucleotide) generally denotes a 5'- and/or 3'-truncated form of a nucleic acid. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the nucleic acid sequence length of said nucleic acid. For example, insofar not exceeding the length of the full-length nucleic acid, a fragment may include a sequence of ≥5 consecutive nucleotides, or ≥10 consecutive nucleotides, or ≥20 consecutive nucleotides, or ≥30 consecutive nucleotides, e.g., ≥40 consecutive nucleotides, such as for example ≥50 consecutive nucleotides, e.g., ≥60, ≥70, ≥80, ≥90, ≥100, ≥200, ≥300, ≥400, ≥500, ≥600, ≥700, ≥800, ≥900, ≥1000, ≥1500, ≥2000, ≥2500, ≥3000, ≥3500 or ≥4000 consecutive nucleotides of the corresponding full-length nucleic acid.

The terms encompass fragments arising by any mechanism, in vivo and/or in vitro, such as, without limitation, by alternative transcription or translation, exo- and/or endo-proteolysis, exo- and/or endo-nucleolysis, or degradation of the peptide, polypeptide, protein or nucleic acid, such as, for example, by physical, chemical and/or enzymatic proteolysis or nucleolysis.

The term "variant" of a protein, polypeptide, peptide or nucleic acid generally refers to proteins, polypeptides or peptides the amino acid sequence of which, or nucleic acids the nucleotide sequence of which, is substantially identical (i.e., largely but not wholly identical) to the sequence of the protein, polypeptide, peptide, or nucleic acid, e.g., at least about 80% identical or at least about 85% identical, e.g., preferably at least about 90% identical, e.g., at least 91% identical, 92% identical, more preferably at least about 93% identical, e.g., at least 94% identical, even more preferably at least about 95% identical, e.g., at least 96% identical, yet more preferably at least about 97% identical, e.g., at least 98% identical, and most preferably at least 99% identical to the sequence of the recited protein, polypeptide, peptide, or nucleic acid. Preferably, a variant may display such degrees of identity to a recited protein, polypeptide, peptide or nucleic acid when the whole sequence of the recited protein, polypeptide, peptide or nucleic acid is queried in the sequence alignment (i.e., overall sequence identity). Sequence identity may be determined using suitable algorithms for performing sequence alignments and determination of sequence identity as know per se. Exemplary but non-limiting algorithms include those based on the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250), for example using the published default settings or other suitable settings (such as, e.g., for the BLASTN algorithm: cost to open a gap=5, cost to extend a gap=2, penalty for a mismatch=−2, reward for a match=1, gap x_dropoff=50, expectation value=10.0, word size=28; or for the BLASTP algorithm: matrix=Blosum62 (Henikoff et al., 1992, Proc. Natl. Acad. Sci., 89:10915-10919), cost to open a gap=11, cost to extend a gap=1, expectation value=10.0, word size=3).

An example procedure to determine the percent identity between a particular amino acid sequence and the amino acid sequence of a query polypeptide will entail aligning the two amino acid sequences using the Blast 2 sequences (Bl2seq) algorithm, available as a web application or as a standalone executable programme (BLAST version 2.2.31+) at the NCBI web site (www.ncbi.nlm.nih.gov), using suitable algorithm parameters. An example of suitable algorithm parameters include: matrix=Blosum62, cost to open a gap=11, cost to extend a gap=1, expectation value=10.0, word size=3). If the two compared sequences share homology, then the output will present those regions of homology as aligned sequences. If the two compared sequences do not share homology, then the output will not present aligned sequences. Once aligned, the number of matches will be determined by counting the number of positions where an identical amino acid residue is presented in both sequences. The percent identity is determined by dividing the number of matches by the length of the query polypeptide, followed by multiplying the resulting value by 100. The percent identity value may, but need not, be rounded to the nearest tenth. For example, 78.11, 78.12, 78.13, and 78.14 may be rounded down to 78.1, while 78.15, 78.16, 78.17, 78.18, and 78.19 may be rounded up to 78.2. It is further noted that the detailed view for each segment of alignment as outputted by Bl2seq already conveniently includes the percentage of identities.

A variant of a protein, polypeptide, peptide or nucleic acid may be a homologue (e.g., orthologue or paralogue) of said protein, polypeptide, peptide or nucleic acid. As used herein, the term "homology" generally denotes structural similarity between two macromolecules from same or different taxons, wherein said similarity is due to shared ancestry.

A variant of a protein, polypeptide, or peptide may comprise one or more amino acid additions, deletions, or substitutions relative to (i.e., compared with) the corresponding protein or polypeptide. For example, a variant (substitution variant) of a protein, polypeptide, or peptide may comprise up to 70 (e.g., not more than one, two, three, four, five, six, seven, eight, nine, ten, 12, 15, 20, 25, 30, 35, 40, 50, 60, or 70) conservative amino acid substitutions relative to (i.e., compared with) the corresponding protein or polypeptide; and/or a variant (substitution variant) of a protein, polypeptide, or peptide may comprise up to 20 (e.g., not more than one, two, three, four, five, six, seven, eight, nine, ten, 11, 12, 13, 14, 15, 16, 17, 18, or 19) non-conservative amino acid substitutions relative to (i.e., compared with) the corresponding protein or polypeptide.

A conservative amino acid substitution is a substitution of one amino acid for another with similar characteristics. Conservative amino acid substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (i.e., basic) amino acids include arginine, lysine and histidine. The negatively charged (i.e., acidic) amino acids include aspartic acid and glutamic acid. Any substitution of one member of the above-mentioned polar, basic, or acidic groups by another member of the same group can be deemed a conservative substitution. By contrast, a non-conservative substitution is a substitution of one amino acid for another with dissimilar characteristics.

Alternatively or in addition, for example, a variant (deletion variant) of a protein, polypeptide, or peptide may lack up to 20 amino acid segments (e.g., one, two, three, four, five, six, seven, eight, nine, ten, 11, 12, 13, 14, 15, 16, 17, 18, 19, or 20 segments) relative to (i.e., compared with) the corresponding protein or polypeptide. The deletion segment(s) may each independently consist of one amino acid, two contiguous amino acids or three contiguous amino acids. The deletion segments may be non-contiguous, or two or more or all of the deletion segments may be contiguous.

A variant of a nucleic acid may comprise one or more nucleotide additions, deletions, or substitutions relative to (i.e., compared with) the corresponding nucleic acid.

Reference to "fragment or variant" or "variant or fragment" of any peptide, polypeptide, protein or nucleic acid, also encompasses fragments of variants of such peptide, polypeptide, protein or nucleic acid, and variants of fragments of such peptide, polypeptide, protein or nucleic acid.

Particularly envisaged are biologically active fragments and/or variants of the recited peptides, polypeptides or proteins. The term "biologically active" is interchangeable with terms such as "functionally active" or "functional", denoting that the fragment and/or variant at least partly retains the biological activity or intended functionality of the respective or corresponding peptide, polypeptide or protein. Reference to the "activity" of a peptide, polypeptide or protein may generally encompass any one or more aspects of the biological activity of the peptide, polypeptide or protein, such as without limitation any one or more aspects of its biochemical activity, enzymatic activity, signaling activity, interaction activity, ligand activity, and/or structural activity, e.g., within a cell, tissue, organ or an organism.

Preferably, a functionally active fragment or variant may retain at least about 20%, e.g., at least about 25%, or at least 30%, or at least about 40%, or at least about 50%, e.g., at least 60%, more preferably at least about 70%, e.g., at least 80%, yet more preferably at least about 85%, still more preferably at least about 90%, and most preferably at least about 95% or even about 100% of the intended biological activity or functionality compared with the corresponding peptide, polypeptide or protein. In certain embodiments, a functionally active fragment or variant may even display higher biological activity or functionality compared with the corresponding peptide, polypeptide or protein, for example may display at least about 100%, or at least about 150%, or at least about 200%, or at least about 300%, or at least about 400%, or at least about 500% of the intended biological activity or functionality compared with the corresponding peptide, polypeptide or protein. By means of an example, where the activity of a given peptide, polypeptide or protein can be readily measured in an assay with a quantitative output, for example an enzymatic assay or a signaling assay or a binding assay producing a quantifiable signal, a functionally active fragment or variant of the peptide, polypeptide or protein may produce a signal which is at least about 20%, or at least about 25%, or at least about 30%, or at least about 40%, or at least about 50%, or at least about 60%, more preferably at least about 70%, or at least about 80%, or at least about 85%, or at least about 90%, or at least about 95%, or at least about 100%, or at least about 150%, or at least about 200%, or at least about 300%, or at least about 400%, or at least about 500% of the signal produced by the corresponding peptide, polypeptide or protein.

By means of an example and not limitation, a biologically active fragment or variant of GPR124, RECK, FZD or LRP polypeptide or protein will at least partly retain one or more aspects of the biological activity of the corresponding native or wild-type GPR124, RECK, FZD or LRP polypeptide or protein, respectively. For example, reference to the biological activity of the GPR124, RECK, FZD or LRP polypeptide or protein may particularly denote the ability to participate in a GPR124/RECK/FZD/LRP complex, e.g., the ability to bind to one or more other component(s) of said complex, and/or the ability to mediate Wnt signaling as part of the GPR124/RECK/FZD/LRP complex.

Hence, the specification in particular discloses an agent capable of activating GPR124/RECK/FZD/LRP-mediated Wnt signaling, wherein said agent does not activate FZD/LRP-mediated Wnt signaling in the absence of RECK and/or GPR124, wherein one or more or preferably all of GPR124, RECK, FZD or LRP is or are native or wild-type GPR124, RECK, FZD or LRP.

The specification further in particular discloses an agent capable of activating GPR124/RECK/FZD/LRP-mediated Wnt signaling, wherein said agent does not activate FZD/LRP-mediated Wnt signaling in the absence of RECK and/or GPR124, wherein one or more or preferably all of GPR124, RECK, FZD or LRP is or are native or wild-type human GPR124, RECK, FZD or LRP.

The specification further in particular discloses an agent capable of activating GPR124/RECK/FZD/LRP-mediated Wnt signaling, wherein said agent does not activate FZD/LRP-mediated Wnt signaling in the absence of RECK and/or GPR124, wherein one or more or preferably all of GPR124, RECK, FZD or LRP is or are native or wild-type human GPR124, RECK, FZD or LRP as annotated under the Genbank or Uniprot entries set forth elsewhere in this specification. The reader is reminded that where Genbank or Uniprot entries provide the sequence of precursor polypeptides or proteins, the corresponding mature forms would be expected to participate in the GPR124/RECK/FZD/LRP complex.

The specification further in particular discloses an agent capable of activating GPR124/RECK/FZD1/LRP5 or LRP6-mediated Wnt signaling, wherein said agent does not activate FZD5/LRP5 or LRP6-mediated Wnt signaling in the absence of RECK and/or GPR124, wherein one or more or preferably all of GPR124, RECK, FZD1, FZD5, LRP5 or LRP6 is or are native or wild-type human GPR124, RECK, FZD1, FZD5, LRP5 or LRP6 as annotated under the Genbank or Uniprot entries set forth elsewhere in this specification.

The specification further in particular discloses an agent capable of activating GPR124/RECK/FZD/LRP-mediated Wnt signaling, wherein said agent does not activate FZD/LRP-mediated Wnt signaling in the absence of RECK and/or GPR124, wherein one or more of GPR124, RECK, FZD or LRP is or are a biologically active fragment or variant of native or wild-type GPR124, RECK, FZD or LRP.

The specification further in particular discloses an agent capable of activating GPR124/RECK/FZD/LRP-mediated Wnt signaling, wherein said agent does not activate FZD/LRP-mediated Wnt signaling in the absence of RECK and/or GPR124, wherein one or more of GPR124, RECK, FZD or LRP is or are a biologically active fragment or variant of native or wild-type human GPR124, RECK, FZD or LRP.

The terms "complex", "protein complex" or "polypeptide complex" are well-understood in the art. By means of further guidance and without limitation, the terms broadly denote a cluster comprising two or more proteins or polypeptides. The cluster may be stabilised by non-covalent bonds, more particularly non-covalent protein-protein interactions, wherein all or only part of the polypeptides present within the cluster physically interact. A protein complex can be comprised entirely of peptides, polypeptides or proteins, or it may include other molecules or macromolecules such as carbohydrates, lipids, glycolipids, nucleic acids, oligonucleotides, nucleoproteins, nucleosides, nucleoside phosphates, enzyme co-factors, porphyrins, metal ions and the like. The terms encompass without limitation protein complexes which may be obligate or non-obligate, transient or permanent, and/or homomultimeric or heteromultimeric. The terms encompass without limitation protein complexes which may be located at the cell membrane (plasma membrane), extracellularly, within cytoplasm, within cellular organelles, or at membranes of cellular organelles. Complexes located at the cell membrane typically contain at least one membrane-anchored or transmembrane protein. The terms also encompass membrane microdomains and membrane-associated macromolecular organelle-like structures known as "signalosome" which compartmentalise a given signaling pathway. Such higher-order protein complexes can be at least partly stabilised by intracellular scaffolds. The terms may thus also denote situations in which certain proteins or polypeptides are locally concentrated or accumulated at a given site of a cell membrane, such as to allow signal transduction through the cell membrane at said site mediated by said proteins or polypeptides.

A GPR124/RECK/FZD/LRP receptor complex broadly denotes a protein complex, particularly a membrane-associated protein complex, more particularly a plasma membrane-associated protein complex comprising at least one GPR124 polypeptide, at least one RECK polypeptide, at least one FZD polypeptide and at least one LRP polypeptide. A GPR124/RECK/FZD/LRP receptor complex, when located at the plasma membrane of a cell containing the downstream members of the Wnt/β-catenin signaling pathway (e.g., Dishevelled (Dvl)), is capable of activating Wnt/β-catenin signaling in said cell in response to extracellularly provided Wnt7 ligand.

A FZD/LRP receptor complex broadly denotes a protein complex, particularly a membrane-associated protein complex, more particularly a plasma membrane-associated protein complex comprising at least one FZD polypeptide and at least one LRP polypeptide. A FZD/LRP receptor complex, when located at the plasma membrane of a cell containing the downstream members of the Wnt/β-catenin signaling pathway (e.g., Dvl), is capable of activating Wnt/β-catenin signaling in said cell in response to extracellularly provided Wnt ligand, such as, but not limited to Wnt7 ligand.

The term "Wnt signaling" as used herein refers to the mechanism by which a biologically active Wnt ligand exerts its effect upon a cell to modulate said cell's activity and/or actions. Biologically active Wnt ligands modulate cell activity and/or action by binding to Wnt receptor(s), such as the FZD/LRP receptor complex. Once activated by binding of the Wnt ligand, the Wnt receptor(s) will activate one or more intracellular signaling pathways. Three Wnt signaling pathways are classically recognized: the canonical (i.e., mediated by β-catenin activation as a transcriptional co-activator) Wnt pathway, the non-canonical planar cell polarity pathway, and the non-canonical Wnt/calcium pathway. All three pathways are typically activated by binding of a Wnt ligand to a FZD receptor. However, the recruitment of the LRP receptor appears to be a prerequisite for inducing canonical (or β-catenin-dependent) Wnt signaling. As known in the art, in the absence of a Wnt/FZD/LRP-complex ("inactive canonical Wnt signaling"), β-catenin is phosphorylated in the cytoplasm by Casein Kinase and glycogen synthase kinase-3 (GSK-3). The interaction between these kinases and β-catenin is facilitated by the scaffolding proteins, Axin and adenomatous polyposis coli (APC). Together, these proteins form a 'degradation complex', which allows phosphorylated β-catenin to be recognized by beta-transducin repeat-containing protein (β-TrCP), targeted for ubiquitination, and degraded by the proteasome. Active canonical (or beta-catenin-dependent) Wnt signaling involves binding of Wnt ligands to a receptor complex of FZD and LRP on the cell surface. During signaling, FZD cooperates with LRP in such a way that binding of the Wnt protein leads to dimerization of the two receptors. It is theorized that this dimerization leads to a conformational change of the FZD and LRP receptors. As a consequence, the cytoplasmic tail of LRP recruits and binds to the scaffold protein Axin in a phosphorylation-dependent manner and leads to formation of a complex involving DVL, Axin, and GSK3. Multimers of receptor-bound DVL and Axin molecules might support the formation of the LRP-FZD dimer. As a result of the recruitment of GSK to the cell membrane, β-catenin phosphorylation is inhibited, releasing β-catenin from the degradation complex and allowing β-catenin to accumulate in the cytoplasm. The accumulation of β-catenin in the cytoplasm allows to β-catenin to enter the nucleus and to interact with TCF/LEF transcription factors.

The present inventors have identified Wnt7-specific RECK/GPR124/Frizzled/LRP-mediated signaling, in which Wnt7 binds specifically to Reck in a FZD-independent manner and GPR124, a RECK binding partner, bridges RECK-bound Wnt7 to the FZD/LRP complex via intracellular DVL scaffolds, thereby assembling Wnt7-ligand specific RECK/GPR124/FZD/LRP signalosomes and activating canonical Wnt signaling.

In view of the above, the skilled person will understand that, as is typically the case for Wnt signaling mediated by the FZD and LRP polypeptides, an FZD/LRP complex might not be formed on a cell's membrane in the absence of or independently of an extracellular agent capable of activating Wnt signaling through said FZD/LRP complex. In other words, the agent may play an active role in assembling or organizing FZD and LRP polypeptides into the FZD/LRP complex, such as by means of protein-protein interactions between the agent and each of FZD and LRP. This results in the formation of the FZD/LRP complex and activation of Wnt signaling mediated by the complex.

Similarly, a GPR124/RECK/FZD/LRP receptor complex might not be formed on a cell's membrane in the absence of or independently of an extracellular agent capable of activating Wnt signaling through said GPR124/RECK/FZD/LRP complex. In other words, the agent may play an active role in assembling or organizing two or more of GPR124, RECK, FZD and LRP polypeptides into the GPR124/RECK/FZD/LRP complex, such as by means of protein-protein interactions between the agent and each of said two or more of GPR124, RECK, FZD and LRP. This results in the formation of the GPR124/RECK/FZD/LRP complex and activation of Wnt signaling mediated by the complex.

Accordingly, the phrase "an agent capable of activating Gpr124/Reck/Frizzled/LRP-mediated Wnt signaling" refers to the ability of the agent to induce Wnt signaling through the Gpr124, Reck, Frizzled and LRP polypeptides. The phrase "an agent capable of activating Gpr124/Reck/Frizzled/LRP-mediated Wnt signaling" does not necessarily imply the existence of a Gpr124/Reck/Frizzled/LRP receptor complex prior to contacting a cell expressing Gpr124, Reck, Frizzled and LRP with the agent. For example and without limitation, the agent may contribute to or facilitate the formation or assembly of a Gpr124/Reck/Frizzled/LRP signaling complex, thus activating Wnt signaling mediated by said complex. Similarly, a phrase "an agent capable of activating Frizzled/LRP-mediated Wnt signaling" refers to the ability of the agent to induce Wnt signaling through the Frizzled and LRP polypeptides. The phrase "an agent capable of activating Frizzled/LRP-mediated Wnt signaling" would not necessarily imply the existence of a Frizzled/LRP receptor complex prior to contacting a cell expressing Frizzled and LRP with such agent. For example and without limitation, such agent might contribute to or facilitate the formation or assembly of a Frizzled/LRP signaling complex, thus activating Wnt signaling mediated by said complex. The phrase "said agent does not activate Frizzled/LRP-mediated Wnt signaling in the absence of Reck and/or Gpr124" does not necessarily imply the existence of a Frizzled/LRP receptor complex in a cell expressing Frizzled and LRP but not Reck and/or Gpr124. For example and without limitation, the agent may fail to contribute to or facilitate the formation or assembly of a Frizzled/LRP signaling complex in such cell, thus failing to activate Wnt signaling mediated by said complex.

The skilled person shall further appreciate that a GPR124/RECK/FZD/LRP receptor complex as envisaged herein may include further component(s), which may or need not functionally modulate the complex. For example, the complex may include Dishevelled (Dvl), forming intracellular scaffolds capable of bridging GPR124 and Frizzled.

In particular embodiments, the cell expressing—GPR124, RECK, FZD and LRP polypeptides at its plasma membrane and containing the downstream members of the Wnt/β-catenin signaling pathway is a cell naturally expressing all GPR124, RECK, FZD and LRP polypeptides at the cell surface, such as a cerebral endothelial cell. In further embodiments, the cell expressing the GPR124, RECK, FZD and LRP polypeptides at its plasma membrane and containing the downstream members of the Wnt/β-catenin signaling pathway is a cell modified (e.g., genetically engineered) in such a way that it expresses all GPR124, RECK, FZD and LRP polypeptides at its surface. For example, the cell may be a cultured cell naturally expressing FZD and LRP but not naturally expressing GPR124 and RECK, and genetically engineered to express the GPR124 and RECK polypeptides (e.g., stably or transiently transfected with expressible nucleic acid(s) encoding said GPR124 and RECK polypeptides. Preferably, the cell is a mammalian cell, more preferably a human cell.

In particular embodiments, the capability of the agent to activate GPR124/RECK/Frizzled/LRP-mediated Wnt signaling, but not activate Frizzled/LRP-mediated Wnt signaling in the absence of RECK and/or GPR124, denotes the capability of the agent to activate canonical Wnt signaling in the presence of RECK and GPR124, but not in the absence of RECK and/or GPR124.

The phrase "the presence of RECK and GPR124" refers to the occurrence of the RECK and GPR124 polypeptides at or close to the cell membrane, preferably in close mutual proximity with the Frizzled and LRP polypeptides. The close mutual proximity can facilitate the formation of the GPR124/RECK/Frizzled/LRP receptor complex under conditions conducive thereto, such as when an agent as taught herein is externally supplied to a cell. On the other hand, the phrase "the absence of RECK and/or GPR124" refers to lack or non-occurrence of the RECK and/or GPR124 polypeptides at the cell membrane. Absence of RECK and/or GPR124 at or close to the cell membrane may occur when a cell does not express, translate, or correctly translocate RECK and/or GPR124. The absence of RECK and/or GPR124 need not denote the complete absence of the RECK and/or GPR124 polypeptide at the cell membrane, but may for example refer to an amount of RECK and/or GPR124 polypeptide which is not detectable by, or falls below the sensitivity range of, conventional protein detection or quantification assays known by the person skilled in the art, such as for example immunoblotting, immunocytochemistry or immunofluorescence.

In particular embodiments, the capability of the agent to activate GPR124/RECK/Frizzled/LRP-mediated Wnt signaling, but not activate Frizzled/LRP-mediated Wnt signaling in the absence of RECK and/or GPR124, denotes the capability of the agent to activate Wnt signalling in cells capable of mediating Wnt signalling by the GPR124/RECK/Frizzled/LRP receptor complex, but not in cells capable of Frizzled/LRP-mediated Wnt signaling which do not express GPR124 and/or RECK.

Cells capable of mediating Wnt signaling by the GPR124/RECK/Frizzled/LRP receptor complex may be cells naturally expressing all cellular components required for GPR124/RECK/Frizzled/LRP-mediated Wnt signaling, such as cerebral endothelial cells or cell lines. Cells capable of mediating Wnt signaling by the GPR124/RECK/Frizzled/LRP receptor complex may also be cells which naturally express none or not all of the cellular components required for GPR124/RECK/Frizzled/LRP-mediated Wnt signaling, which may be modified such as genetically engineered in order to compensate for the missing cellular components required for GPR124/RECK/Frizzled/LRP-mediated Wnt signaling. Such modifications are known in the art and are described elsewhere herein.

Cells capable of mediating Wnt signaling by the GPR124/RECK/Frizzled/LRP receptor complex may be vertebrate cells or cell lines. Non-limiting examples include human embryonic kidney 293 T (HEK239T), human umbilical vein endothelial cells (HUVEC), human dermal microvascular endothelial cells (HDMVEC), human coronary artery endothelial cells (HCAEC), human aortic endothelial cells (HAEC), human brain microvascular endothelial cells (HBMECs), Bend3 cells, Bend5 cells, or hCMEC/D3 cells. HEK293T cells may be obtained from public collections maintained for example by American Type Culture Collection (ATCC) (10801 University Blvd. Manassas, Va. 20110-2209, USA), including without limitation, HEK293T with ATCC acc. No. CRL-3216.

In particular embodiments, the capability of the agent to activate GPR124/RECK/Frizzled/LRP-mediated Wnt signaling, but not activate Frizzled/LRP-mediated Wnt signaling in the absence of RECK and/or GPR124, denotes the capability of the agent to activate Wnt signalling in cells expressing GPR124, RECK, FZ and LRP, but not in cells expressing FZ and LRP but not expressing GPR124 and/or RECK, wherein the cells expressing GPR124, RECK, FZ and LRP and the cells expressing FZ and LRP but not expressing GPR124 and/or RECK are otherwise substantially identical.

In particular embodiments, the capability of the agent to activate GPR124/RECK/Frizzled/LRP-mediated Wnt signaling, but not activate Frizzled/LRP-mediated Wnt signaling in the absence of RECK and/or GPR124, denotes the capability of the agent to activate Wnt signalling in mouse or human brain vascular endothelial cells or cell lines, while not activating Wnt-signalling in mouse or human brain vascular endothelial cells or cell lines in which the RECK and/or GPR124 gene is knocked-out. Determination of the activation of Wnt signalling is known in the art and can be performed as described elsewhere herein. Suitable endothelial cells include for example human brain microvascular endothelial cells (HBMECs), Bend3 cells, Bend5 cells or hCMEC/D3 cells. HBMECs may be obtained from public collections maintained for example by ATCC, including without limitation, HBEC-5i with ATCC acc. no. CRL-3245. Bend3 cells may be obtained from public collections maintained for example by ATCC, including without limitation, bEnd.3 with ATCC acc. No. CRL-2299.

In particular embodiments, the capability of the agent to activate GPR124/RECK/Frizzled/LRP-mediated Wnt signaling, but not activate Frizzled/LRP-mediated Wnt signaling in the absence of RECK and/or GPR124, denotes the capability of the agent to restore the brain vasculature and/or blood-brain barrier in Wnt7aa$^{-/-}$ zebrafish (*Danio rerio*) when being transgenically expressed in the endothelium of said zebrafish, while microinjection of mRNA encoding the agent in a wild-type zebrafish embryo does not induce a posteriorization phenotype, preferably wherein mRNA is injected at a dose of 1 pg to 100 pg, or while microinjection of mRNA encoding the agent in a wild-type *Xenopus* embryo does not induce axis duplication.

The capability of the agent to restore the brain vasculature and/or blood-brain barrier in Wnt7aa$^{-/-}$ zebrafish when being transgenically expressed in the endothelium of said zebrafish can be determined by any method known in the art. For example, restoration of the brain vasculature and/or blood-brain barrier can be evaluated by determining the amount of hindbrain central arteries (CtAs), the aggregate cerebral capillary length, the mean vessel size and/or the average capillary branches. Determining the expression of GLUT1 in the brain region of the Wnt7aa$^{-/-}$ zebrafish transgenically expressing the agent as taught herein (e.g. using in situ hybridization or immunohistochemistry) can be used to visualize the brain vasculature in said zebrafish. Subsequently, the GLUT1 expression pattern in the brain region of the Wnt7aa$^{-/-}$ zebrafish transgenically expressing the agent as taught herein can be compared to the GLUT1 expression pattern in the brain region of a control, such as a wild-type, zebrafish.

In particular embodiments, the brain vasculature and blood-brain barrier of the Wnt7aa$^{-/-}$ zebrafish transgenically expressing the agent as taught herein is considered to be restored if the amount of hindbrain CtAs in Wnt7aa$^{-/-}$ zebrafish transgenically expressing the agent as taught herein is at least 30%, at least 40%, at least 50%, at least 60%, at least 70%, at least 80%, at least 90%, at least 95%, or at least 99% of the amount of hindbrain CtAs in a wild-type zebrafish.

Methods of generating Wnt7aa$^{-/-}$ zebrafish and transgenically expressing an agent in the endothelium of a zebrafish are well known in the art, for example, using CRISPR/Cas-directed gene editing, such as described in Shankaran et al., CRISPR/Cas9-directed gene editing for the generation of loss-of-function mutants in high-throughput zebrafish $F_0$ screens, Curr Protoc Mol Biol., 119:31.9.1-31.9.22 (2017).

Microinjection of mRNA in a zebrafish embryo, preferably a one to four-cell stage zebrafish embryo, as well as the evaluation of the occurrence or absence of a phenotype in zebrafish are well known in the art, for example see Rosen et al., Microinjection of zebrafish embryos to analyse gene function, J Vis Exp. (25): 1115 (2009). The posteriorization phenotype in zebrafish includes posteriorization of the anterior neuroectoderm during gastrulation, loss of forebrain and loss of the eye structure in zebrafish (van de Water et al., Ectopic Wnt signal determines the eyeless phenotype of zebrafish masterblind mutant. Development. 128(20):3877-3888 (2001)).

Evaluation of the occurrence or absence axis duplication upon injection of an agent in a *Xenopus* embryo is well known in the art, for example see Kuhl et al., Dorsal axis duplication as a functional readout for Wnt activity. Methods Mol Biol. 469:467-476 (2008).

As used herein, the term "agent" broadly refers to any chemical (e.g., inorganic or organic), biochemical or biological substance, molecule or macromolecule (e.g., biological macromolecule), a combination or mixture thereof, a sample of undetermined composition, or an extract made from biological materials such as bacteria, fungi, plants, or animal cells or tissues. Preferred though non-limiting "agents" include nucleic acids, oligonucleotides, ribozymes, peptides, polypeptides, proteins, peptidomimetics, antibodies, antibody fragments, antibody-like protein scaffolds, aptamers, photoaptamers, spiegelmers, chemical substances, preferably organic molecules, more preferably small organic molecules, lipids, carbohydrates, polysaccharides, etc., and any combinations thereof. Depending on the context, the term "agent" may denote a "therapeutic agent" or "drug", useful for or used in the treatment, cure, prevention, or diagnosis of a disease.

In particular embodiments, the agent as disclosed herein comprises or is selected from a group consisting of a chemical substance, an antibody, an antibody fragment, an antibody-like protein scaffold, a protein or polypeptide, a peptide, a peptidomimetic, an aptamer, a photoaptamer, a spiegelmer and a nucleic acid, preferably wherein said agent comprises is a protein or polypeptide.

The agent as disclosed herein may comprise a combination of two or more of a chemical substance, an antibody, an antibody fragment, an antibody-like protein scaffold, a protein or polypeptide, a peptide, a peptidomimetic, an aptamer, a photoaptamer, a spiegelmer and a nucleic acid. For example, the agent as disclosed herein may comprise a combination of one or more polypeptide regions and one or more non-polypeptide regions.

In particular embodiments, the agent as disclosed herein comprises or is selected from a group consisting of a protein, polypeptide, or a peptide.

As used herein, the term "chemical substance" is used in its broadest sense and generally refers to any substantially pure substance that has a constant chemical composition and characteristic properties. The chemical substance may be an organic molecule, preferably a small organic molecule. The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da.

The term "antibody" is used herein in its broadest sense and generally refers to any immunologic binding agent, such as a whole antibody, including without limitation a chimeric, humanized, human, recombinant, transgenic, grafted and single chain antibody, and the like, or any fusion proteins, conjugates, fragments, or derivatives thereof that contain one or more domains that selectively bind to an antigen of interest. The term antibody thereby includes a whole immunoglobulin molecule, a monoclonal antibody, a chimeric antibody, a humanized antibody, a human antibody, or an immunologically effective fragment of any of these. The term thus specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest), as well as multivalent and/or multi-specific composites of such fragments. The term "antibody" is not only inclusive of antibodies generated by methods comprising immunisation, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro, in cell culture, or in vivo.

The term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as VHH domains or VH/VL domains, respectively). In addition, the term "sequence" as used herein (for example in terms like "immunoglobulin sequence", "antibody sequence", "variable domain sequence", "VHH sequence" or "protein sequence"), should generally be understood to include both the relevant amino acid sequence as well as nucleic acid sequences or nucleotide sequences encoding the same, unless the context requires a more limited interpretation.

The term "epitope" includes any polypeptide determinant capable of specifically binding to an immunoglobulin or T-cell receptor. Epitope determinants may include chemically active surface groupings of molecules such as amino acids, sugar side chains, phosphoryl, or sulfonyl, and may have specific three dimensional structural characteristics, and/or specific charge characteristics. An epitope is a region of an antigen that is bound by an antibody. An antibody is said to specifically bind an antigen when it preferentially recognizes its target antigen in a complex mixture of proteins and/or macromolecules.

The terms "binding region", "binding site" or "interaction site" shall herein have the meaning of a particular site, part, domain or stretch of amino acid residues that is responsible for binding to an antigen of interest. Such binding region essentially consists of specific amino acid residues of the antibodies described herein, which residues are in contact with the target molecule.

The term "specificity" refers to the number of different types of antigens or antigenic determinants to which a particular antigen-binding molecule or antigen-binding protein (such as an antibody) molecule can bind. The specificity of an antigen-binding protein can be determined based on affinity and/or avidity. The affinity, represented by the equilibrium constant for the dissociation of an antigen with an antigen-binding protein (KD), is a measure for the binding strength between an antigenic determinant and an antigen-binding site on the antigen-binding protein: the lesser the value of the KD, the stronger the binding strength between an antigenic determinant and the antigen-binding molecule (alternatively, the affinity can also be expressed as the affinity constant (KA), which is 1/KD). As will be clear to the skilled person, affinity can be determined in a manner known per se, depending on the specific antigen of interest. Avidity is the measure of the strength of binding between an antigen-binding molecule (such as an antibody) and the pertinent antigen. Avidity is related to both the affinity between an antigenic determinant and its antigen binding site on the antigen-binding molecule and the number of pertinent binding sites present on the antigen-binding molecule. Typically, antigen-binding proteins (such as antibodies) will bind with a dissociation constant (KD) of $10^{-5}$ to $10^{-12}$ moles/liter (M) or less, and preferably $10^{-7}$ to $10^{-12}$ moles/liter (M) or less and more preferably $10^{-8}$ to $10^{-12}$ moles/liter, and/or with an association constant (KA) of at least $10^7$ $M^{-1}$, preferably at least $10^8$ $M^{-1}$, more preferably at least $10^9$ $M^{-1}$, such as at least $10^{12}$ $M^{-1}$. Any KD value greater than $10^{-4}$ M is generally considered to indicate non-specific binding. Preferably, an antibody will bind to the desired antigen with an KD less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art.

A full-length antibody as it exists naturally is an immunoglobulin molecule comprising 2 heavy (H) chains and 2 light (L) chains interconnected by disulfide bonds. The amino terminal portion of each chain includes a variable region of about 100-110 amino acids primarily responsible for antigen recognition via the complementarity determining regions (CDRs) contained therein. The carboxy-terminal portion of each chain defines a constant region primarily responsible for effector function.

The CDRs are interspersed with regions that are more conserved, termed framework regions (FR). Each light chain variable region (LCVR) and heavy chain variable region (HCVR) is composed of 3 CDRs and 4 FRs, arranged from amino-terminus to carboxy-terminus in the following order: FR1, CDR1, FR2, CDR2, FR3, CDR3, FR4. The 3 CDRs of the light chain are referred to as "LCDR1, LCDR2, and LCDR3" and the 3 CDRs of the heavy chain are referred to as "HCDR1, HCDR2, and HCDR3." The CDRs contain most of the residues which form specific interactions with the antigen. The numbering and positioning of CDR amino acid residues within the LCVR and HCVR regions is in accordance with the well-known Kabat numbering convention, which refers to a system of numbering amino acid residues which are more variable (i.e., hypervariable) than other amino acid residues in the heavy and light chain regions of an antibody (Kabat, et al., Ann. NY Acad. Sci. 190:382-93 (1971); Kabat, et al., Sequences of Proteins of Immunological Interest, Fifth Edition, U.S. Department of Health and Human Services, NIH Publication No. 91-3242 (1991)). The positioning of CDRs in the variable region of an antibody follows Kabat numbering or simply, "Kabat."

Light chains are classified as kappa or lambda, and are characterized by a particular constant region as known in the art. Heavy chains are classified as gamma, mu, alpha, delta, or epsilon, and define the isotype of an antibody as IgG, IgM, IgA, IgD, or IgE, respectively. IgG antibodies can be further divided into subclasses, e.g., IgG1, IgG2, IgG3, IgG4. Each heavy chain type is characterized by a particular constant region with a sequence well known in the art.

In certain embodiments, an antibody may be any of IgA, IgD, IgE, IgG and IgM classes, and preferably IgG class antibody.

In certain embodiments, the antibody may be a polyclonal antibody, e.g., an antiserum or immunoglobulins purified there from (e.g., affinity-purified).

In other embodiments, the antibody may be a monoclonal antibody or a mixture of monoclonal antibodies. Monoclonal antibodies can target a particular antigen or a particular epitope within an antigen with greater selectivity and reproducibility.

As used herein, the term "monoclonal antibody" refers to an antibody that is derived from a single copy or clone including, for example, any eukaryotic, prokaryotic, or phage clone, and not the method by which it is produced. Monoclonal antibodies preferably exist in a homogeneous or substantially homogeneous population. Monoclonal antibodies and antigen-binding fragments thereof of the present invention can be produced, for example, by recombinant technologies, phage display technologies, synthetic technologies, e.g., CDR-grafting, or combinations of such technologies, or other technologies known in the art.

By means of example and not limitation, monoclonal antibodies may be made by the hybridoma method first described by Kohler et al. 1975 (Nature 256: 495), or may be made by recombinant DNA methods (e.g., as in U.S. Pat. No. 4,816,567). Monoclonal antibodies may also be made using phage antibody libraries using techniques as described by Clackson et al. 1991 (Nature 352: 624-628) and Marks et al. 1991 (J Mol Biol 222: 581-597).

These latter techniques are based on the phage display technology as described inter alia in U.S. Pat. Nos. 5,837,500, 5,571,698, 5,223,409, 7,118,879, 7,208,293 and 7,413,537. Briefly, therapeutic candidate molecules, e.g., human antibody fragments (e.g., Fabs), peptides, and small proteins, are displayed on the surface of a small bacterial virus called a bacteriophage (or phage). A collection of displayed molecules is known as a library. Phage display enables to search through these libraries to identify molecules that bind, preferably with high specificity and/or affinity, to targets of interest, e.g. therapeutic targets. Non-limiting examples of phage antibody libraries include HuCAL® (Human Combinatorial Antibody Library, Morphosys), Ylanthia® (Morphosys), the human Fab fragment libraries described in WO200070023, and the macaque antibody library as described in WO 1996040878. The Human Combinatorial Antibody Library (Morphosys) has been prepared as described in WO 199708320 using synthetic consensus sequences which cover the structural repertoire of antibodies encoded in the human genome.

The term "antibody fragment" or "antigen-binding moiety" comprises a portion or region of a full length antibody, generally the antigen binding or variable domain thereof. Examples of antibody fragments include Fab, Fab', F(ab)2, Fv, scFv fragments, single domain (sd)Fv, such as $V_H$ domains, $V_L$ domains and $V_{HH}$ domains, diabodies, linear antibodies, single-chain antibody molecules, in particular heavy-chain antibodies; and multivalent and/or multispecific antibodies formed from antibody fragment(s), e.g., dibodies, tribodies, and multibodies. The above designations Fab, Fab', F(ab')2, Fv, scFv etc. are intended to have their art-established meaning.

The term "antigen-binding portion" or "antigen-binding region" refers to one or more fragments of an antibody that retain the ability to specifically bind to an antigen. It has been shown that the antigen-binding function of an antibody may be performed by fragments of a full-length antibody. These may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CHI domains; (ii) a F(ab')2 fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al., Nature, 341: 544-546 (1989); PCT publication WO 90/05144), which comprises a single variable domain; and (vi) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain Fv (scFv) (Bird et al., Science, 242: 423-426 (1988); and Huston et al., Proc. Natl. Acad. Sci., 85: 5879-5883 (1988)). Such single chain antibodies are also intended to be encompassed within the term "antigen-binding portion" of an antibody. Other forms of single chain antibodies, such as diabodies are also encompassed.

Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (Holliger, et al., Proc. Natl. Acad. Sci., 90: 6444-6448 (1993); Poljak, et al., Structure 2: 1121-1123 (1994)). Such antibody binding portions are known in the art (Kontermann and Dubel eds., Antibody Engineering (2001) Springer-Verlag. New York. 790 pp. (ISBN 3-540-41354-5).

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al., Human Antibodies and Hybridomas, 6: 93-101 (1995)) and use of a cysteine residue, a marker peptide and a C-terminal polyhistidine tag to make bivalent and biotinylated scFv molecules (Kipriyanov, et al., Mol. Immunol., 31: 1047-1058 (1994)). Antibody portions, such as Fab and F(ab')2 fragments, may be prepared from whole antibodies using conventional techniques, such as papain or pepsin digestion, respectively, of whole antibodies. Moreover, antibodies, antibody portions and immunoadhesion molecules may be obtained using standard recombinant DNA techniques.

In certain embodiments, the antibody fragment may be a Nanobody®. The terms "Nanobody®" and "Nanobodies®" are trademarks of Ablynx NV (Belgium). The term "Nanobody" is well-known in the art and as used herein in its broadest sense encompasses an immunological binding agent obtained (1) by isolating the $V_{HH}$ domain of a naturally occurring heavy-chain antibody, preferably a heavy-chain antibody derived from camelids; (2) by expression of a nucleotide sequence encoding a naturally occurring $V_{HH}$ domain; (3) by "humanization" of a naturally occurring $V_{HH}$ domain or by expression of a nucleic acid encoding a such humanized $V_{HH}$ domain; (4) by "camelization" of a naturally occurring $V_H$ domain from any animal species, and in particular from a mammalian species, such as from a human being, or by expression of a nucleic acid encoding such a camelized $V_H$ domain; (5) by "camelisation" of a "domain antibody" or "dAb" as described in the art, or by expression of a nucleic acid encoding such a camelized dAb; (6) by using synthetic or semi-synthetic techniques for preparing proteins, polypeptides or other amino acid sequences known per se; (7) by preparing a nucleic acid encoding a Nanobody using techniques for nucleic acid synthesis known per se, followed by expression of the nucleic acid thus obtained; and/or (8) by any combination of one or more of the foregoing. "Camelids" as used herein comprise old world camelids (*Camelus bactrianus* and *Camelus dromaderius*) and new world camelids (for example *Lama paccos, Lama glama* and *Lama vicugna*).

The amino acid sequence and structure of a Nanobody can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively. The total number of amino acid residues in a Nanobody can be in the region of 110-120, and preferably 112-115. It should however be noted that parts, fragments, analogs or derivatives of a Nanobody are not particularly limited as to their length and/or size, as long as such parts, fragments, analogs or derivatives meet the further requirements outlined herein and are preferably suitable for the purposes described herein.

For a general description of heavy chain antibodies and the variable domains thereof, reference is inter alia made to the following references, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and applicant; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551 by applicant and the further published patent applications by applicant; Hamers-Casterman et al., Nature 1993 Jun. 3; 363 (6428): 446-8; Davies and Riechmann, FEBS Lett. 1994 Feb. 21; 339(3): 285-90; Muyldermans et al., Protein Eng. 1994 September; 7(9): 1129-3; Davies and Riechmann, Biotechnology (NY) 1995 May; 13(5): 475-9; Gharoudi et al., 9th Forum of Applied Biotechnology, Med. Fac. Landbouw Univ. Gent. 1995; 60/4a part I: 2097-2100; Davies and Riechmann, Protein Eng. 1996 June; 9(6): 531-7; Desmyter et al., Nat Struct Biol. 1996 September; 3(9): 803-11; Sheriff et al., Nat Struct Biol. 1996 September; 3(9): 733-6; Spinelli et al., Nat Struct Biol. 1996 September; 3(9): 752-7; Arbabi Ghahroudi et al., FEBS Lett. 1997 Sep. 15; 414(3): 521-6; Vu et al., MoI Immunol. 1997 November-December; 34(16-17): 1121-31; Atarhouch et al., Journal of Camel Practice and Research 1997; 4: 177-182; Nguyen et al., J. MoI. Biol. 1998 Jan. 23; 275(3): 413-8; Lauwereys et al., EMBO J. 1998 Jul 1; 17(13): 3512-20; Frenken et al., Res Immunol. 1998 July-August; 149(6): 589-99; Transue et al., Proteins 1998 Sep. 1; 32(4): 515-22; Muyldermans and Lauwereys, J. MoI. Recognit. 1999 March-April; 12 (2): 131-40; van der Linden et al., Biochim. Biophys. Acta 1999 Apr. 12; 1431(1): 37-46; Decanniere et al., Structure Fold. Des. 1999 Apr. 15; 7(4): 361-70; Ngyuen et al., MoI. Immunol. 1999 June; 36(8): 515-24; Woolven et al., Immunogenetics 1999 October; 50 (1-2): 98-101; Riechmann and Muyldermans, J. Immunol. Methods 1999 Dec. 10; 231 (1-2): 25-38; Spinelli et al., Biochemistry 2000 Feb. 15; 39(6): 1217-22; Frenken et al., J. Biotechnol. 2000 Feb. 28; 78(1): 11-21; Nguyen et al., EMBO J. 2000 Mar. 1; 19(5): 921-30; van der Linden et al., J. Immunol. Methods 2000 Jun. 23; 240 (1-2): 185-95; Decanniere et al., J. MoI. Biol. 2000 Jun. 30; 300 (1): 83-91; van der Linden et al., J. Biotechnol. 2000 Jul 14; 80(3): 261-70; Harmsen et al., MoI. Immunol. 2000 August; 37(10): 579-90; Perez et al., Biochemistry 2001 Jan. 9; 40(1): 74-83; Conrath et al., J. Biol. Chem. 2001 Mar. 9; 276 (10): 7346-50; Muyldermans et al., Trends Biochem Sci. 2001 April; 26(4):230-5; Muyldermans S., J. Biotechnol. 2001 June; 74 (4): 277-302; Desmyter et al., J. Biol. Chem. 2001 Jul 13; 276 (28): 26285-90; Spinelli et al., J. MoI. Biol. 2001 Aug. 3; 311 (1): 123-9; Conrath et al., Antimicrob Agents Chemother. 2001 October; 45 (10): 2807-12; Decanniere et al., J. MoI. Biol. 2001 Oct. 26; 313(3): 473-8; Nguyen et al., Adv Immunol. 2001; 79: 261-96; Muruganandam et al., FASEB J. 2002 February; 16 (2): 240-2; Ewert et al., Biochemistry 2002 Mar. 19; 41 (11): 3628-36; Dumoulin et al., Protein Sci. 2002 March; 11 (3): 500-15; Cortez-Retamozo et al., Int. J. Cancer. 2002 Mar. 20; 98 (3): 456-62; Su et al., MoI. Biol. Evol. 2002 March; 19 (3): 205-15; van der Vaart J M., Methods MoI Biol. 2002; 178: 359-66; Vranken et al., Biochemistry 2002 Jul 9; 41 (27): 8570-9; Nguyen et al., Immunogenetics 2002 April; 54 (1): 39-47; Renisio et al., Proteins 2002 Jun. 1; 47 (4): 546-55; Desmyter et al., J. Biol. Chem. 2002 Jun. 28; 277 (26): 23645-50; Ledeboer et al., J. Dairy Sci. 2002 June; 85 (6): 1376-82; De Genst et al., J. Biol. Chem. 2002 Aug. 16; 277 (33): 29897-907; Ferrat et al., Biochem. J. 2002 Sep. 1; 366 (Pt 2): 415-22; Thomassen et al., Enzyme and Microbial Technol. 2002; 30: 273-8; Harmsen et al., Appl. Microbiol. Biotechnol. 2002 December; 60 (4): 449-54; Jobling et al., Nat Biotechnol. 2003 January; 21 (1): 77-80; Conrath et al., Dev. Comp. Immunol. 2003 February; 27 (2): 87-103; Pleschberger et al., Bioconjug. Chem. 2003 March-April; 14 (2): 440-8; Lah et al., J. Biol. Chem. 2003 Apr. 18; 278 (16): 14101-11; Nguyen et al., Immunology. 2003 May; 109 (1): 93-101; Joosten et al., Microb. Cell Fact. 2003 Jan. 30; 2 (1): 1; Li et al., Proteins 2003 Jul 1; 52 (1): 47-50; Loris et al., Biol Chem. 2003 Jul. 25; 278 (30): 28252-7; van Koningsbruggen et al., J. Immunol. Methods. 2003 August; 279 (1-2): 149-61; Dumoulin et al., Nature. 2003 Aug. 14; 424 (6950): 783-8; Bond et al., J. MoI. Biol. 2003 Sep. 19; 332 (3): 643-55; Yau et al., J. Immunol. Methods. 2003 Oct. 1; 281 (1-2): 161-75; Dekker et al., J. Virol. 2003 November; 77 (22): 12132-9; Meddeb-Mouelhi et al., Toxicon. 2003 December; 42 (7): 785-91; Verheesen et al., Biochim. Biophys. Acta 2003 Dec. 5; 1624 (1-3): 21-8; Zhang et al., J MoI Biol. 2004 Jan. 2; 335 (1): 49-56; Stijlemans et al., J Biol Chem. 2004 Jan. 9; 279 (2): 1256-61; Cortez-Retamozo et al., Cancer Res. 2004 Apr. 15; 64 (8): 2853-7; Spinelli et al., FEBS Lett. 2004 Apr. 23; 564 (1-2): 35-40; Pleschberger et al., Bioconjug. Chem. 2004 May-June; 15 (3): 664-71; Nicaise et al., Protein Sci. 2004 Jul; 13 (7): 1882-91; Omidfar et al., Tumour Biol. 2004 July-August; 25 (4): 179-87; Omidfar et al., Tumour Biol. 2004 September-December; 25(5-6): 296-305; Szynol et al., Antimicrob Agents Chemother. 2004 September; 48(9):3390-5; Saerens et al., J. Biol. Chem. 2004 Dec. 10; 279 (50): 51965-72; De Genst et al., J. Biol. Chem. 2004 Dec. 17; 279 (51): 53593-601; Dolk et al., Appl. Environ. Microbiol. 2005 January; 71(1): 442-50; Joosten et al., Appl Microbiol Biotechnol. 2005 January; 66(4): 384-92; Dumoulin et al., J. MoI. Biol. 2005 Feb. 25; 346 (3): 773-88; Yau et al., J Immunol Methods. 2005 February; 297 (1-2): 213-24; De Genst et al., J. Biol. Chem. 2005 Apr. 8; 280 (14): 14114-21; Huang et al., Eur. J. Hum. Genet. 2005 Apr. 13; Dolk et al., Proteins. 2005 May 15; 59 (3): 555-64; Bond et al., J. MoI. Biol. 2005 May 6; 348(3):699-709; Zarebski et al., J. Mol. Biol. 2005 Apr. 21.

In accordance with the terminology used in the above references, the variable domains present in naturally occurring heavy chain antibodies will also be referred to as "VHH domains", in order to distinguish them from the heavy chain variable domains that are present in conventional 4-chain antibodies (which will be referred to herein as "VH domains") and from the light chain variable domains that are present in conventional 4-chain antibodies (which will be referred to herein as "VL domains"). As mentioned in the prior art referred to above, VHH domains have a number of unique structural characteristics and functional properties which make isolated VHH domains (as well as Nanobodies based thereon, which share these structural characteristics and functional properties with the naturally occurring VHH domains) and proteins containing the same highly advantageous for use as functional antigen-binding domains or proteins. In particular, and without being limited thereto, VHH domains (which have been "designed" by nature to functionally bind to an antigen without the presence of, and without any interaction with, a light chain variable domain) and Nanobodies can function as a single, relatively small, functional antigen-binding structural unit, domain or protein. This distinguishes the VHH domains from the VH and VL domains of conventional 4-chain antibodies, which by themselves are generally not suited for practical application as single antigen-binding proteins or domains, but need to be combined in some form or another to provide a functional antigen-binding unit (as in for example conventional antibody fragments such as Fab fragments; in ScFv's fragments, which consist of a VH domain covalently linked to a VL domain).

In certain embodiments, the antibody fragment may be a domain antibody (dAb). For the term "dAb", reference is for example made to Ward et al. (Nature 1989 Oct. 12; 341 (6242): 544-6), to Holt et al., Trends Biotechnol., 2003, 21(11):484-490; as well as to for example WO 06/030220, WO 06/003388 and other published patent applications of Domantis Ltd. Single domain antibodies or single variable domains can be derived from certain species of shark (for example, the so-called "IgNAR domains", see for example WO 05/18629).

In further embodiments, the antibody or antibody fragment may be multispecific (such as a bispecific, trispecific, etc. antibody) comprising at least two (such as two, three, etc.) binding sites, each directed against a different antigen or antigenic determinant.

In some embodiments, the therapeutic agent may be a dual variable domain immunoglobulin (DVD-Ig™).

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), porcine, donkey, rabbit, goat, sheep, guinea pig, monkey (e.g., cynomolus monkeys), camel (e.g., *Camelus bactrianus* and *Camelus dromaderius*) also including camel heavy-chain antibodies, llama (e.g., *Lama paccos, Lama glama* or *Lama vicugna*) also including llama heavy-chain antibodies, or horse.

The term antibody as used herein also encompasses "chimeric antibodies" which originate from at least two animal species. More specifically, the term "chimeric antibody" or "chimeric antibodies" refers to antibodies which comprise heavy and light chain variable region sequences from one species and constant region sequences from another species, such as for example antibodies having murine heavy and light chain variable regions linked to human, non-human primate, canine, equine, or feline constant regions. Chimeric antibodies comprise a portion of the heavy and/or light chain that is identical to or homologous with corresponding sequences from antibodies derived from a particular species or belonging to a particular antibody class or subclass, while the remainder of the chain(s) is identical to or homologous with corresponding sequences in antibodies from another species or belonging to another antibody class or subclass, as well as fragments of such antibodies, exhibiting the desired biological activity (See e.g., U.S. Pat. No. 4,816,567; and Morrison et al., Proc. Natl. Acad. Sci. USA 81:6851-6855 (1984)). Chimeric antibodies are made through merging DNA encoding a portion, such as the Fv region, of a monoclonal antibody from one species, e.g. mouse or monkey, with the antibody-producing DNA from another species, e.g. human.

In certain embodiments, the therapeutic agent may be a "fully human antibody". As used herein, the term "fully human antibody" refers to an antibody of which the encoding genetic information is of human origin. Accordingly, the term "fully human antibody" refers to antibodies having variable and constant regions derived only from human germline immunoglobulin sequences. The term "fully human antibody" is thus not to include antibodies in which CDR sequences derived from the germline of other mammalian species, such as a mouse, have been grafted onto human framework sequences. Fully human antibodies may be derived from phage human antibody libraries as described above, or they may be obtained through immunization of transgenic mice which have been engineered to replace the murine immunoglobulin encoding region as described in Lonberg and Husznar 1995 (Int. Rev. Immunol. 13 (1): 65-93). Fully human antibodies that are made using phage display are preferably produced by recombinant expression in a human cell line resulting in antibodies with a human glycosylation pattern. Non-limiting examples of fully human antibodies are HuCAL® antibodies (Morphosys). The genetic information for constructing a HuCAL® antibody is extracted from the HuCAL® antibody library (Morphosys) and introduced into human PER.C6® cells in the form of a vector (i.e., transfection). The transfected cells translate the genetic information into protein. The protein is further modified by glycosylation and the resulting antibody molecule is finally secreted by the cells into the culture medium.

The term antibody as used herein also encompasses "humanized antibodies", which are antibodies derived from non-human species whose protein sequence have been modified so as to increase their similarity to antibodies produced naturally in humans. More particularly, the term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which non-human CDR sequences are introduced into human VH and VL sequences to replace the corresponding human CDR sequences.

The humanized antibody is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. A humanized antibody comprises substantially all, or at least one, and typically two, variable domains (Fab, Fab', F(ab') 2, FabC, Fv) in which all or substantially all of the CDR regions correspond to those of a non-human immunoglobulin (i.e., donor antibody) and all or substantially all of the framework regions are those of a human immunoglobulin consensus sequence. A humanized antibody also comprises at least a portion of an immunoglobulin constant region (Fc), typically that of a human immunoglobulin. A humanized antibody may contain both the light chain as well as at least the variable domain of a heavy chain. The antibody also may include the CHI, hinge, CH2, CH3, and CH4 regions of the heavy chain. Alternatively, a humanized antibody may only contain a humanized light chain, or a humanized heavy chain. An exemplary humanized antibody contains a humanized variable domain of a light chain and a humanized variable domain of a heavy chain.

Also, for example, humanized antibodies may be derived from conventional antibodies (i.e. an immunoglobulin molecule comprising 2 heavy (H) chains and 2 light (L) chains interconnected by disulfide bonds) from the family Camelidae, in particular from the llama (e.g., *Lama paccos, Lama glama* or *Lama vicugna*), whose variable domains exhibit a high degree of amino acid sequence identity with the variable domains of human antibodies. A suitable platform for the production of such humanized antibodies is the SIMPLE Antibody™ platform (ArGEN-X) as described in WO 2011080350.

A skilled person will understand that an antibody can include one or more amino acid deletions, additions and/or substitutions (e.g., conservative substitutions), insofar such alterations preserve its binding of the respective antigen. For example, mutations may be introduced into the antibody, in particular in the Fc region, to extend in vivo half-life without compromising immunogenicity as described in U.S. Pat. No. 8,323,962.

An antibody may also include one or more native or artificial modifications of its constituent amino acid residues (e.g., glycosylation, etc.).

Methods of producing polyclonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbour Laboratory, New York, 1988; Harlow and Lane, "Using Antibodies: A Laboratory Manual", Cold Spring Harbour Laboratory, New York, 1999, ISBN 0879695447; "Monoclonal Antibodies: A Manual of Techniques", by Zola, ed., CRC Press 1987, ISBN 0849364760; "Monoclonal Antibodies: A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

Methods for immunising animals, e.g., non-human animals such as laboratory or farm animals, using immunising antigens optionally fused to or covalently or non-covalently linked, bound or adsorbed to a presenting carrier, and preparation of antibody or cell reagents from immune sera is well-known per se and described in documents referred to elsewhere in this specification. The animals to be immunised may include any animal species, preferably warm-blooded species, more preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), porcine, donkey, rabbit, goat, sheep, guinea pig, camel, llama or horse. The term "presenting carrier" or "carrier" generally denotes an immunogenic molecule which, when bound to a second molecule, augments immune responses to the latter, usually through the provision of additional T cell epitopes. The presenting carrier may be a (poly)peptidic structure or a non-peptidic structure, such as inter alia glycans, polyethylene glycols, peptide mimetics, synthetic polymers, etc. Exemplary non-limiting carriers include human Hepatitis B virus core protein, multiple C3d domains, tetanus toxin fragment C or yeast Ty particles. Following immunization, the antibody-producing cells from the animals may be isolated and used to generate monoclonal antibody-producing hybridoma cells using techniques well-know in the art.

Methods for producing recombinant antibodies or fragments thereof need a host organism or cell. The terms "host cell" and "host organism" may suitably refer to cells or organisms encompassing both prokaryotes, such as bacteria, and eukaryotes, such as yeast, fungi, protozoan, plants and animals. Contemplated as host organisms or cells for the production of antibodies include inter alia unicellular organisms, such as bacteria (e.g., *E. coli*), and (cultured) animal cells (e.g., mammalian cells or human cells). The advantages of producing antibodies in bacteria are amongst other the relatively safe and straightforward handling of bacterial cells and the rapid replication cycles of microorganisms. Bacteria are particularly suitable for the production of antibody fragments with a simple structure. For the production of full-length immunoglobulins or more complex antibody fragments in prokaryotic cells, the bacterial cells may be transformed with at least two nucleic acids each encoding a different portion of the antibody fragment or the immunoglobulin, e.g., the heavy chain or the light chain, as described in WO 2009021548 for full-length immunoglobulins. In the bacterial cell, the genetic information encoding the antibody is read and translated into a protein. The resulting antibodies accumulate in the periplasmic space and can be harvested upon lysis of the bacterial cells. A further separation step may be performed to purify the antibodies. WO 2009021548 describes an *E. Coli*-based secretion system wherein the bacteria release the antibodies in the surrounding culture medium due to the introduction of a signal sequence into the antibody encoding construct. This enables the easy and convenient purification of the antibodies from the cell culture medium. An exemplary mammalian cell line that can be used for the production of antibodies is the Chinese hamster ovary (CHO) cell line. An exemplary human cell line suitable for the production of antibodies includes the PER.C6® cell line as deposited under ECAC no. 96022940 and described in WO 2000063403 or a derivative thereof. Human cell lines are particularly suitable for the production of fully human antibodies because they produce antibodies with a human glycosylation pattern.

Unless indicated otherwise, all methods, steps, techniques and manipulations that are not specifically described in detail can be performed and have been performed in a manner known per se, as will be clear to the skilled person. Reference is for example again made to standard handbooks as well as to the general background art referred to herein and to the further references cited therein.

The capability of activating Wnt signaling refers to the ability of the agent as disclosed herein to mimic, reproduce or approximate the signal transduction effect and/or activity of a natural Wnt ligand binding to FZD and LRP, such as to a FZD/LRP complex.

Activation of Wnt signaling may be suitably determined and/or quantitated by measuring the expression of one or more Wnt target genes, TCF reporter gene expression, beta-catenin stabilization, LRP phosphorylation, and/or translocation of Axin from cytoplasm to cell membrane as known in the art. For instance, activation of Wnt signaling may be suitably determined and/or quantitated by measuring the expression of TCF gene (e.g., by RT-PCR or any other transcript detection method), a primary output of Wnt signaling (Nature, 1997, vol. 385(6619), 829-33). For example, a TCF reporter assay (also known as TOP/FOP or TOPflash) may be used to assess changes in the transcription of TCF/LEF controlled genes. The TCF reporter assay may be a luciferase reporter assay. Further for example, activation of Wnt signaling may be suitably determined and/or quantitated by measuring the expression of c-myc (He et al., 1998, Science, 281(5382), 1509-12), n-myc (Ten Berge et al., 2008, Development, 135(19), 3247-57), LEF1 (Hovanes et al., 2001, Nat Genet, 28(1), 53-7; Filali et al., 2002, J Biol Chem, 277(36), 33398-410), or c-jun (Mann et al., 1999, Proc Natl Acad Sci USA, 96(4), 1603-8).

Alternatively, activation of Wnt signaling may be determined by measuring the location, level and/or phosphorylation status of β-catenin. A non-limiting example of such an assay is the "13-Catenin Redistribution Assay" (Thermo Scientific) which provides recombinant U2OS cells stably expressing human β-catenin fused to the C-terminus of enhanced green fluorescent protein (EGFP). The assay allows visualization and monitoring of the translocation of a GFP-β-catenin fusion protein from the membrane to the nucleus. Another way of determining activation of Wnt signaling is the visualization of Axin translocation, for example with a GFP-Axin fusion protein.

In particular embodiments, the agent as disclosed herein may be considered capable of activating (canonical) Wnt signaling if the agent enhances Wnt/β-catenin signaling at least 10-fold more, at least 20-fold more, at least 30-fold more, at least 40-fold more, at least 50-fold more, at least 100-fold more, at least 250-fold more, at least 500-fold more, at least 750-fold more, at least 1000-fold more, at least $1\times10^4$-fold more, or at least $1\times10^5$-fold more compared to Wnt/β-catenin signaling baseline or background induced by a neutral substance or negative control, for example as measured in an assay as described elsewhere herein.

In particular embodiments, the agent as disclosed herein may be considered to not activate (canonical) Wnt signaling if the agent enhances Wnt/β-catenin signaling less than 10-fold more, such as particularly at most 5-fold more or at most 2.5-fold more, or if the agent does not enhance or even reduces (e.g., 2-fold less or 5-fold less or 10-fold less) Wnt/β-catenin signaling compared to Wnt/β-catenin signaling baseline or background induced by a neutral substance or negative control, for example as measured in an assay as described elsewhere herein.

In particular embodiments, the agent as disclosed herein may be considered to activate the GPR124/RECK/Frizzled/LRP-mediated Wnt signaling, but not activate Frizzled/LRP-mediated Wnt in the absence of RECK and/or GPR124, if the GPR124/RECK/Frizzled/LRP-mediated Wnt signaling activity induced by said agent is at least 3.5-fold more, at least 5-fold more, at least 10-fold more, at least 15-fold more, at least 20-fold more, at least 25-fold more, at least 50-fold more, at least 100-fold more, at least 500-fold more, at least 1000-fold more, at least $1\times10^4$-fold more, or at least $1\times10^5$-fold more, preferably at least 50-fold more, than the Frizzled/LRP-mediated Wnt signaling activity induced by said agent, in absence of RECK and/or GPR124. Before comparing the GPR124/RECK/Frizzled/LRP-mediated Wnt signaling activity (denoted "activity 1" in this paragraph) and the Frizzled/LRP-mediated Wnt signaling activity in the absence of RECK and/or GPR124 (denoted "activity 2" in this paragraph), activity 1 and activity 2 induced by the agent may be normalized to activity 1 and activity 2 induced by wild-type Wnt7a, respectively, the latter for example set to represent 100% activity.

By means of an example, in an in vitro or in vivo cell assay system comprising 1) cells expressing GPR124, RECK, FZ and LRP and separately 2) cells expressing FZ and LRP but not expressing GPR124 and/or RECK, wherein the cells under 1) and 2) are otherwise substantially identical, the agent may be considered to activate GPR124/RECK/Frizzled/LRP-mediated Wnt signaling, but not activate Frizzled/LRP-mediated Wnt signaling in the absence of RECK and/or GPR124, when the Wnt signaling activity induced by the same quantity of said agent under substantially identical conditions is at least 3.5-fold more, 5-fold more, at least 10-fold more, at least 15-fold more, at least 20-fold more, at least 25-fold more, at least 50-fold more, at least 100-fold more, at least 500-fold more, at least 1000-fold more, at least $1\times10^4$-fold more, or at least $1\times10^5$-fold more in cells under 1) than in cells under 2). For example, the cells under 1) and 2) may be from the same primary cell source, or may be of the same cell line, and may be genetically engineered to differ in expression of GPR124 and/or RECK.

Activation of the Wnt signaling pathway may occur by promoting the close association or mutual proximity of the Frizzled and LRP polypeptides at the cell membrane, thereby forming membrane-associated hetero-oligomers comprising the Frizzled and LRP polypeptides. Upon ligand-driven formation of the Frizzled-LRP hetero-oligomer, the intracellular portion of the LRP polypeptide becomes accessible for phosphorylation, for example by CK1 and GSK-3, which greatly increases its affinity for Axin. Second, when present in a hetero-oligomer with the LRP polypeptide, the intracellular portion of the Frizzled polypeptide is able to induce the phosphorylation and recruitment of DVL. The resulting assembly of an activated LRP-FZD-DVL-Axin complex leads indirectly to the dissociation of the destruction complex of beta-catenin, thereby allowing beta-catenin to accumulate in the cytoplasm and translocate to the cell nucleus where beta-catenin may induce gene transcription.

Accordingly, in particular embodiments, the agent as disclosed herein is capable of inducing heteromerization (such as, preferably, heterodimerization) of Frizzled and LRP polypeptides at a cell membrane in the presence of RECK and GPR124, but not in the absence of RECK and/or GPR124.

In order to achieve heteromerization or close association of the Frizzled and LRP polypeptides at the cell membrane, an agent which is capable of binding concurrently both the Frizzled and the LRP polypeptide, for example by binding the extracellular portions of both the Frizzled and the LRP polypeptide, may be used.

Heteromerization of the Frizzled and LRP polypeptides at the cell membrane may be determined by any method known in the art to determine heteromerization of membrane proteins, such as visualizing the heteromerization of fluorescently labelled membrane proteins by immunofluorescence staining, fluorescence resonance energy transfer (FRET) or determining the occurrence of downstream events of heteromerization of Frizzled and LRP polypeptides, such as detecting the presence and phosphorylation of Dvl.

Accordingly, in particular embodiments, the agent as disclosed herein is capable of concurrently binding to Frizzled and LRP polypeptides at a cell membrane, in the presence of RECK and GPR124, but not in the absence of RECK and/or GPR124.

The terms "bind", "interact", "specifically bind" or "specifically interact" as used throughout this specification mean that an agent binds to or influences one or more desired molecules or analytes substantially to the exclusion of other molecules which are random or unrelated, and optionally substantially to the exclusion of other molecules that are structurally related. The terms do not necessarily require that an agent binds exclusively to its intended target(s). For example, an agent may be said to specifically bind to target(s) of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold or more greater, such as, e.g., at least about 1000-fold or more greater, at least about $1\times10^4$-fold or more greater, or at least about $1\times10^5$-fold or more greater, than its affinity for a non-target molecule.

The binding or interaction between the agent and its intended target(s) may be covalent (i.e., mediated by one or more chemical bonds that involve the sharing of electron pairs between atoms) or, more typically, non-covalent (i.e., mediated by non-covalent forces, such as for example, hydrogen bridges, dipolar interactions, van der Waals interactions, and the like). Preferably, the agent may bind to or interact with its intended target(s) with affinity constant ($K_A$) of such binding $K_A \geq 1\times10^6$ $M^{-1}$, more preferably $K_A \geq 1\times10^7$ $M^{-1}$, yet more preferably $K_A \geq 1\times10^8$ $M^{-1}$, even more preferably $K_A \geq 1\times10^9$ $M^{-1}$, and still more preferably $K_A \geq 1\times10^{10}$ $M^{-1}$ or $K_A \geq 1\times10^{11}$ $M^{-1}$, wherein $K_A = [A\_T]/[A][T]$, A denotes the agent, T denotes the intended target. Determination of $K_A$ can be carried out by methods known in the art, such as for example, using equilibrium dialysis and Scatchard plot analysis.

The binding of an agent as described herein to a target and the affinity and specificity of said binding may be determined by any methods known in the art. Non-limiting examples thereof include co-immunoprecipitation, bimolecular fluorescence complementation, affinity electrophoresis, label transfer, phage display, proximity ligation assay (PLA), Tandem affinity purification (TAP), in-silico docking and calculation of the predicted Gibbs binding energy and competition binding assays.

In particular embodiments, the agent as disclosed herein is capable of binding to one or more different Frizzled polypeptides, such as one or more Frizzled polypeptides selected from the group consisting of Fzd 1, Fzd2, Fzd3, Fzd4, Fzd5, Fzd6, Fzd7, Fzd8, Fzd9, and Fzd10. Preferably, the agent as disclosed herein may be capable of specifically binding to at least Fzd4, and optionally to one or more other Fzd; or may be capable of specifically binding to Fzd4 substantially to the exclusion of other Fzd. Fzd4 is believed to be the dominant Fzd family member in endothelial cells of the central nervous system. More preferably, the agent as disclosed herein is capable of specifically binding to human Fzd4. The agent as disclosed herein may be selective for the one or more preferred Frizzled polypeptides, for example having a specificity for the one or more preferred Frizzled polypeptides of at least 5-fold, at least 10-fold, at least 25-fold, at least 50-fold, at least 100-fold, at least 1000-fold, at least $1\times10^4$-fold, or at least $1\times10^5$-fold, compared to other non-preferred Frizzled polypeptides.

In particular embodiments, the agent as disclosed herein is capable of binding to one or more different LRP polypeptides involved in Wnt signaling. Preferably, the agent as disclosed herein is capable of binding to LRP5 and/or LRP6, e.g., any one or each of LRP5 and LRP6. More preferably, the agent as disclosed herein is capable of binding to human LRP5 and/or LRP6, e.g., any one or each of human LRP5 and human LRP6. The agent as disclosed herein may be selective for the one or more preferred LRP polypeptides, for example having a specificity for the one or more preferred LRP polypeptides of at least 5-fold, at least 10-fold, at least 25-fold, at least 50-fold, at least 100-fold, at least 1000-fold, at least $1\times10^4$-fold, or at least $1\times10^5$-fold, compared to other non-preferred LRP polypeptides.

In particular embodiments, the agent as disclosed herein is capable of binding to the GPR124 and/or the RECK polypeptide.

In particular embodiments, the agent as disclosed herein is capable of concurrently binding to Frizzled and LRP polypeptides, and in addition to the GPR124 and/or the RECK polypeptide.

In particular embodiments, the agent as disclosed herein is capable of binding to the RECK polypeptide.

In particular embodiments, the agent as disclosed herein is capable of concurrently binding to Frizzled, LRP and RECK polypeptides.

RECK is composed of five N-terminal cysteine-knot (CK) motifs or regions (i.e. CK1, CK2, CK3, CK4 and CK5), a cysteine-rich domain (CRD) and three Kazal motifs preceding a Glycosylphosphatidylinositol (GPI)-anchor site. The CK motifs, the CRD and the Kazal motifs are located extracellularly. Accordingly, the agent capable of binding to the RECK polypeptide as disclosed herein may bind the CK1 motif, CK2 motif, CK3 motif, CK4 motif, CK5 motif, CRD, and/or one or more of the Kazal motifs of the RECK polypeptide.

Present inventors found that especially the binding of the agent capable of binding to the RECK polypeptide as disclosed herein to the CK4 and/or CK5 regions of the RECK polypeptide appears important for establishing activation of Wnt signaling mediated by the GPR124/RECK/Frizzled/LRP receptor complex.

Accordingly, in particular embodiments, the agent as disclosed herein is capable of binding to the CK4 and/or CK5 regions of RECK polypeptide.

The CK4 motif spans from amino acid C216 to C263, and the CK5 motif spans from amino acid C292 to C338 of the amino acid sequence of the human RECK protein annotated under NCBI Genbank accession number NP_066934.1 as disclosed elsewhere herein. Accordingly, the CK4 motif of human RECK comprises, consists essentially of or consists of the amino acid sequence CCDRAEDHACQNACK-RILMSKKTEMEIVDGLIEGCKTQPLPQDPLWQC (SEQ ID NO: 5) and the CK5 motif of human RECK comprises, consists essentially of or consists of the amino acid sequence CCSKANTSTCRELCTKLYSMSWGNTQSWQEFDRFC-EYNPVEVSMLTC (SEQ ID NO: 6).

In particular embodiments, the agent as disclosed herein is capable of binding to the amino acid sequence of SEQ ID NO: 5 and/or the amino acid sequence of SEQ ID NO: 6.

The Frizzled receptor is a G protein-coupled receptor protein and ranges in length from about 500 to about 700 amino acids. The N-terminus is predicted to be extracellular and comprises a cysteine rich domain (CRD) of approximately 120 amino acids followed by a hydrophilic linker region of approximately 40-100 amino acids. The Frizzled receptor also comprises seven hydrophobic domains that are predicted to form transmembrane alpha-helices. The intracellular C-terminal domain has a variable length and, though the intracellular domain is overall not well conserved among different family members, it comprises a proximal KTXXXW amino acid motif (SEQ ID NO: 7), wherein X can be any amino acid, which is highly conserved in Frizzled polypeptides and which is required for canonical Wnt signaling.

The Frizzled CRD domain comprises a motif of 10 invariantly spaced cysteines and is largely conserved between the known Frizzled family members, but also in several other proteins, such as RECK, secreted frizzled related proteins (SFRPs), receptor tyrosine kinases (RTKs), and collagen α1 XVIII. The CRD domain is important for ligand (e.g. Wnt) binding to the Frizzled polypeptide, for example by recognition and/or binding of cis-unsaturated fatty acyl groups present in the ligand contact site 1 or the residues located at the Wnt ligand "index" contact site 2

In particular embodiments, the agent as disclosed herein is capable of binding to the cysteine-rich domain (CRD) of the Frizzled polypeptide. In certain embodiments, the agent as disclosed herein is capable of binding to the cis-unsaturated fatty acyl group-binding domain located within the CRD domain of the Frizzled polypeptide or the "index" contact site within the CRD The N-terminal extracellular domain of LRP is composed of four YWTD (SEQ ID NO: 8) repeat domains (or beta-propeller domains), four epidermal growth factor (EGF)-like domains and an LDLR-like domain (LDLRLD). A single YWTD repeat domain comprises six tandem YWTD sequences. The first two, most N-terminal YWPD repeat domains are predicted to bind to Wnt ligands, and the second two sets of YWPD repeat domains are predicted to bind to Dickkopf (DKK). The N-terminal extracellular domain is followed by a single membrane-spanning segment and a cytoplasmic tail harboring between one and three NPXY motifs (SEQ ID NO: 9), wherein X can be any amino acid (e.g. in LRP1, LRP2, LRP4, APOER2, LDLR, LRP9), or between one and five PPPSP motifs (SEQ ID NO: 10) (e.g. in LRP5 and LRP6).

The term "Dickkopf" or "DKK" encompasses any and all members of the DKK family, such as without limitation the known human DKK proteins including DKK1 (RefSeq Protein: NP_036374.1; GeneID: 22943), DKK2 (RefSeq Protein: NP_055236.1; GeneID: 27123), DKK3 (RefSeq Protein: NP_001317149.1; GeneID: 27122), and DKK4 (RefSeq Protein: NP_055235.1; GeneID: 27121). In certain embodiments, the terms may particularly denote DKK1.

In particular embodiments, the agent as disclosed herein is capable of binding to the extracellular domain of the LRP polypeptide.

In particular embodiments, the agent as disclosed herein is capable of binding to the DKK-binding site of the LRP polypeptide. In more particular embodiments, the agent as disclosed herein is capable of binding to the DKK1-binding site of the LRP5 and/or LRP6 polypeptide.

In particular embodiments, the agent as disclosed herein is capable of binding to the Wnt-binding site of the LRP polypeptide. In more particular embodiments, the agent as disclosed herein is capable of binding to the Wnt-binding site of the LRP5 and/or LRP6 polypeptide.

In further particular embodiments, the agent as disclosed herein is capable of binding to the DKK-binding site and the Wnt-binding site of the LRP polypeptide.

In particular embodiments, the agent as disclosed herein is capable of binding to β-propeller-EGF-like domains 1 and 2 (P1E1P2E2) and/or β-propeller-EGF-like domains 3 and 4 (P3E3P4E4) of the LRP polypeptide.

In particular embodiments, the agent as disclosed herein comprises a RECK-binding domain and a Frizzled-binding domain, and optionally a LRP-binding domain. In more particular embodiments, the agent as disclosed herein comprises a RECK-binding domain, a Frizzled-binding domain, and a LRP-binding domain.

The RECK-binding domain of the agent as disclosed herein may be any domain that is capable of binding to a RECK polypeptide at high affinity; such as binding to a RECK polypeptide with a dissociation constant (KD) of at least about $1\times10^{-6}$ M, $1\times10^{-7}$ M, at least $1\times10^{-8}$ M, at least $1\times10^{-9}$ M, at least $1\times10^{-10}$ M, at least $1\times10^{-11}$ M, or at least $1\times10^{-12}$ M. For example, KD of at least about $5\times10^{-6}$ M.

In particular embodiments, said RECK-binding domain comprises a RECK specific antibody or comprises the RECK-binding region, preferably the variable region sequence or CDRs, of one or more RECK specific antibody or antibodies. Preferably, the RECK specific antibody is directed to the extracellular portion of the RECK polypeptide, such as directed to the CK4 and/or CK5 region(s) of the RECK polypeptide. Non-limiting examples of RECK antibodies include antibodies which are known in the art and commercially available, such as from Abcam (e.g. ab88249 and ab89915 specific for human full-length RECK), Cell Signaling Technology (e.g. #3433 specific for human, mouse, rat, monkey RECK (D8C7)), Santa Cruz (e.g. sc-373929 specific for C-terminus of human RECK).

In particular embodiments, the RECK-binding domain comprises at least one, at least two, at least three, at least four, at least five or at least six CDR(s), each independently having at least 70%, at least 75%, at least 80%, at least 85%, at least 90%, at least 95%, or at least 99%, preferably 100%, sequence identity with the respective CDR(s) of a RECK specific antibody.

In particular embodiments, the RECK-binding domain is RECK specific scFv, such as scFv comprising one or more (preferably all 6) CDR(s) of a RECK specific antibody.

In particular embodiments, the RECK-binding domain is RECK specific $V_{HH}$, such as $V_{HH}$ comprising one or more (preferably all 3) CDR(s) of a RECK specific heavy chain antibody.

In particular embodiments, the RECK-binding domain of the agent as disclosed herein may comprise two or more CDR(s) each independently having at least 70%, at least 75%, at least 80%, at least 85%, at least 90%, at least 95%, or at least 99%, preferably 100%, sequence identity with the respective CDR(s) of two or more different RECK specific antibodies.

In particular embodiments, said RECK-binding domain of the agent as disclosed herein comprises, consists essentially of, consists of or is derived from (e.g., is a biologically active fragment and/or variant of) a RECK-binding polypeptide, such as a Wnt ligand or Wnt polypeptide. Preferably, the RECK-binding domain is derived from a Wnt7 polypeptide (e.g., Wnt7a or Wnt7b) as described elsewhere herein, more preferably from a human or murine Wnt7 polypeptide, even more preferably from a human Wnt7 polypeptide (e.g., human Wnt7a or human Wnt7b). For example, in certain embodiments, the RECK-binding domain may comprise, consist essentially of or consist of a RECK-binding fragment of Wnt7 (e.g., Wnt7a or Wnt7b), preferably of human or mouse Wnt7, more preferably of human Wnt7 (e.g., human Wnt7a or human Wnt7b) or variant thereof. In a further example, in certain embodiments, the RECK-binding domain may comprise, consist essentially of or consist of the an amino acid sequence having at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, preferably 100%, sequence identity to the amino acid sequence VEPVRASRNKRPTFLKIKKPLSYRKPMDT (SEQ ID NO: 18) or VEVVRASRLRQPTFLRIKQLRSYQKPMET (SEQ ID NO: 19).

The term "Wnt", "Wnt ligand" or "Wnt polypeptide" encompasses any and all members of the Wnt family. By means of additional guidance, Table 2 presents 19 known human Wnt family members, as annotated in NCBI Genbank and Uniprot.

TABLE 2

| | NCBI Genbank | | | Uniprot |
|---|---|---|---|---|
| | GeneID | mRNA | Protein | Protein |
| WNT1 | 7471 | NM_005430.3 | NP_005421.1 | P04628.1 |
| WNT2 | 7472 | NM_003391.2 | NP_003382.1 | P09544.1 |
| WNT2B | 7482 | NM_004185.4 | NP_004176.2 | Q93097.2 |
| WNT3 | 7473 | NM_030753.4 | NP_110380.1 | P56703.2 |
| WNT3A | 89780 | NM_033131.3 | NP_149122.1 | P56704.1 |
| WNT4 | 54361 | NM_030761.4 | NP_110388.2 | P56705 |
| WNT5A | 7474 | NM_003392.4 | NP_003383.2 | P41221.1 |
| WNT5B | 81029 | NM_030775.2 | NP_110402.2 | Q9H1J7.2 |
| WNT6 | 7475 | NM_006522.3 | NP_006513.1 | Q9Y6F9 |
| WNT7A | 7476 | NM_004625.3 | NP_004616.2 | O00755.2 |
| WNT7B | 7477 | NM_058238.2 | NP_478679.1 | P56706.2 |
| WNT8A | 7478 | NM_001300939.1 | NP_001287868.1 | Q9H1J5.1 |
| WNT8B | 7479 | NM_003393.3 | NP_003384.2 | Q93098.3 |
| WNT9A | 7483 | NM_003395.2 | NP_003386.1 | O14904.2 |
| WNT9B | 7484 | NM_001320458.1 | NP_001307387.1 | E7EPC3 |
| WNT10A | 80326 | NM_025216.2 | NP_079492.2 | Q9GZT5.1 |
| WNT10B | 7480 | NM_003394.3 | NP_003385.2 | O00744.2 |
| WNT11 | 7481 | NM_004626.2 | NP_004617.2 | O96014.2 |
| WNT16 | 51384 | NM_016087.2 | NP_057171.2 | Q9UBV4.1 |

In certain embodiments, the Wnt polypeptide as employed herein is of animal origin, preferably warm-blooded animal origin, more preferably vertebrate origin, yet more preferably mammalian origin, including human origin and non-human mammalian origin, still more preferably human origin.

The Frizzled-binding domain of the agent as disclosed herein may be any domain that is capable of binding to one or more Frizzled polypeptides. Without being limited to any mechanism or theory, the affinity of the Frizzled-binding domain of the agent may be sufficiently high to activate GPR124/RECK/Frizzled/LRP-mediated Wnt signaling (i.e., when binding of the agent to RECK, of RECK to GPR124, and of GPR124 to Frizzled via DVL network ensures the proximity or presentation of the agent and more particularly its Frizzled-binding domain to Frizzled), but sufficiently low to avoid activating (for example, lack of activation or at most minimal activation, such as physiologically inconsequential degree or extent of activation) Frizzled/LRP-mediated Wnt signaling in the absence of RECK and/or GPR124. Without limitation, in certain embodiments the Frizzled-binding domain may be capable of binding to one or more Frizzled polypeptides with a KD lower than about $1\times10^{-9}$ M, lower than about $1\times10^{-8}$ M, or lower than about $1\times10^{-7}$ M, or lower than about $1\times10^{-6}$ M, such as for example between about $1\times10^{-6}$ M and about $1\times10^{-7}$ M, or between about $1\times10^{-6}$ M and about $5\times10^{-6}$ M.

In particular embodiments, the Frizzled-binding domain comprises a Frizzled specific antibody or comprises the Frizzled-binding region, preferably the variable region sequence or CDR, of one or more Frizzled specific antibody or antibodies. Preferably, the Frizzled specific antibody is directed to the extracellular portion of the Frizzled receptor, such as directed to the CRD of the Frizzled receptor. Non-limiting examples of Frizzled antibodies include antibodies which are known in the art and commercially available, such as from Biolegend (e.g. clone CH3A4a7 specific for human Frizzled 4, clone W3C4E11 specific for human Frizzled 9) and antibodies available from Abcam (e.g. ab64636 specific for Frizzled 7, ab83042 specific for human Frizzled 4, ab77379 specific for human Frizzled 7, ab75235 specific for human Frizzled 8, ab102956 specific for human Frizzled 9). For example, the Frizzled-binding domain may comprise the six CDR regions of the pan specific frizzled antibody OMP-18R5 (vantictumab).

In particular embodiments, the Frizzled-binding domain comprises at least one, at least two, at least three, at least four, at least five or at least six CDR(s), each independently having at least 70%, at least 75%, at least 80%, at least 85%, at least 90%, at least 95%, or at least 99%, preferably 100%, sequence identity with the respective CDR(s) of a Frizzled specific antibody.

In particular embodiments, the Frizzled-binding domain is Frizzled specific scFv, such as scFv comprising one or more (preferably all 6) CDR(s) of a Frizzled specific antibody.

In particular embodiments, the Frizzled-binding domain is Frizzled specific $V_{HH}$, such as $V_{HH}$ comprising one or more (preferably all 3) CDR(s) of a Frizzled specific heavy chain antibody.

In particular embodiments, the Frizzled-binding domain may comprise two or more CDR(s) each independently having at least 70%, at least 75%, at least 80%, at least 85%, at least 90%, at least 95%, or at least 99%, preferably 100%, sequence identity with the respective CDR(s) of two or more different Frizzled specific antibodies.

In particular embodiments, the Frizzled-binding domain of the agent as disclosed herein comprises, consists essentially of, consists of or is derived from (e.g., is a biologically active fragment and/or variant of) a Frizzled-binding polypeptide, such as a Wnt ligand or Wnt polypeptide. Preferably, the Frizzled-binding domain is derived from a Wnt7 polypeptide (e.g., Wnt7a or Wnt7b) as described elsewhere herein, more preferably from a human Wnt7 polypeptide (e.g., human Wnt7a or human Wnt7b).

The Frizzled binding region of a Wnt polypeptide, can be determined by modelling a three-dimensional structure of the Wnt polypeptide based on *Xenopus* Wnt8a crystallographic analysis (C. Y. Janda, D. Waghray, A. M. Levin, C. Thomas, K. C. Garcia, Science. 337, 59-64 (2012)).

XWnt8 was shown to bind Frizzled to two discontinued sites. One is called the thumb (site 1) and the other the index (site2). Critical residues of the XWnt8 thumb appear to be K182, I186, S187, G188 and W196. S187 harbors a palmitoleic acid which is critical for binding at site 1. Site 2 contacts appear to be dominated by F317, W319, C321, T322 and V323. In addition, XWnt8 could form higher-order Wnt/Fz multimers though pseudo site 3 composed of: P34, Y37, L38, S41, A42, A45, V46, T70, L71, A74, F147, G150, L151 and T153. It appears that critical amino acid residues in site 1 (especially K182, S187, G188 and W196) and site 2 (especially W319, C321 and V323) are highly conserved between the different Wnt polypeptides, while pseudo-site 3 residues are more divergent. In view thereof, the skilled person will understand that the Frizzled binding region of a Wnt polypeptide can be determined using sequence alignment with XWnt8.

In particular embodiments, the Frizzled-binding domain of the agent as disclosed herein comprises, consists essentially of or consists of the 'thumb' (site 1) of a Wnt ligand, preferably, the Frizzled-binding domain comprises an amino acid sequence XKXXXXSGXXXXXXXW (SEQ ID NO: 11), wherein X can be any amino acid, preferably wherein said amino acid sequence shows at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, preferably 100%, sequence identity to CKCHGVSGSCTTKTCW (SEQ ID NO: 12).

In preferred embodiments, the serine at amino acid position 7 of SEQ ID NO: 11 or SEQ ID NO: 12 is linked to a fatty-acid residue, preferably wherein said serine at amino acid position 7 of SEQ ID NO: 11 or SEQ ID NO: 12 is palmitoylated.

In preferred embodiments, the Frizzled-binding domain of the agent as disclosed herein does not comprise the 'index' (site 2) of a Wnt ligand. More particularly, the Frizzled-binding domain of the agent as disclosed herein preferably does not comprise an amino acid sequence WXCXV (SEQ ID NO: 13), wherein X can be any amino acid.

LRP-binding domain of the agent as disclosed herein may be any domain that is capable of binding to one or more LRP polypeptides. Without being limited to any mechanism or theory, the affinity of the LRP-binding domain of the agent may be sufficiently high to activate GPR124/RECK/Frizzled/LRP-mediated Wnt signaling (i.e., when binding of the agent to RECK, of RECK to GPR124, and of GPR124 to Frizzled via DVL network ensures the proximity or presentation of the agent and more particularly its LRP-binding domain to LRP), but sufficiently low to avoid activating (for example, lack of activation or at most minimal activation, such as physiologically inconsequential degree or extent of activation) Frizzled/LRP-mediated Wnt signaling in the absence of RECK and/or GPR124. Without limitation, in certain embodiments the LRP-binding domain may be capable of binding to one or more LRP polypeptides with a KD lower than about $1 \times 10^{-9}$ M, or lower than about $1 \times 10^{-8}$ M, or lower than about $1 \times 10^{-7}$ M, such as for example between about $1 \times 10^{-3}$ M and about $1 \times 10^{-9}$ M, or between about $1 \times 10^{-3}$ M and about $1 \times 10^{-8}$ M, or between about $1 \times 10^{-3}$ M and about $1 \times 10^{-7}$ M.

In particular embodiments, said LRP-binding domain comprises a LRP specific antibody or the LRP-binding region, preferably the variable region sequence or CDR, of one or more LRP specific antibody or antibodies. Preferably, the LRP specific antibodies are LRP5 and/or LRP6 specific antibodies. Preferably, the LRP specific antibody is directed to the extracellular portion of the LRP polypeptide, such as directed to the DKK-binding domain of LRP5 and/or LRP6. Non-limiting examples of LRP5 specific antibodies include antibodies which are known in the art and commercially available, such as from Abcam (e.g. ab36121 specific for rabbit and human LRP5), or Santa Cruz (e.g. sc-21390 specific for human LRP5). Non-limiting examples of LRP6 specific antibodies include antibodies available from Abcam (e.g. ab134146 specific for mouse, rat and human LRP6), or Santa Cruz (e.g. sc-25317 specific for human LRP6).

In particular embodiments, the LRP-binding domain comprises at least one, at least two, at least three, at least four, at least five or at least six CDR(s), each independently having at least 70%, at least 75%, at least 80%, at least 85%, at least 90%, at least 95%, or at least 99%, preferably 100%, sequence identity with the respective CDR(s) of a LRP specific antibody, preferably a LRP5 or LRP6 specific antibody.

In particular embodiments, the LRP-binding domain is LRP5 or LRP6 specific scFv, such as scFv comprising one or more (preferably all 6) CDR(s) of a LRP5 or LRP6 specific antibody.

In particular embodiments, the LRP-binding domain is LRP5 or LRP6 specific $V_{HH}$, such as $V_{HH}$ comprising one or more (preferably all 3) CDR(s) of a LRP5 or LRP6 specific heavy chain antibody.

In particular embodiments, the LRP-binding domain of the agent as disclosed herein may comprise two or more CDR(s) each independently having at least 70%, at least 75%, at least 80%, at least 85%, at least 90%, at least 95%, or at least 99%, preferably 100%, sequence identity with the respective CDR(s) of two or more different LRP specific antibodies, preferably LRP5 or LRP6 specific antibodies.

In particular embodiments, said LRP-binding domain of the agent as disclosed herein comprises, consists essentially of, consists of or is derived from (e.g., is a biologically active fragment and/or variant of) a LRP-binding polypeptide, such as a Wnt ligand or Wnt polypeptide (e.g., Wnt7a or Wnt7b), a DKK polypeptide (e.g. DKK1, DKK2, DKK3, or DKK4), Sclerostin (or SOST), or Wise (or SOSTDC1), or a variant thereof.

By means of an example, human SOST gene is annotated under NCBI Genbank (http://www.ncbi.nlm.nih.gov/) Gene ID 50964. Human SOST mRNA is annotated under NCBI Genbank accession number NM_025237.2. Nucleotides 48 (start codon) to 689 (stop codon) of NM_025237.2 constitute the SOST coding sequence. Human SOST protein sequence is annotated under NCBI Genbank accession number NP_079513.1, and Uniprot (www.uniprot.org) accession number Q9BQB4.1.

By means of an example, human WISE (or sclerostin domain containing 1 (SOSTDC1)) gene is annotated under NCBI Genbank (http://www.ncbi.nlm.nih.gov/) Gene ID 25928. Human WISE mRNA is annotated under NCBI Genbank accession number NM_015464.2. Nucleotides 182 (start codon) to 802 (stop codon) of NM_015464.2 constitute the WISE coding sequence. Human WISE protein sequence is annotated under NCBI Genbank accession number NP_056279.1, and Uniprot (www.uniprot.org) accession number Q6X4U4.2.

Preferably, the LRP-binding domain of the agent as disclosed herein is derived from a Wnt7 (e.g., Wnt7a or Wnt7b) polypeptide, more preferably from a human Wnt7 polypeptide (e.g., human Wnt7a or human Wnt7b) or a variant thereof.

In particular embodiments, said LRP-binding domain of the agent as disclosed herein comprises, consists essentially of, consists of or is derived from a DKK polypeptide, preferably a DKK1 polypeptide, or a Wnt polypeptide, preferably a Wnt7 polypeptide. In preferred embodiments, said LRP-binding domain of the agent as disclosed herein is derived from a Wnt7 polypeptide.

Ahn V. E. et al. (Ahn V. E. et al., Dev Cell. 2011 Nov. 15; 21(5):862-873) discloses that the C-terminal region of DKK1 is responsible for binding to LRP6. Accordingly, in particular embodiments, said LRP-binding domain of the agent as disclosed herein comprises, consists essentially of, consists of or is derived from the C-terminal domain of DKK1. For example, the C-terminal domain of human DKK1 (human DKK1 is annotated under NCBI Genbank accession number NP_036374.1 and Uniprot accession number O94907.1) comprises amino acid sequence MYHTKGQEGSVCLRSSDCASGLCCARHFWSKICK-PVLKEGQVCTKHRRKGSHGLEIFQRC YCGEGLSCRIQKDHHQASNSSRLHTCQRH (SEQ ID NO: 14).

On the other hand, Bourhis E. et al. (Bourhis, Eric et al., Structure, Volume 19, Issue 10, 1433-1442) identified a LRP5/6 interaction motif NXI/V, wherein X can be any amino acid, at the N-terminal end of DKK1, but also in DKK2, DKK4, WISE, and SOST. In view hereof, LRP-binding domain may comprise NXI or NXV, wherein X can be any amino acid.

Without being limited to any mechanism or theory, the affinity of the Frizzled-binding domain and the LRP-binding domain of the agent may be collectively sufficiently high to activate GPR124/RECK/Frizzled/LRP-mediatied Wnt signaling (i.e., when binding of the agent to RECK, of RECK to GPR124, and of GPR124 to Frizzled via DVL network ensures the proximity or presentation of the agent and more particularly its LRP-binding domain to LRP), but collectively sufficiently low to avoid activating (for example, lack of activation or at most minimal activation, such as physiologically inconsequential degree or extent of activation) Frizzled/LRP-mediated Wnt signaling in the absence of RECK and/or GPR124.

In particular embodiments, the agent as disclosed herein is a protein conjugate.

The terms "fusion protein" or "fusion polypeptide" and "protein conjugate" or "polypeptide conjugate" denote hybrid or chimeric molecules comprising at least two proteins or polypeptides linked, connected or joined together in a manner not normally found in nature. The molecules may be suitably denoted as amino acid-based compounds, i.e., as substances or molecules as including primarily but not necessarily exclusively amino acid residues. Any recombinantly, semi-synthetically or synthetically produced fusions or conjugates are encompassed. The fusions or conjugates may be if desired modified by glycosylation, phosphorylation, sulfonation, methylation, acetylation, lipidation, pegylation or the like.

More particularly, the terms "fusion protein" or "fusion polypeptide" denote genetic fusions, whereby two or more proteins, polypeptides or variants or fragments thereof are joined by a co-linear, covalent linkage via their individual polypeptide backbones, through genetic expression of a single contiguous polynucleotide molecule encoding the fusion product. Typically, to produce the contiguous polynucleotide molecule encoding the fusion product, two or more open reading frames (ORFs) each encoding a given polypeptide segment are joined to form a continuous longer ORF in a manner that maintains the correct reading frame for each original ORF. In the resulting recombinant fusion polypeptide the two or more polypeptide segments encoded by the original ORFs are joined in the same polypeptide molecule, whereas they are not normally so joined in nature. While the reading frame is thus made continuous throughout the fused genetic segments, the so fused polypeptide segments may be physically or spatially separated by, for example, an in-frame polypeptide or peptide linker.

More particularly, the terms "protein conjugate" or "polypeptide conjugate" denote substances or molecules in which two or more proteins, polypeptides or variants or fragments thereof are joined by non-genetic means, whereas they are not normally so joined in nature. The polypeptide segments may be joined via their individual polypeptide backbones or via one or more of their respective amino acid side chains, or one protein segment may be joined via its polypeptide backbone to an amino acid side chain of another polypeptide segment.

In particular embodiments, the RECK-binding domain, the Frizzled-binding domain and/or the LRP-binding domain of the agent as disclosed herein may be coupled by one or more linkers.

In the context of present invention, the term "coupled" as used herein is synonymous with "connected", "bound", "fused", "joined" and refers to a physical link between at least two elements or components.

As used herein, the term "linker" refers to a connecting element that serves to link other elements. The linker may be a rigid linker or a flexible linker. In particular embodiments, the linker is a covalent linker, achieving a covalent bond. The terms "covalent" or "covalent bond" refer to a chemical bond that involves the sharing of one or more electron pairs between two atoms. For many molecules, the sharing of electrons allows each atom to attain the equivalent of a full outer electron shell, corresponding to a stable electronic configuration. Covalent bonds include different types of interactions, including σ-bonds, π-bonds, metal-to-metal bonds, agostic interactions, bent bonds and three-center two-electron bonds.

In particular embodiments, the linker is a (poly) peptide linker or a non-peptide linker, such as a non-peptide polymer, such as a non-biological polymer. Preferably, the linkage(s) between the RECK-binding domain, the Frizzled-binding domain and/or the LRP-binding domain may be hydrolytically stable linkage(s), i.e., substantially stable in water at useful pH values, including in particular under physiological conditions, for an extended period of time, e.g., for days. In particular embodiments, the linker is a peptide linker of one or more amino acids.

The term "amino acid" encompasses naturally occurring amino acids, naturally encoded amino acids, non-naturally encoded amino acids, non-naturally occurring amino acids, amino acid analogues and amino acid mimetics that function in a manner similar to the naturally occurring amino acids, all in their D and L stereoisomers, provided their structure allows such stereo-isomeric forms Amino acids are referred to herein by either their name, their commonly known three letter symbols or by the one-letter symbols recommended by the IUPAC-IUB Biochemical Nomenclature Commission. The term "naturally occurring" generally refers to materials which are found in nature and are not manipulated by man. The terms "non-naturally occurring", "un-natural" and the like generally refer to a material that is not found in nature or that has been structurally modified, semi-synthesised or synthesised by man. A "naturally encoded amino acid" refers to an amino acid that is one of the 20 common amino acids or pyrrolysine, pyrroline-carboxy-lysine or selenocysteine. The 20 common amino acids are: Alanine (A or Ala), Cysteine (C or Cys), Aspartic acid (D or Asp), Glutamic acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr). A "non-naturally encoded amino acid" refers to an amino acid that is not one of the 20 common amino acids or pyrrolysine, pyrroline-carboxy-lysine or selenocysteine. The term includes without limitation amino acids that occur by a modification (such as a post-translational modification) of a naturally encoded amino acid, but are not themselves naturally incorporated into a growing polypeptide chain by the translation complex, as exemplified without limitation by N-acetylglucosaminyl-L-serine, N-acetylglucosaminyl-L-threonine, and O-phosphotyrosine. Further examples of non-naturally encoded, un-natural or modified amino acids include 2-Aminoadipic acid, 3-Aminoadipic acid, beta-Alanine, beta-Aminopropionic acid, 2-Aminobutyric acid, 4-Aminobutyric acid, piperidinic acid, 6-Aminocaproic acid, 2-Aminoheptanoic acid, 2-Aminoisobutyric acid, 3-Aminoisobutyric acid, 2-Aminopimelic acid, 2,4 Diaminobutyric acid, Desmosine, 2,2'-Diaminopimelic acid, 2,3-Diaminopropionic acid, N-Ethylglycine, N-Ethylasparagine, homoserine, homocysteine, Hydroxylysine, allo-Hydroxylysine, 3-Hydroxyproline, 4-Hydroxyproline, Isodesmosine, allo-Isoleucine, N-Methylglycine, N-Methylisoleucine, 6-N-Methyllysine, N-Methylvaline, Norvaline, Norleucine, or Ornithine. Also included are amino acid analogues, in which one or more individual atoms have been replaced either with a different atom, an isotope of the same atom, or with a different functional group. Also included are un-natural amino acids and amino acid analogues described in Ellman et al. Methods Enzymol. 1991, vol. 202, 301-36. The incorporation of non-natural amino acids into proteins or polypeptides may be advantageous in a number of different ways. For example, D-amino acid-containing polypeptides exhibit increased stability in vitro or in vivo compared to L-amino acid-containing counterparts. More specifically, D-amino acid-containing polypeptides may be more resistant to endogenous peptidases and proteases, thereby providing improved bioavailability of the agent and prolonged lifetimes in vivo.

More particularly, the peptide linker may be 1 to 50 amino acids long or 2 to 50 amino acids long or 1 to 45 amino acids long or 2 to 45 amino acids long, preferably 1 to 40 amino acids long or 2 to 40 amino acids long or 1 to 35 amino acids long or 2 to 35 amino acids long, more preferably 1 to 30 amino acids long or 2 to 30 amino acids long. Further preferably, the linker may be 5 to 25 amino acids long or 5 to 20 amino acids long. Particularly preferably, the linker may be 5 to 15 amino acids long or 7 to 15 amino acids long. Hence, in certain embodiments, the linker may be 1, 2, 3 or 4 amino acids long. In other embodiments, the linker may be 5, 6, 7, 8 or 9 amino acids long. In further embodiments, the linker may be 10, 11, 12, 13 or 14 amino acids long. In still other embodiments, the linker may be 15, 16, 17, 18 or 19 amino acids long. In further embodiments, the linker may be 20, 21, 22, 23, 24 or 25 amino acids long. In certain embodiments, the linker is 4-10 or 5-9 or 6-8 or 7 amino acids long. In other embodiments, the linker is 12-18 or 13-17 or 14-16 or 15 amino acids long.

The nature of amino acids constituting the linker is not of particular relevance so long as the biological activity of the polypeptide segments linked thereby is not substantially impaired and the linker provides for the intended spatial separation of the RECK-binding domain, the Frizzled-binding domain and/or the LRP-binding domain of the agent. Preferred linkers are essentially non-immunogenic and/or not prone to proteolytic cleavage.

In certain preferred embodiments, the peptide linker may comprise, consist essentially of or consist of amino acids selected from the group consisting of Glycine, Serine, Alanine, Threonine, and combinations thereof. In even more preferred embodiments, the linker may comprise, consist essentially of or consist of amino acids selected from the group consisting of Glycine, Serine, and combinations thereof. Such linkers provide for particularly good flexibility. In certain embodiments, the linker may consist of only Glycine residues. In certain embodiments, the linker may consist of only Serine residues.

In particular embodiments, the linker is a non-peptide linker. In preferred embodiments, the non-peptide linker may comprise, consist essentially of or consist of a non-peptide polymer. The term "non-peptide polymer" as used herein refers to a biocompatible polymer including two or more repeating units linked to each other by a covalent bond excluding the peptide bond. For example, the non-peptide polymer may be 2 to 200 units long or 2 to 100 units long or 2 to 50 units long or 2 to 45 units long or 2 to 40 units long or 2 to 35 units long or 2 to 30 units long or 5 to 25 units long or 5 to 20 units long or 5 to 15 units long. The non-peptide polymer may be selected from the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, biodegradable polymers such as PLA (poly(lactic acid) and PLGA (polylactic-glycolic acid), lipid polymers, chitins, hyaluronic acid, and combinations thereof. Particularly preferred is poly(ethylene glycol) (PEG). The molecular weight of the non-peptide polymer preferably may range from 1 to 100 kDa, and preferably 1 to 20 kDa. The non-peptide polymer may be one polymer or a combination of different types of polymers. The non-peptide polymer has reactive groups capable of binding to the RECK-binding domain, the Frizzled-binding domain and/or the LRP-binding domain which are to form the conjugate. Preferably, the non-peptide polymer has a reactive group at each end. Preferably, the reactive group is selected from the group consisting of a reactive aldehyde group, a propione aldehyde group, a butyl aldehyde group, a maleimide group and a succinimide derivative. The succinimide derivative may be succinimidyl propionate, hydroxy succinimidyl, succinimidyl carboxymethyl or succinimidyl carbonate. The reactive groups at both ends of the non-peptide polymer may be the same or different. In certain embodiments, the non-peptide polymer has a reactive aldehyde group at both ends. For example, the non-peptide polymer may possess a maleimide group at one end and, at the other end, an aldehyde group, a propionic aldehyde group or a butyl aldehyde group. When a polyethylene glycol (PEG) having a reactive hydroxy group at both ends thereof is used as the non-peptide polymer, the hydroxy group may be activated to various reactive groups by known chemical reactions, or a PEG having a commercially-available modified reactive group may be used so as to prepare the protein conjugate.

The inclusion of one or more linkers increases the spatial separation between the RECK-binding domain, the Frizzled-binding domain and/or the LRP-binding domain of the agent, which can advantageously affect the Wnt signaling activity of the agent.

In particular embodiments, the agent as disclosed herein is provided as a single chain or a multimer. To achieve multimeric forms, RECK-binding domain, Frizzled-binding domain and/or LRP-binding domain may be attached to a scaffold or backbone composed of, for example, dendrimers, antibodies or poly-L-lysine.

In particular embodiments, the agent as disclosed herein comprises a RECK-binding domain, a Frizzled-binding domain and a LRP-binding domain, wherein said RECK-binding domain, said Frizzled-binding domain, and said LRP-binding domain are derived from a Wnt7 polypeptide, such as from a Wnt7a or Wnt7b polypeptide, preferably the human Wnt polypeptide, such as from human Wnt7a or Wnt7b polypeptide.

In particular embodiments, the agent as disclosed herein comprises a RECK-binding domain, a Frizzled-binding domain and a LRP-binding domain, wherein at least one, at least two or all three binding domains are derived from a Wnt7 polypeptide, such as from a Wnt7a or Wnt7b polypeptide, preferably the human Wnt polypeptide, such as from human Wnt7a or Wnt7b polypeptide.

By means of an example, human WNT7A gene is annotated under NCBI Genbank Gene ID 7476. Human WNT7A mRNA (transcript variant 1) is annotated under NCBI Genbank accession number NM_004625.3. Nucleotides 306 (start codon) to 1355 (stop codon) of NM_004625.3 constitute the WNT7A coding sequence. Human WNT7A protein sequence is annotated under NCBI Genbank accession number NP_004616.2, and Uniprot accession number O00755.2, and is further reproduced below (SEQ ID NO: 15):

NP_004616.2 Protein Wnt-7a Precursor [*Homo sapiens*]

MNRKARRCLGHLFLSLGMVYLRIGGFSSVVALGASIICNKIPGLAPRQRA

ICQSRPDAIIVIGEGSQMGLDECQFQFRNGRWNCSALGERTVFGKELKVG

SREAAFTYAIIAAGVAHAITAACTQGNLSDCGCDKEKQGQYHRDEGWKWG

GCSADIRYGIGFAKVFVDAREIKQNARTLMNLHNNEAGRKILEENMKLEC

KCHGVSGSCTTKTCWTTLPQFRELGYVLKDKYNEAVHVEPVRASRNKRPT

FLKIKKPLSYRKPMDTDLVYIEKSPNYCEEDPVTGSVGTQGRACNKTAPQ

ASGCDLMCCGRGYNTHQYARVWQCNCKFHWCCYVKCNTCSERTEMYTCK.

By means of an example, the mature form of human Wnt7a protein (not comprising the signal peptide) comprises an amino sequence as further reproduced below (SEQ ID NO: 51):

LGASIICNKIPGLAPRQRAICQSRPDAIIVIGEGSQMGLDECQFQFRNGR

WNCSALGERTVFGKELKVGSREAAFTYAIIAAGVAHAITAACTQGNLSDC

GCDKEKQGQYHRDEGWKWGGCSADIRYGIGFAKVFVDAREIKQNARTLMN

LHNNEAGRRILEENMKLECKCHGVSGSCTTKTCWTTLPQFRELGYVLKDK

YNEAVHVEPVRASRNKRPTFLKIKKPLSYRKPMDTDLVYIEKSPNYCEED

PVTGSVGTQGRACNKTAPQASGCDLMCCGRGYNTHQYARVWQCNCKFHWC

CYVKCNTCSERTEMYTCK.

By means of an example, human WNT7B gene is annotated under NCBI Genbank Gene ID 7477. Human WNT7B mRNA (transcript variant 1) is annotated under NCBI Genbank accession number NM_058238.2. Nucleotides 375 (start codon) to 1424 (stop codon) of NM_058238.2 constitute the WNT7B coding sequence. Human WNT7B protein sequence is annotated under NCBI Genbank accession number NP_478679.1, and Uniprot accession number P56706.2, and is further reproduced below (SEQ ID NO: 16):

MHRNFRKWIFYVFLCFGVLYVKLGALSSVVALGANIICNKIPGLAPRQRA

ICQSRPDAIIVIGEGAQMGINECQYQFRFGRWNCSALGEKTVFGQELRVG

SREAAFTYAITAAGVAHAVTAACSQGNLSNCGCDREKQGYYNQAEGWKWG

GCSADVRYGIDFSRRFVDAREIKKNARRLMNLHNNEAGRKVLEDRMQLEC

KCHGVSGSCTTKTCWTTLPKFREVGHLLKEKYNAAVQVEVVRASRLRQPT

FLRIKQLRSYQKPMETDLVYIEKSPNYCEEDAATGSVGTQGRLCNRTSPG

ADGCDTMCCGRGYNTHQYTKVWQCNCKFHWCCFVKCNTCSERTEVFTCK

In particular embodiments, said RECK-binding domain comprises, consists essentially of or consists of an amino acid sequence as set forth in HVEPVRASRNKRPTFLKIK-KPLSYRKPMDTDLVYIEKSPNYC (SEQ ID NO: 17), VEPVRASRNKRPTFLKIKKPLSYRKPMDT (SEQ ID NO: 18) or VEVVRASRLRQPTFLRIKQLRSYQKPMET (SEQ ID NO: 19), or an amino acid sequence having at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% sequence identity to the amino acid sequence SEQ ID NO: 17, SEQ ID NO: 18; or SEQ ID NO: 19. In particular embodiments, said RECK-binding domain derived from a Wnt7 polypeptide comprises, consists essentially of or consists of the amino acid sequence SEQ ID NO: 17, SEQ ID NO: 18; or SEQ ID NO: 19.

In particular embodiments, said RECK-binding domain comprises, consists essentially of or consists of the amino acid sequence XXXVXAXRXXXXXFLXIXXXXXYXKXXXX (SEQ ID NO: 20), VXAXRXXXXXFLXIXXXXXYXK (SEQ ID NO: 21), XXXVXAXRXXXXXFLXXXXXXXXXKXXXX (SEQ ID NO: 22) or VXAXRXXXXXFLXXXXXXXXXK (SEQ ID NO: 23), wherein X is any amino acid, preferably wherein the amino acid sequence shows at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, preferably 100%, sequence identity to any one of SEQ ID NO: 18 or SEQ ID NO: 19.

In particular embodiments, said RECK-binding domain is derived from a Wnt7 polypeptide, and the Frizzled-binding domain and LRP-binding domain are not derived from a Wnt7 polypeptide.

In particular embodiments, said RECK-binding domain is derived from a Wnt7 polypeptide, and the Frizzled-binding domain and LRP-binding domain are derived from a Wnt polypeptide selected from the list consisting of Wnt1, Wnt2, Wnt2b, Wnt3, Wnt3a, Wnt4, Wnt5a Wnt5b, Wnt6, Wnt8a, Wnt8b, Wnt9a, Wnt9b, Wnt10a, Wnt10b, Wnt 11 and Wnt16.

In particular embodiments, the agent as disclosed herein is or consists essentially of a fragment of a Wnt7 polypeptide, such as a fragment of a Wnt7a or Wnt7b polypeptide, preferably a fragment of a human Wnt7 polypeptide, such as a fragment of a human Wnt7a or human Wnt7b polypeptide.

In particular embodiments, the fragment of the Wnt7 polypeptide has at least 30%, and preferably at least 40%, at least 50%, at least 60%, at least 70%, at least 80%, at least 90%, at least 95%, at least 99%, preferably 100%, of the GPR124/RECK/Frizzled/LRP-mediated Wnt signaling activity of the full-length Wnt7 polypeptide.

In particular embodiments, the fragment of the Wnt7 polypeptide has a GPR124/RECK/Frizzled/LRP-mediated Wnt signaling activity which is higher (e.g., 1.1-fold, 1.2-fold, 1.3-fold, 1.4-fold, 1.5-fold, 1.6-fold, 1.7-fold, 1.8-fold, 1.9-fold or 2-fold higher or even higher) than the GPR124/RECK/Frizzled/LRP-mediated Wnt signaling activity of the full-length Wnt7 polypeptide.

Present inventors have demonstrated that the N-terminal domain of Wnt7a is capable of binding to RECK and activating Wnt signaling mediated by the GPR124/RECK/Frizzled/LRP receptor complex, while not activating Wnt signaling mediated by the Frizzled/LRP receptor complex in the absence of RECK and/or GPR124.

Hence, in particular embodiments, the fragment of the Wnt7 polypeptide has Frizzled/LRP-mediated Wnt signaling activity in the absence of RECK and/or GPR124 which is at least 10-fold less, or at least 100-fold less, or at least 1000-fold less, or at least 1×10$^4$-fold less, or at least 1×10$^5$-fold less, or at least 1×10$^6$-fold less than the Frizzled/LRP-mediated Wnt signaling activity of the full-length Wnt7 polypeptide in the absence of RECK and/or GPR124.

In particular embodiments, said fragment of the Wnt7 polypeptide is or consists essentially of the N-terminal domain (NTD) of the Wnt7 polypeptide, such as the NTD of a Wnt7a or Wnt7b polypeptide, preferably the NTD of human Wnt7 polypeptide, such as human Wnt7a or Wnt7b. The N-terminal domain of the human Wnt7a or Wnt7b polypeptide typically ranges from the Leucine (L) residue at the position corresponding to position 1 in SEQ ID NO: 24 (Wnt7a) or SEQ ID NO: 25 (Wnt7b) to the cysteine (C) residue at the position corresponding to position 247 in SEQ ID NO: 24 (Wnt7a) or SEQ ID NO: 25 (Wnt7b).

In particular embodiments, said fragment of the Wnt7 polypeptide comprises at least the NTD of the Wnt7 polypeptide and does not comprise the C-terminal domain (CTD) of the Wnt7 polypeptide.

In particular embodiments, the agent as disclosed herein comprises, consists essentially of, or consists of at least 50, at least 75, at least 100, at least 125, at least 150, at least 175, at least 200, at least 225, contiguous amino acids of the NTD of human Wnt7a polypeptide, more particularly, the agent as disclosed herein comprises, consists essentially of or consists of at least 50, at least 75, at least 100, at least 125, at least 150, at least 175, at least 200, at least 225, contiguous amino acids of the amino acid sequence (SEQ ID NO: 24)
LGASIICNKIPGLAPRQRAICQSRPDAIIVIGEGSQMGLDECQFQFRNGR

WNCSALGERTVFGKELKVGSREAAFTYAIIAAGVAHAITAACTQGNLSDC

GCDKEKQGQYHRDEGWKWGGCSADIRYGIGFAKVFVDAREIKQNARTLMN

LHNNEAGRKILEENMKLECKCHGVSGSCTTKTCWTTLPQFRELGYVLKDK

YNEAVHVEPVRASRNKRPTFLKIKKPLSYRKPMDTDLVYIEKSPNYC or (SEQ ID NO: 25)
LGANIICNKIPGLAPRQRAICQSRPDAIIVIGEGAQMGINECQYQFRFGR

WNCSALGEKTVFGQELRVGSREAAFTYAITAAGVAHAVTAACSQGNLSNC

GCDREKQGYYNQAEGWKWGGCSADVRYGIDFSRRFVDAREIKKNARRLMN

LHNNEAGRKVLEDRMQLECKCHGVSGSCTTKTCWTTLPKFREVGHLLKEK

YNAAVQVEVVRASRLRQPTFLRIKQLRSYQKPMETDLVYIEKSPNYC,
preferably SEQ ID NO: 24.

In particular embodiments, the agent as disclosed herein comprises, consists essentially of, or consists of an amino acid sequence as set forth in SEQ ID NO: 24 or SEQ ID NO: 25, preferably SEQ ID NO: 24, or an amino acid sequence having at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, sequence identity to the amino acid sequence SEQ ID NO: 24 or SEQ ID NO: 25, preferably SEQ ID NO: 24.

The skilled person will understand that if it is envisaged to express and secrete the agent as taught herein by a host cell, the nucleic acid encoding the agent as taught herein preferably encodes a precursor form of the agent including an N-terminal signal peptide sequence. Accordingly, the nucleic acid may encode a fragment of the precursor polypeptide of Wnt7 (i.e. including the signal peptide), such as the precursor polypeptide of human Wnt7a or Wnt7b. In particular embodiments, the nucleic acid encodes an agent comprising, consisting essentially of, or consists of an amino acid sequence as set forth in SEQ ID NO: 24 or SEQ ID NO: 25 or an amino acid sequence having having at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% sequence identity to SEQ ID NO: 24 or SEQ ID NO: 25, wherein said amino acid sequence is preceded N-terminally by a signal peptide having an amino acid sequence MNRKARRCLGHLFLSLGMVYL-RIGGFSSVVA (SEQ ID NO: 26) or MHRNFRKWI-FYVFLCFGVLYVKLGALSSVVA (SEQ ID NO: 27), respectively. Alternatively, the nucleic acid encoding the agent as taught herein may be comprised within a vector providing for a signal peptide. The signal peptide may be a homologous or heterologous signal peptide, depending on the host cell used for production of the agent as taught herein. Furthermore, for prokaryotic expression of the agent as taught herein, a protease cleavage site motif may be present C-terminally of said signal peptide and N-terminally of the agent as taught herein.

Present inventors have demonstrated that certain variants of the human or murine Wnt7a polypeptide are as effective or more effective in activating Wnt signaling mediated by the GPR124/RECK/Frizzled/LRP receptor complex, while not activating Wnt signaling mediated by the Frizzled/LRP receptor complex in the absence of RECK and/or GPR124, compared to the wild-type human or murine Wnt7a polypeptide, respectively.

Accordingly, in particular embodiments, the agent as disclosed herein is a variant of a Wnt7 polypeptide, such as a variant of a Wnt7a or Wnt7b polypeptide. In further particular embodiments, the agent as disclosed herein is a variant of the NTD of a Wnt7a or Wnt7b polypeptide.

In certain embodiments, in such variant, the glutamine (Q) residue at the position corresponding to position 17 in SEQ ID NO: 24 or SEQ ID NO: 51; the isoleucine (I) residue at the position corresponding to position 20 in SEQ ID NO: 24 or SEQ ID NO: 51; the proline (P) residue at the position corresponding to position 25 in SEQ ID NO: 24 or SEQ ID NO: 51; the alanine (A) residue at the position corresponding to position 27 in SEQ ID NO: 24 or SEQ ID NO: 51; the isoleucine (I) residue at position corresponding to position 28 in SEQ ID NO: 24 or SEQ ID NO: 51; the glutamate (E) residue at the position corresponding to position 33 in SEQ ID NO: 24 or SEQ ID NO: 51; the methionine (M) residue at the position corresponding to position 37 in SEQ ID NO: 24 or SEQ ID NO: 51; the leucine (L) residue at the position corresponding to position 39 in SEQ ID NO: 24 or SEQ ID NO: 51; the glutamate (E) residue at the position corresponding to position 41 in SEQ ID NO: 24 or SEQ ID NO: 51; the phenylalanine (F) residue at the position corresponding to position 44 in SEQ ID NO: 24 or SEQ ID NO: 51; the arginine (R) residue at the position corresponding to position 50 in SEQ ID NO: 24 or SEQ ID NO: 51; the asparagine (N) residue at the position corresponding to position 52 in SEQ ID NO: 24 or SEQ ID NO: 51; the valine (V) residue at the position corresponding to position 68 in SEQ ID NO: 24 or SEQ ID NO: 51; the isoleucine (I) residue at the position corresponding to position 129 in SEQ ID NO: 24 or SEQ ID NO: 51; the phenylalanine (F) residue at the position corresponding to position 131 in SEQ ID NO: 24 or SEQ ID NO: 51; the lysine (K) residue at the position corresponding to position 133 in SEQ ID NO: 24 or SEQ ID NO: 51; the phenylalanine (F) residue at the position corresponding to position 135 in SEQ ID NO: 24 or SEQ ID NO: 51; the isoleucine (I) residue at the position corresponding to position 141 in SEQ ID NO: 24 or SEQ ID NO: 51; the arginine (R) residue at the position corresponding to position 146 in SEQ ID NO: 24 or SEQ ID NO: 51; the arginine (R) residue at the position corresponding to position 158 in SEQ ID NO: 24 or SEQ ID NO: 51; the lysine (K) residue at the position corresponding to position 159 in SEQ ID NO: 24 or SEQ ID NO: 51; the lysine (K) residue at the position corresponding to position 181 in SEQ ID NO: 24 or SEQ ID NO: 51; the arginine (R) residue at the position corresponding to position 191 in SEQ ID NO: 24 or SEQ ID NO: 51; the lysine (K) residue at the position corresponding to position 198 in SEQ ID NO: 24 or SEQ ID NO: 51; the lysine (K) residue at the position corresponding to position 200 in SEQ ID NO: 24 or SEQ ID NO: 51; the valine (V) residue at the position corresponding to position 205 in SEQ ID NO: 24 or SEQ ID NO: 51; the glutamate (E) residue at the position corresponding to position 208 in SEQ ID NO: 24 or SEQ ID NO: 51; the glutamate (E) residue at the position corresponding to position 208 in SEQ ID NO: 24 or SEQ ID NO: 51; the arginine (R) residue at the position corresponding to position 214 in SEQ ID NO: 24 or SEQ ID NO: 51; the lysine (K) residue at the position corresponding to position 216 in SEQ ID NO: 24 or SEQ ID NO: 51; the proline (P) residue at the position corresponding to position 218 in SEQ ID NO: 24 or SEQ ID NO: 51; the lysine (K) residue at the position corresponding to position 222 in SEQ ID NO: 24 or SEQ ID NO: 51; the isoleucine (I) residue at the position corresponding to position 223 in SEQ ID NO: 24 or SEQ ID NO: 51; the tyrosine (Y) residue at the position corresponding to position 229 in SEQ ID NO: 24 or SEQ ID NO: 51; the proline (P) residue at the position corresponding to position 232 in SEQ ID NO: 24 or SEQ ID NO: 51; the threonine (T) residue at the position corresponding to position 235 in SEQ ID NO: 24 or SEQ ID NO: 51; the glutamate (E) residue at the position corresponding to position 248 in SEQ ID NO: 24 or SEQ ID NO: 51; the arginine (R) residue at the position corresponding to position 289 in SEQ ID NO: 24 or SEQ ID NO: 51; the tryptophan (W) residue at the position corresponding to position 291 in SEQ ID NO: 24 or SEQ ID NO: 51; the threonine (T) residue at the position corresponding to position 307 in SEQ ID NO: 24 or SEQ ID NO: 51; and/or the lysine (K) residue at the position corresponding to position 318 in SEQ ID NO: 24 or SEQ ID NO: 51, is substituted by one or more (preferably not more than three, preferably not more than two, more preferably one) other amino acid residue, such as preferably but without limitation by an alanine (A) residue, an arginine (R) residue or a glutamine (Q) residue, more preferably by an alanine (A) residue. In certain embodiments, in such variant, the glutamine (Q) residue at the position corresponding to position 17 in SEQ ID NO: 24 or SEQ ID NO: 51; the isoleucine (I) residue at the position corresponding to position 20 in SEQ ID NO: 24 or SEQ ID NO: 51; the proline (P) residue at the position corresponding to position 25 in SEQ ID NO: 24 or SEQ ID NO: 51; the isoleucine (I) residue at position corresponding to position 28 in SEQ ID NO: 24 or SEQ ID NO: 51; the glutamate (E) residue at the position corresponding to position 33 in SEQ ID NO: 24 or SEQ ID NO: 51; the methionine (M) residue at the position corresponding to position 37 in SEQ ID NO: 24 or SEQ ID NO: 51; the leucine (L) residue at the position corresponding to position 39 in SEQ ID NO: 24 or SEQ ID NO: 51; the glutamate (E) residue at the position corresponding to position 41 in SEQ ID NO: 24 or SEQ ID NO: 51; the phenylalanine (F) residue at the position corresponding to position 44 in SEQ ID NO: 24 or SEQ ID NO: 51; the arginine (R) residue at the position corresponding to position 50 in SEQ ID NO: 24 or SEQ ID NO: 51; the valine (V) residue at the position corresponding to position 68 in SEQ ID NO: 24 or SEQ ID NO: 51; the isoleucine (I) residue at the position corresponding to position 129 in SEQ ID NO: 24 or SEQ ID NO: 51; the phenylalanine (F) residue at the position corresponding to position 131 in SEQ ID NO: 24 or SEQ ID NO: 51; the lysine (K) residue at the position corresponding to position 133 in SEQ ID NO: 24 or SEQ ID NO: 51; the phenylalanine (F) residue at the position corresponding to position 135 in SEQ ID NO: 24 or SEQ ID NO: 51; the isoleucine (I) residue at the position corresponding to position 141 in SEQ ID NO: 24 or SEQ ID NO: 51; the arginine (R) residue at the position corresponding to position 146 in SEQ ID NO: 24 or SEQ ID NO: 51; the arginine (R) residue at the position corresponding to position 158 in SEQ ID NO: 24 or SEQ ID NO: 51; the lysine (K) residue at the position corresponding to position 181 in SEQ ID NO: 24 or SEQ ID NO: 51; the arginine (R) residue at the position corresponding to position 191 in SEQ ID NO: 24 or SEQ ID NO: 51; the lysine (K) residue at the position corresponding to position 198 in SEQ ID NO: 24 or SEQ ID NO: 51; the lysine (K) residue at the position corresponding to position 200 in SEQ ID NO: 24 or SEQ ID NO: 51; the valine (V) residue at the position corresponding to position 205 in SEQ ID NO: 24 or SEQ ID NO: 51; the glutamate (E) residue at the position corresponding to position 208 in SEQ ID NO: 24 or SEQ ID NO: 51; the glutamate (E) residue at the position corresponding to position 208 in SEQ ID NO: 24 or SEQ ID NO: 51; the arginine (R) residue at the position corresponding to position 214 in SEQ ID NO: 24 or SEQ ID NO: 51; the lysine (K) residue at the position corresponding to position 216 in SEQ ID NO: 24 or SEQ ID NO: 51; the proline (P) residue at the position corresponding to position 218 in SEQ ID NO: 24 or SEQ ID NO: 51; the lysine (K) residue at the position corresponding to position 222 in SEQ ID NO: 24 or SEQ ID NO: 51; the isoleucine (I) residue at the position corresponding to position 223 in SEQ ID NO: 24 or SEQ ID NO: 51; the tyrosine (Y) residue at the position corresponding to position 229 in SEQ ID NO: 24 or SEQ ID NO: 51; the proline (P) residue at the position corresponding to position 232 in SEQ ID NO: 24 or SEQ ID NO: 51; the threonine (T) residue at the position corresponding to position 235 in SEQ ID NO: 24 or SEQ ID NO: 51; the glutamate (E) residue at the position corresponding to position 248 in SEQ ID NO: 24 or SEQ ID NO: 51; the arginine (R) residue at the position corresponding to position 289 in SEQ ID NO: 24 or SEQ ID NO: 51; the tryptophan (W) residue at the position corresponding to position 291 in SEQ ID NO: 24 or SEQ ID NO: 51; the threonine (T) residue at the position corresponding to position 307 in SEQ ID NO: 24 or SEQ ID NO: 51; and/or the lysine (K) residue at the position corresponding to position 318 in SEQ ID NO: 24 or SEQ ID NO: 51, is substituted by an alanine (A) residue; and/or the alanine (A) residue at the position corresponding to position 27 in SEQ ID NO: 24 or SEQ ID NO: 51 is substituted by an arginine (R) residue; and/or the asparagine (N) residue at the position corresponding to position 52 in SEQ ID NO: 24 or SEQ ID NO: 51 is substituted by a glutamine (Q) residue; and/or the lysine (K) residue at the position corresponding to position 159 in SEQ ID NO: 24 or SEQ ID NO: 51 is substituted by an alanine (A), a serine (S) or a leucine (L) residue residue.

In certain embodiments, the variant of the Wnt7 polypeptide comprises two or more (e.g., preferably two, preferably three, more preferably four) of the amino acid substitutions listed above.

In more particular embodiments, the NTD of the Wnt7a or Wnt7b polypeptide comprises two or more (e.g., preferably two, preferably three, more preferably four) of the amino acid substitutions listed above.

Hence, in particular embodiments, the agent as disclosed herein comprises, consists essentially of or consists of an amino acid sequence having at least 50%, at least 55%, at least 60%, at least 65%, at least 70%, at least 75%, at least 80%, at least 85%, at least 90%, at least 95%, or at least 99% sequence identity to the amino acid sequence set forth in SEQ ID NO: 24 or SEQ ID NO:51, wherein the residue at position 17 is not glutamine, the residue at position 20 is not isoleucine, the residue at position 25 is not proline, the residue at position 27 is not alanine, the residue at position 28 is not isoleucine, the residue at position 33 is not glutamate, the residue at position 37 is not methionine, the residue at position 39 is not leucine, the residue at position 41 is not glutamate, the residue at position 44 is not phenylalanine, the residue at position 50 is not arginine, the residue at position 52 is not asparagine, the residue at position 68 is not valine, the residue at position 129 is not isoleucine, the residue at position 131 is not phenylalanine, the residue at position 133 is not lysine, the residue at position 135 is not phenylalanine, the residue at position 141 is not isoleucine, the residue at position 146 is not arginine, the residue at position 158 is not arginine, the residue at position 159 is not lysine, the residue at position 181 is not lysine, the residue at position 191 is not arginine, the residue at position 198 is not lysine, the residue at position 200 is not lysine, the residue at position 205 is not valine, the residue at position 208 is not glutamate, the residue at position 214 is not arginine, the residue at position 216 is not lysine, the residue at position 218 is not proline, the residue at position 222 is not lysine, the residue at position 223 is not isoleucine, the residue at position 229 is not tyrosine, the residue at position 232 is not proline, the residue at position 235 is not threonine, the residue at position 248 is not glutamate, the residue at position 289 is not arginine, the residue at position 291 is not tryptophan, the residue at position 307 is not threonine, and/or the residue at position 318 is not lysine; preferably wherein the residue at position 27 is arginine, the residue at position 28 is alanine, the residue at position 33 is alanine, the residue at position 41 is alanine, the residue at position 44 is alanine, the residue at position 50 is alanine, the residue at position 52 is glutamine, the residue at position 68 is alanine, the residue at position 129 is alanine, the residue at position 131 is alanine, the residue at position 133 is alanine, the residue at position 135 is alanine, the residue at position 141 is alanine, the residue at position 146 is alanine, the residue at position 158 is alanine, the residue at position 159 is alanine, the residue at position 181 is alanine, the residue at position 191 is alanine, the residue at position 198 is alanine, the residue at position 200 is alanine, the residue at position 205 is alanine, the residue at position 208 is alanine, the residue at position 214 is alanine, the residue at position 216 is alanine, the residue at position 218 is alanine, the residue at position 222 is alanine, the residue at position 223 is alanine, the residue at position 229 is alanine, the residue at position 232 is alanine, the residue at position 235 is alanine, the residue at position 248 is alanine, the residue at position 289 is alanine, the residue at position 291 is alanine, the residue at position 307 is alanine, and/or the residue at position 318 is alanine.

In preferred embodiments, the agent as disclosed herein is a variant of the NTD of human Wnt7a comprising, consisting essentially of or consisting of an amino acid sequence having at least 50%, at least 55%, at least 60%, at least 65%, at least 70%, at least 75%, at least 80%, at least 85%, at least 90%, at least 95%, or at least 99% sequence identity to the amino acid sequence set forth in SEQ ID NO: 24, wherein the residue at position 17 is not glutamine, the residue at position 20 is not isoleucine, the residue at position 25 is not proline, the residue at position 27 is not alanine, the residue at position 28 is not isoleucine, the residue at position 33 is not glutamate, the residue at position 37 is not methionine, the residue at position 39 is not leucine, the residue at position 41 is not glutamate, the residue at position 44 is not phenylalanine, the residue at position 50 is not arginine, the residue at position 52 is not asparagine, the residue at position 68 is not valine, the residue at position 129 is not isoleucine, the residue at position 131 is not phenylalanine, the residue at position 133 is not lysine, the residue at position 135 is not phenylalanine, the residue at position 141 is not isoleucine, the residue at position 146 is not arginine, the residue at position 158 is not arginine, the residue at position 159 is not lysine, the residue at position 181 is not lysine, the residue at position 191 is not arginine, the residue at position 198 is not lysine, the residue at position 200 is not lysine, the residue at position 205 is not valine, the residue at position 208 is not glutamate, the residue at position 214 is not arginine, the residue at position 216 is not lysine, the residue at position 218 is not proline, the residue at position 222 is not lysine, the residue at position 223 is not isoleucine, the residue at position 229 is not tyrosine, the residue at position 232 is not proline, and/or the residue at position 235 is not threonine.

In particular embodiments, the agent as disclosed herein comprises, consists essentially of or consists of an amino acid sequence as set forth in SEQ ID NO: 28, 29, 30, 31, 32, 33, 34, 35, 36, 37, 38, 39, 40, 41, 42, 43, 44, 45, 46, 47, 48, 49, 50, 52, 53, 54, 68, 69, 70, 71, 72, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, or 121, preferably SEQ ID NO: 28, 29, 30, 31, 32, 33, 34, 35, 36, 37, 38, 39, 40, 41, 42, 43, 47, 48, 49, 53, 54, 68, 69, 70, 71, 72, 74, 76, 80, 81, 83, 85, 86, 87, 88, 89, 90, 91, 92, 93, 94, 95, 96, 97, 98, 99, 100, 104, 105, 106, 107, 108, 109, 110, 111, 112, 114, 118, 119 or 121, more preferably SEQ ID NO: 28, 29, 30, 31, 32, 33, 34, 35, 36, 37, 38, 39, 40, 41, 42, 43, 47, 48, 49, 53, 54, 68, 69, 70, 71 72, 74, 76, 80, 81 or 83 (FIG. 8).

In preferred embodiments, in such variant, the lysine (K) residue at the position corresponding to position 159 in SEQ ID NO: 24 or SEQ ID NO: 51 is substituted by one or more (preferably not more than three, preferably not more than two, more preferably one) other amino acid residue, such as preferably but without limitation by an alanine (A) residue, a serine (S) or a leucine (L) residue. In more preferred embodiments, the agent as disclosed herein comprises, consists essentially of or consists of an amino acid sequence as set forth in SEQ ID NO: 28, 80, 81, 85, 118 or 119, preferably SEQ ID NO: 28 or 85, more preferably SEQ ID NO: 28.

In particular embodiments, the variant of the Wnt7 polypeptide has at least 35%, preferably at least 40%, at least 50%, at least 60%, at least 70%, at least 80%, at least 90%, at least 95%, at least 99%, preferably 100%, of the GPR124/RECK/Frizzled/LRP-mediated Wnt signaling activity of the full-length wild-type Wnt7 polypeptide. In preferred embodiments, the variant of the Wnt7 polypeptide has at least 70% of the GPR124/RECK/Frizzled/LRP-mediated Wnt signaling activity of the full-length wild-type Wnt7 polypeptide. In particular embodiments, the variant of the Wnt7 polypeptide has a GPR124/RECK/Frizzled/LRP-mediated Wnt signaling activity which is higher (e.g. 1.1-fold, 1.2-fold, 1.3-fold, 1.4-fold, 1.5-fold, 1.6-fold, 1.7-fold, 1.8-fold, 1.9-fold or 2-fold higher or even higher) than the GPR124/RECK/Frizzled/LRP-mediated Wnt signaling activity of the full-length wild-type Wnt7 polypeptide.

In particular embodiments, the agent as disclosed herein is soluble in water. For example, the solubility of the agent can be increased by using a Frizzled-specific antibody or fragment thereof, instead of a palmitoylated Frizzled-binding domain of a Wnt polypeptide.

A further aspect relates to a nucleic acid encoding the agent as disclosed herein, wherein the agent is a protein, polypeptide or a peptide.

By "encoding" is meant that a nucleic acid sequence or part(s) thereof corresponds, by virtue of the genetic code of an organism in question to a particular amino acid sequence, e.g., the amino acid sequence of one or more desired proteins or polypeptides, or to another nucleic acid sequence in a template-transcription product (e.g. RNA or RNA analogue) relationship.

To allow expression of the nucleic acid encoding the agent as disclosed herein, wherein the agent is a protein, polypeptide or a peptide, the nucleic acid may be inserted into a nucleic acid expression cassette and/or vector, as is well-known in the art.

Accordingly, a further aspect relates to a nucleic acid expression cassette comprising the nucleic acid encoding the agent as disclosed herein, operably linked to a promoter and/or transcriptional and translational regulatory signals.

The term "nucleic acid expression cassettes" as used herein refers to nucleic acid molecules, typically DNA, to which nucleic acid fragments, preferably the recombinant nucleic acid molecule as defined herein, may be inserted to be expressed, wherein said nucleic acid molecules comprise one or more nucleic acid sequences controlling the expression of the nucleic acid fragments. Non-limiting examples of such more nucleic acid sequences controlling the expression of the nucleic acid fragments include promoter sequences, open reading frames and transcription terminators.

Preferably, the nucleic acid expression cassette may comprise one or more open reading frames (ORF) encoding said one or more proteins, polypeptides or peptides. An "open reading frame" or "ORF" refers to a succession of coding nucleotide triplets (codons) starting with a translation initiation codon and closing with a translation termination codon known per se, and not containing any internal in-frame translation termination codon, and potentially capable of encoding a protein, polypeptide or peptide. Hence, the term may be synonymous with "coding sequence" as used in the art.

An "operable linkage" is a linkage in which regulatory sequences and sequences sought to be expressed are connected in such a way as to permit said expression. For example, sequences, such as, e.g., a promoter and an ORF, may be said to be operably linked if the nature of the linkage between said sequences does not: (1) result in the introduction of a frame-shift mutation, (2) interfere with the ability of the promoter to direct the transcription of the ORF, (3) interfere with the ability of the ORF to be transcribed from the promoter sequence. Hence, "operably linked" may mean incorporated into a genetic construct so that expression control sequences, such as a promoter, effectively control transcription/expression of a sequence of interest.

The precise nature of transcriptional and translational regulatory sequences or elements required for expression may vary between expression environments, but typically include a transcription terminator, and optionally an enhancer.

Reference to a "promoter" is to be taken in its broadest context and includes transcriptional regulatory sequences required for accurate transcription initiation and where applicable accurate spatial and/or temporal control of gene expression or its response to, e.g., internal or external (e.g., exogenous) stimuli. More particularly, "promoter" may depict a region on a nucleic acid molecule, preferably DNA molecule, to which an RNA polymerase binds and initiates transcription. A promoter is preferably, but not necessarily, positioned upstream, i.e., 5', of the sequence the transcription of which it controls. Typically, in prokaryotes a promoter region may contain both the promoter per se and sequences which, when transcribed into RNA, will signal the initiation of protein synthesis (e.g., Shine-Dalgarno sequence). A promoter sequence can also include "enhancer regions", which are one or more regions of DNA that can be bound with proteins (namely the trans-acting factors) to enhance transcription levels of genes in a gene-cluster. The enhancer, while typically at the 5' end of a coding region, can also be separate from a promoter sequence, e.g., can be within an intronic region of a gene or 3' to the coding region of the gene.

In embodiments, promoters contemplated herein may be constitutive or inducible. A constitutive promoter is understood to be a promoter whose expression is constant under the standard culturing conditions. Inducible promoters are promoters that are responsive to one or more induction cues. For example, an inducible promoter can be chemically regulated (e.g., a promoter whose transcriptional activity is regulated by the presence or absence of a chemical inducing agent such as an alcohol, tetracycline, a steroid, a metal, or other small molecule) or physically regulated (e.g., a promoter whose transcriptional activity is regulated by the presence or absence of a physical inducer such as light or high or low temperatures). An inducible promoter can also be indirectly regulated by one or more transcription factors that are themselves directly regulated by chemical or physical cues. Non-limiting examples of promoters include T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter.

The terms "terminator" or "transcription terminator" refer generally to a sequence element at the end of a transcriptional unit which signals termination of transcription. For example, a terminator is usually positioned downstream of, i.e., 3' of ORF(s) encoding a polypeptide of interest. For instance, where a recombinant nucleic acid contains two or more ORFs, e.g., successively ordered and forming together a multi-cistronic transcription unit, a transcription terminator may be advantageously positioned 3' to the most downstream ORF.

In particular embodiments, the nucleic acid expression cassette comprises the nucleic acid encoding the agent as disclosed herein, operably linked to one or more promoters, enhancers, ORFs and/or transcription terminators.

A further aspect relates to vector comprising the nucleic acid encoding the agent as disclosed herein, or the nucleic acid expression cassette as disclosed herein, such as a viral vector.

The terms "expression vector" or "vector" as used herein refers to nucleic acid molecules, typically DNA, to which nucleic acid fragments, preferably the recombinant nucleic acid molecule as defined herein, may be inserted and cloned, i.e., propagated. Hence, a vector will typically contain one or more unique restriction sites, and may be capable of autonomous replication in a defined cell or vehicle organism such that the cloned sequence is reproducible. A vector may also preferably contain a selection marker, such as, e.g., an antibiotic resistance gene, to allow selection of recipient cells that contain the vector. Vectors may include, without limitation, plasmids, phagemids, bacteriophages, bacteriophage-derived vectors, PAC, BAC, linear nucleic acids, e.g., linear DNA, transposons, viral vectors, etc., as appropriate (see, e.g., Sambrook et al., 1989; Ausubel 1992). Viral vectors may include inter alia retroviral vectors, lentiviral vectors, adenoviral vectors, or adeno-associated viral vectors, for example, vectors based on HIV, SV40, EBV, HSV or BPV. Expression vectors are generally configured to allow for and/or effect the expression of nucleic acids or open reading frames introduced thereto in a desired expression system, e.g., in vitro, in a cell, organ and/or organism. For example, expression vectors may advantageously comprise suitable regulatory sequences.

Factors of importance in selecting a particular vector include inter alia: choice of recipient cell, ease with which recipient cells that contain the vector may be recognised and selected from those recipient cells which do not contain the vector; the number of copies of the vector which are desired in particular recipient cells; whether it is desired for the vector to integrate into the chromosome or to remain extrachromosomal in the recipient cells; and whether it is desirable to be able to "shuttle" the vector between recipient cells of different species.

Expression vectors can be autonomous or integrative. A nucleic acid can be in introduced into a cell in the form of an expression vector such as a plasmid, phage, transposon, cosmid or virus particle. The recombinant nucleic acid can be maintained extrachromosomally or it can be integrated into the cell chromosomal DNA. Expression vectors can contain selection marker genes encoding proteins required for cell viability under selected conditions (e.g., URA3, which encodes an enzyme necessary for uracil biosynthesis, or LEU2, which encodes an enzyme required for leucine biosynthesis, or TRP1, which encodes an enzyme required for tryptophan biosynthesis) to permit detection and/or selection of those cells transformed with the desired nucleic acids. Expression vectors can also include an autonomous replication sequence (ARS). The ARS may comprise a centromere (CEN) and an origin of replication (ORI). For example, the ARS may be ARS18 or ARS68.

Integrative vectors generally include a serially arranged sequence of at least a first insertable DNA fragment, a selectable marker gene, and a second insertable DNA fragment. The first and second insertable DNA fragments are each about 200 (e.g., about 250, about 300, about 350, about 400, about 450, about 500, or about 1000 or more) nucleotides in length and have nucleotide sequences which are homologous to portions of the genomic DNA of the cell species to be transformed. A nucleotide sequence containing a nucleic acid of interest for expression is inserted in this vector between the first and second insertable DNA fragments, whether before or after the marker gene. Integrative vectors can be linearized prior to transformation to facilitate the integration of the nucleotide sequence of interest into the cell genome.

Prior to introducing the vectors into a cell of interest, the vectors can be grown (e.g., amplified) in bacterial cells such as *Escherichia coli* (*E. coli*). The vector DNA can be isolated from bacterial cells by any of the methods known in the art, which result in the purification of vector DNA from the bacterial milieu. The purified vector DNA can be extracted extensively with phenol, chloroform, and ether, to ensure that no *E. coli* proteins are present in the plasmid DNA preparation, since these proteins can be toxic to mammalian cells.

As noted elsewhere, an agent may comprise a protein, polypeptide or peptide. Such may be suitably obtained through expression by host cells or host organisms, transformed with an expression construct encoding and configured for expression of said protein, polypeptide or peptide in said host cells or host organisms, followed by purification of the protein, polypeptide or peptide.

Hence, a further aspect provides a host cell comprising the nucleic acid, nucleic acid expression cassette or vector as taught herein.

In certain embodiments, the host cell may be a bacterial cell, a yeast cell, an animal cell, or a mammalian cell.

The terms "host cell" and "host organism" may suitably refer to cells or organisms encompassing both prokaryotes, such as bacteria, and eukaryotes, such as yeast, fungi, protozoan, plants and animals. Contemplated as host cells are inter alia unicellular organisms, such as bacteria (e.g., *E. coli, Salmonella tymphimurium, Serratia marcescens*, or *Bacillus subtilis*), yeast (e.g., *Saccharomyces cerevisiae* or *Pichia pastoris*), (cultured) plant cells (e.g., from *Arabidopsis thaliana* or *Nicotiana tobaccum*) and (cultured) animal cells (e.g., vertebrate animal cells, mammalian cells, primate cells, human cells or insect cells). Contemplated as host organisms are inter alia multi-cellular organisms, such as plants and animals, preferably animals, more preferably warm-blooded animals, even more preferably vertebrate animals, still more preferably mammals, yet more preferably primates; particularly contemplated are such animals and animal categories which are non-human.

Such protein, polypeptide or peptide may be suitably isolated. The term "isolated" with reference to a particular component (such as for instance a nucleic acid, protein, polypeptide or peptide) generally denotes that such component exists in separation from—for example, has been separated from or prepared and/or maintained in separation from—one or more other components of its natural environment. For instance, an isolated human or animal protein or complex may exist in separation from a human or animal body where it naturally occurs. The term "isolated" as used herein may preferably also encompass the qualifier "purified". As used herein, the term "purified" with reference to peptides, polypeptides, proteins, or nucleic acids does not require absolute purity. Instead, it denotes that such peptides, polypeptides, proteins, or nucleic acids are in a discrete environment in which their abundance (conveniently expressed in terms of mass or weight or concentration) relative to other analytes is greater than in the starting composition or sample. A discrete environment denotes a single medium, such as for example a single solution, gel, precipitate, lyophilisate, etc. Purified nucleic acids, proteins, polypeptides or peptides may be obtained by known methods including, for example, laboratory or recombinant synthesis, chromatography, preparative electrophoresis, centrifugation, precipitation, affinity purification, etc. Purified peptides, polypeptides or proteins may preferably constitute by weight ≥10%, more preferably ≥50%, such as ≥60%, yet more preferably ≥70%, such as ≥80%, and still more preferably ≥90%, such as ≥95%, ≥96%, ≥97%, ≥98%, ≥99% or even 100%, of the protein content of the discrete environment. Protein content may be determined, e.g., by the Lowry method (Lowry et al. 1951. J Biol Chem 193: 265), optionally as described by Hartree 1972 (Anal Biochem 48: 422-427). Purity of peptides, polypeptides, or proteins may be determined by SDS-PAGE under reducing or non-reducing conditions using Coomassie blue or, preferably, silver stain. Quantity of nucleic acids may be determined by measuring absorbance A260. Purity of nucleic acids may be determined by measuring absorbance A260/A280, or by agarose- or polyacrylamide-gel electrophoresis and ethidium bromide or similar staining.

Further, there are several other well-known methods of introducing nucleic acids into animal cells, any of which may be used herein. At the simplest, the nucleic acid can be directly injected into the target cell/target tissue. Other methods include fusion of the recipient cell with bacterial protoplasts containing the nucleic acid, the use of compositions like calcium chloride, rubidium chloride, lithium chloride, calcium phosphate, DEAE dextran, cationic lipids or liposomes or methods like receptor-mediated endocytosis, biolistic particle bombardment ("gene gun" method), infection with viral vectors (i.e. derived from lentivirus, adeno-associated virus (AAV), adenovirus, retrovirus or antiviruses), electroporation, and the like. Other techniques or methods which are suitable for delivering nucleic acid molecules to target cells include the continuous delivery of an NA molecule from poly (lactic-Co-Glycolic Acid) polymeric microspheres or the direct injection of protected (stabilized) NA molecule(s) into micropumps delivering the product. Another possibility is the use of implantable drug-releasing biodegradable microspheres. Also envisaged is encapsulation of NA in various types of liposomes (immunoliposomes, PEGylated (immuno) liposomes), cationic lipids and polymers, nanoparticles or dendrimers, poly (lactic-Co-Glycolic Acid) polymeric microspheres, implantable drug-releasing biodegradable microspheres, etc.; and co-injection of NA with protective agent like the nuclease inhibitor aurintricarboxylic acid. It shall be clear that also a combination of different above-mentioned delivery modes or methods may be used.

In particular embodiments, the vector comprising the nucleic acid as described herein is a viral vector, preferably a viral vector specifically directed towards the central and/or peripheral nervous system (e.g., a brain-specific viral vector). In further particular embodiments, the viral vector is a central nervous system (CNS) neuron-specific adeno-associated virus serotype 9 (AAV9) mutant. For example, the viral vector is the CNS cell-specific AAV-PHP.B or AAV-PHP.eB viral vector displaying the peptide SAQTLAVPFKA (SEQ ID NO: 55) or SDGTLAVPFKA (SEQ ID NO: 56) as described in Deverman et al. (Deverman et al., *Nat Biotechnol*, 34:204-209 (2016) and Chan et al. (Chan et al., Nat Neurosci, 20(8): 1172-1179 (2017)).

In preferred embodiments, the viral vector is a blood brain barrier endothelial cell-specific viral vector. In further preferred embodiments, the viral vector is a blood brain barrier endothelial cell-specific capsid adeno-associated virus serotype 2 (AAV2) mutant. For example, the viral vector is the blood brain barrier endothelial cell-specific AAV-BR1 viral vector displaying the peptide NRGTEWD (SEQ ID NO: 57) as described in Korbelin et al. (Korbelin et al., *EMBO Molecular Medicine*, 8, 609-625 (2016)).

A further aspect relates to a pharmaceutical composition comprising the agent as disclosed herein, the nucleic acid encoding the agent as disclosed herein, the nucleic acid expression cassette as disclosed herein or the vector as disclosed herein, and a pharmaceutically acceptable carrier. Such pharmaceutical formulations or compositions may be comprised in a kit of parts.

The term "pharmaceutically acceptable" as used herein is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, antioxidants, tonicity controlling agents, absorption delaying agents, and the like. The use of such media and agents for pharmaceutical active substances is well known in the art. Except insofar as any conventional media or agent is incompatible with the active substance, its use in the therapeutic compositions may be contemplated.

Illustrative, non-limiting carriers for use in formulating the pharmaceutical compositions include, for example, oil-in-water or water-in-oil emulsions, aqueous compositions with or without inclusion of organic co-solvents suitable for intravenous (IV) use, liposomes or surfactant-containing vesicles, microspheres, microbeads and microsomes, powders, tablets, capsules, suppositories, aqueous suspensions, aerosols, and other carriers apparent to one of ordinary skill in the art.

Pharmaceutical compositions as intended herein may be formulated for essentially any route of administration, such as without limitation, oral administration (such as, e.g., oral ingestion or inhalation), intranasal administration (such as, e.g., intranasal inhalation or intranasal mucosal application), parenteral administration (such as, e.g., subcutaneous, intravenous (I.V.), intramuscular, intraperitoneal or intrasternal injection or infusion), transdermal or transmucosal (such as, e.g., oral, sublingual, intranasal) administration, topical administration, rectal, vaginal or intra-tracheal instillation, and the like. In this way, the therapeutic effects attainable by the methods and compositions can be, for example, systemic, local, tissue-specific, etc., depending of the specific needs of a given application.

For example, for oral administration, pharmaceutical compositions may be formulated in the form of pills, tablets, lacquered tablets, coated (e.g., sugar-coated) tablets, granules, hard and soft gelatin capsules, aqueous, alcoholic or oily solutions, syrups, emulsions or suspensions. In an example, without limitation, preparation of oral dosage forms may be is suitably accomplished by uniformly and intimately blending together a suitable amount of the agent as disclosed herein in the form of a powder, optionally also including finely divided one or more solid carrier, and formulating the blend in a pill, tablet or a capsule. Exemplary but non-limiting solid carriers include calcium phosphate, magnesium stearate, talc, sugars (such as, e.g., glucose, mannose, lactose or sucrose), sugar alcohols (such as, e.g., mannitol), dextrin, starch, gelatin, cellulose, polyvinylpyrrolidine, low melting waxes and ion exchange resins. Compressed tablets containing the pharmaceutical composition can be prepared by uniformly and intimately mixing the agent as disclosed herein with a solid carrier such as described above to provide a mixture having the necessary compression properties, and then compacting the mixture in a suitable machine to the shape and size desired. Moulded tablets maybe made by moulding in a suitable machine, a mixture of powdered compound moistened with an inert liquid diluent. Suitable carriers for soft gelatin capsules and suppositories are, for example, fats, waxes, semisolid and liquid polyols, natural or hardened oils, etc.

For example, for oral or nasal aerosol or inhalation administration, pharmaceutical compositions may be formulated with illustrative carriers, such as, e.g., as in solution with saline, polyethylene glycol or glycols, DPPC, methylcellulose, or in mixture with powdered dispersing agents, further employing benzyl alcohol or other suitable preservatives, absorption promoters to enhance bioavailability, fluorocarbons, and/or other solubilising or dispersing agents known in the art. Suitable pharmaceutical formulations for administration in the form of aerosols or sprays are, for example, solutions, suspensions or emulsions of the agents as taught herein or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Illustratively, delivery may be by use of a single-use delivery device, a mist nebuliser, a breath-activated powder inhaler, an aerosol metered-dose inhaler (MDI) or any other of the numerous nebuliser delivery devices available in the art. Additionally, mist tents or direct administration through endotracheal tubes may also be used.

Examples of carriers for administration via mucosal surfaces depend upon the particular route, e.g., oral, sublingual, intranasal, etc. When administered orally, illustrative examples include pharmaceutical grades of mannitol, starch, lactose, magnesium stearate, sodium saccharide, cellulose, magnesium carbonate and the like, with mannitol being preferred. When administered intranasally, illustrative examples include polyethylene glycol, phospholipids, glycols and glycolipids, sucrose, and/or methylcellulose, powder suspensions with or without bulking agents such as lactose and preservatives such as benzalkonium chloride, EDTA. In a particularly illustrative embodiment, the phospholipid 1,2 dipalmitoyl-sn-glycero-3-phosphocholine (DPPC) is used as an isotonic aqueous carrier at about 0.01-0.2% for intranasal administration of the compound of the subject invention at a concentration of about 0.1 to 3.0 mg/ml.

For example, for parenteral administration, pharmaceutical compositions may be advantageously formulated as solutions, suspensions or emulsions with suitable solvents, diluents, solubilisers or emulsifiers, etc. Suitable solvents are, without limitation, water, physiological saline solution or alcohols, e.g. ethanol, propanol, glycerol, in addition also sugar solutions such as glucose, invert sugar, sucrose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. The agents and pharmaceutically acceptable salts thereof of the invention can also be lyophilised and the lyophilisates obtained used, for example, for the production of injection or infusion preparations. For example, one illustrative example of a carrier for intravenous use includes a mixture of 10% USP ethanol, 40% USP propylene glycol or polyethylene glycol 600 and the balance USP Water for Injection (WFI). Other illustrative carriers for intravenous use include 10% USP ethanol and USP WFI; 0.01-0.1% triethanolamine in USP WFI; or 0.01-0.2% dipalmitoyl diphosphatidylcholine in USP WFI; and 1-10% squalene or parenteral vegetable oil-in-water emulsion. Illustrative examples of carriers for subcutaneous or intramuscular use include phosphate buffered saline (PBS) solution, 5% dextrose in WFI and 0.01-0.1% triethanolamine in 5% dextrose or 0.9% sodium chloride in USP WFI, or a 1 to 2 or 1 to 4 mixture of 10% USP ethanol, 40% propylene glycol and the balance an acceptable isotonic solution such as 5% dextrose or 0.9% sodium chloride; or 0.01-0.2% dipalmitoyl diphosphatidylcholine in USP WFI and 1 to 10% squalene or parenteral vegetable oil-in-water emulsions.

Where aqueous formulations are preferred, such may comprise one or more surfactants. For example, the composition can be in the form of a micellar dispersion comprising at least one suitable surfactant, e.g., a phospholipid surfactant. Illustrative examples of phospholipids include diacyl phosphatidyl glycerols, such as dimyristoyl phosphatidyl glycerol (DPMG), dipalmitoyl phosphatidyl glycerol (DPPG), and distearoyl phosphatidyl glycerol (DSPG), diacyl phosphatidyl cholines, such as dimyristoyl phosphatidylcholine (DPMC), dipalmitoyl phosphatidylcholine (DPPC), and distearoyl phosphatidylcholine (DSPC); diacyl phosphatidic acids, such as dimyristoyl phosphatidic acid (DPMA), dipahnitoyl phosphatidic acid (DPPA), and distearoyl phosphatidic acid (DSPA); and diacyl phosphatidyl ethanolamines such as dimyristoyl phosphatidyl ethanolamine (DPME), dipalmitoyl phosphatidyl ethanolamine (DPPE) and distearoyl phosphatidyl ethanolamine (DSPE). Typically, a surfactant:active substance molar ratio in an aqueous formulation will be from about 10:1 to about 1:10, more typically from about 5:1 to about 1:5, however any effective amount of surfactant may be used in an aqueous formulation to best suit the specific objectives of interest.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquidify and/or dissolve in the rectal cavity to release the drug.

Suitable carriers for microcapsules, implants or rods are, for example, copolymers of glycolic acid and lactic acid.

One skilled in this art will recognize that the above description is illustrative rather than exhaustive. Indeed, many additional formulations techniques and pharmaceutically-acceptable excipients and carrier solutions are well-known to those skilled in the art, as is the development of suitable dosing and treatment regimens for using the particular compositions described herein in a variety of treatment regimens.

In preferred embodiments, the agent, the nucleic acid encoding the agent, the nucleic acid expression cassette comprising the nucleic acid, the vector comprising the nucleic acid or the nucleic acid expression cassette, the host cell or the pharmaceutical composition as taught herein is administered parenterally. More preferably, the agent, the nucleic acid encoding the agent, the nucleic acid expression cassette comprising the nucleic acid or the vector comprising the nucleic acid, the nucleic acid expression cassette, the host cell or the pharmaceutical composition as taught herein is administered intravenously, for example by infusion.

In particular embodiments, the agent, the nucleic acid encoding the agent, or the nucleic acid expression cassette comprising the nucleic acid as taught herein is used in gene therapy. In further particular embodiments, the agent, the nucleic acid encoding the agent, or the nucleic acid expression cassette comprising the nucleic acid as taught herein is used in central and/or peripheral nervous system-directed gene therapy, such as brain-directed gene therapy, more particularly blood brain barrier endothelial cell-directed gene therapy.

Accordingly, also provided herein is a method for gene therapy, in particular central and/or peripheral nervous system-directed gene therapy, in a subject in need of said gene therapy comprising: introducing in the subject, in particular in the central and/or peripheral nervous system of the subject, a nucleic acid expression cassette or a vector as described herein; and expressing a therapeutically effective amount of the agent encoded by the nucleic acid as taught herein in the subject, in particular the central and/or peripheral nervous system of the subject.

The term "gene therapy" as used herein refers to the introduction of an exogenous polynucleotide into a host cell for therapeutic or prophylactic purposes, irrespective of the method used for the introduction. Such methods include a variety of well-known techniques such as vector-mediated gene transfer (by, e.g., viral infection/transfection, or various other protein-based or lipid-based gene delivery complexes) as described elsewhere herein. The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art. For example, the vector-mediated gene transfer of the agent, the nucleic acid encoding the agent, the nucleic acid expression cassette comprising the nucleic acid as taught herein may be performed using a viral vector specifically directed towards the central and/or peripheral nervous system (e.g., AAV-PHP.B and AAV-PHP.eB viral vector) or a viral vector specific for blood brain barrier endothelial cells (e.g., AAV-BR1 viral vector) as described elsewhere herein.

In particular embodiments, the nucleic acid encoding the agent, the nucleic acid expression cassette comprising the nucleic acid, the vector comprising the nucleic acid or the nucleic acid expression cassette or the pharmaceutical composition as taught herein is administered to the subject by the injection (e.g., intravenously) or transplantation of allogeneic cells transformed with the vector comprising the nucleic acid or the nucleic acid expression cassette as taught herein. When administered, the injected or transplanted allogenic cells will transcribe and translate the nucleic acid encoding the agent as taught herein in vivo. The dosage or amount of the agent as taught herein, optionally in combination with one or more other active compounds to be administered, depends on the individual case and is, as is customary, to be adapted to the individual circumstances to achieve an optimum effect. Thus, the unit dose and regimen depend on the nature and the severity of the disorder to be treated, and also on factors such as the species of the subject, the sex, age, body weight, general health, diet, mode and time of administration, immune status, and individual responsiveness of the human or animal to be treated, efficacy, metabolic stability and duration of action of the compounds used, on whether the therapy is acute or chronic or prophylactic, or on whether other active compounds are administered in addition to the agent of the invention. In order to optimize therapeutic efficacy, the agent as taught herein can be first administered at different dosing regimens. Typically, levels of the agent in a tissue can be monitored using appropriate screening assays as part of a clinical testing procedure, e.g., to determine the efficacy of a given treatment regimen. The frequency of dosing is within the skills and clinical judgement of medical practitioners (e.g., doctors, veterinarians or nurses). Typically, the administration regime is established by clinical trials which may establish optimal administration parameters. However, the practitioner may vary such administration regimes according to the one or more of the aforementioned factors, e.g., subject's age, health, weight, sex and medical status. The frequency of dosing can be varied depending on whether the treatment is prophylactic or therapeutic.

Toxicity and therapeutic efficacy of the agent as described herein or pharmaceutical compositions comprising the same can be determined by known pharmaceutical procedures in, for example, cell cultures or experimental animals. These procedures can be used, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Pharmaceutical compositions that exhibit high therapeutic indices are preferred. While pharmaceutical compositions that exhibit toxic side effects can be used, care should be taken to design a delivery system that targets such compounds to the site of affected tissue in order to minimize potential damage to normal cells (e.g., non-target cells) and, thereby, reduce side effects.

The data obtained from the cell culture assays and animal studies can be used in formulating a range of dosage for use in appropriate subjects. The dosage of such pharmaceutical compositions lies generally within a range of circulating concentrations that include the ED50 with little or no toxicity. The dosage may vary within this range depending upon the dosage form employed and the route of administration utilized. For a pharmaceutical composition used as described herein, the therapeutically effective dose can be estimated initially from cell culture assays. A dose can be formulated in animal models to achieve a circulating plasma concentration range that includes the IC50 (i.e., the concentration of the pharmaceutical composition which achieves a half-maximal inhibition of symptoms) as determined in cell culture. Such information can be used to more accurately determine useful doses in humans. Levels in plasma can be measured, for example, by high performance liquid chromatography.

Without limitation, depending on the type and severity of the disease, a typical dosage (e.g., a typical daily dosage or a typical intermittent dosage, e.g., a typical dosage for every two days, every three days, every four days, every five days, every six days, every week, every 1.5 weeks, every two weeks, every three weeks, every month, or other) of the agent as taught herein may range from about 10 µg/kg to about 500 µg/kg body weight of the subject, per dose, depending on the factors mentioned above, e.g., such as 20-400 µg/kg or 20-200 µg/kg or 20-100 µg/kg or 40-80 µg/kg body weight of the subject.

By means of example and without limitation, the agent as taught herein may be administered at about 5 µg/kg, or at about 10 µg/kg, or at about 15 µg/kg, or at about 20 µg/kg, or at about 25 µg/kg, or at about 30 µg/kg, or at about 35 µg/kg, or at about 40 µg/kg, or at about 45 µg/kg, or at about 50 mg/kg, or at about 60 µg/kg, or at about 70 µg/kg, or at about 80 µg/kg, or at about 90 µg/kg, or at about 100 µg/kg, or at about 200 µg/kg, or at about 300 µg/kg, or at about 400 µg/kg, or at about 500 µg/kg per dose.

In particular embodiments, the agent as taught herein is administered using a sustained delivery system, such as a (partly) implanted sustained delivery system. Skilled person will understand that such a sustained delivery system may comprise a reservoir for holding the agent as taught herein, a pump and infusion means (e.g., a tubing system). For example, the sustained delivery system may be a mini-osmotic pump system implanted in the brain.

In particular embodiment, the agent as disclosed herein is the main or only active ingredient of the pharmaceutical composition.

A further aspect relates to the agent as disclosed herein, the nucleic acid encoding the agent as disclosed herein, the nucleic acid expression cassette as disclosed herein, the vector as disclosed herein or the pharmaceutical composition as disclosed herein, for use as a medicament.

A further aspect relates to the agent as disclosed herein, the nucleic acid encoding the agent as disclosed herein, the nucleic acid expression cassette as disclosed herein, the vector as disclosed herein or the pharmaceutical composition as disclosed herein, for use in the prevention or treatment of a neurovascular disorder or a central nervous system (CNS) disorder comprising neurovascular dysfunction.

The terms "treat" or "treatment" encompass both the therapeutic treatment of an already developed disease or condition, such as the therapy of an already developed neurovascular disorder or a central nervous system (CNS) disorder comprising neurovascular dysfunction, as well as prophylactic or preventive measures, wherein the aim is to prevent or lessen the chances of incidence of an undesired affliction, such as to prevent occurrence, development and progression of a neurovascular disorder or a CNS disorder comprising neurovascular dysfunction. Beneficial or desired clinical results may include, without limitation, alleviation of one or more symptoms or one or more biological markers, diminishment of extent of disease, stabilised (i.e., not worsening) state of disease, delay or slowing of disease progression, amelioration or palliation of the disease state, and the like. "Treatment" can also mean prolonging survival as compared to expected survival if not receiving treatment.

The terms "neurovascular disorder" or "neurovascular disease" as used herein refer to a disease or pathological alteration or condition which affects the cerebral vascular system and/or the vascular system supplying the spinal cord. The terms encompass any abnormality of the blood vessels within or supplying the brain and/or spine. Abnormalities may be without limitation (i) narrowing of arteries which reduces blood flow to the brain that may lead to hypoxia, ischemia or stroke and/or (ii) weakening of arteries that may lead to brain aneurysms and increase the risk of intracranial bleeding. Non-limiting examples of neurovascular diseases are ischemic stroke, hemorrhagic stroke, ischemia/reperfusion injury, brain aneurysms, arteriovenous malformations (AVMs), cavernous malformations, vasculitis, cerebral hemorrhage, subarachnoid hemorrhage, spinal vascular malformations, carotid artery stenosis, Moyamoya disease and intracranial atherosclerosis.

The phrases "central nervous system (CNS) disorder comprising neurovascular dysfunction" or "CNS disease comprising neurovascular dysfunction" as used herein refer to a group of neurological disorders that affect the structure and/or function of the brain and/or spinal cord, which collectively form the CNS, that are caused by, contributed to, or typified by neurovascular dysfunction, or which lead to an abnormality of the structure and/or function of the blood vessels within or supplying the brain and/or spine. Non-limiting examples of central nervous system (CNS) disorders comprising neurovascular dysfunction are multiple sclerosis, ischemic stroke, brain cancer, epilepsy, dementia, vascular dementia, HIV-1-associated dementia, Alzheimer's disease, Parkinson's disease, Huntington disease, amyotrophic lateral sclerosis, infectious brain diseases, traumatic brain injuries, migraine and chronic traumatic encephalopathy.

Except when noted, the terms "subject" or "patient" can be used interchangeably and refer to animals, preferably warm-blooded animals, more preferably vertebrates, even more preferably mammals, still more preferably primates, and specifically includes human patients and non-human mammals and primates. Preferred subjects are human subjects. The terms "subject" or "patient" include subjects in need of treatment, more particularly subjects that would benefit from treatment of a given condition, particularly a neurovascular disorder or a central nervous system (CNS) disorder comprising neurovascular dysfunction. Such subjects may include, without limitation, those that have been diagnosed with said condition, those prone to develop said condition and/or those in who said condition is to be prevented.

The products and methods as taught herein allow to administer a therapeutically and/or prophylactically effective amount of an agent as taught herein, a nucleic acid encoding the agent as disclosed herein, a nucleic acid expression cassette as disclosed herein, a vector as disclosed herein or a pharmaceutical composition as disclosed herein, in subjects having a neurovascular disorder or a CNS disorder which will benefit from such treatment. The term "therapeutically effective amount" as used herein, refers to an amount of active compound or pharmaceutical agent that elicits the biological or medicinal response in a subject that is being sought by a surgeon, researcher, veterinarian, medical doctor or other clinician, which may include inter alia alleviation of the symptoms of the disease or condition being treated. The term "prophylactically effective amount" refers to an amount of an active compound or pharmaceutical agent that inhibits or delays in a subject the onset of a disorder as being sought by a researcher, veterinarian, medical doctor or other clinician. Methods are known in the art for determining therapeutically and/or prophylactically effective doses of an agent, a nucleic acid encoding the agent, a nucleic acid expression cassette, or a pharmaceutical composition, as taught herein.

The term "therapeutically effective dose" as used herein refers to an amount of an agent, a nucleic acid encoding the agent, a nucleic acid expression cassette, or a pharmaceutical composition, as taught herein, that when administered brings about a positive therapeutic response with respect to treatment of a patient having a neurovascular disorder or a CNS disorder.

Appropriate therapeutically effective doses of an agent, a nucleic acid encoding the agent, a nucleic acid expression cassette, or a pharmaceutical composition, as taught herein, may be determined by a qualified physician with due regard to the nature of the disease condition and severity, and the age, size and condition of the patient.

A further aspect provides a method of treating a neurovascular disorder or a CNS disorder comprising neurovascular dysfunction in a subject in need of such a treatment, comprising administering a therapeutically effective amount of an agent as disclosed herein, the nucleic acid encoding the agent as disclosed herein, the nucleic acid expression cassette as disclosed herein, the vector as disclosed herein or the pharmaceutical composition as disclosed herein, to the subject.

A further aspect provides the use of an agent as disclosed herein, the nucleic acid encoding the agent as disclosed herein, the nucleic acid expression cassette as disclosed herein, the vector as disclosed herein or the pharmaceutical composition as disclosed herein, for the manufacture of a medicament for the treatment of a neurovascular disorder or a CNS disorder comprising neurovascular dysfunction.

In particular embodiments, said neurovascular disorder is selected from the group consisting of ischemic stroke, hemorrhagic stroke, ischemia/reperfusion injury, brain aneurysms, arteriovenous malformations (AVMs), cavernous malformations, vasculitis, cerebral hemorrhage, subarachnoid hemorrhage, spinal vascular malformations, carotid artery stenosis, Moyamoya disease and intracranial atherosclerosis and combinations thereof.

In particular embodiments, said CNS disorder comprising neurovascular dysfunction is selected from the group consisting of multiple sclerosis, ischemic stroke, brain cancer, epilepsy, dementia, vascular dementia, HIV-1-associated dementia, Alzheimer's disease, Parkinson's disease, Huntington disease, amyotrophic lateral sclerosis, infectious brain diseases, traumatic brain injuries, migraine, chronic traumatic encephalopathy, and combinations thereof.

A further aspect relates to an in vitro method for identifying an agent useful as a therapeutic, such as useful for the prevention or treatment of a neurovascular disorder or a CNS disorder comprising neurovascular dysfunction, said method comprising determining whether a test agent activates Wnt signaling mediated by the GPR124/RECK/Frizzled/LRP receptor complex but not Wnt signaling mediated by the Frizzled/LRP receptor complex in the absence of RECK and/or GPR124. The term "in vitro" generally denotes outside, or external to, a body, e.g., an animal or human body. The term also encompasses "ex vivo". One example of "in vitro" is in tissue cell culture.

The term "test agent" as used herein refers to any chemical (e.g., inorganic or organic), biochemical or biological substance, molecule or macromolecule (e.g., biological macromolecule), a combination or mixture thereof, a sample of undetermined composition, or an extract made from biological materials such as bacteria, fungi, plants, or animal cells or tissues of which it is desired to determine whether it activates GPR124/RECK/Frizzled/LRP-mediated Wnt signaling but not Frizzled/LRP-mediated Wnt signaling in the absence of RECK and/or GPR124.

Determining the activation or lack of activation of Wnt signaling mediated by the GPR124/RECK/Frizzled/LRP receptor complex and Wnt signaling mediated by the Frizzled/LRP receptor complex may be determined as described elsewhere herein. For example, cells transiently transfected with a Super TOPFlash plasmid (e.g. Super 8× TOPFlash plasmid, Addgene plasmid #12456) or a stably transfected Super Top Flash reporter cell line (e.g. HEK293 STF cell line) could be (co-)transfected with plasmids encoding Frizzled, LRP, GPR124 and/or Reck polypeptides, and be used to determine the luciferase activity of the cells in response to addition of the test agent as an indication of the Wnt signaling activity in said cells.

In particular embodiments, the in vitro method for identifying an agent useful as a therapeutic as disclosed herein comprises contacting the test agent with a cell capable of Wnt signaling mediated by the GPR124/RECK/Frizzled/LRP receptor complex and measuring said Wnt signaling, and contacting the test agent with a cell capable of Wnt signaling mediated by the Frizzled/LRP receptor complex but not by the GPR124/RECK/Frizzled/LRP receptor complex, and measuring said Wnt signaling.

The term "contact" or "contacting" as used herein means bringing one or more first components (such as one or more molecules, biological entities, cells, or materials) together with one or more second components (such as one or more molecules, biological entities, cells, or materials) in such a manner that the first component(s) can—if capable thereof—bind or modulate the second component(s) or that the second component(s) can—if capable thereof—bind or modulate the first component(s). Such modulation may occur either directly, i.e., by way of direct interaction between the first and second component(s); or indirectly, e.g., when the first component(s) interact with or modulate one or more further component(s), one or more of which in turn interact with or modulate the second component(s), or vice versa. The term "contacting" may depending on the context be synonymous with "exposing", "incubating", "mixing", "reacting", "treating", or the like.

In particular embodiments, the test agent may be contacted with the cell capable of GPR124/RECK/Frizzled/LRP-mediated Wnt signaling and/or with the cell capable of Frizzled/LRP-mediated Wnt signaling but not GPR124/RECK/Frizzled/LRP-mediated Wnt signaling by transfecting said cell with a nucleic acid encoding the agent, a nucleic acid expression cassette comprising the nucleic acid or a vector comprising the nucleic acid or the nucleic acid expression cassette as taught herein. Measuring Wnt signaling typically denotes determining the activation of Wnt signaling, preferably the activation of canonical or β-catenin-dependent Wnt signaling as described elsewhere herein, for example by the detecting an increase in Wnt-responsive genes or the nuclear localisation of β-catenin. Another way of determining activation of Frizzled/LRP-mediated Wnt signaling is studying the establishment of the dorsal axis duplication during the embryonic development in *Xenopus* upon microinjection of the test agent into one ventral blastomere of the four-cell stage embryo as known in the art. Yet another way of determining activation of Frizzled/LRP-mediated Wnt signaling is studying the establishment of the forebrain and eye structures during the embryonic development in zebrafish (*Danio rerio*) upon microinjection of the test agent into the one to four-cell stage embryo as known in the art. The level of Wnt signaling activity may be compared to a baseline value. The baseline value can be a value for a control sample (e.g. a sample of an unstimulated cell population or a cell population contacted with a control agent).

Cells capable of Wnt signaling mediated by the GPR124/RECK/Frizzled/LRP receptor complex are typically cells that comprise GPR124, RECK, Frizzled, and LRP at its plasma membrane and containing the downstream members of the Wnt/β-catenin signaling pathway. Cells capable of Wnt signaling mediated by the Frizzled/LRP receptor complex but not by the GPR124/RECK/Frizzled/LRP receptor complex, are typically cells that comprise Frizzled and LRP at its plasma membrane and containing the downstream members of the Wnt/β-catenin signaling pathway, but not comprising a GPR124 polypeptide and/or a RECK polypeptide at its plasma membrane.

Cells capable of mediating Wnt signaling by the GPR124/RECK/Frizzled/LRP receptor complex may be cells naturally expressing all cellular components required for GPR124/RECK/Frizzled/LRP-mediated Wnt signaling, such as cerebral endothelial cells or cell lines. Cells capable of mediating Wnt signaling by the GPR124/RECK/Frizzled/LRP receptor complex may also be cells which naturally express none or not all of the cellular components required for GPR124/RECK/Frizzled/LRP-mediated Wnt signaling, which may be modified such as genetically engineered in order to compensate for the missing cellular components required for GPR124/RECK/Frizzled/LRP-mediated Wnt signaling, such as human embryonic kidney 293(HEK293) cells. Such modifications are known in the art and include transfection of the cells with nucleic acids encoding for, for example, the GPR124 and/or RECK polypeptide.

As described elsewhere herein, the absence of, or the not comprising or containing of, a receptor polypeptide does in this context not per se refer to the complete absence of said receptor polypeptide at the cell membrane, but may refer to an amount of the receptor polypeptide which is not detectable by, or falls below the sensitivity range of, protein assays known by the person skilled in the art.

Preliminary screens can be conducted by screening the test agent for its capability of binding to a RECK polypeptide, a Frizzled polypeptide and/or a LRP polypeptide.

In particular embodiments, the in vitro method for identifying an agent useful as a therapeutic as disclosed herein comprises determining whether the test agent is capable of binding to the RECK polypeptide, and optionally determining whether the test agent is capable of binding to the Frizzled polypeptide and/or a LRP polypeptide.

The binding assay may involve contacting a RECK polypeptide, a Frizzled polypeptide and/or a LRP polypeptide with the test agent and allowing sufficient time for the test agent and the RECK polypeptide, the Frizzled polypeptide and/or the LRP polypeptide to from a binding complex. Formation of a binding complex may be detected using any established analytical technique for determining protein-protein binding as described elsewhere herein, such as co-immunoprecipitation, bimolecular fluorescence complementation, label transfer, tandem affinity purification, chemical cross-linking and fluorescence resonance energy transfer. Protein binding assays may be performed in a cell-free system or in a cell lysate or in isolated or cultured cells or in an isolated or cultured tissue, as described elsewhere herein.

In a binding assay, one or more of the agent, RECK polypeptide, Frizzled polypeptide and/or LRP polypeptide may be joined to a label, where the label can directly or indirectly provide a detectable signal. Non-limiting examples of such labels or signals include radioisotopes, fluorescent labels or signals, chemiluminescent labels or signals, enzymes, specific binding molecules, or particles (e.g. magnetic particles).

In particular embodiments, the in vitro method for identifying an agent useful as a therapeutic as disclosed herein may further comprise the use of one or more reagents which improve the efficiency of the assay, facilitate optimal protein-protein binding and/or reduce non-specific or background interactions. Non-limiting examples of such reagents are salts, neutral proteins (e.g. albumin), detergents, protease inhibitors, nuclease inhibitors, and anti-microbial agents.

In particular embodiments, the in vitro method for identifying an agent useful as a therapeutic as disclosed herein comprises contacting the test agent with a cell from 1 hour to 48 hours, from 6 hours to 36 hours, from 12 hours to 24 hours, from 0.5 to 120 minutes, from 1 to 90 minutes, from 5 to 60 minutes, or from 10 to 30 minutes.

In particular embodiments, the in vitro method for identifying an agent useful as a therapeutic as disclosed herein comprises contacting the test agent with a cell at a temperature from 4° C. to 40° C. In certain embodiments, contacting may be performed in isolated or cultured cells or in an isolated or cultured tissue. The term "isolated" as used throughout this specification with reference to a particular component generally denotes that such component exists in separation from—for example, has been separated from or prepared and/or maintained in separation from—one or more other components of its natural environment. More particularly, the term "isolated" as used herein in relation to cells or tissues denotes that such cells or tissues do not form part of an animal or human body. Isolated cells or tissues may be suitably cultured or cultivated in vitro. The terms "culturing" or "cell culture" are common in the art and broadly refer to maintenance of cells and potentially expansion (proliferation, propagation) of cells in vitro. Typically, animal cells, such as mammalian cells, such as human cells, are cultured by exposing them to (i.e., contacting them with) a suitable cell culture medium in a vessel or container adequate for the purpose (e.g., a 96-, 24-, or 6-well plate, a T-25, T-75, T-150 or T-225 flask, or a cell factory), at art-known conditions conducive to in vitro cell culture, such as temperature of 37° C., 5% v/v CO2 and >95% humidity.

The term "medium" as used herein broadly encompasses any cell culture medium conducive to maintenance of cells, preferably conducive to proliferation of cells. Typically, the medium will be a liquid culture medium, which facilitates easy manipulation (e.g., decantation, pipetting, centrifugation, filtration, and such) thereof.

Typically, the medium will comprise a basal medium formulation as known in the art. Many basal media formulations (available, e.g., from the American Type Culture Collection, ATCC; or from Invitrogen, Carlsbad, Calif.) can be used, including but not limited to Eagle's Minimum Essential Medium (MEM), Dulbecco's Modified Eagle's Medium (DMEM), alpha modified Minimum Essential Medium (alpha-MEM), Basal Medium Essential (BME), Iscove's Modified Dulbecco's Medium (IMDM), BGJb medium, F-12 Nutrient Mixture (Ham), Liebovitz L-15, DMEM/F-12, Essential Modified Eagle's Medium (EMEM), RPMI-1640, Medium 199, Waymouth's MB 752/1 or Williams Medium E, and modifications and/or combinations thereof. Compositions of basal media are generally known in the art and it is within the skill of one in the art to modify or modulate concentrations of media and/or media supplements as necessary for the cells cultured.

Such basal media formulations contain ingredients necessary for mammalian cell development, which are known per se. By means of illustration and not limitation, these ingredients may include inorganic salts (in particular salts containing Na, K, Mg, Ca, Cl, P and possibly Cu, Fe, Se and Zn), physiological buffers (e.g., HEPES, bicarbonate), nucleotides, nucleosides and/or nucleic acid bases, ribose, deoxyribose, amino acids, vitamins, antioxidants (e.g., glutathione) and sources of carbon (e.g., glucose, sodium pyruvate, sodium acetate), etc.

For use in culture, basal media can be supplied with one or more further components. For example, additional supplements can be used to supply the cells with the necessary trace elements and substances for optimal growth and expansion. Furthermore, antioxidant supplements may be added, e.g., β-mercaptoethanol. While many basal media already contain amino acids, some amino acids may be supplemented later, e.g., L-glutamine, which is known to be less stable when in solution. A medium may be further supplied with antibiotic and/or antimycotic compounds, such as, typically, mixtures of penicillin and streptomycin, and/or other compounds, exemplified but not limited to, amphotericin, ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Lipids and lipid carriers can also be used to supplement cell culture media. Such lipids and carriers can include, but are not limited to cyclodextrin, cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. Albumin can similarly be used in fatty-acid free formulations.

Also contemplated is supplementation of cell culture media with mammalian plasma or sera. Plasma or sera often contain cellular factors and components that facilitate cell viability and expansion. Optionally, plasma or serum may be heat inactivated. Heat inactivation is used in the art mainly to remove the complement. Heat inactivation typically involves incubating the plasma or serum at 56° C. for 30 to 60 min, e.g., 30 min, with steady mixing, after which the plasma or serum is allowed to gradually cool to ambient temperature. A skilled person will be aware of any common modifications and requirements of the above procedure. Optionally, plasma or serum may be sterilised prior to storage or use. Usual means of sterilisation may involve, e.g., filtration through one or more filters with pore size smaller than 1 μm, preferably smaller than 0.5 μm, e.g., smaller than 0.45 μm, 0.40 μm, 0.35 μm, 0.30 μm or 0.25 μm, more preferably 0.2 μm or smaller, e.g., 0.15 μm or smaller, 0.10 μm or smaller. Suitable sera or plasmas for use in media as taught herein may include human serum or plasma, or serum or plasma from non-human animals, preferably non-human mammals, such as, e.g., non-human primates (e.g., lemurs, monkeys, apes), foetal or adult bovine, horse, porcine, lamb, goat, dog, rabbit, mouse or rat serum or plasma, etc., or any combination of such. In certain preferred embodiments, a medium as taught herein may comprise bovine serum or plasma, preferably foetal bovine (calf) serum or plasma, more preferably foetal bovine (calf) serum (FCS or FBS). When culturing human cells, media may preferably comprise human serum or plasma, such as autologous or allogeneic human serum or plasma, preferably human serum, such as autologous or allogeneic human serum, more preferably autologous human serum or plasma, even more preferably autologous human serum.

In certain preferred embodiments, serum or plasma can be substituted in media by serum replacements, such as to provide for serum-free media (i.e., chemically defined media). The provision of serum-free media may be advantageous particularly with view to administration of the media or fraction(s) thereof to subjects, especially to human subjects (e.g., improved bio-safety). By the term "serum replacement" it is broadly meant any a composition that may be used to replace the functions (e.g., cell maintenance and growth supportive function) of animal serum in a cell culture medium. A conventional serum replacement may typically comprise vitamins, albumin, lipids, amino acids, transferrin, antioxidants, insulin and trace elements. Many commercialized serum replacement additives, such as KnockOut Serum Replacement (KOSR), N2, B27, Insulin-Transferrin-Selenium Supplement (ITS), and G5 are well known and are readily available to those skilled in the art.

Plasma or serum or serum replacement may be comprised in media as taught herein at a proportion (volume of plasma or serum or serum replacement/volume of medium) between about 0.5% v/v and about 40.0% v/v, preferably between about 5.0% v/v and about 20.0% v/v, e.g., between about 5.0% v/v and about 15.0% v/v, more preferably between about 8.0% v/v and about 12.0% v/v, e.g., about 10.0% v/v.

Suitable isolated or cultured cells may be without limitation bacterial cells, fungal cells, including yeast cells, plant cells, animal cells, mammalian cells, human cells, or non-human mammalian cells. Animal cells, such as mammalian cells, human cells, or non-human mammalian cells are preferred. Cells may include primary cells, secondary, tertiary etc. cells, or may include immortalised cell lines, including clonal cell lines. Non-limiting examples of bacterial cells include *Escherichia coli, Yersinia enterocolitica, Brucella* sp., *Salmonella tymphimurium, Serratia marcescens*, or *Bacillus subtilis*. Non-limiting examples of fungal cells include *Yarrowia lipolytica, Arxula adeninivorans, Pichia pastoris, Hansenula polymorpha, Saccharomyces cerevisiae*, or *Schizosaccharomyces pombe*. Non-limiting examples of insect cells include cells derived from *Drosophila melanogaster*, such as Schneider 2 cells, cell lines derived from the army worm *Spodoptera frugiperda*, such as Sf9 and Sf21 cells, or cells derived from the cabbage looper *Trichoplusia ni*, such as High Five cells. Non-limiting example of human cells include the human HeLa (cervical cancer) cell line. Other human cell lines common in tissue culture practice include inter alia human embryonic kidney 293 cells (HEK cells), DU145 (prostate cancer), Lncap (prostate cancer), MCF-7 (breast cancer), MDA-MB-438 (breast cancer), PC3 (prostate cancer), T47D (breast cancer), THP-1 (acute myeloid leukemia), U87 (glioblastoma), SHSYSY (neuroblastoma), or Saos-2 cells (bone cancer). A non-limiting example of primate cells are Vero (African green monkey Chlorocebus kidney epithelial cell line) cells, and COS cells. Non-limiting examples of rodent cells are rat GH3 (pituitary tumor), CHO (Chinese hamster ovary), PC12 (pheochromocytoma) cell lines, or mouse MC3T3 (embryonic calvarium) cell line. Such cells can be obtained from a variety of commercial sources and research resource facilities, such as, for example, the American Type Culture Collection (Rockville, Md.).

In certain embodiments, the cells may have an intact cell membrane. In other embodiments, the cell membrane may be permeabilised (transiently or permanently) to allow diffusion of components across the cell membrane which are not transported or are transported less effectively across an intact cell membrane. Suitable detergents for cell membrane permeabilisation include without limitation saponins (e.g., digitonin), Triton™ X-100, or Polysorbate 20. The cells may be live or viable, or may be non-viable.

Methods for introducing polypeptides and/or nucleic acids into viable cells are known to the person skilled in the art, and may include calcium phosphate co-precipitation, electroporation, microinjection, protoplast fusion, lipofection, exosome-mediated transfection, transfection employing polyamine transfection reagents, bombardment of cells by nucleic acid-coated tungsten micro projectiles, viral particle delivery, etc. Such introduction may also be referred to as delivery, transfection or transformation. Cell penetrating peptides (CPPs) may also be employed for delivering polypeptides or nucleic acids into cells. CPP translocation may be classified into three main entry mechanisms: direct penetration in the membrane, endocytosis-mediated entry, and translocation through the formation of a transitory structure. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. One of the initial CPPs discovered was the trans-activating transcriptional activator (Tat) from Human Immunodeficiency Virus 1 (HIV-1) which was found to be efficiently taken up from the surrounding media by numerous cell types in culture. Since then, the number of known CPPs has expanded considerably and small molecule synthetic analogues with more effective protein transduction properties have been generated. CPPs include but are not limited to Penetratin, Tat (48-60), Transportan, and (R-AhX-R4) (Ahx=aminohexanoyl). U.S. Pat. No. 8,372,951, provides a CPP derived from eosinophil cationic protein (ECP) which exhibits highly cell-penetrating efficiency and low toxicity. Aspects of delivering the CPP with its cargo into a vertebrate subject are also provided. Further aspects of CPPs and their delivery are described in U.S. Pat. Nos. 8,575,305; 8,614,194 and 8,044,019. CPPs can be conjugated or complex with the cargo as known in the art, e.g., via a thioether bond or via formation of particles.

Expressible nucleic acid molecules, such as for example expression cassettes or expression vectors, encoding polypeptides or RNAs of interest can be provided as generally known in the art. An expressible nucleic acid molecule may typically comprise a nucleic acid molecule encoding the polypeptide of interest and/or a nucleic acid molecule encoding the RNA molecule of interest and a promoter(s) operably linked to said nucleic acid molecule(s). The promoter may be selected or configured to effect expression of the polypeptide and/or RNA of interest in a cell of interest, such as a bacterial cell, fungal cell, yeast cell, plant cell, animal cell, mammalian cell, human cell, or non-human mammalian cell.

The cells may be contacted with the test agent by adding the test agent to the culture medium in which the cells are being cultured. Nucleic acids encoding the test agent may be provided to the cells comprised within a vector under conditions known by the person skilled in the art and as described elsewhere herein. Alternatively, nucleic acids encoding the test agent may be provided to the cells via a viral vector, i.e. the cells are contacted with viral particles comprising nucleic acids encoding the test agent. The viral vectors have typically been modified to lack the ability of producing viral proteins required for productive infection. In particular embodiments, the test agent may be identified as an agent useful as a therapeutic as disclosed herein if the agent enhances Wnt/β-catenin signaling mediated by the GPR124/RECK/Frizzled/LRP receptor complex at least 10-fold more, at least 20-fold more, at least 30-fold more, at least 40-fold more, at least 50-fold more, at least 100-fold more, at least 250-fold more, at least 500-fold more, at least 750-fold more, at least 1000-fold more, at least $1\times10^4$-fold more, or at least $1\times10^5$-fold more compared to GPR124/RECK/Frizzled/LRP-mediated Wnt/β-catenin signaling baseline or background induced by a neutral substance or negative control, for example as measured in an assay as described elsewhere herein.

In particular embodiments, the test agent may be identified as an agent useful as a therapeutic as disclosed herein if the GPR124/RECK/Frizzled/LRP-mediated Wnt signaling activity induced by said agent is at least 3.5-fold more, at least 5-fold more, at least 10-fold more, at least 15-fold more, at least 20-fold more, at least 25-fold more, at least 50-fold more, at least 100-fold more, at least 500-fold more, at least 1000-fold more, at least $1\times10^4$-fold more, or at least $1\times10^5$-fold more t than the Frizzled/LRP-mediated Wnt signaling activity induced by said agent, in absence of RECK and/or GPR124.

Test agents that are initially identified as useful as a therapeutic as disclosed herein by any of the foregoing screening methods can be further tested to validate the apparent activity in vitro, in vivo or ex vivo, by animal models suitable for mimicking neurovascular disorders or central nervous system (CNS) disorders comprising neurovascular dysfunction in human.

The present application also provides aspects and embodiments as set forth in the following Statements:

Statement 1. An agent capable of activating G-protein coupled receptor (GPR)124/RECK/Frizzled/lipoprotein receptor-related protein (LRP)-mediated Wnt signaling, wherein said agent does not activate Frizzled/LRP-mediated Wnt signaling in the absence of RECK and/or GPR124.

Statement 2. The agent according to Statement 1, wherein said agent is capable of inducing heteromerization of Frizzled and LRP polypeptides at a cell membrane in the presence of RECK and GPR124, but not in the absence of RECK and/or GPR124.

Statement 3. The agent according to Statement 2, wherein said agent is capable of concurrently binding to Frizzled and LRP polypeptides at a cell membrane in the presence of RECK and GPR124, but not in the absence of RECK and/or GPR124.

Statement 4. The agent according to any one of Statements 1 to 3, wherein said agent is capable of binding to the GPR124 and/or the RECK polypeptide.

Statement 5. The agent according to any one of Statements 1 to 4, wherein said agent is capable of binding to the RECK polypeptide.

Statement 6. The agent according to Statement 5, wherein said agent is capable of binding to the cysteine knot 4 (CK4) region, to the CK5 region or to the CK4 and CK5 regions, of RECK polypeptide.

Statement 7. The agent according to any one of Statements 1 to 6, wherein said agent is capable of binding to the cysteine-rich domain (CRD) of the Frizzled polypeptide.

Statement 8. The agent according to any one of Statements 1 to 7, wherein said agent is capable of binding to the DKK-binding site and/or the Wnt-binding site of the LRP polypeptide.

Statement 9. The agent according to any one of Statements 1 to 8, wherein the agent comprises or is selected from a group consisting of a chemical substance, an antibody, an antibody fragment, an antibody-like protein scaffold, a protein or polypeptide, a peptide, a peptidomimetic, an aptamer, a photoaptamer, a spiegelmer and a nucleic acid, preferably wherein said agent comprises is a protein or polypeptide.

Statement 10. The agent according to any one of Statements 1 to 9, wherein said agent comprises a RECK-binding domain, a Frizzled-binding domain and a LRP-binding domain, wherein said RECK-binding domain, said Frizzled-binding domain, and said LRP-binding domain are derived from a Wnt7 polypeptide, such as from a Wnt7a or Wnt7b polypeptide.

Statement 11. The agent according to Statement 10, wherein said RECK-binding domain comprises:
- an amino acid sequence having at least 25% sequence identity to the amino acid sequence HVEPVRASRNKRPTFLKIKKPLSYRKPMDTDLVYIEKSPNYC (SEQ ID NO: 17); or
- an amino acid sequence having at least 25% sequence identity to the amino acid sequence VEPVRASRNKRPTFLKIKKPLSYRKPMDT (SEQ ID NO: 18); or
- an amino acid sequence having at least 25% sequence identity to the amino acid sequence VEVVRASRLRQPTFLRIKQLRSYQKPMET (SEQ ID NO: 19); or
- an amino acid sequence XXXVXAXRXXXXXFLXIXXXXXYXKXXXX (SEQ ID NO: 20), VXAXRXXXXXFLXIXXXXXYXK (SEQ ID NO: 21), XXXVXAXRXXXXXFLXXXXXXXXXKXXXX (SEQ ID NO: 22) or VXAXRXXXXXFLXXXXXXXXXK (SEQ ID NO: 23) wherein X is any amino acid, preferably wherein the amino acid sequence shows at least 50% sequence identity to any one of SEQ ID NO: 18 or SEQ ID NO: 19.

Statement 12. The agent according to any one of Statements 1 to 11, wherein said agent is or consists essentially of a fragment of a Wnt7 polypeptide, such as a fragment of a Wnt7a or Wnt7b polypeptide.

Statement 13. The agent according to Statements 12, wherein said fragment is or consists essentially of the N-terminal domain (NTD) of the Wnt7 polypeptide.

Statement 14. The agent according to any one of Statements 1 to 13, wherein said agent is a variant of a Wnt7 polypeptide, such as a variant of a Wnt7a or Wnt7b polypeptide.

Statement 15. The agent according to Statement 14, wherein
- the glutamine (Q) residue at the position corresponding to position 17 in SEQ ID NO: 24 or SEQ ID NO: 51 is substituted by one or more amino acid residues other than glutamine (Q), preferably by an alanine (A) residue;
- the isoleucine (I) residue at the position corresponding to position 20 in SEQ ID NO: 24 or SEQ ID NO: 51 is substituted by one or more amino acid residues other than isoleucine (I), preferably by an alanine (A) residue;
- the proline (P) residue at the position corresponding to position 25 in SEQ ID NO: 24 or SEQ ID NO: 51 is substituted by one or more amino acid residues other than proline (P), preferably by an alanine (A) residue;
- the alanine (A) residue at the position corresponding to position 27 in SEQ ID NO: 24 or SEQ ID NO: 51 is substituted by one or more amino acid residues other than alanine (A), preferably by an arginine (R) residue;
- the isoleucine (I) residue at position corresponding to position 28 in SEQ ID NO: 24 or SEQ ID NO: 51 is substituted by one or more amino acid residues other than isoleucine (I), preferably by an alanine (A) residue;
- the glutamate (E) residue at the position corresponding to position 33 in SEQ ID NO: 24 or SEQ ID NO: 51 is substituted by one or more amino acid residues other than glutamate (E), preferably by an alanine (A) residue;
- the methionine (M) residue at the position corresponding to position 37 in SEQ ID NO: 24 or SEQ ID NO: 51 is substituted by one or more amino acid residues other than glutamate (E), preferably by an alanine (A) residue;
- the leucine (L) residue at the position corresponding to position 39 in SEQ ID NO: 24 or SEQ ID NO: 51 is substituted by one or more amino acid residues other than glutamate (E), preferably by an alanine (A) residue;
- the glutamate (E) residue at the position corresponding to position 41 in SEQ ID NO: 24 or SEQ ID NO: 51 is substituted by one or more amino acid residues other than glutamate (E), preferably by an alanine (A) residue;
- the phenylalanine (F) residue at the position corresponding to position 44 in SEQ ID NO: 24 or SEQ ID NO: 51 is substituted by one or more amino acid residues other than phenylalanine (F), preferably by an alanine (A) residue;
- the arginine (R) residue at the position corresponding to position 50 in SEQ ID NO: 24 or SEQ ID NO: 51 is substituted by one or more amino acid residues other than arginine (R), preferably by an alanine (A) residue;
- the asparagine (N) residue at the position corresponding to position 52 in SEQ ID NO: 24 or SEQ ID NO: 51 is substituted by one or more amino acid residues other than asparagine (N), preferably by an glutamine (Q) residue;
- the valine (V) residue at the position corresponding to position 68 in SEQ ID NO: 24 or SEQ ID NO: 51 is substituted by one or more amino acid residues other than valine (V), preferably by an alanine (A) residue;
- the isoleucine (I) residue at the position corresponding to position 129 in SEQ ID NO: 24 or SEQ ID NO: 51 is substituted by one or more amino acid residues other than isoleucine (I), preferably by an alanine (A) residue;
- the phenylalanine (F) residue at the position corresponding to position 131 in SEQ ID NO: 24 or SEQ ID NO: 51 is substituted by one or more amino acid residues other than phenylalanine (F), preferably by an alanine (A) residue;
- the lysine (K) residue at the position corresponding to position 133 in SEQ ID NO: 24 or SEQ ID NO: 51 is substituted by one or more amino acid residues other than lysine (K), preferably by an alanine (A) residue;

the phenylalanine (F) residue at the position corresponding to position 135 in SEQ ID NO: 24 or SEQ ID NO: 51 is substituted by one or more amino acid residues other than phenylalanine (F), preferably by an alanine (A) residue;

the isoleucine (I) residue at the position corresponding to position 141 in SEQ ID NO: 24 or SEQ ID NO: 51 is substituted by one or more amino acid residues other than isoleucine (I), preferably by an alanine (A) residue;

the arginine (R) residue at the position corresponding to position 146 in SEQ ID NO: 24 or SEQ ID NO: 51 is substituted by one or more amino acid residues other than arginine (R), preferably by an alanine (A) residue;

the arginine (R) residue at the position corresponding to position 158 in SEQ ID NO: 24 or SEQ ID NO: 51 is substituted by one or more amino acid residues other than arginine (R), preferably by an alanine (A) residue;

the lysine (K) residue at the position corresponding to position 159 in SEQ ID NO: 24 or SEQ ID NO: 51 is substituted by one or more amino acid residues other than lysine (K), preferably by an alanine (A), serine (S) or leucine (L) residue;

the lysine (K) residue at the position corresponding to position 181 in SEQ ID NO: 24 or SEQ ID NO: 51 is substituted by one or more amino acid residues other than lysine (K), preferably by an alanine (A) residue;

the arginine (R) residue at the position corresponding to position 191 in SEQ ID NO: 24 or SEQ ID NO: 51 is substituted by one or more amino acid residues other than arginine (R), preferably by an alanine (A) residue;

the lysine (K) residue at the position corresponding to position 198 in SEQ ID NO: 24 or SEQ ID NO: 51 is substituted by one or more amino acid residues other than lysine (K), preferably by an alanine (A) residue;

the lysine (K) residue at the position corresponding to position 200 in SEQ ID NO: 24 or SEQ ID NO: 51 is substituted by one or more amino acid residues other than lysine (K), preferably by an alanine (A) residue;

the valine (V) residue at the position corresponding to position 205 in SEQ ID NO: 24 or SEQ ID NO: 51 is substituted by one or more amino acid residues other than valine (V), preferably by an alanine (A) residue;

the glutamate (E) residue at the position corresponding to position 208 in SEQ ID NO: 24 or SEQ ID NO: 51 is substituted by one or more amino acid residues other than glutamate (E), preferably by an alanine (A) residue;

the arginine (R) residue at the position corresponding to position 214 in SEQ ID NO: 24 or SEQ ID NO: 51 is substituted by one or more amino acid residues other than arginine (R), preferably by an alanine (A) residue;

the lysine (K) residue at the position corresponding to position 216 in SEQ ID NO: 24 or SEQ ID NO: 51 is substituted by one or more amino acid residues other than lysine (K), preferably by an alanine (A) residue;

the proline (P) residue at the position corresponding to position 218 in SEQ ID NO: 24 or SEQ ID NO: 51 is substituted by one or more amino acid residues other than proline (P), preferably by an alanine (A) residue;

the lysine (K) residue at the position corresponding to position 222 in SEQ ID NO: 24 or SEQ ID NO: 51 is substituted by one or more amino acid residues other than lysine (K), preferably by an alanine (A) residue;

the isoleucine (I) residue at the position corresponding to position 223 in SEQ ID NO: 24 or SEQ ID NO: 51 is substituted by one or more amino acid residues other than isoleucine (I), preferably by an alanine (A) residue;

the tyrosine (Y) residue at the position corresponding to position 229 in SEQ ID NO: 24 or SEQ ID NO: 51 is substituted by one or more amino acid residues other than tyrosine (Y), preferably by an alanine (A) residue;

the proline (P) residue at the position corresponding to position 232 in SEQ ID NO: 24 or SEQ ID NO: 51 is substituted by one or more amino acid residues other than proline (P), preferably by an alanine (A) residue;

the threonine (T) residue at the position corresponding to position 235 in SEQ ID NO: 24 or SEQ ID NO: 51 is substituted by one or more amino acid residues other than threonine (T), preferably by an alanine (A) residue;

the glutamate (E) residue at the position corresponding to position 248 in SEQ ID NO: 24 or SEQ ID NO: 51 is substituted by one or more amino acid residues other than glutamate (E), preferably by an alanine (A) residue;

the arginine (R) residue at the position corresponding to position 289 in SEQ ID NO: 24 or SEQ ID NO: 51 is substituted by one or more amino acid residues other than arginine (R), preferably by an alanine (A) residue;

the tryptophan (W) residue at the position corresponding to position 291 in SEQ ID NO: 24 or SEQ ID NO: 51 is substituted by one or more amino acid residues other than tryptophan (W), preferably by an alanine (A) residue;

the threonine (T) residue at the position corresponding to position 307 in SEQ ID NO: 24 or SEQ ID NO: 51 is substituted by one or more amino acid residues other than threonine (T), preferably by an alanine (A) residue; and/or the lysine (K) residue at the position corresponding to position 318 in SEQ ID NO: 24 or SEQ ID NO: 51 is substituted by one or more amino acid residues other than lysine (K), preferably by an alanine (A) residue.

Statement 16. A nucleic acid encoding the agent according to any one of Statements 1 to 15, wherein said agent is a protein, polypeptide or a peptide.

Statement 17. A nucleic acid expression cassette comprising the nucleic acid according to Statement 16, operably linked to a promoter and/or transcriptional and translational regulatory signals.

Statement 18. A vector comprising the nucleic acid according to Statement 16 or the nucleic acid expression cassette according to Statement 17, such as a viral vector.

Statement 19. A host cell comprising the nucleic acid according to Statement 16, the nucleic acid expression cassette according to Statement 17 or the vector according to Statement 18.

Statement 20. A pharmaceutical composition comprising the agent according to any one of Statements 1 to 15, the nucleic acid according to Statement 16, the nucleic acid expression cassette according to Statement 17, the vector according to Statement 18, or the host cell according to Statement 19 and a pharmaceutically acceptable carrier.

Statement 21. The agent according to any one of Statements 1 to 15, the nucleic acid according to Statement 16, the nucleic acid expression cassette according to Statement 17, the vector according to Statement 18, the host cell according to Statement 19, or the pharmaceutical composition according to Statement 20, for use as a medicament.

Statement 22. The agent according to any one of Statements 1 to 15, the nucleic acid according to Statement 16, the nucleic acid expression cassette according to Statement 17, the vector according to Statement 18, the host cell according to Statement 19, or the pharmaceutical composition according to Statement 20, for use in the prevention or treatment of a neurovascular disorder or a central nervous system (CNS) disorder comprising neurovascular dysfunction.

Statement 23. The agent for use according to Statement 22, wherein said neurovascular disorder is selected from the group consisting of ischemic stroke, hemorrhagic stroke, ischemia/reperfusion injury, brain aneurysms, arteriovenous malformations (AVMs), cavernous malformations, vasculitis, cerebral hemorrhage, subarachnoid hemorrhage, spinal vascular malformations, carotid artery stenosis, Moyamoya disease and intracranial atherosclerosis and combinations thereof, or said CNS disorder is selected from the group consisting of multiple sclerosis, ischemic stroke, brain cancer, epilepsy, dementia, vascular dementia, HIV-1-associated dementia, Alzheimer's disease, Parkinson's disease, Huntington disease, amyotrophic lateral sclerosis, infectious brain diseases, traumatic brain injuries, migraine and chronic traumatic encephalopathy and combinations thereof.

Statement 24. An in vitro method for identifying an agent useful as a therapeutic, such as useful for the prevention or treatment of a neurovascular disorder or a CNS disorder comprising neurovascular dysfunction, said method comprising determining whether a test agent activates GPR124/RECK/Frizzled/LRP-mediated Wnt signaling but not Frizzled/LRP-mediated Wnt signaling in the absence of RECK and/or GPR124.

Statement 25. The in vitro method according to Statement 24, comprising:
contacting the test agent with a cell capable of GPR124/RECK/Frizzled/LRP-mediated Wnt signaling and measuring said Wnt signaling, and
contacting the test agent with a cell capable of Frizzled/LRP-mediated Wnt signaling but not GPR124/RECK/Frizzled/LRP-mediated Wnt signaling, and measuring said Wnt signaling.

Statement 26. The in vitro method according to Statement 24 or 25, wherein the method further comprises determining whether the test agent is capable of binding to the RECK polypeptide.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as follows in the spirit and broad scope of the appended claims.

The herein disclosed aspects and embodiments of the invention are further supported by the following non-limiting examples.

EXAMPLES

Example 1. A Molecular Mechanism for Wnt Ligand-Specific Signaling

1. Material and Methods
   1.1. Zebrafish Lines
   Zebrafish (*Danio rerio*) were maintained at 28° C. on a 14 h light/10 h dark cycle. Embryos were obtained and raised under standard conditions in accordance with European and national ethical and animal welfare guidelines (protocol approval number: CEBEA-IBMM-2017-22:65). Staging was performed according to Kimmel et al. (C. B. Kimmel, W. W. Ballard, S. R. Kimmel, B. Ullmann, T. F. Schilling, Dev. Dyn. 203, 253-310 (1995)). The characterized transgenic and mutant lines Tg(kdrl:GFP)s843, Tg(kdrl:ras-mCherry)s896 and gpr124s984 (*Danio rerio*) lines were used in this study (B. Vanhollebeke et al., Elife. 4, 1-25 (2015); S.-W. Jin, D. Beis, T. Mitchell, J.-N. Chen, D. Y. R. Stainier, *Development*. 132, 5199-209 (2005); N. C. Chi et al., Genes Dev. 22, 734-739 (2008)).

1.2. Morpholinos, RNA Constructs and Microinjection
   Splice-blocking morpholinos against gpr124 (5'-ACTGATATTGATTTAACTCACCACA-3') (SEQ ID NO. 122) (B. Vanhollebeke et al., Elife. 4, 1-25 (2015)) were obtained from Gene Tools (Eugene, OR) and injected at the one-cell stage at 2 ng. Synthetic mRNAs were transcribed from pCS2 plasmids after NotI digestion using the mMessage mMachine SP6 Kit (Ambion, Carlsbad, CA) and injected into one-cell stage zebrafish embryo 1.4. Expression Plasmid Constructs
   All Wnt signaling components and other constructs were expressed from the CMV promoter of the pCS2 vector after recombination using In-Fusion cloning (Takara, Mountain View, Calif.) except for Fz1 (addgene #42253) and Fz5 (addgene #42267). Single-point mutation variants, deletions and chimeras were generated using In-Fusion cloning and tandem overlapping PCR products. All constructs were confirmed by Sanger sequencing. Deletions of Reck variants correspond to the following amino acids: ReckΔCK1: 46-93; ReckΔCK2: 113-150; ReckΔCK3: 160-206; ReckΔCK4: 225-272; ReckΔCK5: 301-347; ReckΔCK1-5: 46-347; ReckΔCRD: 352-484 and ReckΔKAZAL: 636-798. The HA tag was inserted after residue 22 in Reck, residue 49 in Gpr124 and residue 22 in Fz5. The FLAG tag was inserted after residue 49 in Gpr124.

1.5. Cell Culture and HEK293(T) Mutant Cell Lines
   HEK293T cells were obtained from ATCC (CRL-3216) and the HEK293 STF cell line was kindly provided by Jeremy Nathans (John Hopkins). WT and mutant cells were cultured in DMEM/F12 medium (Lonza, Basel, Switzerland) supplemented with 10% fetal bovine serum and maintained in a humidified incubator equilibrated with 5% CO2. GPR124 and RECK were genetically invalidated using CRISPR/Cas9 approaches in HEK293 STF cells and LRP5, LRP6 and FZ were similarly invalidated in HEK293T cells. CRISPR/Cas9 guide sequences were designed using the http://crispr.mit.edu/website and were cloned into pSpCas9 (BB)-2AGFP (F. A. Ran et al., Nat. Protoc. 8, 2281-308 (2013).). The top 1% of GFP+ cells was isolated by FACS (AriaIII, BD Biosciences, San Jose, Calif.) 48 h after transfection and distributed in 96-well plates for clonal expansion. In order to facilitate the genetic characterization of the mutant cell lines, clones generating multiple-peak derivative melt curves in high-resolution melt analyses were counter-selected. For each target site, mutations were identified by Sanger sequencing of both ~1000 bp PCR products centered on the protospacer adjacent motif (PAM) site as well as at least eight subclones of the PCR product in pCR™-Blunt II-TOPO® (Thermo Fisher Scientific, Waltham, Mass.). The mutant cell lines were obtained through iterative CRISPR/Cas9-mediated mutagenesis.

1.6. STF Dual Luciferase Assays
   Cells were plated into 96-well plates and transfected after 24 h in triplicate with Lipofectamine 2000 (Life Technologies, Carlsbad, Calif.). The amount of plasmid DNA transfected per well was optimized for each expression vector: *Renilla* luciferase (0.5 ng) (was kindly provided by Jeremy Nathans (John Hopkins)), Wnt ligands (20 ng), Fz receptors (5 ng), Lrp (2.5 ng), Gpr124 (10 ng), Reck (5 ng) and Dkk-1 (10 ng) unless otherwise indicated. The total amount of DNA was adjusted to 100 ng per well with the empty pCS2 vector. Dual luciferase assays were performed using the STF cell line or by co-transfecting 20 ng of M50 Super 8x TOPFlash plasmid (Addgene plasmid #12456). Cells were harvested in passive lysis buffer (E1960, Promega, Wis.) and the activities of the Firefly and *Renilla* luciferases were measured sequentially using the Dual-Luciferase Reporter Assay system (E1960, Promega, Madison, Wis.) 48 h post-transfection. The competition assays of FIG. 1C were performed by plating cells as a 1:1:1 mixture at 90% confluency in 96-well plates 24 h after transfection. Luciferase activity was measured 24 h after co-culture.

1.7. Immunofluorescence and Proximity Ligation Assay

Cells were grown in glass-coated chambers (IBIDI, Martinsried, Germany) and transfected after 24 h with Lipofectamine 2000 (Life Technologies, Carlsbad, Calif.). Cells were fixed with 4% paraformaldehyde for 10 min at room temperature (RT) 48 h post transfection. For immunofluorescence staining (IF), cells were blocked in 1% BSA-PBS for 30 min before being exposed to primary antibodies for 1 h at RT. After three PBS washes, cells were incubated with secondary antibodies for 1 h at RT. For anti-V5 staining of Wnt ligands, cells were additionally washes for 10 min in PBS 0.1% Tween 20 before incubation with the secondary antibody solution. For the proximity ligation assay (PLA) (Sigma-Aldrich, St. Louis, Mo.), cells were blocked for 30 min at 37° C. with the Blocking solution provided by the manufacturer before being incubated with the primary antibodies for 1 h at RT. Cells were washed three times and incubated with the PLA probes anti-rabbit PLUS and anti-mouse MINUS for 1 h at 37° C. After two PBS washes, cells were incubated with the Duolink Ligation solution for 30 min at 37° C. After two PBS washes, cells were incubated with the Duolink Amplification solution for 100 min at 37° C. The following antibodies were used: mouse monoclonal anti-V5 (R96025, Life Technologies, Carlsbad, Calif.) at 1:500 for IF and PLA, purified polyclonal rabbit anti-HA (H6908, St. Louis, Mo.) at 1:400 for IF and PLA and anti-mouse Alexa488-conjugated secondary antibody (Thermo Fisher Scientific, Waltham, Mass.) at 1:5000. Cells were stained for 2 min with Hoechst diluted to 10 µg ml-1 in PBS.

1.8. Western Blotting, Dotblot and Co-Immunoprecipitation

The following antibodies were used: rabbit anti-DVL2 (1:1000, 3216, Cell Signaling Technology, Leiden, Netherlands), rabbit anti-DVL2-phospho T224 (1:1000, ab124941, Abcam, Cambridge, UK) and anti-mouse β-actin (1:50,000, A5441, Sigma-Aldrich, St. Louis, Mo.), chicken anti-GFP (1:5000, GFP-1010, Ayes, Tigard, Oreg.) and mouse monoclonal anti-FLAG M2 (1:1000, F1804, Sigma-Aldrich, St. Louis, Mo.). Dot blot analyses were performed according to standard protocols with a BioDot SF apparatus (Bio-Rad, Munich, Germany). Serial dilutions of supernatant were spotted onto a nitrocellulose membrane (GE Healthcare, Little Chalfont, UK). After drying, the membrane was incubated with the antibodies as described above for the Western blots. For the co-immunoprecipitation, transfected HEK293T cells from 6-well plates were washed twice and detached from the plate with PBS. The cells were pelleted by centrifugation and lysed in lysis buffer (150 mM NaCl, 25 mM Tris (pH 7.5), 1% NP40) containing protein inhibitor (ThermoFisher Scientific, Waltham, Mass.) for 30 min at 4° C. After centrifugation, the supernatant was incubated with anti-FLAG M2 affinity gel (A2220, Sigma, St. Louis, Mo.) for 3 h at 4° C. Beads were washed five times with the lysis buffer and boiled in equal amount of 2x Laemmli Sample buffer.

1.9. Microscopy and Images Processing

Cells and zebrafish embryos were imaged with an LSM710 confocal microscope and images were processed in ImageJ. Images of eye fusion phenotypes were taken on Leica M165 FC. Representations of brain vasculature were generated using Imaris software (BitPlane, Zurich, Switzerland). The percentage of PLA positive (PLA+) areas and DAPI positive (DAPI+) areas were calculated using ImageJ on images containing about 50 to 100 cells. The PLA+ area was measured after manually applying a fixed threshold. The DAPI+ area was measured after applying the "default" thresholding method in Image J.

1.10. Structural Modeling

The structure of *Xenopus* Wnt8a (PDB ID: 4F0A) (C. Y. Janda, D. Waghray, A. M. Levin, C. Thomas, K. C. Garcia, Science. 337, 59-64 (2012)) was used as a starting model for Wnt7a. Missing residues and substitutions were modeled using the program Modeller (B. Webb, A. Sali, *Current Protocols in Bioinformatics* (John Wiley & Sons, Inc., Hoboken, N.J., USA, 2016), vol. 54, p. 5.6.1-5.6.37.). The modeling strategy included accounting for existing disulphide bridges as observed in Wnt8. The initial best models were subjected to a conjugate-gradient energy minimization in vacuum with the Ca restrained and then freed in a second minimization step. These models were then embedded in a water box and electric neutrality was achieved by adding Na+ counter ions at 150 mM. The whole system was again energy minimized in 3000 steps. The molecular dynamics simulation was carried out for 0.5 ns with the program NAMD 2.7 at constant temperature (310 K) and constant pressure (1 atm), with periodic boundaries and using CHARMM36 as force field (J. C. Phillips et al., J. Comput. Chem. 26, 1781-1802 (2005). A time step of 2 fs was used to integrate the equations of motion. The short-range interactions were cut at 12 Å and the smooth-particle mesh Ewald method was used to calculate electrostatic interactions. Hydrogen atoms were constrained using the SHAKE algorithm. The resulting model is an average representation of the stable simulation.

1.11. Recombinant Proteins and Synthetic Peptides

Reck-CK-Fc fusion proteins were recovered in serum-free FreeStyle 293 Expression Medium (Thermo Fisher Scientific, Waltham, Mass.) from the supernatant of HEK293T cell cultures 72 h post transfection with Lipofectamine 2000 (Life Technologies, Carlsbad, Calif.). After collection, the supernatants were either concentrated 50 times by centrifugation (GE Healthcare, Little Chalfont, UK) or submitted to Protein G affinity purification (Protein G Sepharose 4 Fast Flow, Sigma-Aldrich, St. Louis, Mo.). Protein purity was assessed using Coomassie blue staining after PAGE. Synthetic Wnt linker peptides were obtained from Chinapeptide Co., Ltd at purities over 90%.

1.12. Isothermal Titration Calorimetry

ITC titrations were carried out on an Affinity ITC (TA Instruments). Prior to the measurement, Reck-CK-Fc and all Reck-CK-Fc fusions were dialyzed to Tris-NaCl buffer (50 mM Tris pH8, 300 mM NaCl). In each case Wnt-derived peptides were prepared with buffer from the last step of protein dialysis. The samples were filtered and degassed before being examined in the calorimeter and the titrations were performed 25° C. All the experiments consisted of injection of constant volumes of 2 µL of titrant into the cell (200 µL) with a stirring rate of 75 rpm. Nominal sample concentrations were between 20 μM and 40 μM in the cell and 400 μM to 1.0 mM in the syringe. Actual sample concentrations were determined after dialysis or buffer exchange by measurement of their absorption at 280 nm or the BCA method. All data were analyzed using the MicroCal Origin ITC 7.0, and NanoAnalyze software packages.

1.13. Atomic Force Microscopy

Glass coverslips coated with a thin gold layer were cleaned in an ultraviolet radiation and ozone (UV-0) cleaner (Jetlight) for 15 min and subsequently immersed overnight in an ethanol solution containing 1 mM 16-mercaptododecahexanoic acid and 1-mercapto-1-undecanol at a 1:99 volumetric reatio. Substrates were then rinsed with ethanol, dried with N2 and added to a solution containing equal volumes of 20 mg ml$^{-1}$ N-hydroxysuccinimide (NHS) and 50 mg ml$^{-1}$ 1-ethyl-3-(3-dimethylaminopropyl)-arbodiimide (EDC) for 30 min. The obtained NHS activated surfaces were rinsed with ultrapure water and incubated with 100 μl of a 10 ng ml$^{-1}$ protein G solution for 1 hour at RT. Samples were then washed with washing buffer (3×5 min) and further incubated at 100 μl blocking buffer for 1 hour at RT. Finally, 50 μl of a 0.2 ng ml$^{-1}$ Reck-CK-Fc solution was added to the substrates for 1 hour, rinsed with washing buffer and subsequently used for AFM experiments. Single-molecule force spectrometry (SMFS) measurements were performed in PBS buffer at RT using a Nanoscope VIII Multimode AFM (Bruker). Triangular AFM cantilevers (MSCT, Bruker) with silicon nitride tips and a nominal spring constant between 0.01-0.06 N m$^{-1}$ were used. Cantilevers were calibrated at the end of each experiment using the thermal noise method as described in Butt et al. Calculation of thermal noise in atomic force microscopy. Nanotechnology 6, 1-7 (1995). Functionalized tips were derivatized using a NHS-PEG27-Malemide linker, following a protocol as described in Wildling et al., Probing binding pocket of serotonin transporter by single molecular force spectroscopy on living cells. J. Biol. Chem. 287, 105-113 (2012), to covalently attach the Pep7b linking the cysteine residue added at the C terminus. After functionalization, the cantilevers were washed with PBS (3×5 min) and stored in individual wells of a multiwall dish containing 2 ml of PBS per well at 4° C. until used in AFM experiments. Force-distance curves were recorded as 32×32 pixel arrays over 1×1 μm$^2$ areas, using an applied force of 250 pN, a contact time of 0.25 s and a constant approach and retraction speed of 1 μm s$^{-1}$. For dynamic force spectroscopy measurements, the retraction speed of the cantilever was varied as follows: 20 nm s$^{-1}$, 100 nm s$^{-1}$, 200 nm s$^{-1}$, 1 μm s$^{-1}$, 2 μm s$^{-1}$, 10 μm s$^{-1}$ and 20 μm s$^{-1}$. Typically, at least 2000 force-distance curves were performed for each cantilever at a particular retraction speed. The collected date were analyzed using the Nanoscope Analysis software (Bruker) The retraction segment of each curve was analyzed and unbinding events were considered as specific if they occurred at a distance between 5-50 nm from the contact point. The minimum adhesion force was further used to calculate binding probabilities and build force distribution histograms. To reconstruct the energy landscape of the measured interactions, loading rates were calculated from the force vs time curve, as the slope of the adhesion event before the tip cantilever jumps off to surface. The dependency of the force with the loading rate was then plotted in dynamic force spectroscopy plots.

1.14. Statistical Analysis

Statistical analysis was performed using GraphPad software. Data represent mean±SD. Pvalues were calculated by the one-way ANOVA (post hoc Dunnett's test) and Student's t test for multiple and single comparisons of normally distributed data (STF and PLA assays) and by the Kruskal-Wallis (post hoc Dunn's test) for multiple comparisons of non-normally distributed data (CtA quantifications); *p<0.05; p<0.01; *p<0.001.

2. Results 2.1. Reck is a Frizzled-Independent Wnt7-Specific Receptor Wnt/Fz binding relationships are promiscuous, with multiple Wnts competing for binding to individual Fzs and several Fzs capable of responding to a single Wnt. Recent crystallographic studies confirmed that the Wnt/Fz interaction chemistry is incompatible with unambiguous Wnt and Fz pairing, with Wnt/Fz contact being dominated by conserved residues or identical chemical modifications (C. Y. Janda, D. Waghray, A. M. Levin, C. Thomas, K. C. Garcia, Science. 337, 59-64 (2012)). These observations raise the question of how cells interpret the spatially and temporarily overlapping expression patterns of multiple Wnt ligands that sometimes have opposing biological functions.

A pertinent example is the exclusive control of mammalian forebrain and ventral spinal cord vascular development by Wnt7a and Wnt7b (J. M. Stenman et al., Science. 322, 1247-1250 (2008); R. Daneman et al., Proc. Natl. Acad. Sci. U.S.A. 106, 641-646 (2009); S. Liebner et al., J. Cell Biol. 183, 409-417 (2008)). Specifically, in order to respond to neural progenitor-derived Wnt7 and activate Wnt/β-catenin signaling, cerebral endothelial cells (ECs) must express Gpr124, an orphan member of the adhesion class of G protein-coupled receptors (M. Cullen et al., Proc. Natl. Acad. Sci. U.S.A. 108, 5759-5764 (2011); F. Kuhnert et al., Science. 330, 985-989 (2010); K. D. Anderson et al., Proc. Natl. Acad. Sci. U.S.A. 108, 2807-2812 (2011); Y. Zhou, J. Nathans, Dev. Cell. 31, 248-256 (2014); E. Posokhova et al., Cell Rep. 10, 123-130 (2015); B. Vanhollebeke et al., Elife. 4, 1-25 (2015)) as well as the GPI-anchored glycoprotein Reck (B. Vanhollebeke et al., 2015; F. Ulrich et al., Development. 143, 147-159 (2015)). Gpr124 and Reck physically interact and synergistically stimulate Wnt7-specific responses (B. Vanhollebeke et al., 2015; C. Cho, P. M. Smallwood, J. Nathans, Neuron. 95, 1056-1073 (2017)) but it is unknown how this signaling module can discriminate Wnt7 from other, locally expressed, Wnt ligands.

Figure 1:
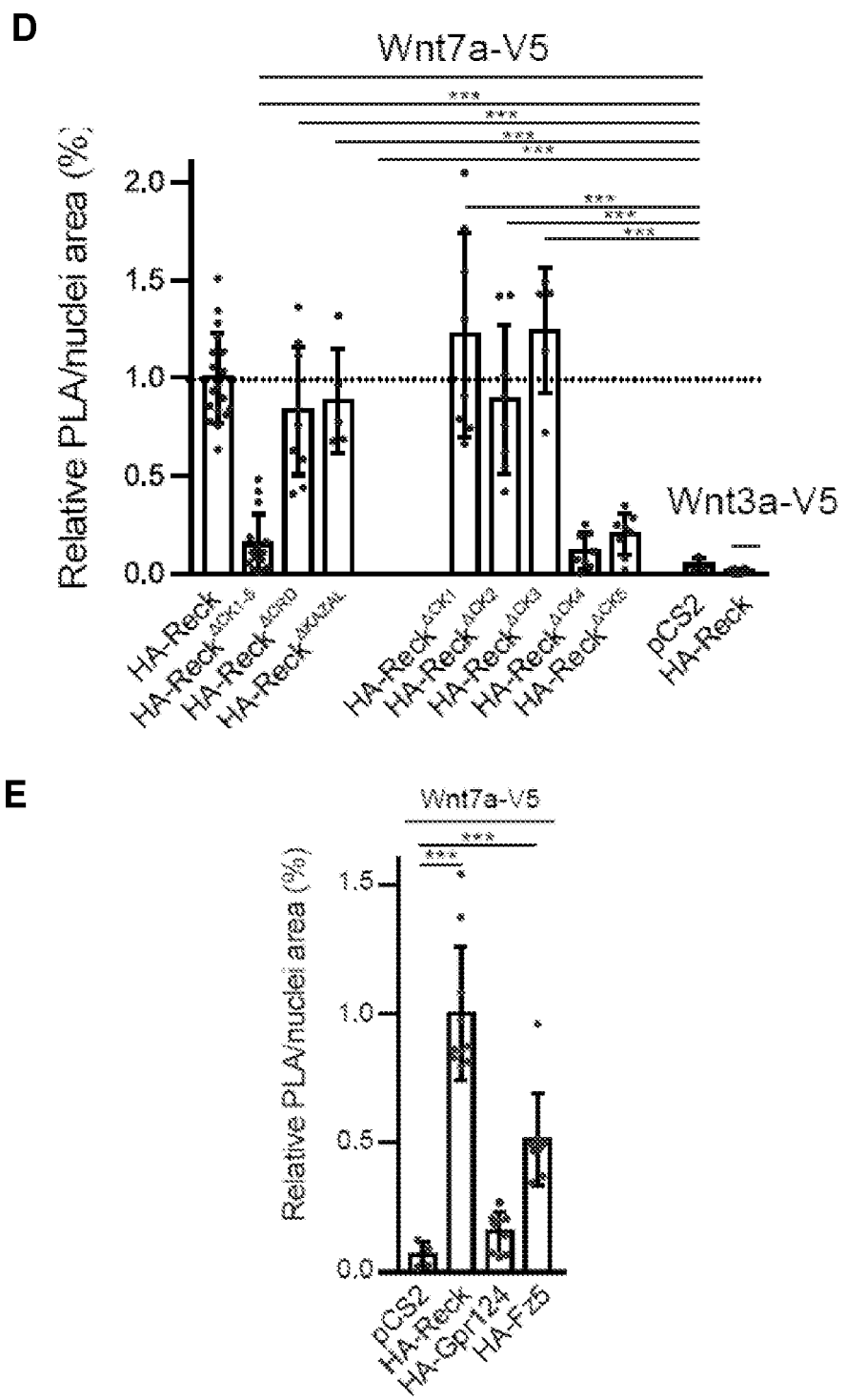
FIG. 1 illustrates (A) anti-V5 immunostaining of transiently-expressed Wnt7a-V5 or Wnt3a-V5 in non-permeabilized WT, $FZ_{1-10}^{-/-}$, $LRP5^{-/-}$;$LRP6^{-/-}$ and $GPR124^{-/-}$; $RECK^{-/-}$ cells. (B) Same as (A) in $GPR124^{-/-}$;$RECK^{-/-}$ cells transiently co-expressing Wnt7a-V5 and the indicated (co)-receptors. (C) Ligand capture assay in triple (1:1:1) co-cultures. Super top-flash luciferase (STF) activities of HEK293-STF reporter cells transfected with Fz5 and stimulated in a paracrine manner by co-cultured Wnt7a or Wnt3a emitting cells in the presence of $FZ_{1-10}^{-/-}$ HEK293T competing cells transfected with various (co)-receptors as indicated. (D) Quantification of PLA signals of in situ PLA using anti-V5 and anti-HA primary antibodies targeting Wnt7a-V5 and HA-Reck or its variants co-expressed in $GPR124^{-/-}$; $RECK^{-/-}$ cells. (E) Quantification of PLA signals of in situ PLA using anti-V5 and anti-HA primary antibodies directed against Wnt7a-V5 and the indicated HA-tagged (co)-receptors co-expressed in $GPR124^{-/-}$;$RECK^{-/-}$ cells. Scale bar: 10 µm. (F) Quantification of the anti-V5/anti-HA PLA signals of $GPR124^{-/-}$;$RECK^{-/-}$ cells co-transfected with Wnt7a-V5 or Wnt3a-V5 and the indicated HA-tagged Reck variants with (y-axis) or without Gpr124 (x-axis). (G) Schematics of Reck and its Gpr124 and Wnt7 binding motifs. *p<0.05, ***P<0.001; data represent mean±SD.

It was determined how Wnt7 is specifically recognized within this signaling module, a question inherently complicated by the ubiquitous expression of Frizzled receptors and their Lrp5/6 co-receptors in vertebrate cells. Therefore, a first set of cell lines genetically depleted of the receptor complex components at defines nodes was generated by targeting (i) all ten FZ genes ($FZ_{1-10}^{-/-}$), (ii) LRP5 and LRP6 ($LRP5^{-/-};LRP6^{-/-}$) or (iii) GPR124 and RECK ($GPR124^{-/-};RECK^{-/-}$), through multiplexed CRISPR/Cas9 mutagenesis in HEK293 cells. To identify the determinants of Wnt7 binding, V5-tagged Wnt ligands were transiently expressed in these cell lines. Wnt7a-V5 but not Wnt3a-V5 could be immunodetected at the plasma membrane of WT, $FZ_{1-10}^{-/-}$ and $LRP5^{-/-};LRP6^{-/-}$ cells, but not at those of $GPR124^{-/-};RECK^{-/-}$ cells (FIG. 1A). Ectopic restoration of Reck expression, alone or in combination with Gpr124, was sufficient to specifically restore Wnt7a-V5 membrane labeling in these cells, while Gpr124 expression alone was not (FIG. 1B). As expected, Fz5 was competent for Wnt7a-V5 binding, reflecting the competence of this Frizzled receptor to mediate baseline Wnt7 signaling.

Using cellular competition experiments it was found that Reck recruits Wnt7a in the absence of Fz, as the co-culture of $FZ_{1-10}^{-/-}$ cells ectopically expressing Reck but not $Gpr124^{\Delta ICD}$ could drastically reduce Wnt7a-Fz5 signaling in neighboring $GPR124^{-/-};RECK^{-/-}$ Super Top Flash (STF)

reporter cells (FIG. 1C). Of note, in this ligand capture assay, Gpr124 was lacking its C-terminal ICD domain to restrict the analysis to the surface exposed parts of the Gpr124/Reck complex. Next, PLA was used to map the domains of Reck required for Wnt7a binding. Reck is composed of five N-terminal cysteine-knot (CK) motifs, a cysteine-rich domain (CRD) and three Kazal motifs interspersed with EGF-like motifs preceding the GPI-anchor site. A collection of HA epitope-tagged deletion variants was generated for each domain of Reck and PLA signals were quantified. This analysis revealed that the N-terminal cysteine-knot domain, and more particularly CK4 and CK5 were required for binding (FIG. 1D). In agreement with these results, Reck$^{\Delta cK4}$ expression was also inactive in competition assays (FIG. 1C).

Although Reck appears to be the dominant Wnt7 binding determinant, its function in Wnt signaling is known to rely on its capacity to form a complex with Gpr124 through its N-terminal CK domain (Y. Zhou, J. Nathans, *Dev. Cell.* 31, 248-256 (2014); B. Vanhollebeke et al., *Elife.* 4, 1-25 (2015)), a domain that is shown herein to be additionally implicated in Wnt7a binding. In contrast to HA-Reck and HA-Fz5, HA-Gpr124 does not generate PLA signals when expressed with Wnt7a-V5 (FIG. 1E). However, a 4-fold increase in Wnt7a-V5/HA-Reck PLAs signals was detected upon co-expression of untagged Gpr124 (FIG. 1F). This binding stimulation by Gpr124 was dependent on Reck CK1 and CK2, in agreement with the role of the N-terminal CK1 motifs in the formation of the Gpr124/Reck complex (C. Cho, P. M. Smallwood, J. Nathans, *Neuron.* 95, 1056-1073 (2017)). In sum, with the tacit assumption that PLAs act as a valid proxy for direct interaction between a diffusible extracellular ligand and its membrane receptor, these results suggest that Reck constitutes the first reported Fz-independent Wnt ligand-specific receptor, whose binding to Wnt7 is reinforced by the proximal binding of Gpr124 within the CK domain (FIG. 1G).

2.2. Wnt7 Recognition Involves a Highly-Divergent and Intrinsically Disorder Linker Region of Wnt Ligands Wnt ligands are notoriously refractory to high level recombinant production, preventing cell-free biochemical or biophysical interaction studies between full-length recombinant Wnt7 and Reck.

Wnt ligands adopt a two-domain structure reminiscent of a human hand pinching the globular Fz cysteine-rich domain (CRD) via the palmitoylated 'thumb' of the ligand N-terminal domain (NTD) and hydrophobic residues of the 'index' C-terminal domain (CTD). The structures involved in Fz binding are mainly located at the extremities of the 'thumb' and 'index'. The two domains are connected through a flexible inter-domain linker region of the NTD.

Figure 2:
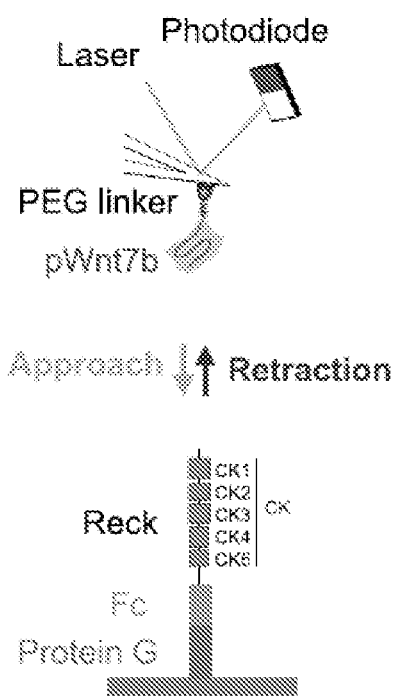
FIG. 2 illustrates (A) Schematic representation of Wnt7a, the V5-tagged Wnt7a variants and paralogues examined in the PLAs quantified in (B) using anti-V5 and anti-HA primary antibodies in $GPR124^{-/-}$;$RECK^{-/-}$ cells co-expressing HA-Reck. (C) Gpr124/Reck-dependent relative STF luciferase activities in HEK293-STF cells of signaling of 101 different single-residue variants of Wnt7a and their position on the Wnt7a structure (x-axis and structure models below). The relative luciferase activities are normalized to the WT Wnt7a values. All Wnt7a residues are mutated to alanine, expect alanine residues that are changed to arginine. (D) Alignment of the Wnt7 linker domain across the vertebrate clade. Mm, *Mus musculus*; Gg, *Gallus gallus*; Xl, *Xenopus laevis*; Dr, *Danio rerio*. The eight Wnt7a variants (falling within amino acid region pWnt7a 238-266), which reduced Gpr124/Reck-dependent signaling to less than 10%, are underlined. The activities of the corresponding single-residue variants and their activity class are determined in (C). The sequences of the Mm Wnt3a and quadruple Wnt7a variant (Wnt7$^{4A}$) linker regions appear below. (E) Anti-V5/HA PLAs between Wnt7a-V5 or Wnt7a$^{4A}$-V5 and HA-Reck. Ligand secretion was evaluated by means of semi-quantitative anti-V5 dot blot analysis of serially diluted cell supernatant. Ponceau S staining was used as the loading control. Scale bars, 10 µm. *P<0.05, ***P<0.001; data represent mean±SD (F) Probing the interaction between purified recombinant Reck-CK-Fc and the synthetic pWnt7a peptide using isothermal titration calorimetry (ITC). ITC of pWnt7a, pWnt7a$^{4A}$ and pWnt3a into recombinant Reck-CK-Fc (upper panels). ITC of Reck-CK-Fc, Reck-CK$^{\Delta CK1}$-Fc, Reck-CK$^{\Delta CK2}$-Fc, Reck-CK$^{\Delta CK3}$-Fc, Reck-CK$^{ACK4}$-Fc and Reck-CK$^{\Delta CK5}$-Fc to pWnt7b (middle and bottom panels). (G) Probing Reck-CK-Fc/pWnt7b interaction by use of SMFS. Principle of force-distance curve-based atomic force microscopy (FD-based AFM) is shown. An AFM tip functionalized with a polyethylene glycol (PEG) spacer fused to the pWnt7b peptide is approached and retracted from a surface coated with Reck-CK-Fc.

A collection of Wnt7 variants deleted for specific domains or residues, or that were engineered to carry selected domains from other Wnt ligands (FIG. 2A) were generated. These chimeric ligands were each applied to PLAs, revealing that Reck binding occurs exclusively in the Wnt7a NTD. Strikingly, the Wnt7a$^{NTD}$ alone bound to Reck as potently as full-length Wnt7a, while Wnt7a' did not (FIG. 2B). The palmitoleic acid implicated in Fz binding was not involved in Reck interaction as the mutant Wnt7a$^{S206A}$ incapable of being palmitoylated at Serine 206 bound Reck efficiently. The NTD recognition mode of Wnt7a by Reck was confirmed by chimeric Wnt7a ligands in which CTDs were swapped with equivalent domains of *Xenopus* Wnt8a (XWnt8a) and murine Wnt4 and Wnt16. These binding assays reveal that Reck discriminates between Wnt ligands by recognizing a motif embedded in the Wnt7a NTD, at sites distinct from those engaged by Fz.

Smaller NTD variants lacking the linker region, Wnt7a$^{1-212}$ and Wnt7$_{1-237}$, did not bind Reck. This mutational analysis combined to the spatial segregation of the Wnt7a linker region away from the Fz binding sites, suggest that Reck decodes Wnt7a, at least in part, through this linker motif. The linker region, which is the most variable motif across the Wnt ligand family, exhibits strong evolutionary conservation amongst Wnt7 orthologues throughout the vertebrate clade (FIG. 2D). To precisely map the interaction site, the present inventors analyzed Gpr124/Reck-dependent STF signaling of a collection of 101 single residue variants of Wnt7a (FIG. 2C). The mutated residues corresponded to surface-exposed NTD residues strictly or chemically conserved between Wnt7a and Wnt7b, but not found in XWnt8a or any of the other Wnt ligands. As shown in FIG. 2C, while ~80% of the examined variants were as active as WT Wnt7a, only eight Wnt7a variants (underlined) reduced Gpr124/Reck-dependent signaling to less than 10%. All but one (137) critical residues clustered on the top or back of the predicted Wnt7a structure, with six further mapping to the linker domain. All critical residues are strictly conserved amongst Wnt7 orthologues from human to fish and absent in any other Wnt, including Wnt3a (FIG. 2D). Present inventors further investigated whether inactivity of the Wnt7 linker variants might result from defective binding to LRP5/6, Reck, or both. In line with a function in Reck binding, Wnt7a$^{4A}$, a four-residue variant of Wnt7a (V241A, F251A, L252A, K262A; wherein the substitutions indicate the amino acid position in mWnt7a precursor polypeptide) within a linker region, showed reduced Reck PLA signals as compared with that of WT Wnt7a. This lower activity occurred despite slightly improved secretion rates (FIG. 2E).

To investigate Reck-Wnt7 binding in a cell-free system, highly pure Reck-CK-Fc fusion proteins (and variants thereof, namely HA-Reck-CK$^{\Delta CK1}$-Fc, HA-Reck-CK$^{\Delta CK2}$-Fc; HA-Reck-CK$^{\Delta CK3}$-Fc; HA-Reck-CK$^{\Delta CK4}$-Fc; and HA-Reck-CK$^{\Delta CK5}$-Fc) were recovered from HEK293T cells supernatants and titrated with purified 29 amino-acid long synthetic Wnt7a and Wnt7b linker peptides (pWnt7a and pWnt7b) by isothermal titration calorimetry (ITC). ITC confirmed that pWnt7a and pWnt7b directly bind Reck with affinities of 7 µM and 1.2 µM, respectively (FIG. 2F). As controls, the synthetic peptides corresponding to Wnt7a' (pWnt7a$^{4A}$) as well as equivalent linker peptides of Wnt3a (pWnt3a) showed no binding to Reck-CK-Fc. pWnt7b binding required Reck CK4 and CK5, but not CK1, CK2 and CK3, strikingly mirroring the PLA results in cultured cells. To corroborate the results provided by the ITC analysis, present inventors used single-molecule force spectroscopy (SMFS) to measure binding affinities at the single-molecule level (FIG. 2G). Binding of pWnt7b to Reck-CK-Fc was detectable with a measured dissociation constant ($K_D$) of 5 µM. Despite the fundamental differences between the two techniques, ITC and SMFS thus provided a close match between measured binding affinity values.

Altogether, these data demonstrate that Wnt7 is recognized by Reck at least in part through its 'signature' linker motif. However, Reck-bound Wnt7 must be functionally integrated into efficient signal activation and transduction machineries in order for cells to display potentiated Wnt7-specific cellular responses.

2.3. Gpr124 does not Act as a Classical Signal Transducing GPCR During Wnt7 Signaling and Brain Angiogenesis Reck itself, by virtue of its GPI-anchoring mode to the sole external leaflet of the plasma membrane, has limited potential to transduce Wnt7 signals across the membrane bilayer, and therefore signal transduction must rely on other components of the receptor complex, i.e. Gpr124 and/or Fz/Lrp5/6.

To uncover this signal transduction mechanism, the functional relationship between Gpr124 and Fz/Lrp5/6 complexes was evaluated in cultured cells. Using "Fz-free" and "Lrp5/6-free" cells, it was genetically established that the function of Gpr124/Reck strictly relies on Fz and Lrp5/6 function (FIG. 3A-E). It was further established that their respective CRD and DKK1-sensitive Wnt ligand binding domains are essential for signaling, implying that Wnt7 binds and activates Fz/Lrp5/6 in a classical manner.

The development of the zebrafish CNS vasculature has been shown to strictly rely on Reck/Gpr124 signaling, in a process of angiogenic sprouting that can be readily quantified. It therefore constitutes a prime setting to perform structure-function analysis in vivo in response to physiological Wnt7 input levels (B. Vanhollebeke et al., *Elife.* 4, 1-25 (2015); N. Bostaille, A. Gauquier, L. Twyffels, B. Vanhollebeke, *Biol. Open.* 5, 1874-1881 (2016)). Using injections of synthetic mRNA at the one-cell stage WT or gpr124$^{-/-}$ embryos, the present inventors started by evaluating the activity of three Gpr124 variants (FIG. 4A) lacking the N-terminal extracellular part (Gpr124$^{\Delta ECD}$) the seven-span moiety (Gpr124$^{\Delta TM2-7}$) or the C-terminal cytoplasmic extension (Gpr124$^{\Delta ICD}$). While ectopic expression of Gpr124$^{\Delta ECD}$ and Gpr124$^{\Delta ICD}$ did not restore brain angiogenesis in gpr124 mutants, Gpr124$^{\Delta TM2-7}$ activity was sufficient to trigger brain angiogenesis in vivo (FIG. 4B, C) and Wnt activity in in vitro STF assays (FIG. 4D).

This retained competence of Gpr124$^{\Delta TM2-7}$ was unanticipated: Gpr124 is a GPCR, a receptor super-family classically relaying extracellular stimuli within the cell by ligand-induced conformational remodeling of the seven transmembrane spans, which are absent in the engineered Gpr124$^{\Delta TM12-7}$ mutant protein. Based on these results, it appears that Gpr124 may not act as a classical GPCR when promoting Wnt7 signaling, as it does not require signal transduction across the membrane.

Instead, Gpr124 seemingly acts in this module as a signaling-deficient transmembrane protein whose activity relies on the Reck-binding extracellular domain (ECD) and the conformationally uncoupled intracellular domain (ICD). Present inventors hypothesized that the Gpr124 ICD might operate through Dishevelled, the crucial effector of Wnt signaling interacting with Fz. This 'Dvl hypothesis' is rooted in the findings that Gpr125, an adhesion GPCR closely related to Gpr124, was shown to physically interact with Dvl via its C-terminal ICD domain (X. Li et al., *Development.* 140, 3028-3039 (2013)) and that Gpr124/125 hybrids in which the ICD of Gpr124 is replaced with the ICD of Gpr125 are able to promote brain angiogenesis in zebrafish (B. Vanhollebeke et al., *Elife.* 4, 1-25 (2015)) (see also FIG. 4E). Similarly, Gpr124/Fz2 hybrids (Gpr124$^{ICDFz2}$) in which the Gpr124 ICD was replaced with the Fz2 ICD, known to bind Dvl, were competent. In contrast, full-length Fz2 was not. Notably, the activity of Gpr124$^{ICDFz2}$ was dependent on the KTxxW and ETTV motifs Dvl binding sites within the Fz2 ICD (FIG. 4E).

2.4. Dvl Polymers Assemble Ligand-Specific Wnt Signalosomes by Linking Fz and Gpr124

Figure 5:
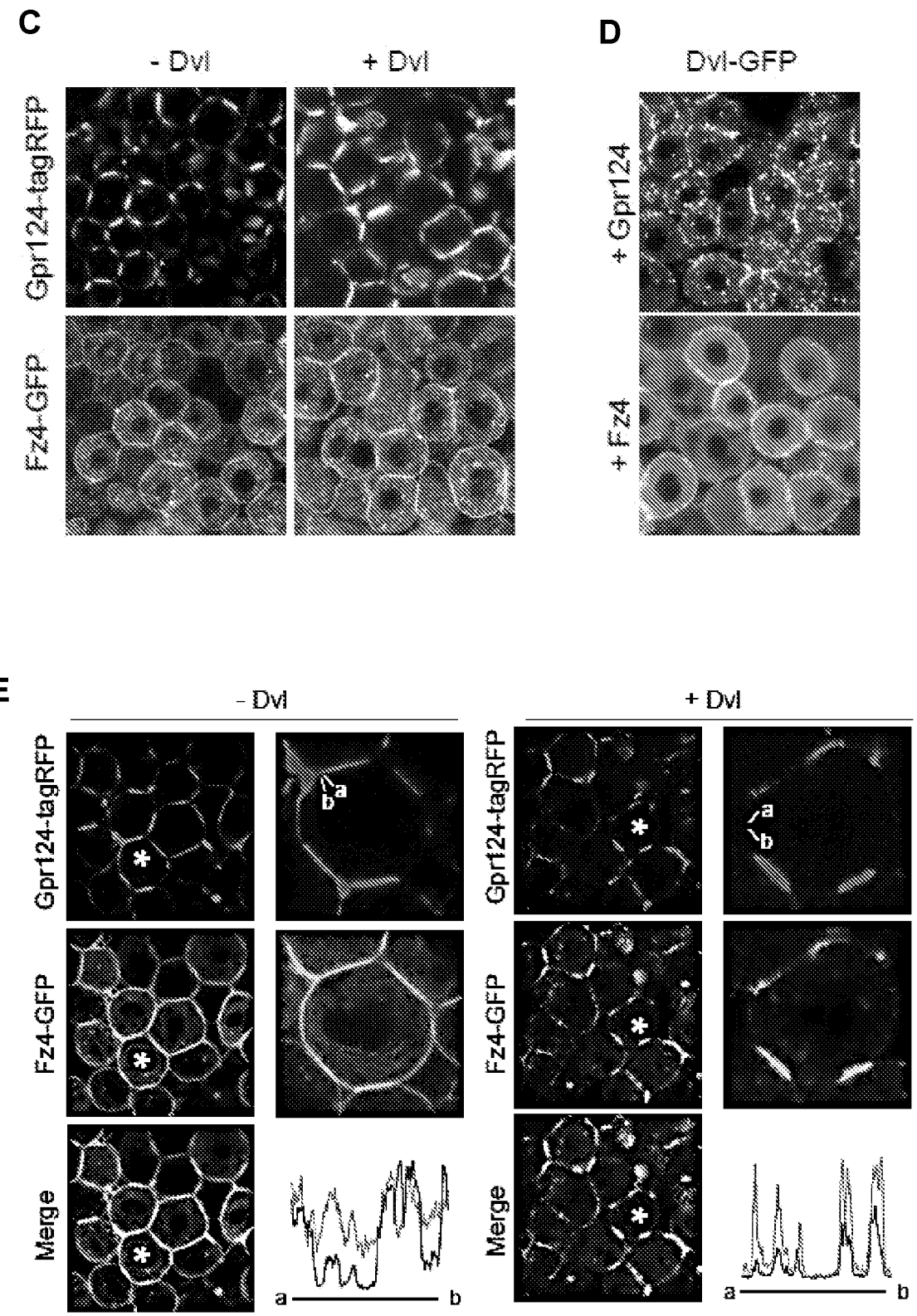
FIG. 5 illustrates (A) Anti-FLAG co-immunoprecipitation assays in total lysates of cells co-expressing Dvl-GFP and N-terminal FLAG-tagged versions of Gpr124 or its ICD variants. (B) Immunoblot of DVL2 and p-DVL2 (T224) in whole cell lysates from FZ1-10 −/− and WT HEK293T cells transfected with the indicated combination of plasmids.

Co-immunoprecipitation experiments performed between N-terminal FLAG-tagged Gpr124 and Dvl-GFP in FZ$_{1-10}$$^{-/-}$ HEK293T cells confirmed the interaction between Gpr124 and Dvl (FIG. 5A), even in the absence of the C-terminal ETTV Unlike Fz, Gpr124 did not yield a detectable increase in phosphorylated Dvl levels, an early indicator of Wnt signaling activation upstream of β-catenin stabilization (S. I. Yanagawa, F. Van Leeuwen, A. Wodarz, J. Klingensmith, R. Nusse, *Genes Dev.* 9, 1087-1095 (1995); X. Huang et al., *Science.* 339, 1441-1445 (2013)) (FIG. 5B). This absence of Gpr124-induced Dvl activation is consistent with the experiments of FIG. 4 that identified Gpr124 as a signaling-deficient protein. Taken together, these experiments identify Dvl as a constitutive Gpr124 binding partner that could mediate its Wnt7 signaling activities.

Gpr124, Reck and Fz/Lrp5/6 have been proposed to form higher-order receptor complexes in cultured cells (C. Cho, P. M. Smallwood, J. Nathans, *Neuron.* 95, 1056-1073 (2017)). Present inventors reasoned that the Gpr124 ICD might assemble this complex via Dvl. Dvl molecules indeed assemble signalosomes through dynamic polymerization via head-to-tail self-assemblies of their N-terminal Dix domains. These self-associations allow the local concentration of various cytoplasmic Wnt signaling regulatory proteins, including kinases and components of the endocytic machinery (M. Gammons, M. Bienz, *Curr. Opin. Cell Biol.* 51, 42-49 (2018), M. Bienz, *Trends Biochem. Sci.* 39, 487-495 (2014)). As Dvl physically interacts with both Gpr124 and Fz, Gpr124 and the associated Reck-bound Wnt7 might thus become trapped in dynamic Wnt signalosomes, thereby increasing the local concentration of Wnt7 ligands available for Fz signaling.

Wnt signalosomes are readily detected by light microscopy as large, punctate structures enriched in Dvl that form at or below the plasma membrane (M. Bienz, *Trends Biochem. Sci.* 39, 487-495 (2014); J. Bilic et al., *Science.* 316, 1619-1622 (2007); M. V. Gammons, M. Renko, C. M. Johnson, T. J. Rutherford, M. Bienz, *Mol. Cell.* 64, 92-104 (2016)). To determine whether Fz and Gpr124 co-distribute in Wnt signalosomes in a Dvl-dependent manner, the localization of individually expressed Fz-GFP and Gpr124-tagRFP was first examined in blastula deep layer (DEL) cells. Fz4 decorated the entire plasma membrane periphery while, instead, Gpr124-tagRFP accumulated at cellular contacts. This differential membrane localization was retained upon Dvl expression (FIG. 5C). Consistent with their Dvl binding capacity, both receptors recruited Dvl to their respective membrane compartment (FIG. 5D). However, when Gpr124-tagRFP and Fz4-GFP were co-expressed, Gpr124-tagRFP remained anchored at the intercellular junctions but Fz4-GFP quantitatively relocalized to the Gpr124 membrane subdomains in a Dvl-dependent manner (FIG. 5E), where the proteins colocalized in Wnt signalosome-reminiscent punctate structures particularly evident at EVL cell membranes (FIG. 5F). Present inventors used bimolecular fluorescence complementation as an assay to test for Dvl-dependent Fz/Gpr124 interaction in DEL cells. Co-injection of Gpr124-VN$_{155}$ (I152L) and Fz1-VC$_{155}$ indeed generated bright junctional signals in a Dvl-dependent manner (FIG. 5G), demonstrating that Fz and Gpr124 indirectly interacts via the Dvl scaffold protein. This provides a molecular mechanism for spatial clustering of Fz/Lrp5/6 and Gpr124 together with the associated Reck-bound Wnt7 within Wnt signalosomes endowed with Wnt ligand discrimination potential, thereby explaining the Wnt7-specific responses of Gpr124/Reck-positive cells (see final model, FIG. 6).

In summary, this work sheds the first structural and mechanistic insights onto the Wnt decoding capacities of vertebrate cells. It also demonstrates that the evolutionarily constrained Wnt structure retained enough diversity and intrinsic plasticity to allow ligand-specific cellular responses, a property so far thought to require structurally unrelated Frizzled ligands like Norrin (M. B. Lai et al., *Cell Rep.* 19, 2809-2822 (2017)). These structural insights onto Wnt evolution and function immediately suggest that additional Wnt decoding modules exist, enabling fine-tuning of cellular behaviors in response to other Wnt or Fz family members.

Example 2: Molecular Recognition of Wnt7 by Reck Minimizes Wnt/Fz Interaction Requirements 1. Materials and Methods
   1.1. Zebrafish Lines
   Zebrafish (*Danio rerio*) were raised and handled under standard conditions following the rules of the State of Belgium (protocol approval number: CEBEA-IBMM-2017-22:65). The following line was used: Tg(-17.0neurog1: EGFP)$^{w61}$ (McGraw et al., *J. Neurosci* 28(47):12558-69 (2008)).
   1.2. Morpholinos, RNA Constructs and Microinjection
   The following splice-blocking morpholino (MOs) (Gene-Tools, Eugene, OR) were injected into embryos at the one-cell stage: wnt7aa (TTCCATTTGACCCTACTTACC-CAAT, 6 ng) (SEQ ID NO.: 123). Synthetic mRNAs were transcribed from pCS2 plasmids after NotI digestion using the mMessage mMachine SP6 Kit (Ambion, Carlsbad, CA) and injected into one-cell stage zebrafish embryo. For *Xenopus laevis* microinjection, 15 pg of wnt7a or wnt7a$^{K190A}$ or wnt7a$^{1-278}$ mRNA were injected into one ventral blastomere of the four-cell stage embryo.
   1.3. Expression Plasmid Constructs
   All Wnt signaling components and other expression constructs were expressed from the CMV promoter of the pCS2 vector after recombination using In-Fusion cloning (Takara, Mountain View, Calif.) except for Fz1 (addgene #42253) and Fz5 (addgene #42267). Single-point mutation variants and deletions were generated using In-Fusion cloning and tandem overlapping PCR products. All constructs were confirmed by sequencing.
   1.4. Cell Culture and HEK293 Mutant Cell Lines
   HEK293T cells were obtained from ATCC (CRL-3216) and the HEK293 STF cell line was kindly provided by Jeremy Nathans (John Hopkins) Cells were cultured in DMEM/F12 medium (Lonza, Basel, Switzerland) supplemented with 10% fetal bovine serum and maintained in a humidified incubator equilibrated with 5% $CO_2$. 7B.
   1.5. STF Dual Luciferase Assays
   Cells were plated into 96-well plates and transfected after 24 h in triplicate with Lipofectamine 2000 (Invitrogen, Carlsbad, Calif.). The amount of plasmid DNA transfected per well was optimized for each expression vector: *Renilla* luciferase (0.5 ng), Wnt (20 ng), Fz (5 ng), LRP (2.5 ng), Gpr124 (10 ng), Reck (10 ng) unless otherwise indicated. The total amount of DNA was adjusted to 100 ng per well with the empty pCS2 vector. Cells were harvested in passive lysis buffer (E1960, Promega, Wisconsin) and the activities of the Firefly and *Renilla* luciferases were measured sequentially using the Dual-Luciferase Reporter Assay system (E1960, Promega, Madison, Wis.) 48 h post-transfection.
   1.6. Microscopy and Images Processing
   zebrafish embryos were imaged with an LSM710 confocal microscope and images were processed in ImageJ. Images of zebrafish development phenotypes were taken on Leica M165 FC. *Xenopus* larvae were imaged with an Olympus SZX16.
   1.7. Statistical Analysis
   Statistical analysis was performed using GraphPad software. Data represent mean±SD. p-values were calculated by the one-way ANOVA (post hoc Dunnett's test) and Student's t test for multiple and single comparisons of normally distributed data (STF assays) and by the Kruskal-Wallis (post hoc Dunn's test) for multiple comparisons of non-normally distributed data (DRG quantifications); *$p<0.05$; $p<0.01$; *$p<0.001$.
2. Results
   The present inventors identified in Experiment 1 that Reck discriminates between Wnt ligands by recognizing a linker within the Wnt7a, at sites distinct from those engaged by Fz. The binding mechanism appears thus compatible with the formation of a higher-order Wnt7/Reck/Gpr124/Fz/LRP5/6 complex held together by intracellular scaffolds, in which Wnt7 is engaged simultaneously by Fz, Reck and LRP5/6. The present inventors further revealed that the N-terminal domain of Wnt7a (Wnt7a$^{1-278}$) still binds Reck.
   Next, the STF activity of these truncated variants of Wnt7a for Fz5 and Gpr124/Reck/Fz/LRP signaling were evaluated (FIG. 7A). Wnt signaling through Fz5 required the preservation of both Wnt/Fz contact sites and all Wnt7a variants lacking either one, through truncation or by the absence of the palmitoleic acid, were unable to stimulate Fz5 signaling (FIG. 7A). Gpr124/Reck/Fz1 signaling was equally sensitive towards Wnt7a truncations or mutations, with one notable exception: the single domain Wnt7a$^{1-278}$ maintained ~40% signaling capacity via Gpr124/Reck/Fz1 (FIG. 7A, arrowhead). The present inventors proposed that within a complex formed by Wnt7, Fz, LRP5/6 and Reck, the additional contact point provided by Reck is compensating for the missing Wnt/Fz interaction at the ligand index.
   To differentiate the residues that are essential within Wnt7a for Gpr124/Reck/Fz/LRP signaling from Fz5 signaling, Gpr124/Reck/Fz/LRP or Fz5-dependent STF signaling of a collection of single residue variants of Wnt7a were analyzed (FIG. 7B, 7C). Forty-two full-length mWnt7a variants (in box in 7B) were identified that are inactive for Fz5 signaling but still activate Gpr124/Reck/Fz/LRP-mediated Wnt signaling, more particularly activate Gpr124/Reck/Fz/LRP-mediated Wnt signaling by at least 35% of the Gpr124/Reck/Fz/LRP-mediated Wnt signaling activity of the wild-type mature full-length Wnt7a (FIG. 7B-7C, see table 3). Thirty-one of these variants, more particularly, Wnt7a variants Q48A (Q17A), I51A (I20A), P56A (P25A), A58R (A27R); I59A (I28A); E64A (E33A); M68A (M37A), L70A (L39A), E72A (E41A); F75A (F44A); V99A (V68A); I160A (I129A); F162A (F131A); K164A (K133A); I172A (I141A); R189A (R158A); K190A (K159A); K190L (K159L); K212A (K181A); R222A (R191A); K229A (K198A); K231A (K200A); V236A (V205A); E239A (E208A); P249A (P218A); Y260A (Y229A); P263A (P232A); T266A (T235A); W322A (W291A); T338A (T307A) and N83Q (N52Q) (wherein the substitutions indicate the amino acid position in mWnt7a precursor polypeptide (and wherein the substitutions between brackets indicate the amino acid position in mWnt7a mature polypeptide, see table 3) were able to activate Gpr124/Reck/Fz/LRP-mediated Wnt signaling by at least 70% of the Gpr124/Reck/Fz/LRP-mediated Wnt signaling activity of the wild-type mature full-length Wnt7a (FIG. 7 B-C).
   In vitro, Wnt7a$^{1-278}$ and Wnt7a$^{K190A}$ (one of the thirty-one selective variants for Gpr124/Reck Fz/LRP signaling) failed to signal through any Fz in the absence of Gpr124/Reck (FIG. 7D). Accordingly, upon mRNA injection in the zebrafish zygote, Wnt7a$^{1-278}$ and Wnt7a$^{K190A}$ were well tolerated and did not reveal posteriorizing or gross anatomical alterations up to 1 ng and 100 pg, respectively (FIG. 7D-E). By contrast, 3 pg of wnt7a mRNA induced the loss of forebrain and eye structures by ectopic activation of Wnt signaling (Kim et al., Nature 407(6806):913-6 (2000)) and lead to dysmorphic embryos at doses higher than 10 pg (FIG. 7E-F).

Similarly, when injected in Xenopus embryos, Wnt7a caused axis duplication, a classical Wnt/β-catenin signaling outcome, while Wnt7a$^{1-278}$ and Wnt7a$^{K190A}$ did not (FIG. 7G). The lack of any discernable developmental defects induced by Wnt7A$^{1-278}$ and Wnt7a$^{K190A}$, allowed for significant DRG rescues in wnt7aa morphants after 100 pg mRNA injections, while wnt7aa mRNA injected at its highest tolerated dose of 10 pg, revealed only marginal restoration of DRG neurons (FIG. 7H). Together, these experiments identify Wnt7a$^{1-278}$ and Wnt7a$^{K190A}$ as Gpr124/Reck/Fz/LRP-selective agonists that elicit Gpr124/Reck/Fz/LRP-dependent responses in vivo without demonstrating off target activity on alternative Fz pathways, thereby providing a proof of concept that ligand-specific Fz signaling pathways can be tailored to develop novel Wnt agonists with drastically increased selectivity. The positions of the amino acid substitutions in the Wnt7a polypeptide variants in the experimental section are indicated in respect of the amino acid sequence of the Wnt7a precursor polypeptide (i.e. including the signal peptide). Table 3 shows the position of amino acid substitutions in the amino acid sequence of the Wnt7a precursor polypeptide and their corresponding position in the amino acid sequence of the mature Wnt7a polypeptide.

Transgenic endothelial expression of mouse Wnt7a$^{K190A}$ or Wnt7a$^{1-278}$ triggered GPR124/RECK-dependent brain angiogenesis and restored blood-brain barrier (as evaluated by GLUT1 expression) in Wnt7aa$^{-/-}$ mutant zebrafish (FIG. 9 A-C). Mouse Wnt7, Wnt7a$^{K190A}$ and Wnt7a$^{1-278}$ were transiently expressed in the endothelium of Wnt7aa$^{-/-}$ embryos under the control of an endothelial-specific kdrl (Vascular endothelial growth factor receptor kdr-like) promoter. The Wnt7 ligands were expressed as a biscistronic construct with BFP (Blue Fluorescent Protein) as transgenesis marker. In contrast to uninjected embryos, all three ligands restore CtAs formation. Anti-GLUT1 immunofluorescence staining of the CtAs after transgenic expression of Wnt7, Wnt7a$^{K190A}$ and Wnt7a$^{1-278}$ in 60 hpf Wnt7aa$^{-/-}$ embryos revealed blood-brain barrier maturation.

In view of the above, the Wnt7a variants are GPR124/RECK-selective agonists that elicit GPR124/RECK-dependent responses in vivo without demonstrating off target activity on alternative Fz pathways.

TABLE 3

| Amino acid position in mWnt7a precursor polypeptide | Amino acid position in mature mWnt7a polypeptide |
| --- | --- |
| Q48A | Q17A |
| I51A | I20A |
| P56A | P25A |
| A58R | A27R |
| I59A | I28A |
| E64A | E33A |
| M68A | M37A |
| L70A | L39A |
| E72A | E41A |
| F75A | F44A |
| V99A | V68A |
| R81A | R50A |
| N83Q | N52Q |
| I160A | I129A |
| F162A | F131A |
| K164A | K133A |
| F166A | F135A |
| I172A | I141A |
| R177A | R146A |
| R189A | R158A |
| K190A | K159A |
| K190L | K159L |
| K190S | K159S |
| K212A | K181A |
| R222A | R191A |
| K229A | K198A |
| K231A | K200A |
| V236A | V205A |
| E239A | E208A |
| R245A | R214A |
| K247A | K216A |
| P249A | P218A |
| K253A | K222A |
| I254A | I223A |
| Y260A | Y229A |
| P263A | P232A |
| T266A | T235A |
| E279A | E248A |
| R320A | R289A |
| W322A | W291A |
| T338A | T307A |
| K349A | K318A |

It is noted that the primary amino acid sequences of mouse and human wild-type full-length mature Wnt7a are identical.

Example 3: Viral Vector Delivery of MouseWnt7a$^{K190A}$ in Mice Subjected to a Model of Stroke (Transient Middle Cerebral Artery Occlusion (tMCAO))

1. Materials and Methods 1.1. Generation of the AAV Plasmid Constructs (AAV-PHP.eB-CAG-mWnt7a$^{K190A}$-p2A-EGFP) The full-length mWnt7a$^{K190A}$ variant was cloned into the pAAV transgene vector containing flanking ITRs sequences under the regulatory elements of the pCAG promoter. The Wnt7 variant was expressed as a fusion to EGFP by the intermediate of the auto-cleaving p2A peptide. The AAV vector was produced and purified as described in Körbelin et al., 2016 by triple co-transfection of HEK293 cells with the pAAV-transgene plasmids, the helper plasmid (encoding the AAV-PHP.eB capsid variant+rep+insertion sequences) and the adenoviral helper plasmid.

It is noted that K190A of "Wnt7a$^{K190A}$" indicates the amino acid position in mWnt7a precursor polypeptide.

1.2. Animal Studies

Ten C57BL/6 mice were intravenously injected into the periorbital vein with 50 µl of concentrated vectors ($1 \times 10^{11}$ vg/mouse) containing the AAV-PHP.eB-CAG-mWnt7a$^{K190A}$-p2A-EGFP or AAV-PHP.eB control vector ($1 \times 10^{11}$ vg/mouse). Two weeks post infection, the EGFP signal was assessed in CNS endothelial cells to confirm transgene expression.

Mice were subjected to tMCAO for 1 hour and infarct size was measured through TTC (2,3,5-Triphenyltetrazolium chloride) staining 5 days post tMCAO. Leakage assays at the level of the blood brain barrier (BBB) was performed 1 hour post reperfusion by measuring endogenous plasma protein leakage (immunoglobulin and fibrinogen). The survival of the mice was evaluated 5 days post perfusion after tMCAO.

2. Results

A GFP encoding construct was used to demonstrate widespread transgenic expression in the mouse brain (FIG. 10 A).

To assess the effect of mouse Wnt7a$^{K190A}$ on stroke in vivo, brain specific adeno-associated vectors were generated that express mouse Wnt7a$^{K190A}$.

All mice injected with a vector comprising mouse Wnt7a$^{K190A}$ showed reduced stroke volume (FIG. 10 B).

Example 4: Viral Vector Delivery of Wnt7a$^{K190S}$ or Wnt7a$^{K190L}$ in Mice Subjected to a Mouse Model of Stroke (Transient Middle Cerebral Artery Occlusion (tMCAO))

1. Materials and Methods 1.1. Generation of the AAV plasmid constructs (AAV-PHP.eB-CAG-mWnt7a$^{K190S}$-p2A-EGFP and AAV-PHP.eB-CAG-mWnt7a$^{K190L}$-p2A-EGFP)

AAV plasmid constructs are generated as described in example 3, section 1.1.

It is noted that K190S of "Wnt7a$^{K190S}$" and in K190L "Wnt7a$^{K190L}$", indicate the amino acid position in mWnt7a precursor polypeptide.

1.2. Animal Studies

Animal studies are performed as described in example 3, section 1.1.

2. Results

Stroke volume reduction is measured in mice injected with a vector comprising mouse Wnt7a$^{K190S}$ or Wnt7a$^{K190L}$.

Example 5: Viral Vector Delivery of Wnt7a Variant Agonists in Mice Subjected to a Mouse Model of Stroke (Transient Middle Cerebral Artery Occlusion (tMCAO))

1. Materials and Methods

AAV plasmid constructs are generated as described in example 3, section 1.1 and animal studies are performed as described in example 3, section 1.1.

2. Results

Stroke volume reduction is measured in mice injected with a vector comprising mouse Wnt7a$^{Q48A}$, Wnt7a$^{I51A}$, Wnt7a$^{P56A}$, Wnt7a$^{A58P}$, Wnt7a$^{I59A}$, Wnt7a$^{E64A}$, Wnt7a$^{M68A}$, Wnt7a$^{L70A}$, Wnt7a$^{E72A}$, Wnt7a$^{F75A}$, Wnt7a$^{R81A}$, Wnt7a$^{N83Q}$, Wnt7a$^{V99A}$, Wnt7a$^{I160A}$, Wnt7a$^{F162A}$, Wnt7a$^{K164A}$, Wnt7a$^{F166A}$, Wnt7a$^{I172A}$, Wnt7a$^{P177A}$, Wnt7a$^{R189A}$, Wnt7a$^{K212A}$, Wnt7a$^{R222A}$, Wnt7a$^{K229A}$, Wnt7a$^{K231A}$, Wnt7a$^{V236A}$, Wnt7a$^{E239A}$, Wnt7a$^{R245A}$, Wnt7a$^{K247A}$, Wnt7a$^{E249A}$, Wnt7a$^{K253A}$, Wnt7a$^{I254A}$, Wnt7a$^{Y260A}$, Wnt7a$^{P263A}$, Wnt7a$^{T266A}$, Wnt7a$^{E279A}$, Wnt7a$^{R320A}$, Wnt7a$^{W322A}$, Wnt7a$^{T338A}$ or Wnt7a$^{K349A}$.

As a negative control, stroke volume reduction is measured in mice injected with a vector comprising mouse Wnt7a$^{R49A}$, Wnt7a$^{E103A}$ or Wnt7a$^{T192A}$.

It is noted that the substitutions refer to the amino acid position in mWnt7a precursor polypeptide.

The invention claimed is:

1. A nucleic acid encoding a Wnt7 polypeptide or a fragment thereof capable of activating G-protein coupled receptor (GPR)124/RECK/Frizzled/lipoprotein receptor-related protein (LRP)-mediated Wnt signaling, wherein said Wnt7 polypeptide or fragment thereof does not activate Frizzled/LRP-mediated Wnt signaling in the absence of RECK and/or GPR124, wherein said Wnt7 polypeptide or a fragment thereof comprises the amino acid sequence of SEQ ID NO:24 with an amino acid substitution or the amino acid sequence of SEQ ID NO:51 with an amino acid substitution, and wherein the amino acid substitution is selected from the group consisting of:

a glutamine (Q) residue of the Wnt7 polypeptide or fragment at a position corresponding to position 17 in SEQ ID NO: 24 or SEQ ID NO: 51 is substituted by an alanine (A) residue;

an isoleucine (I) residue of the Wnt7 polypeptide or fragment at a position corresponding to position 20 in SEQ ID NO: 24 or SEQ ID NO: 51 is substituted by an alanine (A) residue;

a proline (P) residue of the Wnt7 polypeptide or fragment at a position corresponding to position 25 in SEQ ID NO: 24 or SEQ ID NO: 51 is substituted by an alanine (A) residue;

an alanine (A) residue of the Wnt7 polypeptide or fragment at a position corresponding to position 27 in SEQ ID NO: 24 or SEQ ID NO: 51 is substituted by an arginine (R) residue;

an isoleucine (I) residue of the Wnt7 polypeptide or fragment at a position corresponding to position 28 in SEQ ID NO: 24 or SEQ ID NO: 51 is substituted by an alanine (A) residue;

a glutamate (E) residue of the Wnt7 polypeptide or fragment at a position corresponding to position 33 in SEQ ID NO: 24 or SEQ ID NO: 51 is substituted by an alanine (A) residue;

a methionine (M) residue of the Wnt7 polypeptide or fragment at a position corresponding to position 37 in SEQ ID NO: 24 or SEQ ID NO: 51 is substituted by an alanine (A) residue;

a leucine (L) residue of the Wnt7 polypeptide or fragment at a position corresponding to position 39 in SEQ ID NO: 24 or SEQ ID NO: 51 is substituted by an alanine (A) residue;

a glutamate (E) residue of the Wnt7 polypeptide or fragment at a position corresponding to position 41 in SEQ ID NO: 24 or SEQ ID NO: 51 is substituted by an alanine (A) residue;

a phenylalanine (F) residue of the Wnt7 polypeptide or fragment at a position corresponding to position 44 in SEQ ID NO: 24 or SEQ ID NO: 51 is substituted by an alanine (A) residue;

an arginine (R) residue of the Wnt7 polypeptide or fragment at a position corresponding to position 50 in SEQ ID NO: 24 or SEQ ID NO: 51 is substituted by an alanine (A) residue;

an asparagine (N) residue of the Wnt7 polypeptide or fragment at a position corresponding to position 52 in SEQ ID NO: 24 or SEQ ID NO: 51 is substituted by a glutamine (Q) residue;

a valine (V) residue of the Wnt7 polypeptide or fragment at a position corresponding to position 68 in SEQ ID NO: 24 or SEQ ID NO: 51 is substituted by an alanine (A) residue;

an isoleucine (I) residue of the Wnt7 polypeptide or fragment at a position corresponding to position 129 in SEQ ID NO: 24 or SEQ ID NO: 51 is substituted by an alanine (A) residue;

a phenylalanine (F) residue of the Wnt7 polypeptide or fragment at a position corresponding to position 131 in SEQ ID NO: 24 or SEQ ID NO: 51 is substituted by an alanine (A) residue;

a lysine (K) residue of the Wnt7 polypeptide or fragment at a position corresponding to position 133 in SEQ ID NO: 24 or SEQ ID NO: 51 is substituted by an alanine (A) residue;

a phenylalanine (F) residue of the Wnt7 polypeptide or fragment at a position corresponding to position 135 in SEQ ID NO: 24 or SEQ ID NO: 51 is substituted by an alanine (A) residue;

an isoleucine (I) residue of the Wnt7 polypeptide or fragment at a position corresponding to position 141 in SEQ ID NO: 24 or SEQ ID NO: 51 is substituted by an alanine (A) residue;

an arginine (R) residue of the Wnt7 polypeptide or fragment at a position corresponding to position 146 in SEQ ID NO: 24 or SEQ ID NO: 51 is substituted by an alanine (A) residue;

an arginine (R) residue of the Wnt7 polypeptide or fragment at a position corresponding to position 158 in SEQ ID NO: 24 or SEQ ID NO: 51 is substituted by an alanine (A) residue;

a lysine (K) residue of the Wnt7 polypeptide or fragment at a position corresponding to position 159 in SEQ ID NO: 24 or SEQ ID NO: 51 is substituted by an alanine (A), serine (S) or leucine (L) residue;

a lysine (K) residue of the Wnt7 polypeptide or fragment at a position corresponding to position 181 in SEQ ID NO: 24 or SEQ ID NO: 51 is substituted by an alanine (A) residue;

an arginine (R) residue of the Wnt7 polypeptide or fragment at a position corresponding to position 191 in SEQ ID NO: 24 or SEQ ID NO: 51 is substituted by an alanine (A) residue;

a lysine (K) residue of the Wnt7 polypeptide or fragment at a position corresponding to position 198 in SEQ ID NO: 24 or SEQ ID NO: 51 is substituted by an alanine (A) residue;

a lysine (K) residue of the Wnt7 polypeptide or fragment at a position corresponding to position 200 in SEQ ID NO: 24 or SEQ ID NO: 51 is substituted by an alanine (A) residue;

a valine (V) residue of the Wnt7 polypeptide or fragment at a position corresponding to position 205 in SEQ ID NO: 24 or SEQ ID NO: 51 is substituted by an alanine (A) residue;

a glutamate (E) residue of the Wnt7 polypeptide or fragment at a position corresponding to position 208 in SEQ ID NO: 24 or SEQ ID NO: 51 is substituted by an alanine (A) residue;

an arginine (R) residue of the Wnt7 polypeptide or fragment at a position corresponding to position 214 in SEQ ID NO: 24 or SEQ ID NO: 51 is substituted by an alanine (A) residue;

a lysine (K) residue of the Wnt7 polypeptide or fragment at a position corresponding to position 216 in SEQ ID NO: 24 or SEQ ID NO: 51 is substituted by an alanine (A) residue;

a proline (P) residue of the Wnt7 polypeptide or fragment at a position corresponding to position 218 in SEQ ID NO: 24 or SEQ ID NO: 51 is substituted by an alanine (A) residue;

a lysine (K) residue of the Wnt7 polypeptide or fragment at a position corresponding to position 222 in SEQ ID NO: 24 or SEQ ID NO: 51 is substituted by an alanine (A) residue;

an isoleucine (I) residue of the Wnt7 polypeptide or fragment at a position corresponding to position 223 in SEQ ID NO: 24 or SEQ ID NO: 51 is substituted by an alanine (A) residue;

a tyrosine (Y) residue of the Wnt7 polypeptide or fragment at a position corresponding to position 229 in SEQ ID NO: 24 or SEQ ID NO: 51 is substituted by an alanine (A) residue;

a proline (P) residue of the Wnt7 polypeptide or fragment at a position corresponding to position 232 in SEQ ID NO: 24 or SEQ ID NO: 51 is substituted by an alanine (A) residue;

a threonine (T) residue of the Wnt7 polypeptide or fragment at a position corresponding to position 235 in SEQ ID NO: 24 or SEQ ID NO: 51 is substituted by an alanine (A) residue;

a glutamate (E) residue of the Wnt7 polypeptide or fragment at a position corresponding to position 248 in SEQ ID NO: 51 is substituted by an alanine (A) residue;

an arginine (R) residue of the Wnt7 polypeptide or fragment at a position corresponding to position 289 in SEQ ID NO: 51 is substituted by an alanine (A) residue;

a tryptophan (W) residue of the Wnt7 polypeptide or fragment at a position corresponding to position 291 in SEQ ID NO: 51 is substituted by an alanine (A) residue;

a threonine (T) residue of the Wnt7 polypeptide or fragment at a position corresponding to position 307 in SEQ ID NO: 51 is substituted by an alanine (A) residue; or a lysine (K) residue of the Wnt7 polypeptide or fragment at a position corresponding to position 318 in SEQ ID NO: 51 is substituted by an alanine (A) residue.

2. A nucleic acid expression cassette comprising the nucleic acid according to claim 1, operably linked to a promoter and/or transcriptional and translational regulatory signals.

3. A vector comprising the nucleic acid according to claim 1.

4. A pharmaceutical composition comprising the nucleic acid according to claim 1.

* * * * *